US012752093B2

(12) United States Patent
Shauver et al.

(10) Patent No.: US 12,752,093 B2
(45) Date of Patent: Oct. 6, 2026

(54) MEDICAL CONNECTORS

(71) Applicant: ICU Medical, Inc., San Clemente, CA (US)

(72) Inventors: Erik Scott Shauver, Tustin, CA (US); Trent Spencer Wells, Santa Ana, CA (US); David Nelson, Lake Forest, CA (US)

(73) Assignee: ICU Medical, Inc., San Clemente, CA (US)

( * ) Notice: Subject to any disclaimer, the term of this patent is extended or adjusted under 35 U.S.C. 154(b) by 688 days.

(21) Appl. No.: 18/194,442

(22) Filed: Mar. 31, 2023

(65) Prior Publication Data

US 2023/0310824 A1 Oct. 5, 2023

Related U.S. Application Data

(60) Provisional application No. 63/326,612, filed on Apr. 1, 2022.

(51) Int. Cl.
*A61M 39/10* (2006.01)
*A61M 39/22* (2006.01)

(52) U.S. Cl.
CPC ............ *A61M 39/10* (2013.01); *A61M 39/22* (2013.01)

(58) Field of Classification Search
CPC ...... A61M 39/10; A61M 39/22; A61M 39/26; A61M 2039/1061; A61M 2039/268; F16L 29/04
See application file for complete search history.

(56) References Cited

U.S. PATENT DOCUMENTS 2,254,997 A 9/1941 Fisher
2,419,453 A 4/1947 Kocevar
(Continued)

FOREIGN PATENT DOCUMENTS

CA 2747283 7/2002
DE 20 2014 103247 U1 8/2014
(Continued)

OTHER PUBLICATIONS

International Preliminary Report on Patentability, re PCT Application No. PCT/US2023/080155, issued Apr. 29, 2025.
(Continued)

*Primary Examiner* — Laura A Bouchelle
(74) *Attorney, Agent, or Firm* — Knobbe, Martens, Olson & Bear, LLP

(57) ABSTRACT

A breakaway medical connector can include a housing with engagement features that interface with corresponding engagement features on a breakaway member so that the breakaway is attached to the housing. A second connector can couple to the breakaway member to provide a fluid connection between the first connector and the second connector. If a force above a threshold is applied that pulls the second connector apart from the breakaway connector, the engagement features can be overcome and the breakaway member can detach from the housing. The second connector can detach from the first connector along with the breakaway member. The connector can have a valve that closes the fluid pathway upon the separation of the breakaway member from the housing. In some embodiments, the breakaway member can be reattached to the housing, such as to reestablish fluid communication between the breakaway medical connector and the second medical connector.

38 Claims, 59 Drawing Sheets

(56) References Cited

U.S. PATENT DOCUMENTS

| | | | |
|---|---|---|---|
| 2,456,045 | A | 12/1948 | Brock |
| 2,457,052 | A | 12/1948 | Clair |
| 2,485,006 | A | 10/1949 | Main, Jr. et al. |
| 2,842,382 | A | 7/1958 | Franck |
| 2,931,668 | A | 4/1960 | Baley |
| 2,968,497 | A | 1/1961 | Treleman |
| 3,127,892 | A | 4/1964 | Bellamy, Jr. et al. |
| 3,191,972 | A | 6/1965 | Collar |
| 3,304,047 | A | 2/1967 | Martin |
| 3,334,860 | A | 8/1967 | Bolton, Jr. |
| 3,538,950 | A | 11/1970 | Porteners |
| 3,707,972 | A | 1/1973 | Villari et al. |
| 3,729,031 | A | 4/1973 | Baldwin |
| 3,824,556 | A | 7/1974 | Berkovits et al. |
| 3,986,508 | A | 10/1976 | Barrington |
| 4,055,179 | A | 10/1977 | Manschot et al. |
| 4,066,067 | A | 1/1978 | Micheli |
| 4,076,285 | A | 2/1978 | Martinez |
| 4,080,965 | A | 3/1978 | Phillips |
| 4,084,606 | A | 4/1978 | Mittleman |
| 4,121,585 | A | 10/1978 | Becker, Jr. |
| 4,133,441 | A | 1/1979 | Mittleman et al. |
| 4,143,853 | A | 3/1979 | Abramson |
| 4,150,845 | A | 4/1979 | Kopacz et al. |
| 4,187,848 | A | 2/1980 | Taylor |
| 4,195,632 | A | 4/1980 | Parker et al. |
| 4,233,982 | A | 11/1980 | Bauer et al. |
| 4,245,635 | A | 1/1981 | Kontos |
| 4,286,640 | A | 9/1981 | Knox |
| 4,324,239 | A | 4/1982 | Gordon et al. |
| 4,334,551 | A | 6/1982 | Pfister |
| 4,340,049 | A | 7/1982 | Munsch |
| 4,379,458 | A | 4/1983 | Bauer et al. |
| 4,387,879 | A | 6/1983 | Tauschinski |
| 4,397,442 | A | 8/1983 | Larkin |
| 4,405,312 | A | 9/1983 | Gross et al. |
| 4,430,073 | A | 2/1984 | Bemis et al. |
| 4,432,759 | A | 2/1984 | Gross et al. |
| 4,436,125 | A | 3/1984 | Blenkush |
| 4,452,473 | A | 6/1984 | Ruschke |
| 4,457,749 | A | 7/1984 | Bellotti et al. |
| 4,473,369 | A | 9/1984 | Lueders et al. |
| 4,511,359 | A | 4/1985 | Vaillancourt |
| 4,538,836 | A | 9/1985 | Kruetten |
| 4,541,457 | A | 9/1985 | Blenkush |
| 4,576,359 | A | 3/1986 | Oetiker |
| 4,596,571 | A | 6/1986 | Bellotti et al. |
| 4,607,868 | A | 8/1986 | Harvey et al. |
| 4,610,469 | A | 9/1986 | Wolff-Mooij |
| 4,619,640 | A | 10/1986 | Potolsky et al. |
| 4,623,332 | A | 11/1986 | Lindmayer et al. |
| 4,629,159 | A | 12/1986 | Wellenstam |
| 4,660,803 | A | 4/1987 | Johnston et al. |
| 4,662,878 | A | 5/1987 | Lindmayer |
| 4,673,400 | A | 6/1987 | Martin |
| 4,700,744 | A | 10/1987 | Rutter et al. |
| 4,723,603 | A | 2/1988 | Plummer |
| 4,723,948 | A | 2/1988 | Clark et al. |
| 4,728,075 | A | 3/1988 | Paradis |
| 4,745,950 | A | 5/1988 | Mathieu |
| 4,758,023 | A | 7/1988 | Vermillion |
| 4,774,964 | A | 10/1988 | Bonaldo |
| 4,774,965 | A | 10/1988 | Rodriguez et al. |
| 4,781,702 | A | 11/1988 | Herrli |
| 4,804,015 | A | 2/1989 | Albinsson |
| 4,816,024 | A | 3/1989 | Sitar et al. |
| 4,819,692 | A | 4/1989 | Olson et al. |
| 4,834,271 | A | 5/1989 | Litwin |
| 4,844,512 | A | 7/1989 | Gahwiler |
| 4,862,913 | A | 9/1989 | Wildfang |
| 4,863,201 | A | 9/1989 | Carstens |
| 4,883,483 | A | 11/1989 | Lindmayer |
| 4,915,687 | A | 4/1990 | Sivert |
| 4,917,669 | A | 4/1990 | Bonaldo |
| 4,935,010 | A | 6/1990 | Cox et al. |
| 4,949,745 | A | 8/1990 | McKeon |
| 4,950,260 | A | 8/1990 | Bonaldo |
| 4,969,879 | A | 11/1990 | Lichte |
| D313,277 | S | 12/1990 | Haining |
| D314,050 | S | 1/1991 | Sone |
| 5,006,114 | A | 4/1991 | Rogers et al. |
| 5,021,059 | A | 6/1991 | Kensey et al. |
| 5,047,021 | A | 9/1991 | Utterberg |
| 5,053,015 | A | 10/1991 | Gross |
| 5,065,783 | A | 11/1991 | Ogle, II |
| 5,066,286 | A | 11/1991 | Ryan |
| 5,070,885 | A | 12/1991 | Bonaldo |
| 5,083,819 | A | 1/1992 | Bynum |
| 5,098,385 | A | 3/1992 | Walsh |
| 5,108,376 | A | 4/1992 | Bonaldo |
| 5,122,123 | A | 6/1992 | Vaillancourt |
| 5,139,483 | A | 8/1992 | Ryan |
| 5,147,333 | A | 9/1992 | Raines |
| 5,154,703 | A | 10/1992 | Bonaldo |
| 5,176,406 | A | 1/1993 | Straghan |
| RE34,223 | E | 4/1993 | Bonaldo |
| 5,199,948 | A | 4/1993 | McPhee |
| 5,201,717 | A | 4/1993 | Wyatt et al. |
| 5,201,725 | A | 4/1993 | Kling |
| 5,203,775 | A | 4/1993 | Frank et al. |
| 5,211,634 | A | 5/1993 | Vaillancourt |
| 5,215,537 | A | 6/1993 | Lynn et al. |
| 5,215,538 | A | 6/1993 | Larkin |
| 5,224,939 | A | 7/1993 | Holman et al. |
| 5,242,393 | A | 9/1993 | Brimhall et al. |
| 5,242,425 | A | 9/1993 | White et al. |
| 5,251,873 | A | 10/1993 | Atkinson et al. |
| 5,269,771 | A | 12/1993 | Thomas et al. |
| 5,273,533 | A | 12/1993 | Bonaldo |
| 5,279,571 | A | 1/1994 | Larkin |
| 5,281,206 | A | 1/1994 | Lopez |
| 5,284,475 | A | 2/1994 | Mackal |
| 5,295,657 | A | 3/1994 | Atkinson |
| 5,301,686 | A | 4/1994 | Newman |
| 5,306,243 | A | 4/1994 | Bonaldo |
| 5,312,377 | A | 5/1994 | Dalton |
| 5,322,518 | A | 6/1994 | Schneider et al. |
| 5,324,270 | A | 6/1994 | Kayan et al. |
| 5,330,235 | A | 7/1994 | Wagner et al. |
| 5,330,450 | A | 7/1994 | Lopez |
| 5,334,159 | A | 8/1994 | Turkel |
| 5,344,414 | A | 9/1994 | Lopez et al. |
| 5,360,413 | A | 11/1994 | Leason et al. |
| 5,370,636 | A | 12/1994 | Von Witzleben |
| 5,380,306 | A | 1/1995 | Brinon |
| 5,385,372 | A | 1/1995 | Utterberg |
| 5,390,898 | A | 2/1995 | Smedley et al. |
| 5,391,150 | A | 2/1995 | Richmond |
| 5,395,348 | A | 3/1995 | Ryan |
| 5,397,314 | A | 3/1995 | Farley et al. |
| 5,400,500 | A | 3/1995 | Behnke et al. |
| 5,401,245 | A | 3/1995 | Haining |
| 5,402,826 | A | 4/1995 | Molnar et al. |
| 5,402,982 | A | 4/1995 | Atkinson et al. |
| 5,405,323 | A | 4/1995 | Rogers et al. |
| 5,405,331 | A | 4/1995 | Behnke et al. |
| 5,405,333 | A | 4/1995 | Richmond |
| D358,882 | S | 5/1995 | Metz et al. |
| 5,411,499 | A | 5/1995 | Dudar et al. |
| 5,417,673 | A | 5/1995 | Gordon |
| 5,423,791 | A | 6/1995 | Bartlett |
| 5,425,465 | A | 6/1995 | Healy |
| 5,433,330 | A | 7/1995 | Yatsko et al. |
| 5,439,451 | A | 8/1995 | Collinson et al. |
| 5,441,487 | A | 8/1995 | Vedder |
| 5,445,623 | A | 8/1995 | Richmond |
| 5,447,177 | A | 9/1995 | Ricken et al. |
| 5,456,668 | A | 10/1995 | Ogle, II |
| 5,456,675 | A | 10/1995 | Wolbring et al. |
| 5,462,255 | A | 10/1995 | Rosen et al. |
| 5,464,399 | A | 11/1995 | Boettger |
| 5,470,319 | A | 11/1995 | Mayer |
| 5,470,327 | A | 11/1995 | Helgren et al. |
| 5,474,536 | A | 12/1995 | Bonaldo |

(56) References Cited

U.S. PATENT DOCUMENTS

| | | | |
|---|---|---|---|
| 5,480,393 | A | 1/1996 | Bommarito |
| 5,489,274 | A | 2/1996 | Chu et al. |
| 5,492,147 | A | 2/1996 | Challender et al. |
| 5,501,426 | A | 3/1996 | Atkinson et al. |
| 5,507,744 | A | 4/1996 | Tay et al. |
| 5,514,177 | A | 5/1996 | Kurz et al. |
| 5,518,026 | A | 5/1996 | Benjey |
| 5,520,665 | A | 5/1996 | Fleetwood |
| 5,520,666 | A | 5/1996 | Choudhury et al. |
| 5,527,284 | A | 6/1996 | Ohnemus et al. |
| 5,531,695 | A | 7/1996 | Swisher |
| 5,533,708 | A | 7/1996 | Atkinson et al. |
| 5,533,983 | A | 7/1996 | Haining |
| 5,533,996 | A | 7/1996 | Murphey et al. |
| 5,535,785 | A | 7/1996 | Werge et al. |
| 5,540,661 | A | 7/1996 | Tomisaka et al. |
| 5,549,566 | A | 8/1996 | Elias et al. |
| 5,549,577 | A | 8/1996 | Siegel et al. |
| 5,549,583 | A | 8/1996 | Sanford et al. |
| 5,549,651 | A | 8/1996 | Lynn |
| 5,552,118 | A | 9/1996 | Mayer |
| 5,555,908 | A | 9/1996 | Edwards et al. |
| 5,569,235 | A | 10/1996 | Ross et al. |
| 5,573,516 | A | 11/1996 | Tyner |
| 5,575,769 | A | 11/1996 | Vaillancourt |
| 5,578,059 | A | 11/1996 | Patzer |
| 5,584,819 | A | 12/1996 | Kopfer |
| 5,591,137 | A | 1/1997 | Stevens |
| 5,591,143 | A | 1/1997 | Trombley, III et al. |
| 5,597,536 | A | 1/1997 | Mayer |
| 5,616,129 | A | 4/1997 | Mayer |
| 5,616,130 | A | 4/1997 | Mayer |
| 5,620,210 | A | 4/1997 | Eyster et al. |
| 5,620,427 | A | 4/1997 | Werschmidt et al. |
| RE35,539 | E | 6/1997 | Bonaldo |
| 5,643,224 | A | 7/1997 | Szapiro et al. |
| 5,645,538 | A | 7/1997 | Richmond |
| 5,651,776 | A | 7/1997 | Appling et al. |
| D382,958 | S | 8/1997 | Wolff |
| 5,658,260 | A | 8/1997 | Desecki et al. |
| 5,674,206 | A | 10/1997 | Allton et al. |
| 5,676,346 | A | 10/1997 | Leinsing |
| 5,685,866 | A | 11/1997 | Lopez |
| 5,685,868 | A | 11/1997 | Lundquist |
| 5,699,821 | A | 12/1997 | Paradis |
| 5,700,248 | A | 12/1997 | Lopez |
| 5,702,374 | A | 12/1997 | Johnson |
| 5,709,243 | A | 1/1998 | Wells et al. |
| 5,735,826 | A | 4/1998 | Richmond |
| 5,738,144 | A | 4/1998 | Rogers |
| 5,741,084 | A | 4/1998 | Del Rio et al. |
| 5,749,861 | A | 5/1998 | Guala et al. |
| D395,502 | S | 6/1998 | Deily et al. |
| RE35,841 | E | 7/1998 | Frank et al. |
| 5,782,816 | A | 7/1998 | Werschmidt et al. |
| 5,784,750 | A | 7/1998 | Sankovic et al. |
| 5,785,693 | A | 7/1998 | Haining |
| 5,788,215 | A | 8/1998 | Ryan |
| 5,806,831 | A | 9/1998 | Paradis |
| 5,810,398 | A | 9/1998 | Matkovich |
| 5,814,024 | A | 9/1998 | Thompson et al. |
| 5,820,601 | A | 10/1998 | Mayer |
| 5,820,614 | A | 10/1998 | Erksine et al. |
| 5,830,189 | A | 11/1998 | Chang |
| 5,830,195 | A | 11/1998 | Peters et al. |
| 5,839,715 | A | 11/1998 | Leinsing |
| 5,848,994 | A | 12/1998 | Richmond |
| 5,855,568 | A | 1/1999 | Battiato et al. |
| 5,947,954 | A | 9/1999 | Bonaldo |
| 5,984,373 | A | 11/1999 | Fitoussi et al. |
| 6,029,946 | A | 2/2000 | Doyle |
| 6,036,171 | A | 3/2000 | Weinheimer et al. |
| 6,039,302 | A | 3/2000 | Cote, Sr. et al. |
| 6,041,805 | A | 3/2000 | Gydesen et al. |
| 6,050,978 | A | 4/2000 | Orr et al. |
| 6,063,062 | A | 5/2000 | Paradis |
| 6,068,011 | A | 5/2000 | Paradis |
| 6,068,617 | A | 5/2000 | Richmond |
| 6,079,432 | A | 6/2000 | Paradis |
| 6,082,401 | A | 7/2000 | Braun et al. |
| 6,099,519 | A | 8/2000 | Olsen et al. |
| 6,106,502 | A | 8/2000 | Richmond |
| 6,113,068 | A | 9/2000 | Ryan |
| 6,142,446 | A | 11/2000 | Leinsing |
| 6,152,913 | A | 11/2000 | Feith et al. |
| 6,168,137 | B1 | 1/2001 | Paradis |
| 6,170,522 | B1 | 1/2001 | Tanida |
| 6,171,287 | B1 | 1/2001 | Lynn et al. |
| 6,183,464 | B1 | 2/2001 | Sharp et al. |
| 6,189,859 | B1 | 2/2001 | Rohrbough et al. |
| 6,206,860 | B1 | 3/2001 | Richmond |
| 6,221,029 | B1 | 4/2001 | Mathis et al. |
| 6,224,578 | B1 | 5/2001 | Davis et al. |
| 6,224,588 | B1 | 5/2001 | Jentzen |
| 6,231,552 | B1 | 5/2001 | Jentzen |
| 6,242,393 | B1 | 6/2001 | Ishida et al. |
| 6,245,048 | B1 | 6/2001 | Fangrow et al. |
| 6,290,206 | B1 | 9/2001 | Doyle |
| 6,299,132 | B1 | 10/2001 | Weinheimer et al. |
| 6,325,100 | B1 | 12/2001 | Bunschoten et al. |
| 6,332,633 | B1 | 12/2001 | Fitoussi et al. |
| 6,402,207 | B1 | 6/2002 | Segal et al. |
| 6,428,520 | B1 | 8/2002 | Lopez |
| 6,431,219 | B1 | 8/2002 | Redler et al. |
| 6,439,276 | B1 | 8/2002 | Wood et al. |
| D465,843 | S | 11/2002 | Guala |
| 6,485,472 | B1 | 11/2002 | Richmond |
| 6,499,719 | B1 | 12/2002 | Clancy et al. |
| D469,530 | S | 1/2003 | Gomez |
| 6,508,792 | B2 | 1/2003 | Szames et al. |
| 6,508,807 | B1 | 1/2003 | Peters |
| 6,541,802 | B2 | 4/2003 | Doyle |
| 6,543,745 | B1 | 4/2003 | Enerson |
| 6,581,906 | B2 | 6/2003 | Pott et al. |
| 6,585,229 | B2 | 7/2003 | Cote et al. |
| 6,595,964 | B2 | 7/2003 | Finley et al. |
| 6,595,981 | B2 | 7/2003 | Huet |
| 6,605,076 | B1 | 8/2003 | Jepson |
| 6,609,696 | B2 | 8/2003 | Enerson |
| 6,612,624 | B1 | 9/2003 | Segal et al. |
| 6,666,852 | B2 | 12/2003 | Niedospial, Jr. |
| 6,673,059 | B2 | 1/2004 | Guala |
| 6,681,803 | B2 | 1/2004 | Taneya et al. |
| 6,695,817 | B1 | 2/2004 | Fangrow |
| 6,745,998 | B2 | 6/2004 | Doyle |
| 6,808,161 | B1 | 10/2004 | Hishikawa |
| 6,840,501 | B2 | 1/2005 | Doyle |
| 6,843,513 | B2 | 1/2005 | Guala |
| 6,869,426 | B2 | 3/2005 | Ganem |
| 6,875,205 | B2 | 4/2005 | Leinsing |
| 6,893,056 | B2 | 5/2005 | Guala |
| 6,899,315 | B2 | 5/2005 | Mailville et al. |
| 6,911,025 | B2 | 6/2005 | Miyahara |
| 6,916,051 | B2 | 7/2005 | Fisher |
| 6,955,669 | B2 | 10/2005 | Curutcharry |
| 6,964,406 | B2 | 11/2005 | Doyle |
| 6,991,608 | B2 | 1/2006 | Young et al. |
| 6,997,917 | B2 | 2/2006 | Niedospial, Jr. et al. |
| 7,004,934 | B2 | 2/2006 | Vaillancourt |
| 7,037,302 | B2 | 5/2006 | Vaillancourt |
| 7,040,598 | B2 | 5/2006 | Raybuck |
| 7,044,441 | B2 | 5/2006 | Doyle |
| 7,100,891 | B2 | 9/2006 | Doyle |
| 7,125,396 | B2 | 10/2006 | Leinsing et al. |
| 7,137,654 | B2 | 11/2006 | Segal et al. |
| 7,140,592 | B2 | 11/2006 | Phillips |
| 7,160,272 | B1 | 1/2007 | Eyal et al. |
| D536,958 | S | 2/2007 | Ruhlander |
| 7,182,313 | B2 | 2/2007 | Doyle |
| 7,195,228 | B2 | 3/2007 | Tiberghien et al. |
| 7,244,249 | B2 | 7/2007 | Leinsing et al. |
| 7,306,197 | B2 | 12/2007 | Parrino et al. |
| 7,306,198 | B2 | 12/2007 | Doyle |
| 7,306,566 | B2 | 12/2007 | Raybuck |

(56) References Cited

U.S. PATENT DOCUMENTS 7,316,679 B2 1/2008 Bierman
7,347,458 B2 3/2008 Rome et al.
7,350,764 B2 4/2008 Raybuck
7,350,834 B2 4/2008 Ryhman et al.
7,361,164 B2 4/2008 Simpson et al.
D569,973 S 5/2008 Oren et al.
7,396,051 B2 7/2008 Baldwin et al.
7,448,653 B2 11/2008 Jensen et al.
7,497,484 B2 3/2009 Ziman
7,503,596 B2 3/2009 Rome et al.
D590,022 S 4/2009 Misumi
D595,420 S 6/2009 Suzuki et al.
D595,421 S 6/2009 Suzuki et al.
D595,863 S 7/2009 Suzuki et al.
7,559,530 B2 7/2009 Korogi et al.
7,588,563 B2 9/2009 Guala
7,600,515 B2 10/2009 Matlock
7,628,781 B2 12/2009 Roy et al.
7,645,274 B2 1/2010 Whitley
7,651,481 B2 1/2010 Raybuck
7,666,170 B2 2/2010 Guala
D612,939 S 3/2010 Boone, III et al.
7,670,326 B2 3/2010 Shemesh
7,717,874 B2 5/2010 Landau et al.
7,722,090 B2 5/2010 Burton et al.
7,758,566 B2 7/2010 Simpson et al.
7,762,524 B2 7/2010 Cawthon et al.
7,763,013 B2 7/2010 Baldwin et al.
7,766,304 B2 8/2010 Phillips
7,766,897 B2 8/2010 Ramsey et al.
7,770,939 B2 8/2010 Jensen et al.
7,803,139 B2 9/2010 Fangrow, Jr.
7,803,140 B2 9/2010 Fangrow, Jr.
7,806,139 B2 10/2010 Packham et al.
7,815,614 B2 10/2010 Fangrow, Jr.
7,837,658 B2 11/2010 Cote et al.
7,857,805 B2 12/2010 Raines
7,867,215 B2 1/2011 Akerlund et al.
7,875,019 B2 1/2011 Barron et al.
D636,079 S 4/2011 Leypold et al.
7,976,532 B2 7/2011 Kitani et al.
7,998,134 B2 8/2011 Fangrow et al.
8,066,692 B2 11/2011 Simpson et al.
8,113,546 B2 2/2012 Jensen et al.
8,123,738 B2 2/2012 Vaillancourt
8,162,013 B2 4/2012 Rosenquist et al.
8,162,914 B2 4/2012 Kraushaar et al.
8,177,760 B2 5/2012 Rome et al.
D662,122 S 6/2012 Goodwin et al.
8,196,606 B2 6/2012 Kitagawa
8,196,614 B2 6/2012 Kriheli
8,197,452 B2 6/2012 Harding et al.
8,197,466 B2 6/2012 Yokota et al.
8,211,069 B2 7/2012 Fangrow, Jr.
8,225,826 B2 7/2012 Horppu et al.
8,231,567 B2 7/2012 Tennican et al.
8,235,426 B2 8/2012 Pisula, Jr. et al.
8,251,346 B2 8/2012 Stroup
8,262,628 B2 9/2012 Fangrow, Jr.
8,277,424 B2 10/2012 Pan et al.
8,281,824 B2 10/2012 Molema et al.
8,286,936 B2 10/2012 Kitani et al.
8,287,513 B2 10/2012 Ellstrom et al.
8,287,518 B2 10/2012 Kitani et al.
8,298,195 B2 10/2012 Peppel
8,336,587 B2 12/2012 Rosenquist et al.
8,337,483 B2 12/2012 Harding et al.
8,361,408 B2 1/2013 Lynn
8,366,676 B2 2/2013 Harding et al.
8,372,059 B2 2/2013 Ziman
8,377,010 B2 2/2013 Harding et al.
8,392,756 B2 3/2013 Nakayama et al.
8,397,756 B2 3/2013 Packham et al.
8,403,894 B2 3/2013 Lynn et al.
8,403,905 B2 3/2013 Yow
8,408,226 B2 4/2013 Raines et al.
8,409,165 B2 4/2013 Niedospial, Jr. et al.
8,414,554 B2 4/2013 Garfield et al.
8,414,555 B2 4/2013 Garfield et al.
8,448,994 B2 5/2013 Pisula, Jr. et al.
8,454,579 B2 6/2013 Fangrow, Jr.
8,479,370 B2 7/2013 Grant
8,500,717 B2 8/2013 Becker
8,529,524 B2 9/2013 Newton et al.
8,556,868 B2 10/2013 Simpson et al.
8,596,688 B2 12/2013 Pisula, Jr. et al.
8,603,047 B2 12/2013 Stroup
8,628,516 B2 1/2014 Naftalovitz et al.
8,641,685 B2 2/2014 Mansour et al.
8,647,310 B2 2/2014 Fangrow, Jr. et al.
8,667,997 B2 3/2014 Costanzo
8,671,964 B2 3/2014 Py
8,679,090 B2 3/2014 Anderson et al.
8,684,994 B2 4/2014 Lev et al.
8,702,675 B2 4/2014 Imai
8,715,222 B2 5/2014 Truitt et al.
8,715,247 B2 5/2014 Mansour et al.
8,721,614 B2 5/2014 Takemoto
8,721,627 B2 5/2014 Albert
8,721,628 B2 5/2014 Ziman
8,746,278 B2 6/2014 Py
8,764,731 B2 7/2014 Burgess et al.
8,777,908 B2 7/2014 Fangrow, Jr.
8,777,909 B2 7/2014 Fangrow, Jr.
8,777,931 B2 7/2014 Davis et al.
8,790,327 B2 7/2014 Takemoto
8,790,330 B2 7/2014 Rosenquist
8,795,256 B1 8/2014 Smith
8,801,678 B2 8/2014 Panian et al.
8,834,432 B2 9/2014 Winsor et al.
8,864,725 B2 10/2014 Ranalletta et al.
8,864,737 B2 10/2014 Hasegawa et al.
8,870,832 B2 10/2014 Raday et al.
8,870,846 B2 10/2014 Davis et al.
8,876,784 B2 11/2014 Coete, Sr. et al.
8,882,742 B2 11/2014 Dikeman et al.
8,888,758 B2 11/2014 Mansour et al.
8,899,267 B2 12/2014 Diodati et al.
8,910,919 B2 12/2014 Bonnal et al.
8,951,233 B2 2/2015 Mansour
8,968,261 B2 3/2015 Kimball et al.
8,968,271 B2 3/2015 Guala
8,974,425 B2 3/2015 Tachizaki et al.
8,979,804 B2 3/2015 Ho et al.
9,017,295 B2 4/2015 Pan
9,032,997 B2 5/2015 Abura et al.
9,039,047 B2 5/2015 Imai
9,044,554 B2 6/2015 Wu et al.
9,044,585 B2 6/2015 Masuda et al.
9,061,130 B2 6/2015 Truitt et al.
9,067,049 B2 6/2015 Panian et al.
9,089,680 B2 7/2015 Ueda et al.
9,089,681 B2 7/2015 Ueda et al.
9,114,242 B2 8/2015 Fangrow et al.
9,114,244 B2 8/2015 Yeh et al.
9,119,950 B2 9/2015 Mansour et al.
9,126,028 B2 9/2015 Fangrow et al.
9,126,029 B2 9/2015 Fangrow et al.
9,138,572 B2 9/2015 Zeytoonian et al.
9,149,622 B2 10/2015 Bonnet et al.
9,168,203 B2 10/2015 Rosenquist et al.
9,168,366 B2 10/2015 Fangrow et al.
9,198,831 B2 12/2015 Rogers
9,220,882 B2 12/2015 Belley et al.
9,234,616 B2 1/2016 Carrez et al.
9,238,128 B2 1/2016 Yamaguchi et al.
9,308,317 B2 4/2016 Poncon
9,314,604 B2 4/2016 Bonnal et al.
9,345,641 B2 5/2016 Kraus et al.
9,351,906 B2 5/2016 Garfield et al.
9,358,182 B2 6/2016 Garfield et al.
9,358,379 B2 6/2016 Fangrow
9,393,398 B2 7/2016 Truitt et al.
9,409,007 B2 8/2016 Yeh

(56) References Cited

U.S. PATENT DOCUMENTS

| | | | |
|---|---|---|---|
| 9,433,768 | B2 | 9/2016 | Tekeste et al. |
| 9,541,227 | B2 | 1/2017 | Okiyama |
| 9,592,344 | B2 | 3/2017 | Simpson et al. |
| 9,636,492 | B2 | 5/2017 | Fangrow, Jr. |
| 9,683,683 | B2 | 6/2017 | Reuter |
| 9,707,346 | B2 | 7/2017 | Simpson et al. |
| D793,553 | S | 8/2017 | Stillson |
| 9,724,504 | B2 | 8/2017 | Fangrow, Jr. et al. |
| 9,726,308 | B2 | 8/2017 | Williams et al. |
| D799,938 | S | 10/2017 | Lowitz |
| D799,939 | S | 10/2017 | Lowitz |
| 9,775,979 | B2 | 10/2017 | Okiyama |
| 9,795,736 | B2 | 10/2017 | Okiyama |
| 9,814,870 | B2 | 11/2017 | Jin et al. |
| 9,833,605 | B2 | 12/2017 | Sanders et al. |
| 9,861,805 | B2 | 1/2018 | Dennis et al. |
| 9,884,177 | B2 | 2/2018 | Ueda et al. |
| 9,895,290 | B2 | 2/2018 | Cederschiöld et al. |
| 9,907,944 | B2 | 3/2018 | Liebe et al. |
| 9,913,945 | B2 | 3/2018 | Simpson et al. |
| 9,933,094 | B2 | 4/2018 | Fangrow |
| 9,950,152 | B2 | 4/2018 | Guala |
| 9,968,771 | B2 | 5/2018 | Wong |
| 9,974,939 | B2 | 5/2018 | Fangrow, Jr. |
| 9,974,940 | B2 | 5/2018 | Fangrow, Jr. |
| 9,987,407 | B2 | 6/2018 | Grant et al. |
| 9,993,634 | B2 | 6/2018 | Christensen et al. |
| 10,022,531 | B2 | 7/2018 | Shemesh |
| 10,046,154 | B2 | 8/2018 | Fangrow et al. |
| 10,098,816 | B2 | 10/2018 | Carney et al. |
| 10,105,492 | B2 | 10/2018 | Simpson |
| 10,149,940 | B2 | 12/2018 | Yagi et al. |
| 10,149,949 | B2 | 12/2018 | Tekeste et al. |
| 10,156,306 | B2 | 12/2018 | Fangrow |
| 10,188,847 | B2 | 1/2019 | Tohse et al. |
| 10,201,693 | B2 | 2/2019 | Tsai |
| 10,206,853 | B2 | 2/2019 | Sanders et al. |
| 10,207,096 | B2 | 2/2019 | Jensen et al. |
| 10,279,159 | B2 | 5/2019 | Andreen et al. |
| 10,279,160 | B2 | 5/2019 | Guala |
| 10,286,201 | B2 | 5/2019 | Mckinnon et al. |
| D851,759 | S | 6/2019 | Jones et al. |
| 10,315,024 | B1 | 6/2019 | Vitello et al. |
| 10,357,643 | B2 | 7/2019 | Buchanan |
| 10,369,347 | B2 | 8/2019 | Lauer |
| D859,650 | S | 9/2019 | Steele et al. |
| 10,398,887 | B2 | 9/2019 | Fangrow, Jr. et al. |
| 10,473,246 | B2 | 11/2019 | Herrema et al. |
| D870,881 | S | 12/2019 | Mullani |
| 10,500,327 | B2 | 12/2019 | Grant et al. |
| 10,500,390 | B2 | 12/2019 | Ueda et al. |
| 10,500,391 | B2 | 12/2019 | Takeuchi |
| 10,518,076 | B2 | 12/2019 | Christie et al. |
| 10,518,077 | B2 | 12/2019 | Wong |
| 10,518,078 | B2 | 12/2019 | Stjernberg Bejhed et al. |
| 10,537,726 | B2 | 1/2020 | Guala |
| 10,556,099 | B2 | 2/2020 | Takeuchi |
| 10,569,073 | B2 * | 2/2020 | Hallisey ................ A61M 39/26 |
| 10,569,074 | B2 | 2/2020 | Stenzel et al. |
| D879,956 | S | 3/2020 | Klenner et al. |
| 10,655,768 | B2 | 5/2020 | Jones et al. |
| 10,682,505 | B2 | 6/2020 | Shemesh |
| 10,682,506 | B2 | 6/2020 | Iwakata et al. |
| 10,695,549 | B2 | 6/2020 | Roxas et al. |
| 10,697,570 | B2 * | 6/2020 | Fangrow ............... A61M 39/18 |
| 10,716,928 | B2 | 7/2020 | Fangrow et al. |
| 10,744,317 | B2 | 8/2020 | Davis et al. |
| 10,842,982 | B2 | 11/2020 | Fangrow, Jr. |
| 10,842,983 | B2 | 11/2020 | Ubaldi et al. |
| 10,850,086 | B2 | 12/2020 | Ueda et al. |
| 10,857,346 | B2 | 12/2020 | Dennis et al. |
| 10,864,362 | B2 | 12/2020 | Jones et al. |
| 11,168,818 | B2 | 11/2021 | Fangrow |
| 11,213,668 | B2 | 1/2022 | Mansour et al. |
| 11,266,785 | B2 | 3/2022 | Simpson et al. |
| 11,291,822 | B2 | 4/2022 | Jones et al. |
| 11,445,954 | B2 | 9/2022 | Jones et al. |
| 11,478,624 | B2 | 10/2022 | Fangrow et al. |
| 11,523,970 | B1 | 12/2022 | Vitello et al. |
| D976,982 | S | 1/2023 | Meyer |
| D982,140 | S | 3/2023 | Mitrovic |
| 11,648,383 | B2 | 5/2023 | Hallisey et al. |
| 11,701,040 | B2 | 7/2023 | Jones et al. |
| 11,708,924 | B2 | 7/2023 | Mansour et al. |
| 11,786,715 | B2 | 10/2023 | Fangrow, Jr. et al. |
| 11,808,389 | B2 | 11/2023 | Fangrow |
| 11,857,751 | B1 | 1/2024 | Vitello |
| D1,029,247 | S | 5/2024 | Janzen |
| D1,037,443 | S | 7/2024 | Kawachi |
| D1,038,388 | S | 8/2024 | Kawachi |
| D1,038,389 | S | 8/2024 | Kawachi |
| D1,038,390 | S | 8/2024 | Kawachi |
| D1,038,391 | S | 8/2024 | Kawachi |
| 12,072,049 | B2 | 8/2024 | Mansour et al. |
| D1,042,800 | S | 9/2024 | Sender et al. |
| D1,042,817 | S | 9/2024 | Fangrow |
| D1,042,822 | S | 9/2024 | Sender et al. |
| 12,076,522 | B2 | 9/2024 | Erekovcanski et al. |
| 12,109,387 | B2 | 10/2024 | Feith |
| 12,134,500 | B2 | 11/2024 | Wurm |
| D1,059,589 | S | 1/2025 | Reed et al. |
| D1,065,524 | S | 3/2025 | Kawachi |
| D1,069,110 | S | 4/2025 | Hund |
| D1,071,162 | S | 4/2025 | Neby |
| D1,071,169 | S | 4/2025 | Consolaro et al. |
| D1,071,202 | S | 4/2025 | Ubbesen |
| 12,280,230 | B2 | 4/2025 | Fangrow et al. |
| D1,073,939 | S | 5/2025 | Sender et al. |
| D1,075,002 | S | 5/2025 | Yang |
| D1,077,216 | S | 5/2025 | Kawachi |
| 12,320,453 | B2 | 6/2025 | Fangrow |
| D1,100,189 | S | 10/2025 | Fangrow |
| D1,105,422 | S | 12/2025 | Shauver |
| 2001/0029355 | A1 | 10/2001 | Szames et al. |
| 2001/0049490 | A1 | 12/2001 | Slanda et al. |
| 2002/0066715 | A1 | 6/2002 | Niedospial, Jr. |
| 2002/0153503 | A1 | 10/2002 | Newton et al. |
| 2003/0060804 | A1 | 3/2003 | Vaillancourt |
| 2003/0066978 | A1 | 4/2003 | Enerson |
| 2003/0111623 | A1 | 6/2003 | Enerson |
| 2003/0136932 | A1 | 7/2003 | Doyle |
| 2003/0151256 | A1 | 8/2003 | Guala |
| 2003/0201639 | A1 | 10/2003 | Korkor |
| 2003/0208165 | A1 | 11/2003 | Christensen et al. |
| 2004/0074541 | A1 | 4/2004 | Sharpe |
| 2004/0124388 | A1 | 7/2004 | Kiehne |
| 2004/0124389 | A1 | 7/2004 | Phillips |
| 2004/0238776 | A1 | 12/2004 | Peters et al. |
| 2004/0244848 | A1 | 12/2004 | Maldavs |
| 2005/0015075 | A1 | 1/2005 | Wright et al. |
| 2005/0033268 | A1 | 2/2005 | Decaria |
| 2005/0090805 | A1 | 4/2005 | Shaw et al. |
| 2005/0124942 | A1 | 6/2005 | Richmond |
| 2005/0212292 | A1 | 9/2005 | Parrino et al. |
| 2005/0228362 | A1 | 10/2005 | Vaillancourt |
| 2005/0245872 | A1 | 11/2005 | Simpson et al. |
| 2006/0025751 | A1 | 2/2006 | Roy et al. |
| 2006/0058734 | A1 | 3/2006 | Phillips |
| 2006/0129109 | A1 | 6/2006 | Shaw et al. |
| 2006/0142730 | A1 | 6/2006 | Proulx et al. |
| 2006/0149213 | A1 | 7/2006 | Raybuck |
| 2006/0157971 | A1 | 7/2006 | Baldwin et al. |
| 2006/0161115 | A1 | 7/2006 | Fangrow |
| 2006/0192164 | A1 | 8/2006 | Korogi et al. |
| 2006/0202146 | A1 | 9/2006 | Doyle |
| 2006/0211996 | A1 | 9/2006 | Trinchera et al. |
| 2006/0253084 | A1 | 11/2006 | Nordgren |
| 2007/0043334 | A1 | 2/2007 | Guala |
| 2007/0066965 | A1 | 3/2007 | Coambs et al. |
| 2007/0088292 | A1 | 4/2007 | Fangrow |
| 2007/0088293 | A1 | 4/2007 | Fangrow |
| 2007/0088294 | A1 | 4/2007 | Fangrow |
| 2007/0088327 | A1 | 4/2007 | Guala |
| 2007/0102923 | A1 | 5/2007 | Niemela |

(56) References Cited

U.S. PATENT DOCUMENTS

2007/0179453 A1 8/2007 Lim et al.
2007/0179454 A1 8/2007 Ziman et al.
2008/0067807 A1 3/2008 deCler et al.
2008/0103485 A1 5/2008 Kruger
2008/0125756 A1 5/2008 Dicarlo et al.
2008/0140020 A1 6/2008 Shirley
2008/0190485 A1 8/2008 Guala
2008/0200900 A1 8/2008 Aeschlimann et al.
2008/0290657 A1 11/2008 McKeon, III
2009/0001720 A1 1/2009 Cheon et al.
2010/0211019 A1 8/2010 Greco
2010/0249723 A1 9/2010 Fangrow, Jr.
2010/0253070 A1 10/2010 Cheon et al.
2010/0264343 A1 10/2010 Jeory
2010/0292673 A1 11/2010 Korogi et al.
2011/0046572 A1 2/2011 Fangrow
2011/0062703 A1 3/2011 Lopez
2011/0074148 A1 3/2011 Imai
2011/0175347 A1 7/2011 Okiyama
2011/0306931 A1 12/2011 Kamen et al.
2011/0319859 A1 12/2011 Zeytoonian et al.
2012/0022468 A1 1/2012 Silver
2012/0031515 A1 2/2012 Whitaker
2012/0046636 A1 2/2012 Kriheli
2012/0089101 A1 4/2012 Carlyon et al.
2012/0109077 A1 5/2012 Ryan
2012/0153201 A1 6/2012 Larose et al.
2012/0220955 A1 8/2012 Maseda et al.
2012/0220984 A1 8/2012 Christensen et al.
2012/0271246 A1 10/2012 Guala
2012/0277688 A1 11/2012 Rogier
2012/0316536 A1 12/2012 Carrez et al.
2013/0006211 A1 1/2013 Takemoto
2013/0053815 A1 2/2013 Mucientes et al.
2013/0060205 A1 3/2013 Mansour et al.
2013/0076019 A1 3/2013 Takemoto
2013/0079730 A1 3/2013 Mosler et al.
2013/0197453 A1 8/2013 Yeh
2013/0317483 A1 11/2013 Reichart et al.
2014/0020792 A1 1/2014 Kraus et al.
2014/0174578 A1 6/2014 Bonnal et al.
2014/0246616 A1 9/2014 Fangrow
2014/0265319 A1 9/2014 Clark et al.
2014/0358033 A1 12/2014 Lynn
2014/0358073 A1 12/2014 Panian et al.
2014/0371686 A1 12/2014 Sano et al.
2015/0008664 A1 1/2015 Tachizaki
2015/0045746 A1 2/2015 Macy, Jr. et al.
2015/0073380 A1 3/2015 Mansour et al.
2015/0148756 A1 5/2015 Lynn
2015/0157848 A1 6/2015 Wu et al.
2015/0196749 A1 7/2015 Ziv et al.
2015/0202424 A1 7/2015 Harton
2015/0209233 A1 7/2015 Fukuoka
2015/0258324 A1 9/2015 Chida et al.
2015/0258325 A1 9/2015 Panian et al.
2015/0265829 A1 9/2015 Truitt et al.
2015/0320992 A1 11/2015 Bonnet et al.
2016/0030729 A1 2/2016 McLean
2016/0114147 A1 4/2016 Siopes et al.
2016/0144109 A1 5/2016 Stroup
2016/0158518 A1 6/2016 Hallynck et al.
2016/0250102 A1 9/2016 Garfield et al.
2016/0250415 A1 9/2016 Yagi et al.
2016/0263369 A1 9/2016 Naftalovitz et al.
2016/0354288 A1 12/2016 Uehara et al.
2017/0191595 A1 7/2017 Van Scyoc
2017/0296801 A1 10/2017 Fangrow, Jr.
2017/0304547 A1 10/2017 Simpson
2018/0015275 A1 1/2018 Fangrow, Jr. et al.
2018/0036524 A1 2/2018 Fangrow, Jr.
2018/0085286 A1 3/2018 Kim et al.
2018/0133451 A1 5/2018 Takeuchi
2018/0172190 A1 6/2018 Fangrow
2018/0193566 A1 7/2018 Simpson
2018/0207418 A1 7/2018 Ueda
2018/0214683 A1 8/2018 Ueda
2018/0289920 A1 10/2018 Harding et al.
2018/0303720 A1 10/2018 Kennard et al.
2018/0339146 A1 11/2018 Schrauder et al.
2019/0053980 A1 2/2019 West et al.
2019/0076319 A1 3/2019 Okiyama
2019/0078712 A1 3/2019 Fangrow
2019/0224468 A1 7/2019 Jones
2019/0247642 A1 8/2019 Karthikeyan et al.
2019/0275314 A1 9/2019 Jeffrey
2019/0282794 A1 9/2019 Carlsson et al.
2019/0321564 A1 10/2019 Kim et al.
2020/0000979 A1 1/2020 Myers
2020/0016391 A1 1/2020 Di Ubaldi
2020/0094036 A1 3/2020 Wong
2020/0101237 A1 4/2020 Biggers et al.
2020/0114139 A1 4/2020 Mills et al.
2020/0271171 A1 8/2020 Leung
2020/0316361 A1 10/2020 Kakinoki et al.
2020/0316362 A1 10/2020 Jeffrey
2020/0345996 A1 11/2020 DeMeritt et al.
2020/0384256 A1 12/2020 Hopkinson
2021/0252267 A1 8/2021 Fangrow, Jr.
2021/0283343 A1 9/2021 Mills et al.
2021/0372551 A1 12/2021 Clark et al.
2022/0008294 A1 1/2022 Sanders et al.
2022/0288378 A1 9/2022 Mermelshtein et al.
2022/0296869 A1 9/2022 Jones et al.
2022/0370697 A1 11/2022 Parikh et al.
2023/0001172 A1 1/2023 Wine et al.
2023/0040378 A1 2/2023 Jones et al.
2023/0045573 A1 2/2023 Nelson et al.
2023/0059045 A1 2/2023 Feith et al.
2023/0139756 A1 5/2023 Wine et al.
2023/0149689 A1 5/2023 Armstrong et al.
2023/0321425 A1 10/2023 Jadhav et al.
2023/0355946 A1 11/2023 Kuriyama
2023/0372691 A1 11/2023 Kuriyama et al.
2024/0011588 A1 1/2024 Fangrow
2024/0024652 A1 1/2024 Fangrow, Jr.
2024/0042188 A1 2/2024 Wine et al.
2024/0050728 A1 2/2024 Jadhav et al.
2024/0151338 A1 5/2024 Desai et al.
2024/0157110 A1 5/2024 Shafiq et al.
2024/0157112 A1 5/2024 Feith et al.
2024/0167602 A1 5/2024 Wine
2024/0173531 A1 5/2024 Kumar et al.
2024/0173537 A1 5/2024 Nalawade et al.
2024/0204452 A1 6/2024 Wine
2024/0207594 A1 6/2024 Jadhav et al.
2024/0238578 A1 7/2024 Wine et al.
2024/0245898 A1 7/2024 Malviya et al.
2024/0261555 A1 8/2024 Nelson et al.
2024/0269452 A1 8/2024 Wells et al.
2024/0293657 A1 9/2024 Kuriyama
2024/0316330 A1 9/2024 Kumar et al.
2024/0325715 A1 10/2024 Cai et al.
2024/0328553 A1 10/2024 Austin et al.
2024/0328555 A1 10/2024 Austin et al.
2024/0358988 A1 10/2024 Gaffney et al.
2024/0358989 A1 10/2024 Gaffney et al.
2024/0377007 A1 11/2024 Kakaraparthi et al.
2025/0018165 A1 1/2025 Callahan et al.
2025/0032769 A1 1/2025 Callahan et al.
2025/0114587 A1 4/2025 Wells
2025/0161649 A1 5/2025 Fangrow
2025/0172226 A1 5/2025 Fangrow

FOREIGN PATENT DOCUMENTS

EP 0 158 030 10/1985
EP 0 368 473 5/1990
EP 0 791 371 8/1997
EP 0 795 342 9/1997
EP 1 050 318 11/2000
EP 1 904 152 4/2008
EP 1 917 996 5/2008
EP 1 946 792 7/2008

(56) References Cited

FOREIGN PATENT DOCUMENTS

| | | | |
|---|---|---|---|
| EP | 2 123 322 | | 11/2009 |
| EP | 3 381 502 | | 10/2018 |
| EP | 3 884 990 | | 9/2021 |
| GB | 2 116 277 | | 9/1983 |
| GB | 2 118 440 | | 11/1983 |
| GB | 2 353 078 | | 2/2001 |
| JP | 56-72659 | U1 | 6/1981 |
| JP | 58-13216 | | 1/1983 |
| JP | 59-41429 | | 3/1984 |
| JP | 60-89488 | | 6/1985 |
| JP | 62-65779 | | 4/1987 |
| JP | 63-175383 | | 11/1988 |
| JP | 11-311234 | | 11/1999 |
| JP | 2001-187990 | A | 7/2001 |
| JP | 2003-192100 | | 7/2003 |
| JP | 2004-000483 | A | 1/2004 |
| WO | WO 1988/08499 | | 11/1988 |
| WO | WO 1995/32748 | | 12/1995 |
| WO | WO 1996/33762 | | 10/1996 |
| WO | WO 1998/22178 | | 5/1998 |
| WO | WO 2001/03756 | | 1/2001 |
| WO | WO 2001/23026 | | 4/2001 |
| WO | WO 2002/066100 | | 8/2002 |
| WO | WO 2002/096500 | | 12/2002 |
| WO | WO 2004/060474 | | 7/2004 |
| WO | WO 2004/082756 | | 9/2004 |
| WO | WO 2006/076656 | | 7/2006 |
| WO | WO 2006/088858 | | 8/2006 |
| WO | WO 2006/124756 | | 11/2006 |
| WO | WO 2009/095760 | | 8/2009 |
| WO | WO 2013/036854 | | 3/2013 |
| WO | WO 2015/065958 | | 5/2015 |
| WO | WO 2023/014720 | | 2/2023 |
| WO | WO 2023/018737 | | 2/2023 |
| WO | WO 2023/193007 | | 10/2023 |
| WO | WO 2024/100671 | | 5/2024 |
| WO | WO 2024/108047 | | 5/2024 |
| WO | WO 2025/076278 | | 4/2025 |

OTHER PUBLICATIONS

Air Embolism and Exsanguination from Separation of Two-Piece Side Port/Hemostasis Valve Cardiac Catheter Introducers, ECRI Institute, Jan. 1995, in 2 pages, http://www.mdsr.ecri.org/summary/detail.aspx?doc_id=8098.

Assignee websited, products/pharmacy preparations/closed system transfer devices/chemolock, product literature—oncology intravesical administration, Jan. 1, 2021, https://www.icumed.com/media/Ofqhrnkl/p23-6036-2-intravesical-administration-brochure-v2.pdf (Year: 2021).

Injection Site, Molded Products, Inc., Apr. 2, 2004, in 1 page, https://web.archive.org/web/20040402123354/https://www.moldedproducts.com/injectionsite.htm.

International Search Report for PCT/US2006/026124, dated Mar. 3, 2007 in 5 pgs.

International Written Opinion for PCT/US2006/026124, dated Jan. 10, 2008 in 11 pgs.

International Search Report and Written Opinion of International Application No. PCT/US2008/063797 mailed on Dec. 30, 2008 in 21 pages.

International Preliminary Report on Patentability, International Application No. PCT/US2008/063797 mailed on Nov. 17, 2009 in 11 pages.

International Search Report and Written Opinion re PCT App. No. PCT/US2009/068857, dated (mailed) Apr. 8, 2010.

International Preliminary Report on Patentability re PCT App. No. PCT/US2009/068857, issued, Jun. 21, 2011 in 8 pages.

International Search Report and Written Opinion re PCT App. No. PCT/US2011/034854, mailed Mar. 28, 2012.

International Preliminary Report on Patentability re PCT App. No. PCT/US2011/034854, issued Nov. 6, 2012, 2012.

International Search Report and Written Opinion for International Application No. PCT/US2004/042723, issued on Jun. 28, 2005 in 16 pages.

International Written Opinion of International Application No. PCT/US2004/042723 issued on Jul. 3, 2006 in 10 pages.

International Search Report and Written Opinion re PCT Application No. PCT/US2012/054289, mailed Jan. 24, 2013.

International Preliminary Report on Patentability and Written Opinion re PCT Application No. PCT/US2012/054289, mailed Mar. 12, 2014.

International Search Report and Written Opinion, re PCT Application No. PCT/US2022/039183, mailed Oct. 28, 2022.

International Search Report and Written Opinion, re PCT Application No. PCT/US2023/080155, mailed Mar. 20, 2024.

International Search Report and Written Opinion, re PCT Application No. PCT/US2023/065237, mailed Sep. 25, 2023.

International Search Report and Written Opinion, re PCT Application No. PCT/US2024/049865, mailed Jan. 7, 2025.

* cited by examiner

MEDICAL CONNECTORS

CROSS-REFERENCE TO RELATED APPLICATIONS

This application claims the benefit under 35 U.S.C. § 119(e) of U.S. Provisional Patent Application No. 63/326,612, filed on Apr. 1, 2022, and titled MEDICAL CONNECTORS. The contents of each of the above-identified patent application(s) is hereby incorporated by reference in their entirety and is made a part of this specification for all that they discloses.

BACKGROUND

Field of the Disclosure

Some embodiments disclosed herein relate to medical connectors.

Description of the Related Art

Although various medical connectors exist, there remains a need for improved medical connectors.

SUMMARY OF CERTAIN ASPECTS

The innovations described herein each have several aspects, no single one of which is solely responsible for its desirable attributes. Without limiting the scope of the claims, some prominent aspects of this disclosure will now be briefly described.

Various aspects can relate to a breakaway medical connector, which can include a base portion, a projection that extends distally from the base portion, a distal opening at a distal end of the projection, a proximal end with a proximal opening, and a fluid pathway that extends between the distal opening and the proximal opening. The fluid pathway can extend inside the projection. A valve can be disposed inside the projection and can have a closed configuration that closes the distal opening of the fluid pathway and an open configuration that opens the distal opening of the fluid pathway. The connector can have an outer wall that extends distally further than the distal end of the projection. A cavity can be formed between the projection and the outer wall. The connector can have one or more first engagement features and a breakaway member disposed in the cavity between the projection and the outer wall, and the breakaway member can include one or more second engagement features that are configured to engage with the first engagement features to retain the breakaway member in the cavity. The breakaway member can have a coupling interface configured to couple to a second medical connector and to position the second medical connector to open the valve and to establish fluid communication between the second medical connector and fluid pathway when the second medical connector is coupled to the breakaway member when the second engagement features are engaged with the first engagement features. The first engagement features and the second engagement features can be configured to disengage if a force above a threshold pulls the breakaway member in a distal direction, to thereby provide a breakaway disconnection.

The breakaway medical connector can include a face seal disposed outside the projection. The face seal can have a first configuration with the distal end of the face seal substantially flush with the distal end of the projection and/or substantially flush with the distal end of the valve. Connecting the second medical connector can move the face seal to a second configuration with the face seal displaced proximally from the distal end of the projection. The face seal can be configured to form a seal with the proximal end of the second connector when the second connector is coupled to the breakaway member. The projection can include a widened portion, and a proximal portion of the face seal can be configured to engage the widened portion of the projection. Connection of the second connector to the breakaway member can move the proximal end of the face seal in a proximal direction. The breakaway medical connector can include an activation member, which can be configured to move proximally with the proximal movement of the proximal end of the face seal. The activation member can be configured to pull the valve proximally to open the valve. The activation member can be biased distally. The activation member can be configured to push the valve distally to close the valve upon breakaway disconnection of the second connector. The base portion can include openings, and the activation member can include a body portion on a first side of the base portion and posts that extend through the openings of the base portion.

The breakaway member can be configured to be reattached after the breakaway disconnection to reestablish fluid communication between the second medical connector and the fluid pathway of the breakaway medical connector. The outer wall can define an opening that is sufficiently large to permit swabbing of the distal ends of the projection and the distal end of the valve before reattachment. The coupling interface on the breakaway member can include internal threading, which can be configured to engage threads of a standard female luer lock. The breakaway medical connector can be configured to form a seal with the second connector without using a standard luer taper connection. The valve can be a dual-mode valve that is configured to open when either: i) a projection of the second medical connector is inserted into the distal opening of the projection of the breakaway connector to push the valve proximally, or ii) a housing of the second medical connector pushes an activation member proximally when the activation member is coupled to the valve to thereby pull the valve proximally. The valve can include a flexible shaft. The outer wall can have a distal opening formed by a continuous distal surface with no slits. The distal opening can be configured to permit the breakaway member to pass therethrough. The outer wall can have no openings that connect the cavity to the area outside the connector, other than the distal opening. The outer wall can have a distal opening having a first shape, and the breakaway member can have a second shape that is keyed with the first shape to impede rotation of the breakaway member relative to the outer wall, and/or to align the second engagement features with the first engagement features.

Various aspects of the disclosure can relate to a medical connector, which can include a housing having an outer wall, a first opening, a second opening, a fluid pathway between the first opening and the second opening, and a hollow projection that defines an interior cavity that forms a portion of the fluid pathway. The projection can be disposed inward of the outer wall to form a cavity between the projection and the outer wall. A valve can be disposed inside the projection. The valve can have a closed position with an end of the valve substantially flush with an end of the projection to close the fluid pathway and an open position with the end of the valve recessed inside the projection to open the fluid pathway. The connector can include a cover disposed in the cavity between the projection and the outer wall. The cover can have a first configuration with the cover disposed substantially flush with the end of the valve and substantially flush with the end of the projection.

The medical connector can include a breakaway member that can be configured to removably couple to the housing and to receive a second medical connector to establish fluid communication between the second medical connector and the fluid pathway. The breakaway member can be configured to disengage from the housing when a threshold amount of force pulls the breakaway member or the second medical connector away from the medical connector. The breakaway member can be configured to reengage the housing after the disengagement to reestablish fluid communication between the second medical connector and the fluid pathway of the breakaway medical connector. The end of the valve, the end of the projection, and the end of the cover can provide a substantially flush swabbing surface upon disengagement. The outer wall can have an opening that is at least about 6 mm wide to provide access to the swabbing surface. The cover can be configured to be pushed along an exterior of the projection when a second medical connector is coupled to the medical connector. The cover can be configured to form a seal with a housing of the second medical connector. The medical connector can include an activation member configured to move with the cover. The activation member can be configured to pull the valve to the open position. The activation member can be biased so that the activation member is configured to push the valve to the closed position upon breakaway disconnection from a second connector. The medical connector can include a hub that divides an interior of the connector into a first portion and a second portion, and the hub can include one or more openings. The activation member can include a body portion on a first side of the hub and one or more posts that extend through the openings in the hub. The fluid pathway can extend through the activation member. The valve can include a shaft that is made of a resilient material. Pressing on an end of the shaft can cause the shaft to bend so that the end of the shaft is recessed within the projection to open the valve.

Various aspects of the disclosure can relate to a method of using a breakaway medical connector. The method can include accessing a first medical connector that includes a main body with a fluid pathway and a breakaway member attached to the main body and coupling a second medical connector to the breakaway member. Coupling the second medical connector to the breakaway member can establish fluid communication between the second medical connector and the fluid pathway of the main body. The method can include detaching the breakaway member and the second medical connector from the main body of the first medical connector by pulling the second connector away from the first connector. The breakaway member can remain coupled to the second medical connector after the detachment. In some implementations, the method can include reattaching the breakaway member to the main body of the first medical connector, such as without needing the use of a tool, for example by pushing the breakaway member into the main body of the first medical connector, to reestablish fluid communication between the second medical connector and the fluid pathway of the main body of the first medical connector.

The method can include swabbing the main body of the first medical connector with a disinfectant before reattaching. The main body of the first connector can include a projection, a valve internal to the projection, and a face seal external to the projection. The end of the projection, the end of the valve, and the end of the face seal can be substantially flush after the detaching. The main body of the first medical connector can include an outside wall that creates a cavity. The projection, valve, and face seal can be recessed within the cavity. The cavity can have an opening that is at least about 6 mm wide to facilitate the swabbing. The method can include moving an activation member within the first medical connector with a housing of the second medical connector when the second medical connector is attached to the first medical connector, and moving the activation member can pull a valve to an open position to open the fluid pathway. The activation member can be biased so that is closes the valve upon detachment of the second medical connector from the main body of the first medical connector. Coupling a second medical connector to the breakaway member can include rotating the second medical connector relative to the breakaway member so that threading on the second medical connector engages threading on the breakaway member. The connector can include any combination of the various connector features disclosed herein.

Various aspects of the disclosure can relate to a breakaway connector system, which can include a first connector having a first housing having a first opening (e.g., at a first end), a second opening (e.g., at a second end), and a fluid pathway between the first opening and the second opening. The first connector can include a first engagement structure. A second connector can include a second housing having a first opening (e.g., at a first end), a second opening (e.g., at a second end), and a fluid pathway between the first opening and the second opening. An adapter or breakaway member can be coupled to the second housing (e.g., by a threaded or non-threaded interface). The adapter can includes a second engagement structure, which can be configured to engage the first engagement structure to couple the second connector to the first connector. The first and second engagement structures can be configured to disconnect the second connector from the first connector, such as when a force (e.g., above a disconnection threshold force) pulls the first and second connectors apart.

The adapter can be configured to remain coupled to the second connector after the disconnection. The adapter can be configured to be coupled to the first connector before the first and second connectors are connected. The first valve can be configured to automatically close the fluid pathway of the first connector upon disconnection of the first connector from the second connector.

The first connector can have a first valve, which can have a closed configuration that closes the fluid pathway and an open configuration that opens the fluid pathway. The first valve can be configured to automatically close the fluid pathway of the first connector upon disconnection of the first connector from the second connector. The second connector can have a second valve, which can have a closed configuration that closes the fluid pathway and an open configuration that opens the fluid pathway. The second valve can be configured to automatically close the fluid pathway of the second connector upon disconnection of the first connector from the second connector.

The first and second engagement features can be configured to disconnect the second connector from the first connector without rotation of the first connector relative to the second connector. The disconnection threshold force can be between about 0.5 pounds and about 15 pounds, between about 2 pounds and about 8 pounds, or various other values or ranges as disclosed. The second connector can include exposed threading that can be inserted into the first housing of the first connector without engaging the first connector.

The second connector can include a twist-to-connect engagement structure, and wherein the adapter can be configured to convert the second connector to a push-to-connect engagement. In some embodiments, the adapter can have threading to engage the threading of the second connector. The second connector can include a standard female luer taper, and the first connector can be configured to form a seal with the second connector without using (e.g., without sealing against) the standard female luer taper. The second connector housing can seal against a face seal of the first connector, which can be disposed outside of a projection. The projection can include an opening to the fluid pathway, and a valve inside the projection can selective open and close the fluid pathway (e.g., at the opening).

In some implementations, the adapter can include a body portion that can circumferentially surround the second housing of the second connector. The body portion can abut against a first outer surface of the second housing to impede the adapter from moving in a first direction relative to the second housing. The adapter can include one or more arms extending from the body portion, wherein the one or more arms can abut against a second surface on the second housing to impede the adapter from moving relative to the second housing in a second direction. The adapter can include a first tapered surface that decreases in width along a first direction and a second tapered surface that decreases in width along a second direction. The one or more arms can be configured to flex outwardly. The first tapered surface and the second tapered surface can be on the body portion. The first tapered surface and the second tapered surface can be on the one or more arms. The first engagement structure of the first connector can include one or more protrusions that abut against the first tapered surface of the adapter, such as to couple the first connector to the second connector. The one or more protrusions can be configured to flex outward when the threshold disconnection force is applied to permit the first tapered surface of the adapter to move past the one or more protrusions. The first connector can include a shroud positioned outward of the first housing. In some implementations, the shroud can be movable relative to the first housing between an advanced position and a retracted position. In some embodiments, the shroud can be stationary relative to the first housing. The shroud can include the first engagement structure. The shroud can be an outer wall or outer housing portion. A biasing structure can be configured to bias the shroud to the advanced position. The connector can include a locking mechanism, which can be configured to lock the shroud in the advanced position when the locking mechanism is engaged. The locking mechanism can be configured to permit movement of the shroud to the retracted position when disengaged.

Various aspects of the disclosure can relate to a medical connector, which can include a housing having a first opening (e.g., at a first end), a second opening (e.g., at a second end), and a fluid pathway between the first opening and the second opening. The connector can include a valve having a closed configuration that closes the fluid pathway and an open configuration that opens the fluid pathway. The connector can include a shroud, which can be movable relative to the housing between an advanced position and a retracted position in some implementations, and in some cases the shroud can be stationary relative to the housing or can be a portion of the housing (e.g., an outer wall portion). The shroud can have an engagement structure configured to provide a breakaway connection to another connector. For example, the engagement structure can be configured to release from the other connector in response to force that pulls the other connector away from the medical connector.

The medical connector can include a biasing structure, which can be configured to bias the shroud to the advanced position. The connector can include a locking mechanism, which can be configured to lock the shroud in the advanced position when the locking mechanism is engaged. The locking mechanism can be configured to permit movement of the shroud to the retracted position when disengaged. The housing can be recessed within the shroud by at least about 5 mm (e.g., when the shroud is in the advanced position, for the movable shroud implementations). Aa distal end of the shroud can be retracted at least sufficiently to be flush with a distal end of the housing when the shroud is in the retracted position (e.g., for the movable shroud implementations). The housing can be recessed within the shroud (e.g., by less than about 5 mm) when the shroud is in the retracted position. In some cases, the shroud can have an opening that is sufficiently wide (e.g., at least about 6 mm, about 8 mm, about 10 mm, or other values or ranges discussed herein) to enable swabbing inside the connector (e.g., of a protrusion, valve, and/or face seal), such as without movement of the shroud.

The shroud can includes a sidewall portion and a ring portion coupled to the sidewall portion by a neck portion. The ring portion can include a first protrusion extending inward from a first location on the ring portion and a second protrusion extending inward from a second location on the ring portion that is substantially opposite the first location. A first gap can be disposed between the first location on the ring portion and the sidewall portion. A second gap can be disposed between the second location on the ring portion and the sidewall portion. In some implementations, the shroud or outer wall can have no lateral openings. In some implementations the shroud or outer wall can have no openings other than the opening (e.g., distal opening) that receive the second connector and/or breakaway member or adapter. The shroud or outer wall can be configured to flex or deform to enable the breakaway disconnection, without slits in the shroud or other wall.

The first protrusion and the second protrusion can include angled distal surfaces so that pressing longitudinally on the distal surfaces can cause the first and second protrusions to be displaced laterally outward. The connector can include a hollow projection that defines an interior cavity that forms a portion of the fluid pathway. The valve can include a shaft disposed inside the projection. The shaft can be made of a resilient material, wherein an end of the shaft is substantially flush with an end of the projection when the valve is in the closed configuration, and wherein pressing on an end of the shaft causes the shaft to bend so that the end of the shaft is recessed within the projection to open the valve. The valve can include a flange that extends laterally from the shaft, and the flange can includes one or more openings, which can form part of the fluid pathway in some cases. In some implementations, the flange can abut against a portion of the housing when the valve is in the closed configuration to impede fluid from flowing through the openings in the flange. The flange can be spaced away from the portion of the housing when the valve is in the open configuration to permit fluid to flow through the openings in the flange. In some cases the fluid pathway through the flange can be open regardless of whether the valve is open and/or regardless of whether the second connector is attached to the first connector.

The housing can include an outer wall with a cavity formed between the projection and the outer wall. The connector can include a cover disposed in the cavity between the projection and the outer wall. Therein the cover can have a first configuration with the cover disposed substantially flush with an end of the projection and/or with an end of the outer wall. The cover can have a second configuration with the cover recessed into the cavity. The connector can include a biasing structure configured to bias the cover toward the first configuration.

Various aspects of the disclosure can relate to a medical connector, which can include a housing, a first opening, a second opening, and a fluid pathway between the first opening and the second opening. The connector can have a hollow projection that defines an interior cavity that forms a portion of the fluid pathway. A valve that includes a shaft can be disposed inside the projection. The shaft can have a closed position with an end of the shaft substantially flush with an end of the projection, such as to close the fluid pathway and an open position with the end of the shaft recessed inside the projection to open the fluid pathway. The connector can have a cover outside the projection. The cover can have a first configuration with the cover disposed substantially flush with the end of the shaft, and with the end of the projection. The cover can have a second configuration with the cover retracted along the projection.

In some implementations, the housing can have an outer wall. The projection can be disposed inward of the outer wall to form a cavity between the projection and the outer wall. The cover can be disposed in the cavity between the projection and the outer wall. In some implementations the cover can be flush with an end of the outer wall in the first configuration. The cover can be recessed into the cavity in the second configuration.

The shaft can be made of a resilient material. Pressing on the end of the shaft can cause the shaft to bend so that the end of the shaft is recessed within the projection to open the valve. The valve can include a flange that extends laterally from the shaft. The flange can include one or more openings. In some implementations, the flange can abuts against a portion of the housing when the shaft is in the closed configuration to impede fluid from flowing through the openings in the flange. The flange can be spaced away from the portion of the housing when the shaft is in the open configuration to permit fluid to flow through the openings in the flange.

The connector can include a biasing structure configured to bias the cover toward the first configuration. The connector can include an engagement structure configured to provide a breakaway connection to another connector, and can be configured to release from the other connector in response to force that pulls the other connector away from the connector. The connector can include a shroud, which can be movable between a first position and a second position, in some implementations. The end of the shaft, the end of the projection, the end of the outer wall, and/or the cover (or any combination thereof) can be recessed inside the shroud by a first distance (e.g., when the shroud is in the first position, the movable shroud implementations). The end of the shaft, the end of the projection, the end of the outer wall, and/or the cover (or any combination thereof) can be recessed inside the shroud by a second distance less than the first distance when the shroud is in the second position (e.g., for the movable shroud implementations). The end of the shaft, the end of the projection, the end of the outer wall, and/or the cover (or any combination thereof) can be positioned flush with or can extend past an end of the shroud (e.g., when the shroud is retracted in the second position for the movable shroud implementations).

Various aspects of the disclosure can relate to a medical connector which can include a housing, which can have a first opening, a second opening, and a fluid pathway between the first opening and the second opening. An adapter can be configured to couple to the housing. The adapter can include an engagement structure, which can be configured to engage an engagement structure of another connector to couple the connector to the other connector and to provide a breakaway connection to the other connector.

In some cases, the engagement structure can be configured to release from the other connector in response to force that pulls the other connector away from the medical connector. In some cases, the adapter can be configured to release from the medical connector and remain attached to the other connector in response to force that pulls the other connector away from the medical connector. In some cases, a valve can have a closed configuration that closes the fluid pathway and an open configuration that opens the fluid pathway. The adapter can be spaced away from the first end of the housing and spaced away from the second end of the housing, in some implementations. The engagement structure can be configured to disconnect the other connector from the medical connector without rotation of the other connector relative to the medical connector. The connector can include a female luer lock fitting with external threading configured to couple a male luer lock fitting. The adapter can provide an alternative engagement mechanism to bypass the external threading to couple to the other connector. The adapter can include a body portion that circumferentially surrounds at least a portion of the housing of the connector. The body portion can abut against a first outer surface of the second housing to impede the adapter from moving in a first direction relative to the second housing, in some cases. One or more arms can extend from the body portion. The one or more arms can abut against a second surface on the second housing to impede the adapter from moving relative to the second housing in a second direction. The adapter can have a first tapered surface that decreases in width along a first direction and a second tapered surface that decreases in width along a second direction. The one or more arms can be configured to flex outwardly. The first tapered surface and the second tapered surface can be on the body portion. The first tapered surface and the second tapered surface can be on the one or more arms.

Various aspects of the disclosure can relate to an adapter for use with a medical connector. The adapter can include a body portion that can be configured to circumferentially surrounds at least a portion of the housing of the connector. One or more arms can extending longitudinally from the body portion. The one or more arms can be configured to flex laterally outward. The adapter can include a first tapered surface that decreases in width along a first direction, and a second tapered surface that decreases in width along a second direction that is opposite the first direction. The first tapered surface and the second tapered surface can be on the body portion. The first tapered surface and the second tapered surface can be on the one or more arms.

Various aspects of the disclosure can relate to a medical connector, which can include at least one engagement structure configured to provide a breakaway connection to another connector. The breakaway connection can be configured to release the connector from the other connector in response to force that pulls the other connector away from the connector. The medical connector can include any combination of the various aspects and features disclosed herein.

DETAILED DESCRIPTION OF CERTAIN EMBODIMENTS

The various features and advantages of the systems, devices, and methods of the technology described herein will become more fully apparent from the following description of the examples illustrated in the figures. These examples are intended to illustrate the principles of this disclosure, and this disclosure should not be limited to merely the illustrated examples. The features of the illustrated examples can be modified, combined, removed, and/or substituted as will be apparent to those of ordinary skill in the art upon consideration of the principles disclosed herein.

Various embodiments disclosed herein can relate to breakaway fluid connectors. The fluid connectors can be medical connectors configured to transport medical fluids, such as blood or other bodily fluids, medication, saline, parenteral nutrients, etc.

Figure 1:
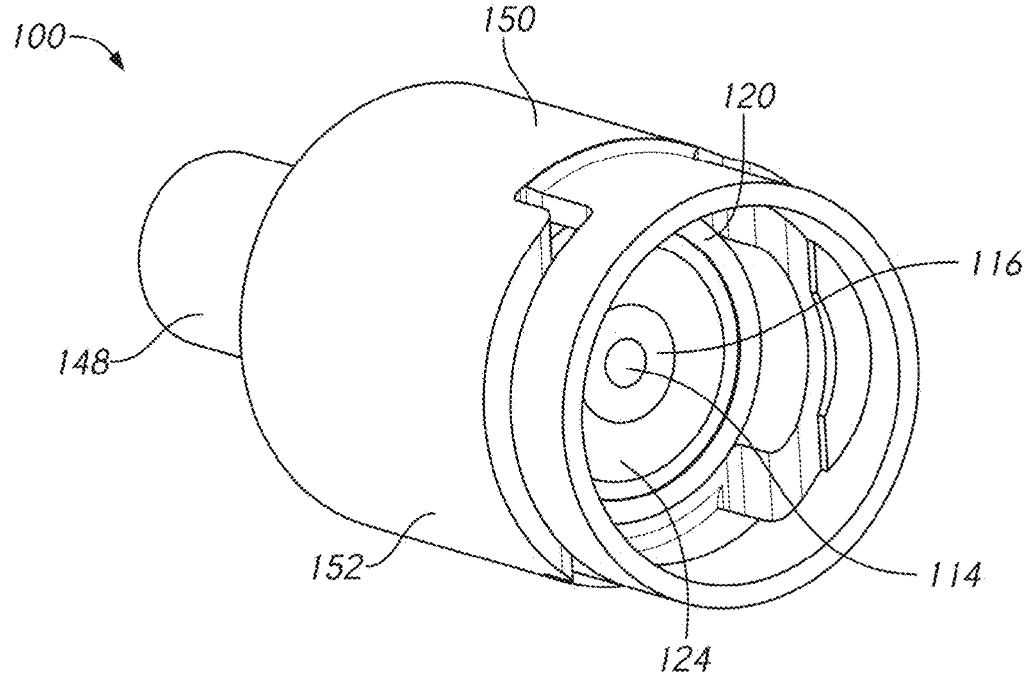
FIG. 1 shows a perspective view of an example embodiment of a first connector.
Figure 2:
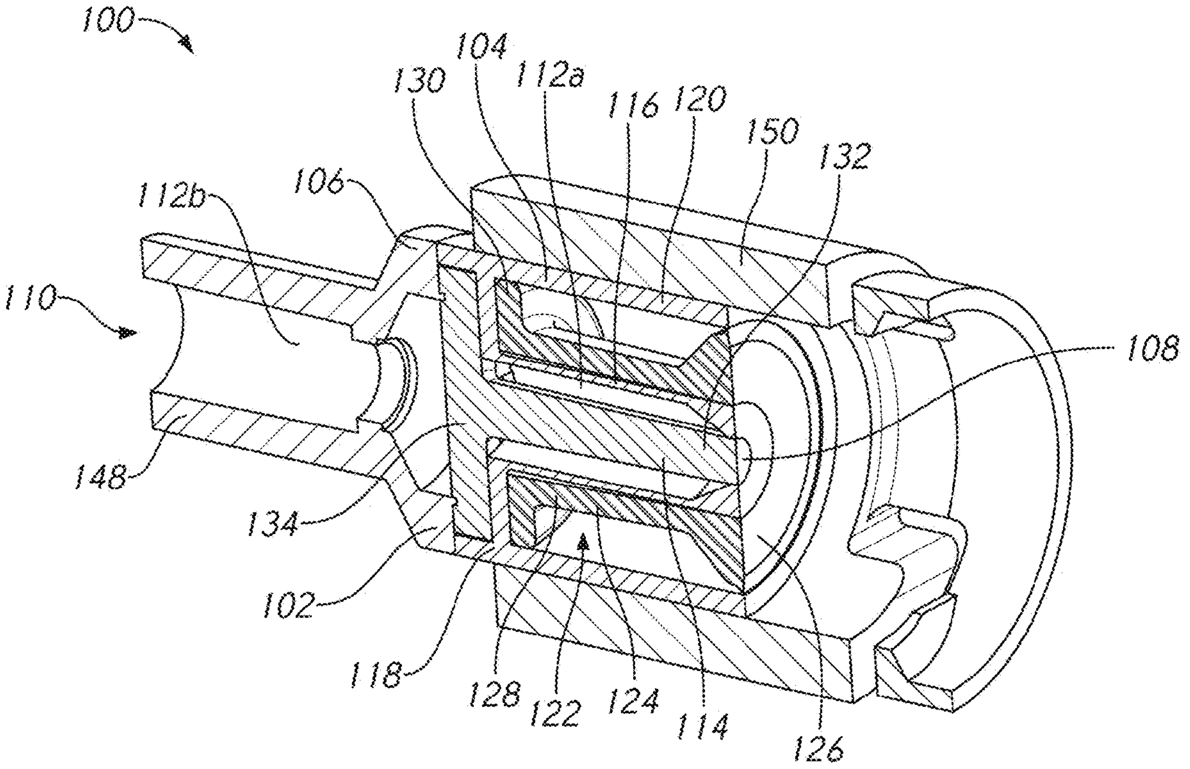
FIG. 2 shows a perspective cross-sectional view of the example first connector of FIG. 1.

FIG. 1 shows a perspective view of an example embodiment of a first connector 100. FIG. 2 shows a perspective cross-sectional view of the example first connector 100 of FIG. 1. The first connector 100 can have a housing 102. The housing 102 can include a first (e.g., distal) housing portion 104 and a second (e.g., proximal) housing portion 106, which can be coupled together, such as by sonic welding, a threaded engagement, a snap-fit engagement, a friction engagement, or any other suitable coupling mechanism. The housing 102 (e.g., the first housing portion 104) can have a first (e.g., distal) opening 108. The housing 102 (e.g., the second housing portion 106) can have a second (e.g., proximal) opening 110. A fluid pathway 112 can connect the first opening 108 to the second opening 110. A first portion **112*a* of the fluid pathway can extend through the first housing portion 104, and a second portion 112*b* of the fluid pathway can extend through the second housing portion 106. The connector 100 can include a valve 114, which can have a closed configuration that closes the fluid pathway 112 and an open configuration that opens the fluid pathway 112**, as discussed herein.

The connector 100, such as the housing 102 (e.g., the first housing portion 104), can have a projection 116, which can extend distally from a base portion 118 of the housing 102. The projection 116 can be hollow, and the interior of the projection 116 can form a portion **112*a* of the fluid pathway through the connector 100. The end of the projection 116 can have the first opening 108. The projection 116 can have a generally cylindrical shape. The projection 116 can have a sidewall. The sidewall thickness can increase towards the distal end of the projection 116, for example, such that the diameter of the interior of the projection 116 can decrease at the distal end. The interior projection 116 can be tapered or sloped inward at the distal end. The distal end of the projection 116 can be configured to guide the valve 114 to the closed configuration, in some embodiments. The projection 116 can have a proximal portion, which can have a substantially uniform interior diameter, which can be larger than the inner diameter(s) along the distal end. The projection 116 can have a substantially uniform outer diameter. The outer surface of the projection can be configured so that it does not provide a luer connection (e.g., with a standard female luer device). In other configurations, the projection can be a male luer fitting, which can be configured to couple to a female luer of another connector. For example, the outside surface of the projection 116** can be tapered, such as having a standard luer taper.

The housing 102 (e.g., the first housing portion 104) can have an outer wall 120, which can extend distally from the base portion 118. The distal end of the outer wall 120 and the distal end of the projection 116 can be substantially aligned along the same plane. The outer wall 120 and the projection 116 can extend distally from the base portion 118 by substantially the same distance. The outer wall 120 can be spaced radially outward from the projection 116 to form a cavity 122 therebetween. The base portion 118 can extend between the outer wall 120 and the projection 116, for example so that the cavity 122 is closed at the proximal end thereof. The cavity 122 can be open at the distal end thereof. The connector 100 can be configured to receive a portion of another connector 200 into the cavity 122, in some cases so that the projection 116 is inserted into the portion of the other connector 200. The projection 116 can be a male projection for a male/female connector engagement.

A cover 124 can be disposed inside the cavity 122 between the projection 116 and the outer wall 120. The cover 124 can be configured to cover the exterior of the projection 116 when in its default configuration. The cover 124 can be movable between a default configuration and an actuated configuration. When the portion of the another connector 200 is inserted into the cavity 122, the portion of the other connector 200 can compress or displace the cover 124 proximally, such as to transition the cover 124 from its default configuration to its actuated configuration. The cover 124 can be biased so that it returns to its default configuration when the other connector 200 is removed or detached from the connector 100.

Figure 3:
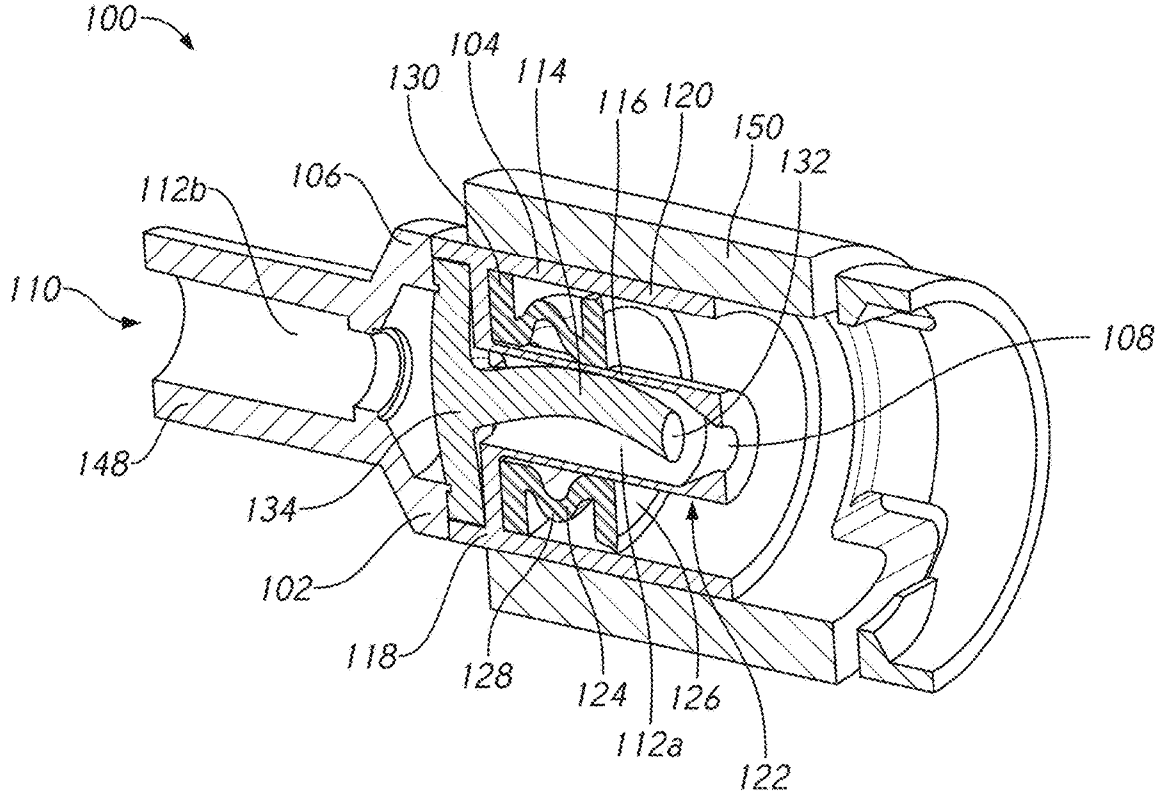
FIG. 3 shows the cover in the actuated configuration and the valve in the open configuration.

FIGS. 1 and 2 show the cover 124 in the default configuration and the valve 114 in the closed configuration. FIG. 3 shows the cover 124 in the actuated configuration and the valve 114 in the open configuration. Another connector 200 can move the valve 114 to the open configuration and/or the cover 124 to the actuated position when the other connector 200 is coupled to the connector 100. The other connector 200 is not shown in FIG. 3, for simplicity.

The cover 124 can include a distal portion, which can extend from the protrusion 116 to the outer wall 120. The distal portion of the cover 124 can be a wiper 126, which can be configured to wipe the exterior of the projection 116 and/or the interior of the outer wall 124 as it moves between the actuated and default configurations. The cover 124 can have a biasing structure 128. The biasing structure 128 can be a resilient sleeve that at least partially surrounds the projection 116. The resilient sleeve 128 can buckle, flex, compress, or otherwise deform as the wiper 124 is displaced proximally. The resilient sleeve 128 can resiliently return to its undeformed shape to return the wiper 124 to its default position. As the wiper 124 moves distally, it can wipe the fluid off of the exterior of the projection 116 and/or off of the interior of the outer wall 120, which can impede microbial growth in the connector 100 or other contaminants. When in the default position, the cover 124 can impede contamination of the interior of the connector 100 (e.g., the cavity 122, the exterior of the projection 116, and/or the inside of the exterior wall 120). Various biasing structures can be used, such as a coil spring, a compression spring, another type of spring, a resiliently compressible O-ring, etc. The cover 124 can have a base portion 130, which can extend between the protrusion 116 and the outer wall 120. The base portion 130 of the cover can be disposed at the proximal end of the cavity 122 or next to the base portion 118 of the first housing portion 104. The cover 124 can be coupled to the housing 100, such as to impede the cover 124 from being pulled out of the cavity 122. The base portion 130 of the cover 124 can be compressed between the outer wall 120 and the projection 116, such as to form a friction fitting. The cover 124 can be made of silicone or any other suitable elastomeric or resilient material. The cover 124 (e.g., the base portion 130) could be coupled to the housing 100 by an adhesive or in any other suitable manner. In some embodiments, the cover 124 could be omitted.

Figure 4:
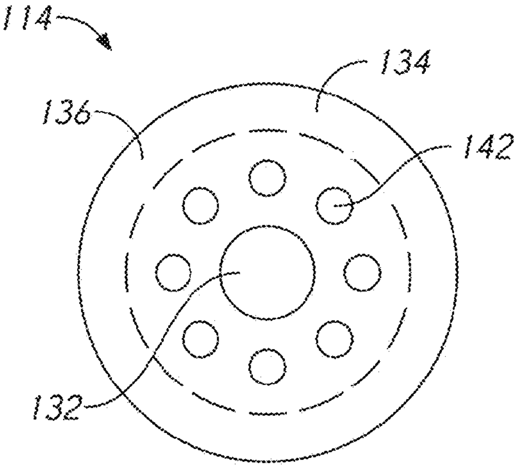
FIG. 4 illustrates an example embodiment of the valve, shown top-down from the distal to proximal direction.
Figure 5:
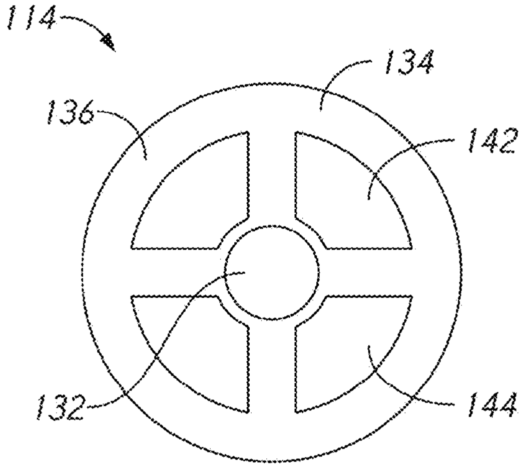
FIG. 5 illustrates another example embodiments of a valve, also shown top-down from the distal to proximal direction.
Figure 7:
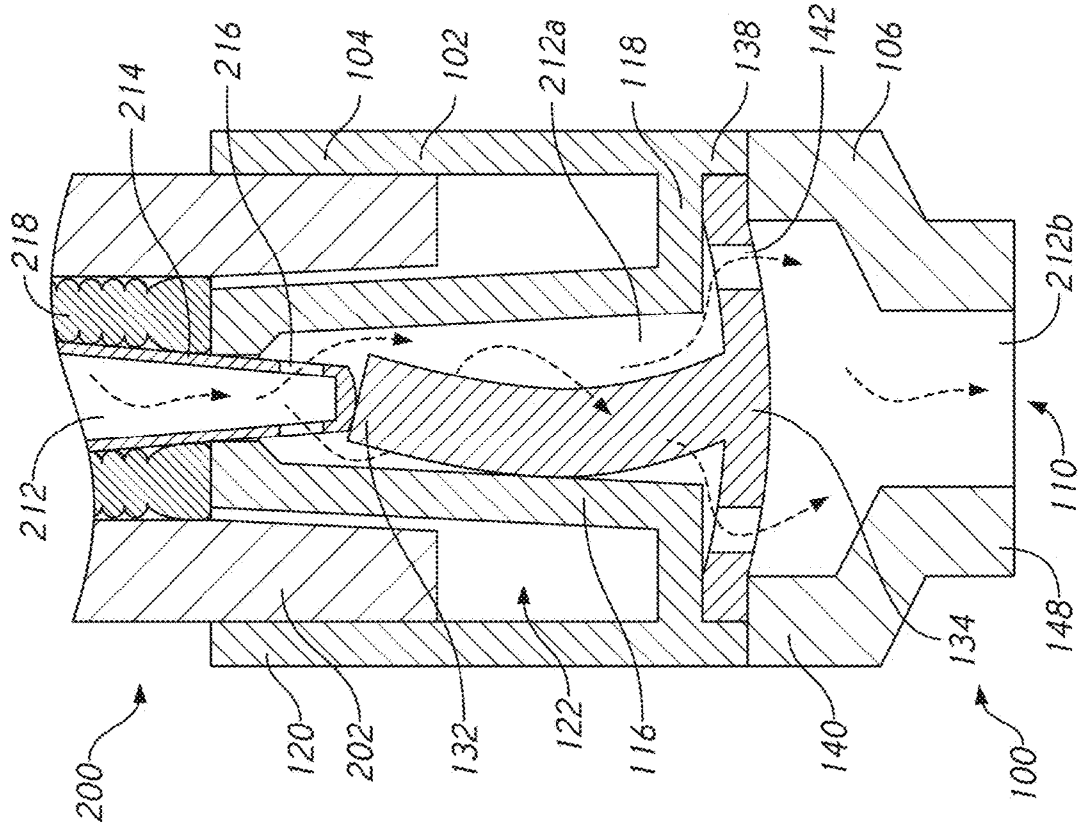
FIG. 7 shows a cross-section of an example embodiment of the connector with the valve in an open configuration.
Figure 6:
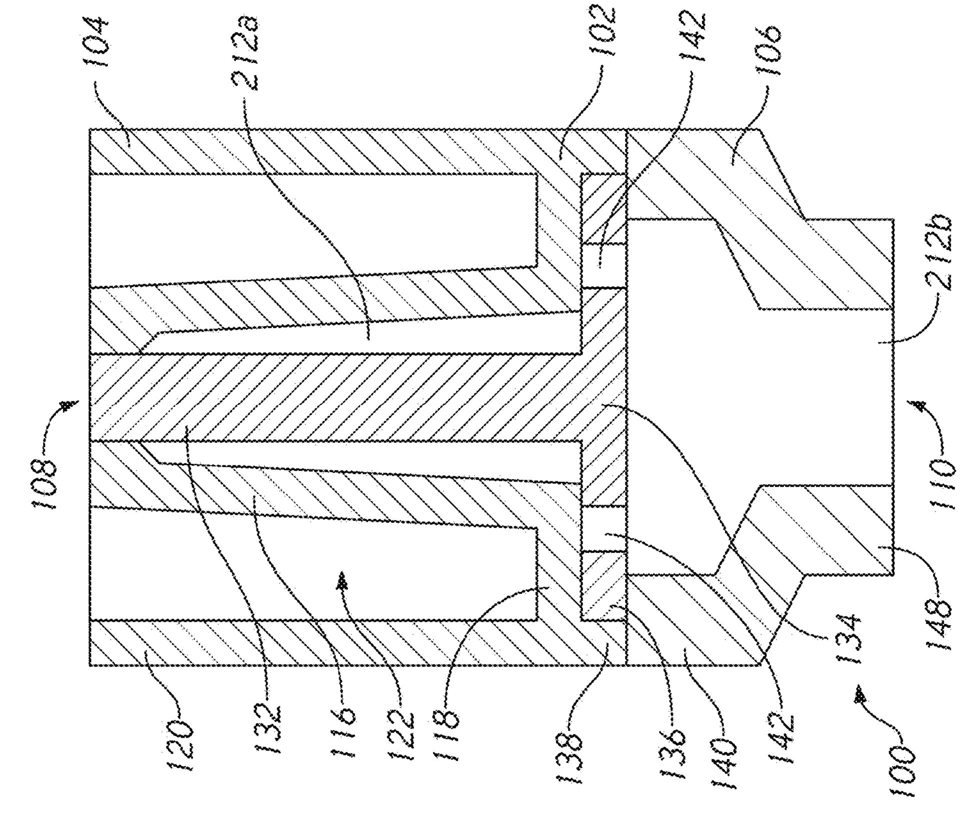
FIG. 6 shows a cross-section of an example embodiment of a connector with the valve in a closed configuration.

FIG. 4 illustrates an example embodiment of the valve 114, shown top-down from the distal to proximal direction. FIG. 5 illustrates another example embodiments of a valve 114, also shown top-down from the distal to proximal direction. FIG. 6 shows a cross-section of an example embodiment of a connector 100 with the valve 114 in a closed configuration. FIG. 7 shows a cross-section of an example embodiment of the connector 100 with the valve 114 in an open configuration. In FIGS. 6 and 7, the shroud and the cover 124 are omitted from view.

The valve 114 can have a shaft 132, which can extend axially, and a flange 134, which can extend laterally from a proximal end of the shaft 132. The valve 114 (e.g., the flange 134) can be coupled to the housing 100. The flange 134 can have a coupling portion 136, which can be the radially outer portion of the flange 134 (e.g., outside the dashed line in FIG. 4). The coupling portion 136 of the flange 134 can be pressed between the first housing portion 104 and the second housing portion 106. The first housing portion 104 can have a wall 138 (e.g., proximal wall portion) that extends proximally from the base portion 118. The wall 138 can couple with a corresponding wall 140 (e.g., distal wall portion) of the second housing portion 106 (e.g., by sonic welding, adhesive, or any other suitable coupling). The wall 140 on the second housing portion 106 can have a wider thickness than the wall 138 on the first housing portion 104. A gap can be formed between the proximal side of the base portion 118 and the portion of the wall 140 that extends further inwardly than the wall 138. The height of the gap can be defined by the longitudinal height of the wall 138. The height of the gap can be smaller than a thickness of the flange 134 in an uncompressed state. The coupling portion 136 of the flange 134 can be compressed between the base portion 118 and the wall 140, such as to secure the valve 114 to the housing 100.

The flange 134 can have one or more openings 142, which can permit fluid to pass through the flange 134. FIG. 4 shows an example embodiment with 8 opening 142, although any suitable number of openings can be used (e.g., 1, 2, 3, 4, 6, 8, 12, 16, 20 openings, or any values or ranges therebetween). In some embodiments, the one or more openings 142 can be positioned on the flange 134 so that the base portion 118 covers the one or more openings 142 when the flange is in the closed configuration (e.g., having a default or undeformed shape and/or position), as shown in FIG. 6, which can impede fluid from flowing through the openings 142 in the flange 134. FIG. 7 shows an open configuration of the valve 114, in which the flange 134 can be displaced (e.g., flexed or resiliently deformed) so that the one or more openings 142 are spaced away from the base portion 118, which can enable fluid to flow through the openings 142 in the flange 134. Various configurations for the openings 142 are possible. The openings 142 can be circular in shape or generally wedge shaped. With reference to FIG. 5, for example, the flange 134 can include openings 142 that extend from the coupling portion 136 to the shaft 134. In some cases, one or more spokes 144 can separate the openings 142. The one or more openings 142 can cover about 10%, about 15%, about 20%, about 25%, about 30%, about 35%, about 40%, about 45%, about 50%, about 55%, about 60%, about 70%, about 75%, about 80%, about 85%, about 90%, or more of the area of the flange 134 between the coupling portion 136 and the shaft 132, or any values or ranges between any of these values (e.g., between about 20% and 70%), although other configurations are possible. In some embodiments, at least some portions of the opening(s) 142 are uncovered when the flange 134 is against the base portion 118. For example, a portion of the one or more openings can extend inwardly past the base portion 118.

The shaft 132 can extend distally from the flange 134, such as along a longitudinal axis of the connector 100. The shaft 132 can be positioned inside the projection 116, such as inside the fluid pathway first portion 112*a*. The shaft 132 can have a diameter or thickness that is smaller than a diameter or width of the fluid pathway first portion 112*a* or hollow inside of the projection 116. The distal end of the fluid pathway first portion 112*a* can narrow to accommodate the distal tip of the shaft 132 so that the shaft 132 can close or seal the fluid pathway 112 (e.g., at the distal opening 108) when in the closed (e.g., default or undeformed) configuration. The narrowed distal end of the fluid pathway first portion 112*a* can have the same diameter or width as the diameter or thickness of the distal tip of the shaft 132.

The shaft 132 (e.g., at least the distal tip thereof) can be displaced proximally when another connector 200 is coupled to the connector 100, which can open the distal opening 108. As shown in FIG. 7, the other connector 200 can include a projection 214 (e.g., an internal cannula), which can be inserted into the opening 108 at the distal end of the projection 116 when the connector 200 is coupled to the connector 100. The projection 214 can push the distal end of the shaft 132 proximally to open the opening 108, such as to permit fluid to flow to or from the first connector 100. The shaft 132 can be compliant or resilient so that it can buckle, bend, compress, or otherwise deform, so that the distal end of the shaft 132 can disengage from the opening 108. The shaft 132 can be resilient and can return to the closed position (e.g., the default or undeformed position) when the other connector 200 is detached. The valve 114 can be made of silicone, or any other suitable elastomeric or resilient material. The fluid pathway first portion 112*a* in the projection 116 having a larger diameter or width than the shaft 132 can permit the shaft to bend or buckle. In some embodiments, the shaft 132 can be have sufficient rigidity to push a portion of the flange 134 proximally when the connectors 100, 200 are coupled. For example, a portion of the flange 134 at or near the junction with the shaft 132 (e.g., a center portion) can be pushed proximally by the shaft 132 when the projection 214 presses on the shaft 132. The flange 134 can be moved so that the flange 134 disengages from the base portion 118 to open the openings 142 through the flange 134.

In some embodiments, the shaft 132 can deform without moving the flange 134, and the openings 142 can be exposed (e.g., extending inward past the base portion 118 of the housing) to let fluid flow through the connector 100. In some embodiments, the flange 134 can be omitted from the valve 114. The valve 114 can have two seal stages, with one formed by the shaft sealing the opening 108, and another formed by the openings sealing against the housing (e.g., the base portion 118). The in some embodiments, the connector 100 can include a valve with only one of the seal stages. In some embodiments, the shaft 132 can be rigid so that it does not bend or deform when it is opened. The rigid shaft 132 can be pushed proximally enough to disengage the shaft from the opening 108 to open the fluid pathway 112. The rigid shaft 132 may push a flange 134 proximally to open the one or more openings 142. The shaft 132 and/or the distal opening 108 can have a circular cross-sectional shapes, but other cross-sectional shaped configurations could be used (e.g., square, rectangle, oval, hexagon, or other polygons). Many other suitable valve configurations may be used to open and close the connector 100.

The projection 214 can be tapered, with its diameter or width decreasing along the proximal direction. The exterior surface of the projection 214 can abut against the opening 108 (e.g., against the narrowed portion of the interior of the projection 116), which can form a fluid seal between the connector 100 and the connector 200, although a fluid seal can be formed at other locations, and various other configurations are possible. For example, in some embodiments, the outer surface of the projection 116 can be tapered (e.g., with a standard male luer taper, 6%, or any other suitable configuration). The inner surface of the housing 202 can be tapered (e.g., with a standard female luer taper, 6%, or any other suitable configuration) to make a sealing engagement with the projection 116. A portion of the housing 202 of the connector 200 can be inserted into cavity 122 between the projection 116 and the outer wall 120. In some embodiments, the housing 202 can actuate (e.g., depress or move) the cover 124, which is omitted from view in FIG. 7. The projection 116 of the first connector 100 can be inserted into the housing 202 of the second connector 200. The projection 214 can include a fluid pathway 212 and one or more openings 216, which can permit fluid to flow to or from the fluid pathway 212. The projection 214 can be inserted so that the one or more openings 216 can be inside the projection 214 (e.g., in the fluid pathway 112 of the first connector 100). The second connector 200 can include a valve 218, which can have an open configuration (e.g., shown in FIG. 7) and a closed configuration. In the closed configuration, the valve 218 can cover the openings 216 on the projection 214 so that fluid is impeded from flowing to or from the connector 200. The projection 116 of the first connector 100 can push the valve 218 (e.g., at least the proximal end thereof) distally as the connectors 100, 200 are coupled, so that the opening(s) 216 are exposed to permit fluid flow. When the connectors 100, 200 are disconnected, the valve 218 can resiliently return to its closed configuration. Many other suitable valve configurations may be used to open and close the connector 200.

As shown in FIG. 7, when the connectors 100, 200 are coupled, fluid can flow from the second connector 200 to the first connector 100 (e.g., such as for drawing a bodily fluid from a patient). The fluid can flow through a fluid pathway 212 of the second connector 200, through the opening(s) 216 and into the fluid pathway first portion 112*a* in the projection 116. The fluid can flow around the shaft 132, and through opening(s) 142 in the flange 134, through the fluid pathway second portion 112*b* in the second housing portion 106, and out the opening 110. In some embodiments, a catheter, tubing, another connector, or other medical implement can be attached to the proximal end of the connector 100 (e.g., to receive the fluid that flows out the opening 100. The fluid can flow in the other direction as well (e.g., such as for infusing a medication or other fluid into a patient).

When the connectors 100, 200 are disconnected, the valve 114 can resiliently return to the closed configuration to impede fluid from entering or exiting the connector first 100, which can impede contaminants from entering the fluid, loss of fluid, and unintended exposure to the fluid, etc. The inside surface of the projection 116 can be tapered inward at the distal end, such as to guide the tip of the shaft 132 when it moves distally to the closed configuration. When the connectors 100, 200 are disconnected, the valve 218 can resiliently return to the closed configuration to impede fluid from entering or exiting the second connector 200, which can impede contaminants from entering the fluid, loss of fluid, and unintended exposure to the fluid, etc.

Figure 9:
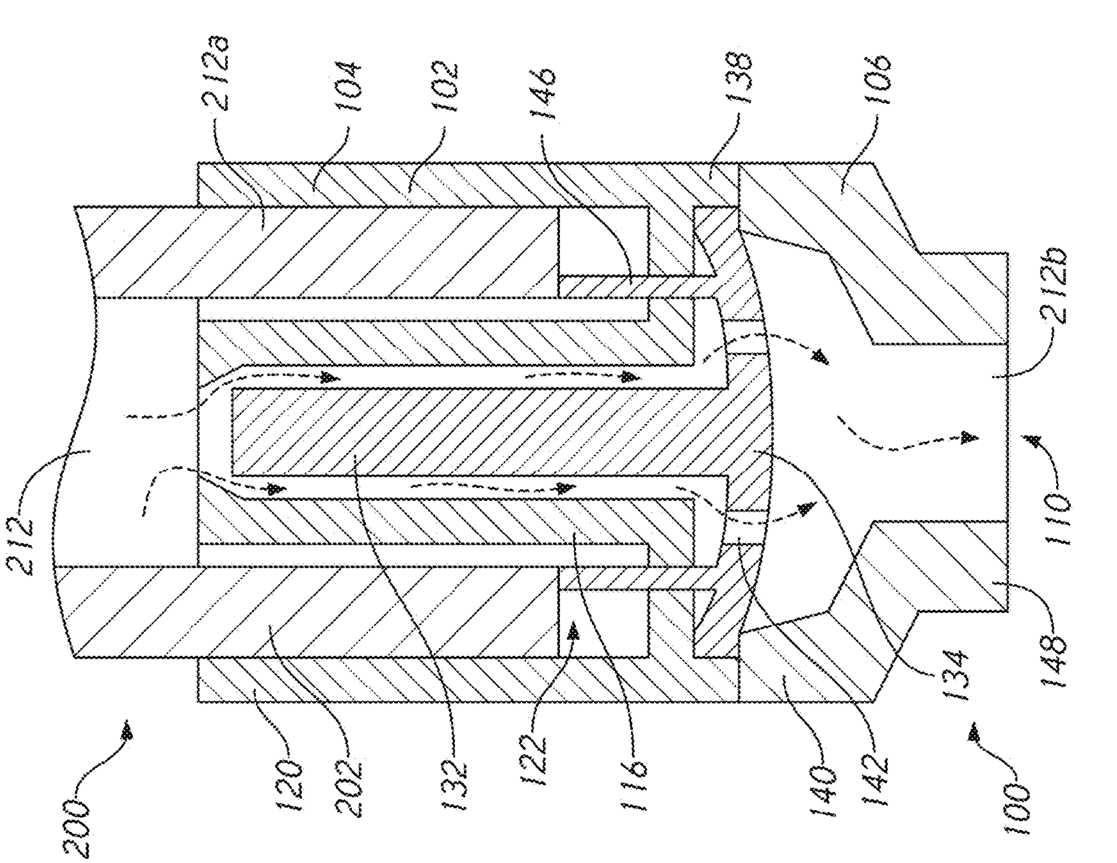
FIG. 9 shows a cross-section of an example embodiment of the connector with the valve in an open configuration
Figure 8:
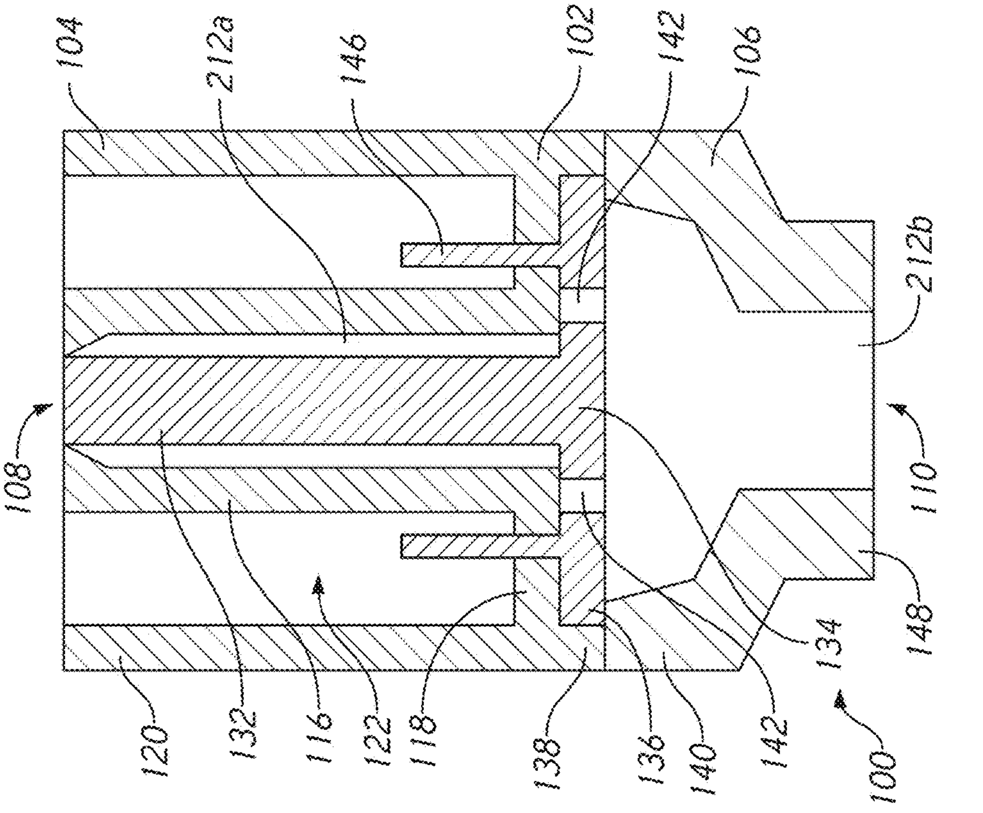
FIG. 8 shows a cross-section of another example embodiment of a connector with the valve in a closed configuration.

In some embodiments, the first connector 100 can be compatible with other second connectors 200 that do not include a projection 214. FIG. 8 shows a cross-section of another example embodiment of a connector 100 with the valve 114 in a closed configuration. FIG. 9 shows a cross-section of an example embodiment of the connector 100 with the valve 114 in an open configuration. In FIGS. 8 and 9, the shroud and the cover 124 are omitted from view. The embodiments of FIGS. 8 and 9 can be similar to the other embodiments disclosed herein, except as described. The valve 214 can include one or more posts 146, which can extend distally from the flange 134. The posts 146 can extend substantially parallel with the shaft 132 of the valve 114. The shaft 132 can extend further than the one or more posts 146 in the distal direction. The cross-section in FIGS. 8 and 9 show two posts 146, but any suitable number of posts 146 could be used (e.g., 1, 2, 3, 4, 6, 8, 10 posts or more, or any values or ranges between any of these values). The post(s) 146 can extend through holes in the base portion 118 of the housing 102, and into the cavity 122. When the second connector 200 is being coupled to the first connector 100, a portion of the housing 202 of the second connector 200 can be inserted into the cavity 122 so that it pushes the posts 146 proximally, which posts 146 can push on the flange 134, such that at least a portion of the flange 134 is displaced proximally. Proximal displacement of the flange 134 can open the openings 142 through the flange 134. Proximal displacement of the flange 134 can pull the shaft 132 proximally, which can cause the shaft 132 to disengage from the opening 108 to open the connector 100. When the second connector 200 is disconnected from the first connector 100, the valve 214 can return to its default or undeformed configuration. The flange 134 can move distally to its default position and the one or more posts can be pushed distally to their starting positions. In some embodiments, the shaft 132 can be rigid, although resilient material could also be used.

When the connector 100 is in the closed configuration, the distal ends of the outer wall 120, the cover 124, the projection 116, the valve 114, or any combination thereof, can be substantially flush with each other, for example to facilitate swabbing of the closed connector surface (e.g., with alcohol or other disinfectant) before and/or after use.

The connector 100 can include a connection fitting 148, such as at the proximal end or second portion 106 of the housing 102. The connection fitting 148 can be configured to couple to tubing, some other conduit, or other medical implement, which can be used to transport fluid (e.g., medical fluids). The tubing or other device can be coupled to the connection fitting 148 by a clamp, friction fitting, adhesive, threading, or any other suitable coupling mechanism. In some embodiments, the connection fitting 148 can be configured to couple to an additional connector that is configured to engage the connection fitting 148. For example, the connection fitting 148 can be female luer connection fitting, which can be configured to engage a male luer fitting on an additional connector. Although not shown, the connection fitting 148 can have threading (e.g., external thread(s)) for coupling to another connector, such as for a luer lock engagement). In some configurations, the connector 100 can be added to an existing fluid line and connector to add a breakaway connection feature to the system.

Figure 10:
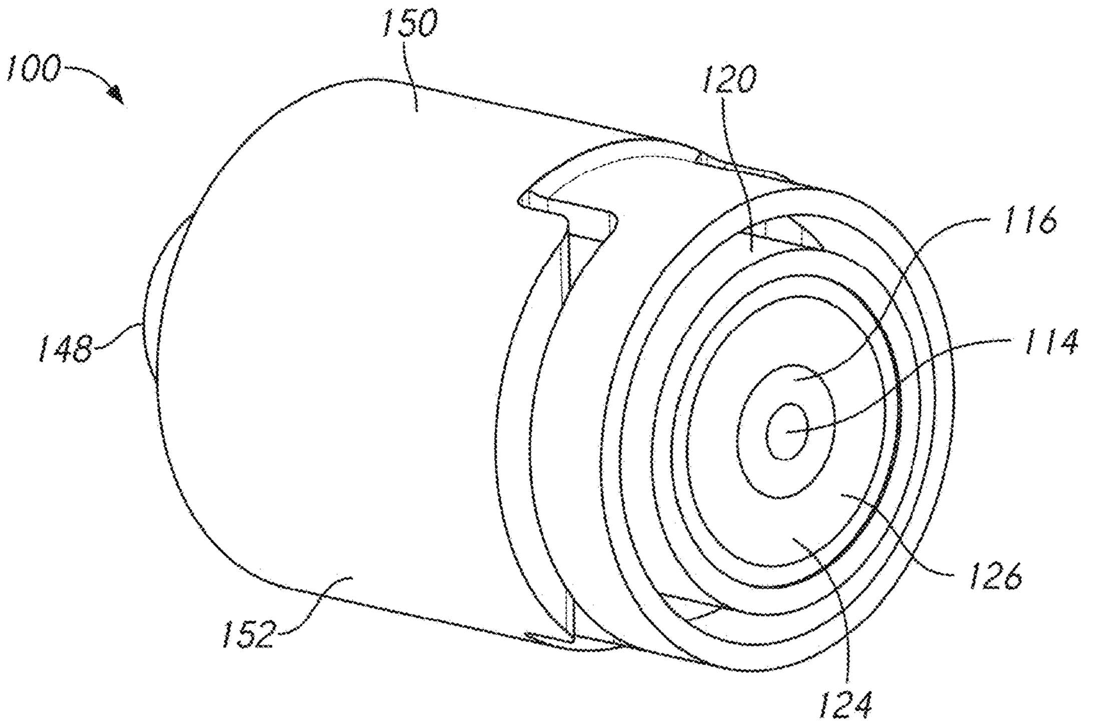
FIG. 10 shows a perspective view of an example embodiment of a first connector.
Figure 11:
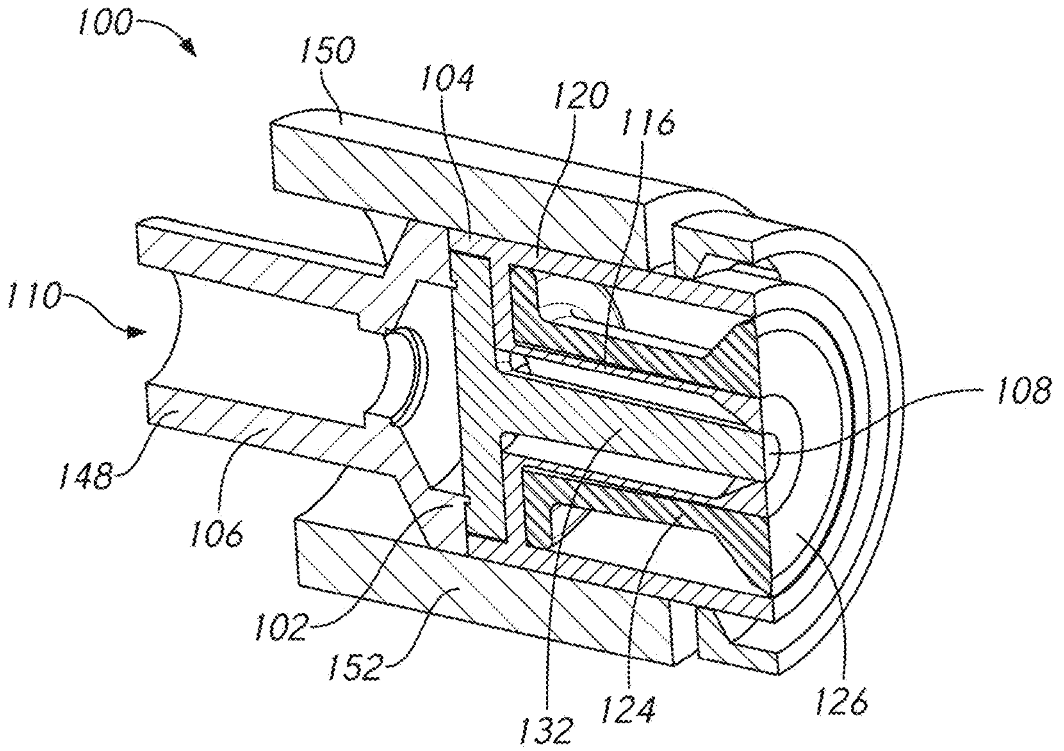
FIG. 11 shows a perspective cross-sectional view of the example first connector of FIG. 10.

In some embodiments, the first connector 100 can include a shroud 150. The shroud 150 can be configured to move (e.g., axially) relative to the housing 102, such as between an advanced (e.g., distal) position and a retracted (e.g., proximal) position. FIGS. 1, 2, and 3 show the connector 100 with the shroud 150 in an advance position. FIGS. 10 and 11 shows the connector 100 with the shroud 150 in a retracted position. In the advanced or distal position, the shroud 150 can surround the distal end of the housing 102 and can impede contaminants from reaching the housing 100 (e.g., the valve 114, the projection 116, the cover 124, and/or the outer wall 120). For example, in some instances when the connectors 100, 200 become disconnected (such as when connectors 100, 200 are pulled apart by movement of the patient and/or a fluid supply container), the first connector 100 (e.g., which can be coupled at the end of a fluid delivery tube) can fall onto the floor or other non-sterile surface. When the shroud 150 is in the advanced or distal position, the shroud can tend to contact the floor or other non-sterile surface, thereby insulating the distal portion of the housing 100 from the contaminants. In some cases, the distal end of the shroud 150 can extend distally past the distal end(s) of the housing 102, the valve 114, the projection 116, the cover 124, and/or the outer wall 120 by about 5 mm, about 7 mm, about 10 mm, about 12 mm, about 15 mm, about 17 mm, about 20 mm, about 25 mm, about 30 mm, or any values therebetween, or any ranges between any of these values, although other configurations are possible.

With the shroud 150 in the retracted or proximal position, the distal end of the housing 102 (e.g., the valve 114, the projection 116, the cover 124, and/or the outer wall 120) can be exposed for disinfection, such as by swabbing with alcohol or some other disinfectant. In some cases, after disconnection of the connectors 100, 200, the user can retract the shroud 150, disinfect the connector 100, and recouple the connectors 100, 200. In some cases, the second connector 200 can be coupled to a catheter, and can remain coupled to the catheter upon disconnection from the connector 100, which can impede the connector 200 from falling onto the floor or other unsterile surface. However, the second connector 200 can be disinfected (e.g., by swabbing) before reconnection to the first connector 100.

In some implementations, the shroud 150 can be configured to retract fully proximally of the distal end of the housing 102. The distal end(s) of the housing 102, the valve 114, the projection 116, the cover 124, and/or the outer wall 120 can be disposed distally of or flush with the distal end the shroud 150, when the shroud is in the retracted or proximal position. In some cases, the distal end of the shroud 150 can extend distally past the distal end(s) of the housing 102, the valve 114, the projection 116, the cover 124, and/or the outer wall 120 by a small amount (e.g., about 5 mm, about 4 mm, about 3 mm, about 2 mm, about 1 mm, or less, or any values or ranges therebetween), which still enables the user to perform the swabbing or other disinfection action.

The shroud 150 can have a generally cylindrical shape. A side wall 152 can define a cavity, which can contain at least a portion of the housing 102. The cavity can be open at the proximal side and/or can be open at the distal side. The interior of the cavity can be configured to be slidable relative to the exterior surface of the housing 102 (e.g., the exterior wall 120). In some embodiments, the shroud 150 can include a recess (e.g., groove) or protrusion, which can engage a corresponding protrusion or recess (e.g., groove) on the housing 102 to impede rotation between the shroud 150 and the housing 102, while permitting axial movement therebetween. In some embodiments, the shroud 150 can be permitted to rotate relative to the housing 102 (e.g., about the longitudinal axis of the connector 100). The shroud 150 can include an engagement structure configured to provide a breakaway connection to the second connector 200, as discussed herein.

Figure 12:
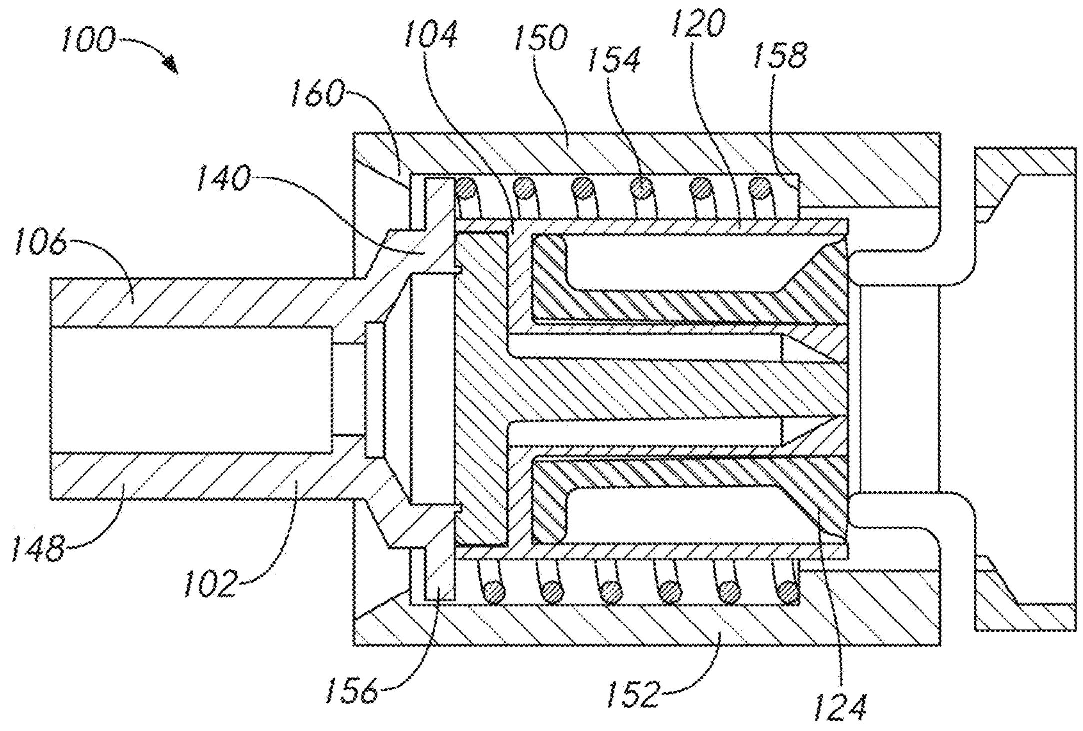
FIG. 12 is a cross-section view of an example embodiments of a first connector with a biasing mechanism configured to bias the shroud toward the advance or distal position.

In some embodiments, the shroud 150 can be biased toward the advanced or distal position (e.g., shown in FIGS. 1-3). FIG. 12 is a cross-section view of an example embodiments of a first connector 100 with a biasing mechanism 154 configured to bias the shroud 150 toward the advance or distal position. The biasing mechanism 154 can be a coil spring, although any suitable biasing mechanism can be used, such as a resiliently compressible O-ring or other member, a compression spring, an extension spring, or another type of spring, etc.

With reference to FIG. 12, the housing 102 can have a ledge 156 that extends laterally outward (e.g., past the outer wall 120). For example, the wall 140 at the distal end of the second housing portion 106 can extend laterally outward past the proximal end of the first housing portion 104. Various other configurations are possible. For example, the ledge 156 can be formed as a ridge on the exterior of the outer wall 120 on the first housing portion 104. The inside of the shroud 150 can have a step 158, which can for a proximally facing surface. The spring 154 can be contained between the step 158 and the ledge 156. When a force moves the shroud 150 proximally, the step 158 can move toward the ledge 156, which can compress the spring 154. When the force is removed, the spring 154 can push the shroud 150 distally relative to the housing 102 back to the advanced or distal position. The spring 154 can be contained in a cavity between the outer wall 120 of the housing 102 and the side wall 152 of the shroud 150. The shroud 150 can include at least one protrusion 160 that can extend laterally inward from side wall 152. The protrusion 160 can be a ridge that can extend around a circumference of the inside of the side wall 152. In some embodiments, two, three, four, or any suitable number of protrusions 160 can be spaced around the circumference of the shroud 150. The protrusion 160 can have a distal side that is configured to abut against the proximal side of the ledge 156, such as to limit movement of the shroud 150 relative to the housing 102 in the distal direction. The spring 154 can be held in a partially compressed state when the shroud 150 is at its most distal position, with the protrusion(s) 160 abutting the ledge 156. In some embodiments, a first end of the spring 154 can be secured to the shroud 150 (e.g., to the step 158), and a second end of the spring 154 can be secured to the housing 102 (e.g., to the ledge 156). Moving the shroud 150 proximally relative to the housing 102 can stretch the spring 150. When the shroud 150 is released, the spring 154 can pull the shroud distally. In some embodiments, the spring can be replaced by an elastic or resilient member.

The shroud 150 can be biased forward by an elastic member. The shroud 150 may be temporarily pushed back to expose the male luer for disinfection, which can stretch or compress the elastic member. The elastic member can return the shroud to its forward position when the shroud 150 is no longer being pushed back.

The proximal side of the protrusion(s) 160 can have a surface where a line normal to the surface can extend substantially parallel to the longitudinal axis. The distal side of the protrusion(s) can be angled or tapered, which can facilitate assembly of the shroud 150 and housing 102. A line normal to the proximal side of the protrusion(s) can be angled relative to the longitudinal axis by about 30 degrees, about 40 degrees, 45 degrees, 50 degrees, 60 degrees, or any values therebetween or any ranges between any of these values (e.g., between about 30 and 60 degrees), although other configurations are possible. By way of example, the shroud 150 can start detached from the housing 102, and the housing 102 can be inserted into the proximal side of the shroud 150 until the protrusion(s) 160 contact the ledge 156. Pressing the housing 102 distally and/or the shroud 150 proximally can cause the protrusions 156 to deform or flex apart so that the protrusion(s) 160 can move past the ledge 156. Once the protrusion(s) 160 clear the ledge 156 they can snap back inward. The angled or tapered surface(s) on the proximal side of the protrusion(s) 160 can facilitate the snap-fit engagement, for example.

In some embodiments, the shroud 150 can be lockable in the advance or distal position. The shroud 150 can be locked forward until disinfection is to be performed. The user can unlock the shroud 150, move the shroud 150 to the retracted or proximal position, perform the disinfection action, return the shroud 150 to the advance or distal position, and relock the shroud 150 relative to the housing 102.

Figure 13:
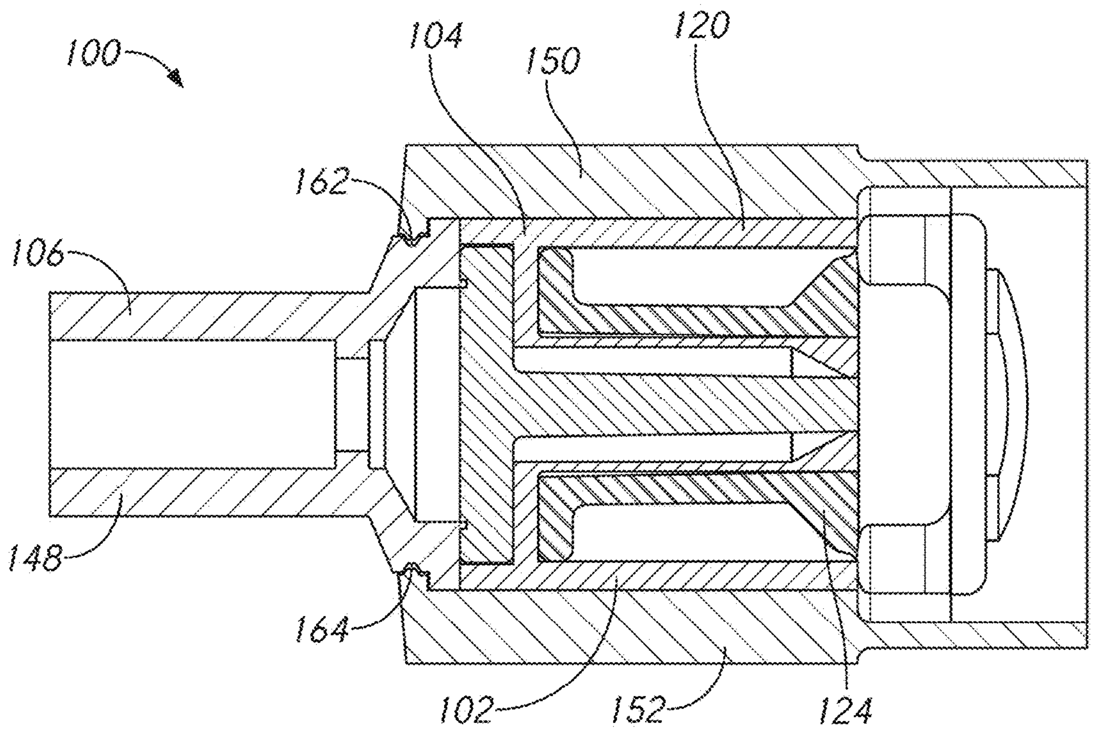
FIG. 13 shows a cross-sectional view of an example embodiment of a first connector.

FIG. 13 shows a cross-sectional view of an example embodiment of a first connector 100. The connector 100 can have a detent or snap engagement feature that can lock the shroud 150 in the advanced or distal position until a threshold amount of force is applied, which can disengage the detent or snap engagement to enable the shroud 150 to move (e.g., proximally) relative to the housing 102, such as to facilitate disinfection as discussed herein. In FIG. 13, the housing 102 (e.g., the second housing portion 106) can have at least one recess 162, which can be a groove that extends around the circumference of the connector 100, or a plurality of recesses 162 spaced apart around the circumference, or a single recess 162 could be used. The recess 162 can be formed on an outer surface of the housing 102 (e.g., on the wall 140). The shroud 150 can include at least one protrusion 164, which can be a ridge that extends around a circumference of the shroud 150, or a plurality of protrusions 164 can be spaced around the circumference, or a single protrusion 164 could be used. The at least one protrusion 164 can be formed on an inside surface of the shroud 150. The at least one protrusion 164 can be configured to engage with the at least one recess 162, such as to form a snap-fit engagement, when the shroud 150 is in the advance or distal position. The engagement of the at least one protrusion 164 and at least one recess 162 can lock the shroud 150 against axial movement relative to the housing 102 until a force above a threshold is applied. The threshold force can be higher than a typical force that would be experienced by dropping the connector 100 on the ground (e.g., upon unintended disconnection from another connector 200). For example, a threshold force to release the shroud 150 can be about 0.5 pounds, about 1 pound, about 2 pounds, about 3 pounds, about 4 pounds, about 5 pounds, about 6 pounds, about 7 pounds, about 8 pounds, about 10 pounds, about 12 pounds, about 15 pounds, or about 20 pounds of force, or any values therebetween, or any ranges between any pair of these values (e.g., between about 2 pounds and about 8 pounds), although other configurations are possible. When a force above the threshold is applied the at least one protrusion 164 can disengage from the at least one recess 162 so that the shroud 150 can move (e.g., proximally) relative to the housing 102. A force (e.g., above the threshold) can be applied to reengage the at least one protrusion 164 with the at least one recess 162. The at least one recess 162 and at least one protrusion 164 can be swapped. In some embodiments, the shroud 150 can have at least one recess 162 and the housing 102 can have at least one protrusion 164. The detent or snap fit engagement between the shroud 150 and housing 102 can be formed at various other suitable locations, such as on the exterior of the outer wall 120.

Figure 14A:
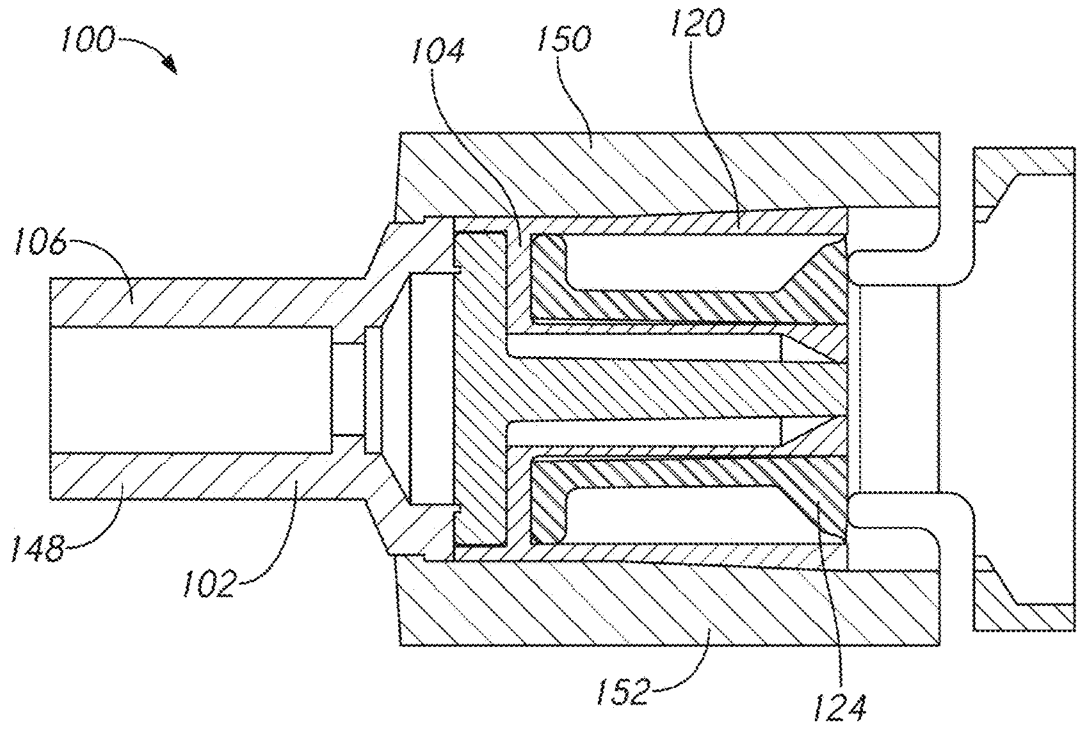
FIG. 14A shows an example embodiment of a connector with the shroud in a locked, forward, or distal position.
Figure 14B:
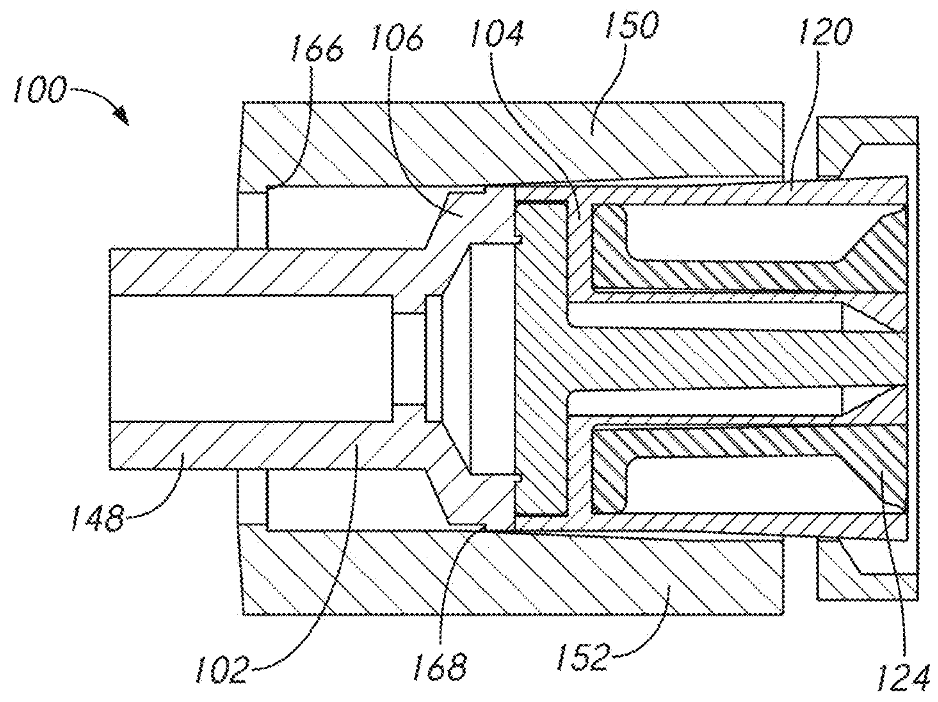
FIG. 14B shows an example embodiments of a connector with the shroud in an unlocked, retracted, or proximal position

In some embodiments, the shroud 150 can be locked axially relative to the housing 102 by a taper lock. FIG. 14A shows an example embodiment of a connector 100 with the shroud 150 in a locked, forward, or distal position. FIG. 14B shows an example embodiments of a connector 100 with the shroud 150 in an unlocked, retracted, or proximal position. The exterior surface of the outer wall 120 of the housing 102 can be tapered. The outer diameter of the outer wall 120 can increase moving distally. The inner surface of the side wall 152 of the shroud 150 can have a corresponding tapered shape. The inner diameter of the side wall 152 can increase moving distally. When the tapered surfaces are engaged (e.g., with the shroud 150 in the forward position), a force above a threshold is needed to move the shroud 150 axially relative to the housing 102. The threshold force can be more than would typically be experienced by dropping the connector 100 on the ground (e.g., upon unintentional disconnection). To unlock the shroud 150 from the housing 102, a user can rotate the shroud 150 relative to the housing 102 to break the engagement between the tapered surfaces. Rotating the shroud 150 relative to the housing 102 can overcome the static friction of the engaged tapered surfaces. Once unlocked, the shroud 150 can be retracted (e.g., proximally), such as to facilitate disinfection. The shroud 150 can be returned to the locked configuration by moving the shroud 150 distally to reengage the taper lock between the tapered surfaces.

Figure 15:
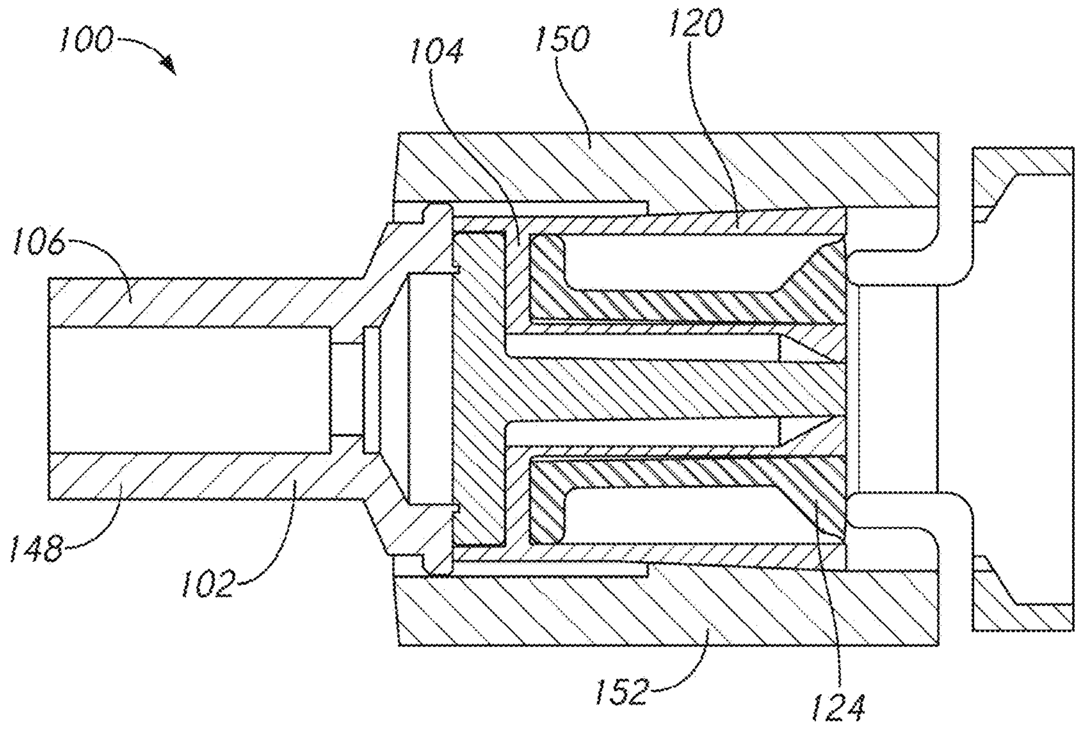
FIG. 15 shows a cross-sectional view of an example connector.

In some embodiments, the shroud 150 can have a step 166, which can abut against a step 168 on the housing 102 to limit movement of the shroud 150 (e.g., distally) relative to the housing 102. The connector 100 can be configured so that the steps 166, 168 can engage each other to impede further distal movement of the shroud 150 relative to the housing 102 at substantially the same time or position that the tapered surfaces engage to impeded further distal movement of the shroud 150 relative to the housing. In some embodiments, the tapered surfaces can be omitted, and the steps 166, 168 can limit movement of the shroud 150 in the distal direction relative to the housing 102. In some embodiments, the steps 166, 168 can be omitted, as shown for example in FIG. 15. In some embodiments, the tapered surfaces can be omitted, and the steps 166, 168 (or other protrusions or engagement structures on the shroud 150 and housing 102) can abut or otherwise engage to limit the distal movement of the shroud 150 relative to the housing 102.

Figure 16A:
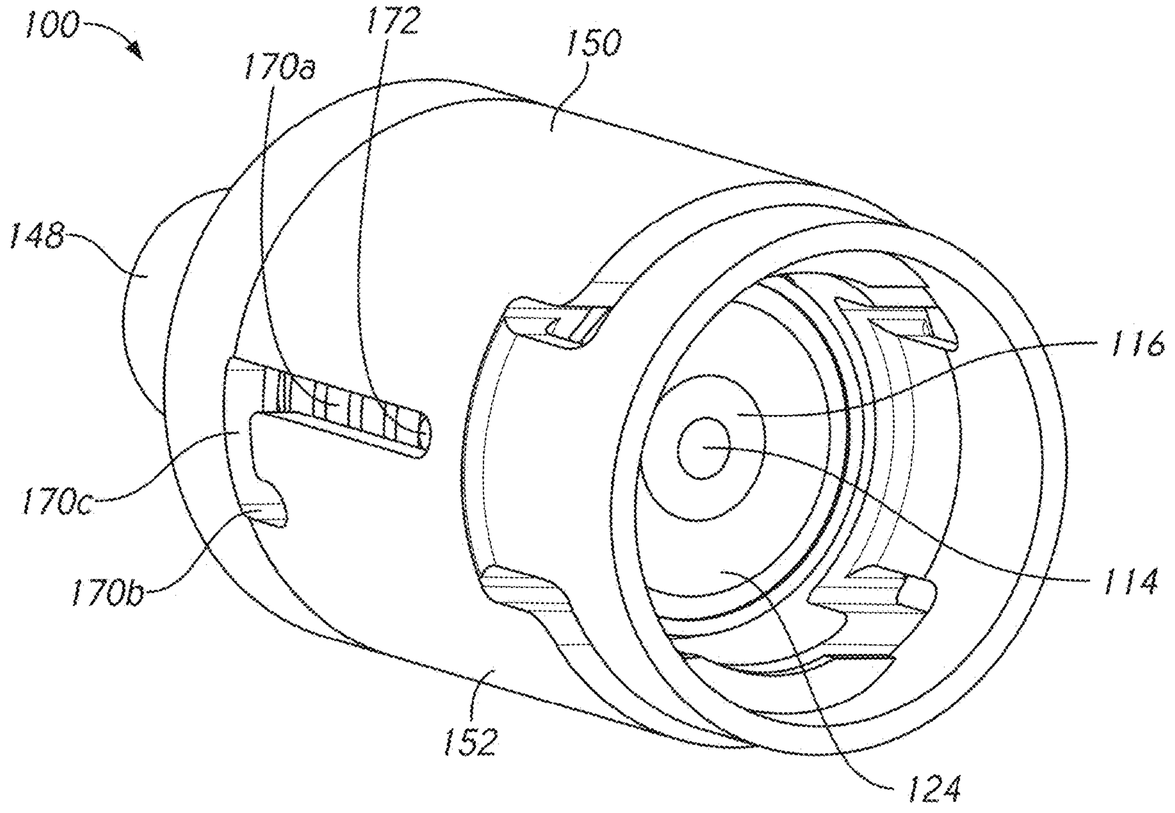
FIG. 16A shows a perspective view of an example connector.
Figure 16B:
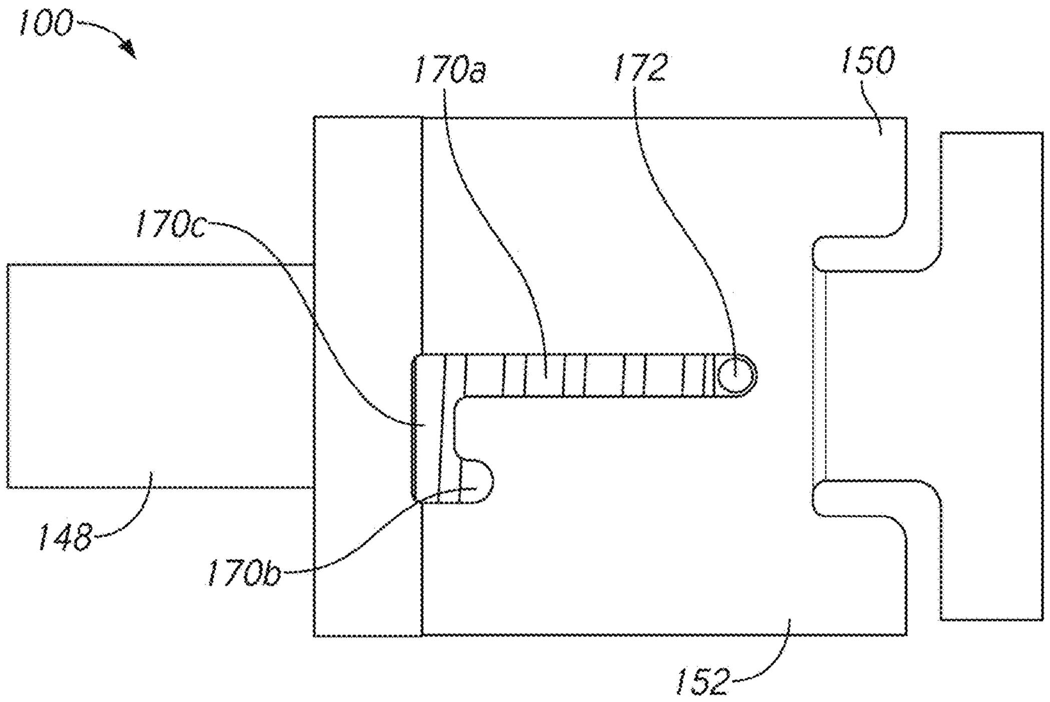
FIG. 16B shows a cross-sectional view of an example connector.

FIGS. 16A and 16B illustrate an example embodiment of a connector 100, which can have a bayonet style mechanism to control movement between the shroud 150 and the housing 102. The shroud 150 can include a J-shaped slot 170. The housing 102 can include a protrusion 172, which can be configured to fit into the slot 170. The slot 170 can have a first portion 170*a* that is longer than a second portion 170*b*, and an intermediate (e.g., curved) portion of the slot can couple the first portion 170*a* to the second portion 170*b*. The shroud 150 can be positioned at the advanced, distal, or locked position when the protrusion 172 is positioned at a first end of the slot 170 (e.g., at the end of the second portion 170*b*), as shown in FIGS. 16A and 16B. In this position pressing the shroud 150 proximally would not move the shroud 150 because the protrusion 172 would abut against the end of the slot second portion 170*b*. To move the shroud to the retracted or proximal position, the shroud 150 is first moved distally and rotated so that the protrusion 172 transitions from the second portion 170*b*, through the intermediate (e.g., curved) portion 170*c*, to the first portion 170*a*. The first portion 170*a* of the slot can extend further distally than the second portion 170*b* of the slot, so that the shroud 150 can be moved further proximally when the protrusion 172 is in the first portion 170*a* than when it is in the second portion 170*b* of the slot 170. The protrusion can abut against the distal end of the first slot portion 170*a* when the shroud is in the retracted or proximal position. The user can move the shroud 150 distally, rotate the shroud 150 (e.g., in a first direction), and then move the shroud 150 proximally to expose the distal end of the housing 102 for disinfection. The user can move the shroud 150 distally, rotate the shroud 150 (e.g., in a second direction opposite the first direction), and then move the shroud 150 proximally to move the shroud 150 back to the locked or advanced position.

Figure 17:
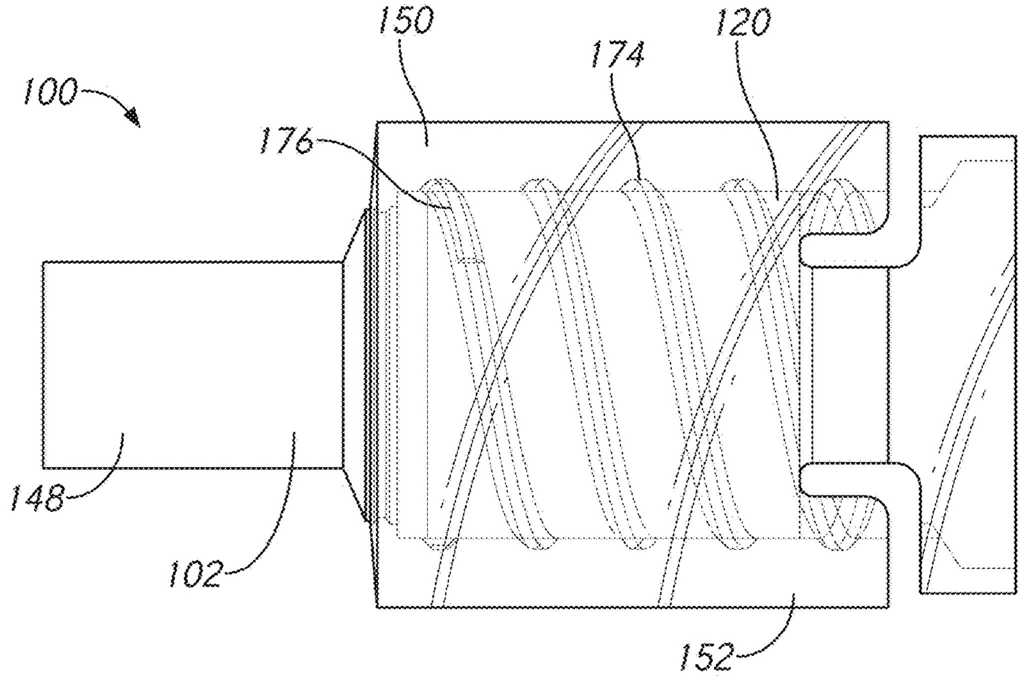
FIG. 17 shows an example embodiment with a threaded engagement between the shroud and the housing.

In some embodiments, the shroud 150 and housing 102 can be threaded together. Rotating the shroud 150 relative to the housing 102 can move the shroud 150 axially relative to the housing 102, such as between an advanced or distal position and a retracted or proximal position. FIG. 17 shows an example embodiment with a threaded engagement between the shroud 150 and the housing 102. The inside of the shroud 150 can have threading 174. The exterior of the outside wall 120 can have threading 176 that is configured to engage the threading 174 on the shroud 150. In FIG. 17, the shroud 150 is shown semi-transparent to facilitate illustration. When the shroud 150 is rotated relative to the housing 102 in a first direction as far as the threading 174 and/or 176 permit, the shroud 150 can be in an advanced or distal position (e.g., as shown in FIG. 17). When the shroud 150 is rotated relative to the housing 102 in a second direction as far as the threading 174 and/or 176 permit, the shroud 150 can be in a retracted or proximal position, which can facilitate a disinfection action, as discussed herein. In some embodiments, a detent can be used to lock the shroud 150 in the advanced or distal position, unless a sufficient amount of force is applied to disengage the detent. The detent feature can be similar to the embodiment of FIG. 13, for example. In some embodiments, the detent engagement can provide tactile feedback that the shroud 150 is locked into the advanced or distal position, which can be configured to impede contamination, as discussed herein. In some embodiments, the detent feature can be incorporated into the threading. The thread can have a narrow section or a wide section that resists the threaded engagement unless an increased rotational force is applied, and the increased rotation force can cause engagement or disengagement of the narrow or wide section of the thread, which can provide tactile feedback of engagement into the locked position, and which can resist unintended movement of the shroud 150 away from the locked position.

In some embodiments, the outer wall 120 can have one or more protrusions 176 that engage the threading on the shroud 150, rather than both sides being threaded. In some cases, the protrusions 176 can form a partial thread. The thread 174 on the shroud 150 can be formed as a groove. Many variations are possible for the threaded engagement. The thread 174 on the shroud can be a protrusion that engages a recess on the housing 102 (e.g., a recessed thread).

Figure 18:
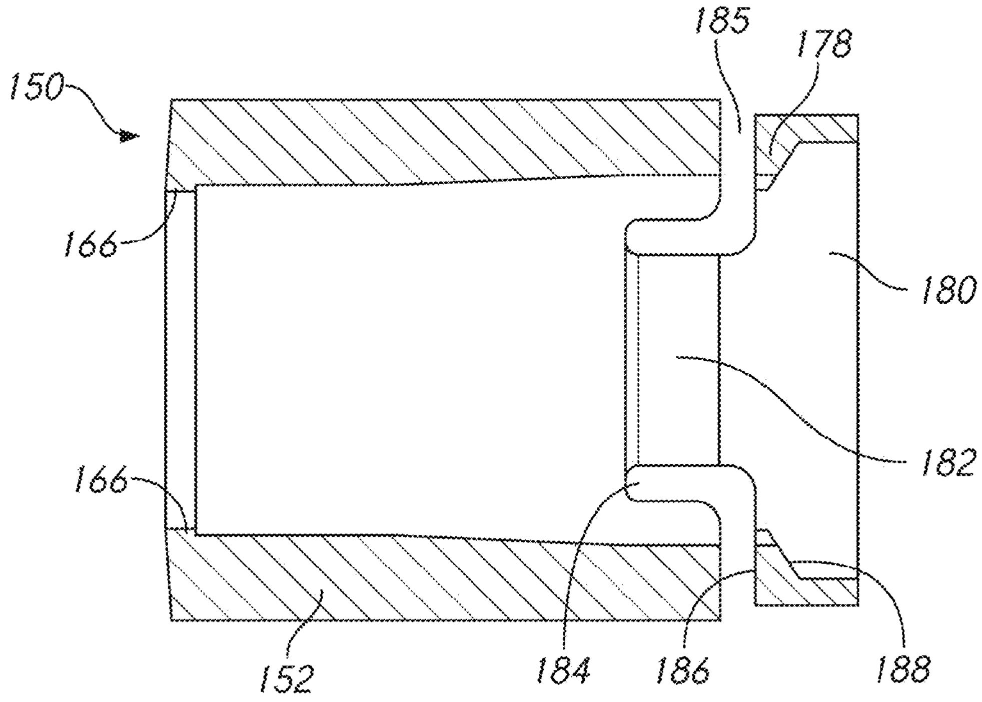
FIG. 18 is a cross-sectional view of an example embodiments of a shroud.
Figure 19:
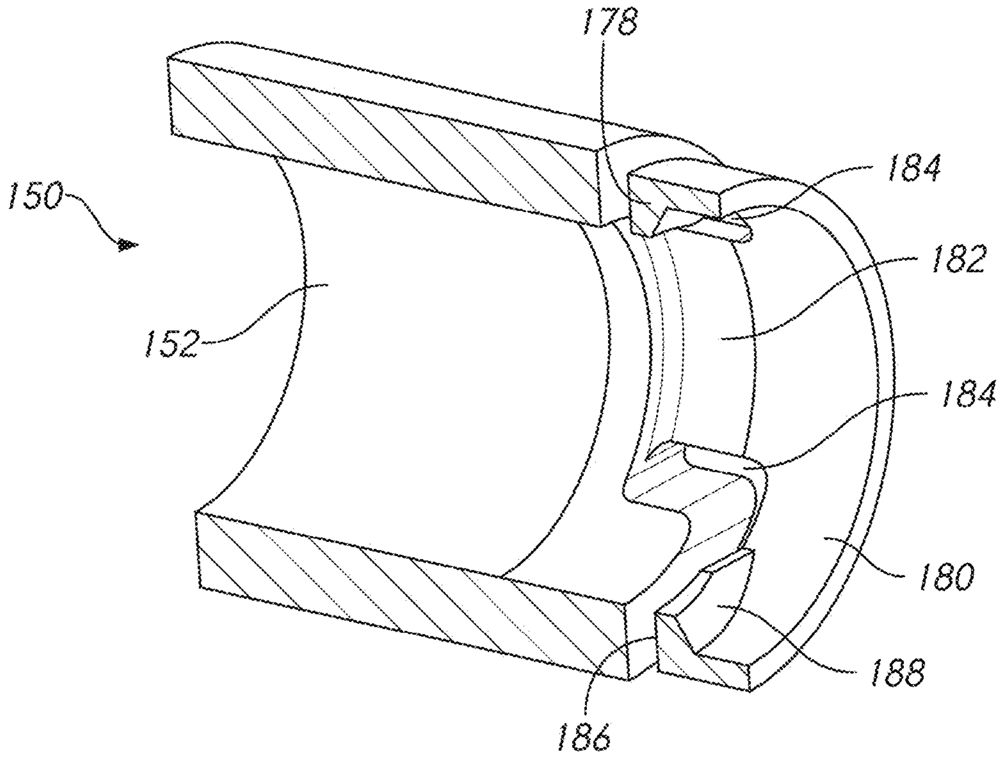
FIG. 19 is a perspective cross-sectional view of an example embodiments of a shroud.

The shroud 150 can include a breakaway engagement feature configured to couple the first connector 100 to the second connector 200 in a manner the permits the connectors 100, 200 to be decoupled when a sufficient force is applied that pulls the connectors 100, 200 apart (e.g., longitudinally). FIG. 18 is a cross-sectional view of an example embodiments of a shroud 150. FIG. 19 is a perspective cross-sectional view of an example embodiments of a shroud 150. The shroud 150 can have a sidewall 152, which can define an interior cavity. The sidewall 152 can be generally cylindrical. The shroud 150 can have one or more protrusions 178, which can extend laterally inward. The one or more protrusions 178 can engage a corresponding structure on the second connector 200 to couple the connectors 100, 200. When the connectors 100, 200 are pulled apart, the one or more protrusions 178 can be displaced (e.g., laterally outwardly) to disengage from the corresponding structure on the second connector 200, to permit disconnection of the first connector 100 from the second connector 200. In some embodiments, the shroud 150 can include two protrusions 178, which can be disposed one generally opposite sides of the shroud 150. The two protrusions 178 can be between about 150 degrees and 210 degrees apart, or about 170 degrees to about 190 degrees apart, or about 180 degrees apart, although various other values or ranges therebetween could be used, and other configurations are possible.

The protrusions 178 can be disposed on a ring 180, which can be configured to flex or deform to enable displacement of the one or more protrusions 178. The ring 180 can be coupled to the sidewall 152 by one or more neck portions 182. The shroud 150 can include two neck portions 182, which can be disposed generally opposite each other. The two neck portions 182 can be between about 150 degrees and 210 degrees apart, or about 170 degrees to about 190 degrees apart, or about 180 degrees apart, although various other values or ranges therebetween could be used, and other configurations are possible. At least a portion of the ring 180 can be separated from the side wall 152 by one or more gaps 184. The gaps 184 can facilitate flexing of the ring 180, such as by enabling the ring 180 to deform substantially independently of the side wall 152. In some embodiments, the shroud 150 can have two gaps 184. Each protrusion 178 can have a separate gap 184. The one or more gaps 184 can be disposed between the one or more protrusions 178 and the sidewall 152 of the shroud 150. The gaps 184 can be separated by the neck portions 182. The gaps 184 can be generally L-shaped. A longitudinal portion of the gap 184 can extend adjacent the neck portion 182 (e.g., from the side wall 150 to the ring 180), and a circumferential portion of the gap 184 can extend along a circumference of the shroud 150, and can extend under a corresponding protrusion 178.

The ring 180 can have a substantially circular shape by default (e.g., when not flexed or deformed). When the protrusions 178 are pushed outward, the circular shape of the ring 180 can change to have an oblong (e.g., generally elliptical or oval) shape. When the ring is flexed or deformed, the distance between opposite sides of the ring 180 next to the protrusions 178 can be larger than the distance between opposite sides of the ring 180 next to the neck portions 182. The neck portions 182 can be offset from the protrusions 178 by about 70 degrees to about 110 degrees, or by about 80 degrees to 100 degrees, or by about 90 degrees, or any other values or ranges between these values, although other configurations are possible. The ring 180 can be thinner than the sidewall 152, such as to facilitate deformation of the ring 180. The neck portion(s) 182 can also be thinner than the sidewall 152. The sidewall 152 can be about 1.5 times, about 2 times, about 2.5 times, about 3 times, about 4 times, or about 5 times thicker, or more, than the ring 180 and/or than the neck portion(s) 182, or any values or ranges therebetween, although other configurations are possible.

The protrusion(s) 178 can have a proximal side 186 and a distal side 188. The proximal side 186 can be flat (e.g., extending laterally). A line normal to the proximal side or surface 186 can extend substantially parallel to the longitudinal axis of the connector, or within about 2 degrees, about 5 degrees, about 10 degrees, or any values or ranges therebetween, although other configurations are possible. The distal side or surface 188 can be angled. A line normal to the distal side or surface 188 can be angled inwardly by an angle of about 30 degrees, about 40 degrees, 45 degrees, 50 degrees, 60 degrees, or any values therebetween or any ranges between any of these values (e.g., between about 30 and 60 degrees), although other configurations are possible. When the second connector 200 is being coupled to the first connector 100 a structure on the second connector 200 can press proximally on the distal surface 188, and the angled surface can facilitate displacing the protrusion(s) 178 outwardly as the structure slides along the distal surface 188. When the structure on the second connector 200 clears the protrusions 178, the protrusions 178 can move inward (e.g., to their unflexed positions), which can couple the connectors 100, 200. The proximal side or surface 186 can abut against a portion of the second connector 200 to impede the second connector 200 from moving proximally away from the connector 100 (e.g., unless sufficient force is applied to implement the breakaway disconnection feature, which can push the protrusions 178 outward to release the second connector 200 from the first connector 100).

Figure 20:
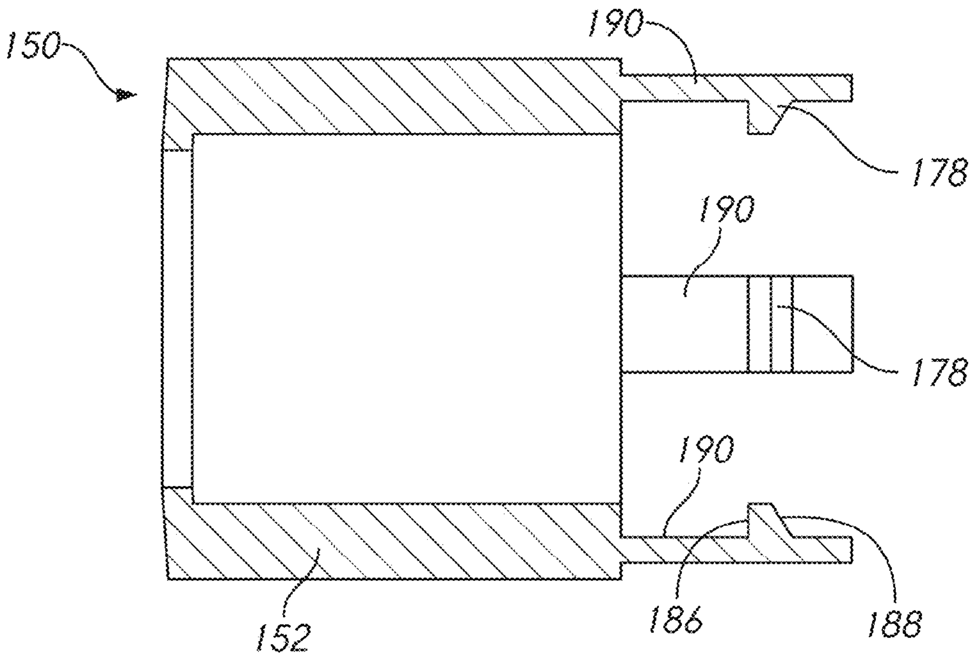
FIG. 20 shows a cross-sectional view of another example embodiment of a shroud

FIG. 20 shows a cross-sectional view of another example embodiment of a shroud 150. The shroud 150 can have one or more protrusions 178 on one or more arms 190, which can extend longitudinally from the sidewall 152 of the shroud 150. The arm(s) 190 can be configured to flex so that the protrusion(s) 178 can be displaced (e.g., laterally outward), such as during connecting to or disconnecting from the second connector 200. The arm(s) 190 can be thinner than the sidewall 152. The sidewall 152 can be about 1.5 times, about 2 times, about 2.5 times, about 3 times, about 4 times, or about 5 times thicker, or more, than the ring 180 and/or than the arm(s) 190, or any values or ranges therebetween, although other configurations are possible. The shroud can include four arms 190 and protrusions 178, which can be spaced around the shroud 150 (e.g., offset by about 90 degrees each), but any suitable number of arm(s) 190 and protrusion(s) 178 can be used (e.g., 1, 2, 3, 4, 6, 8, 12, etc.). Because the protrusions 178 in the embodiment of FIG. 20 are not interconnected by a ring 180, the protrusions 178 can be displaced independently, which can permit the use of more protrusions 178, which can more evenly distribute the forces during connecting and/or disconnecting. The sidewall 152 can be formed with enough longitudinal height that the housing 102 can be recessed proximally therein to insulate the housing 102 from contaminants.

Figure 21:
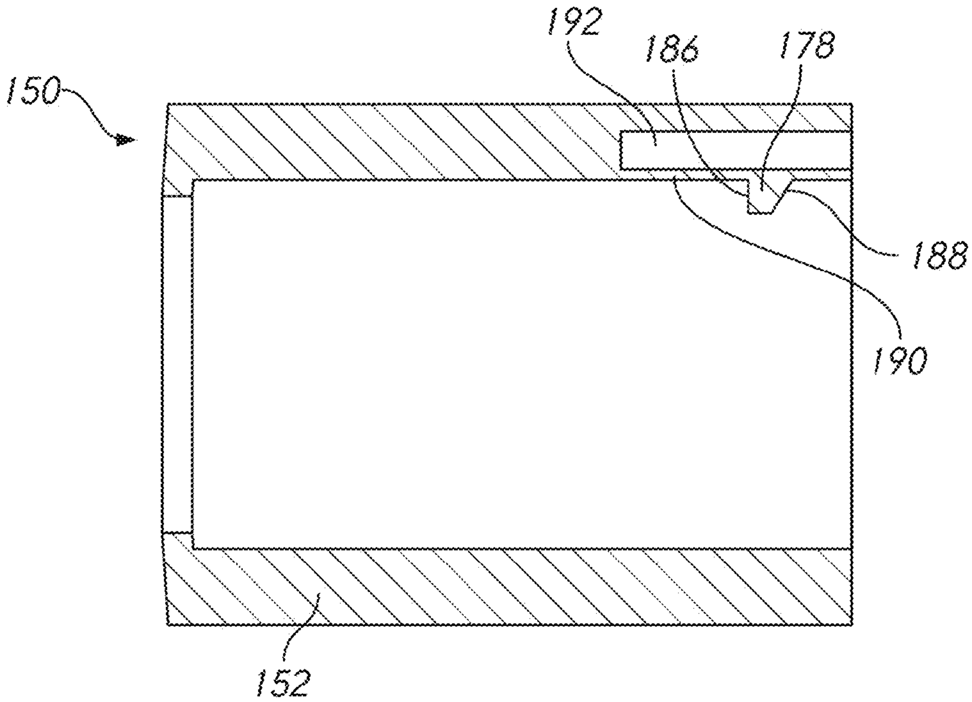
FIG. 21 shows a cross-sectional view of another example embodiment of a shroud.

FIG. 21 shows a cross-sectional view of another example embodiment of a shroud 150. The shroud 150 can have a sidewall 152 that extends distally to or past the protrusion(s) 178. In some implementations, the sidewall 152 can have no openings or slots that are proximal of the protrusion(s). This configuration can provide improved resistance to contaminants entering the connector 100. The protrusion(s) 178 can be disposed on a flexible member (e.g., an arm 190 as shown, or a ring 180). One or more cavities 192 can be formed laterally outward of one or more protrusions 178 and/or the one or more flexible members 190. The cavity 192 can provide room for the protrusion 178 and/or flexible member 190 to be displaced outwardly, such as during connection to or disconnection from the second connector 200. In some embodiments, such as shown in FIG. 21, a single protrusion 178 can be used, although any suitable number could be used, as discussed herein. In some embodiments, the protrusions 178 can be configured to deform to permit connection to and/or disconnection from the second connector 200.

Figure 23:
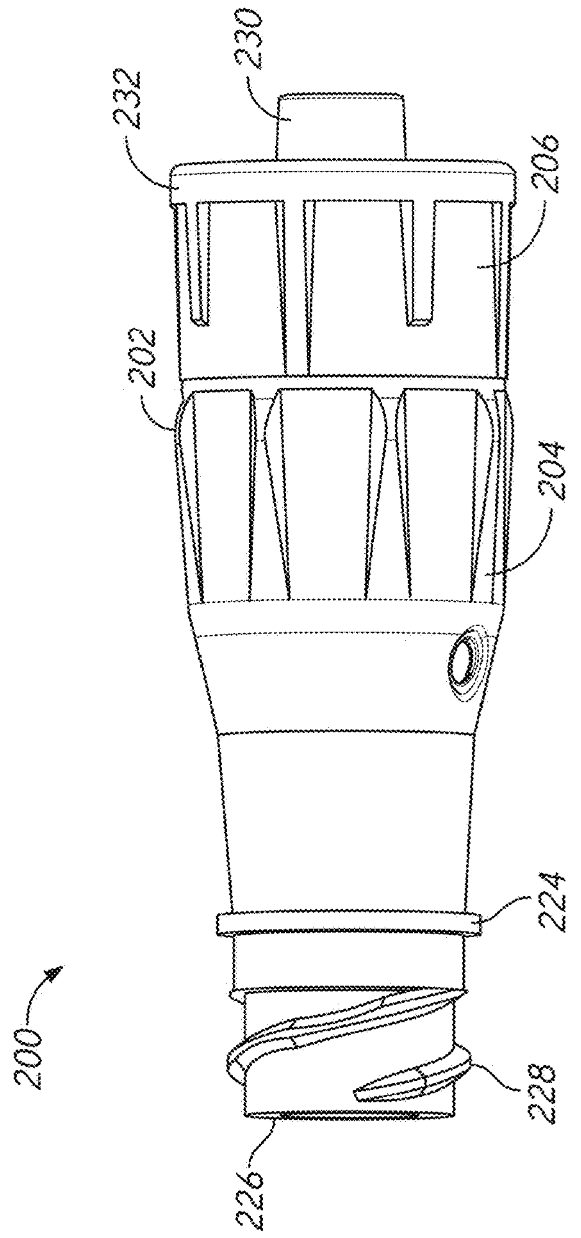
FIG. 23 shows a side view of an example embodiments of a second connector, without the adapter coupled thereto.
Figure 22:
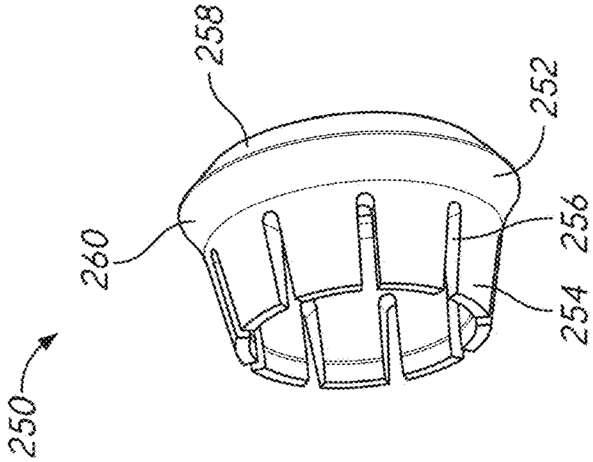
FIG. 22 shows a perspective view of an example embodiments of an adapter, which can be configured for use with a second connector.
Figure 24:
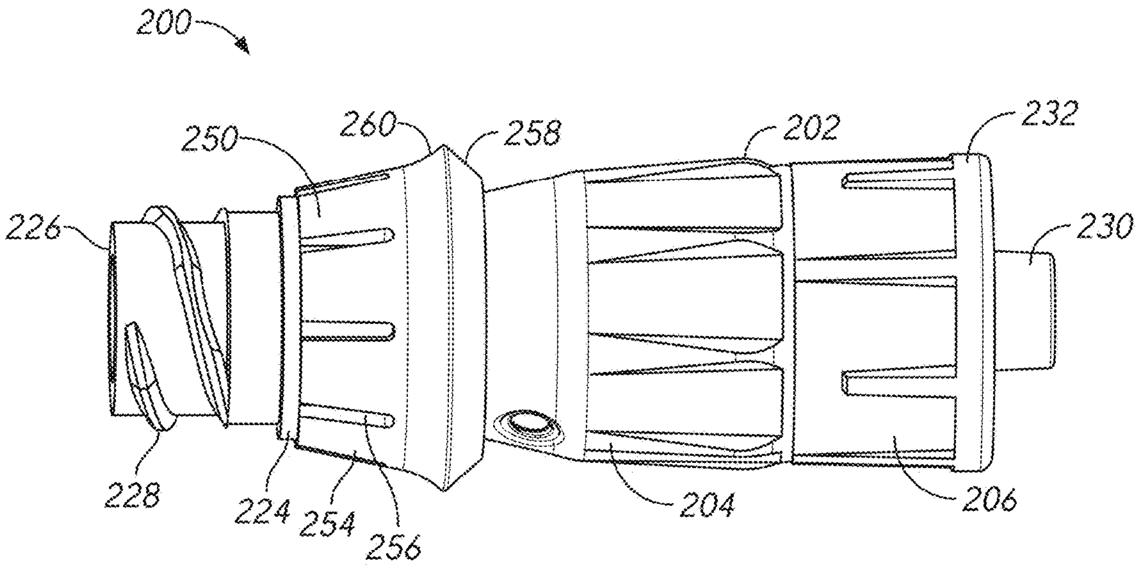
FIG. 24 shows a side view of an example embodiments of a second connector, with the adapter coupled thereto.
Figure 25:
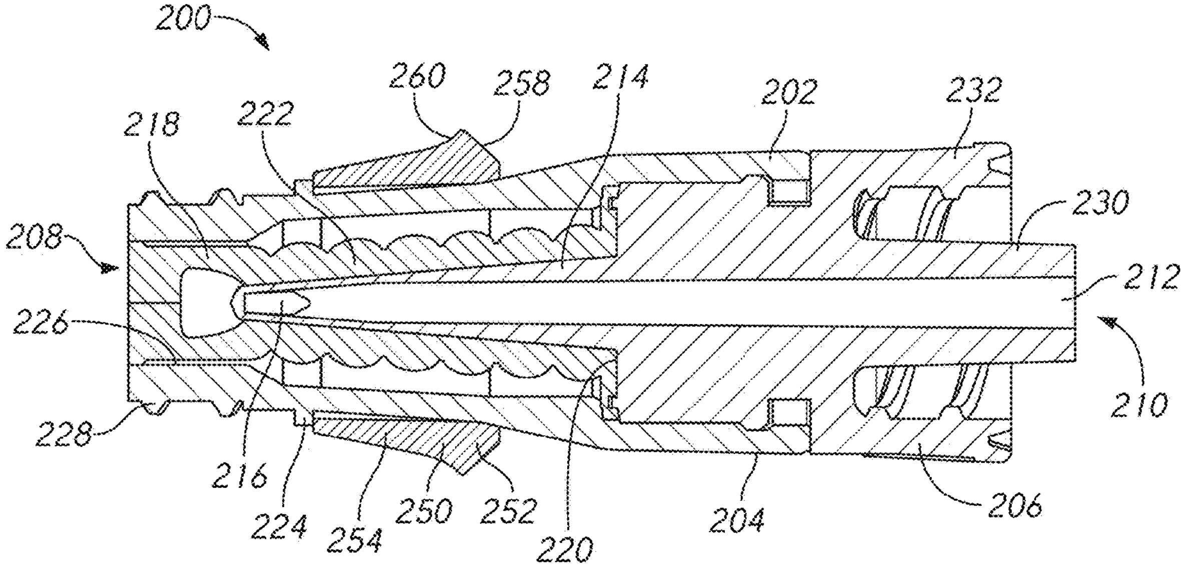
FIG. 25 shows a cross-sectional view of the second connector, with the adapter coupled thereto.
Figure 26:
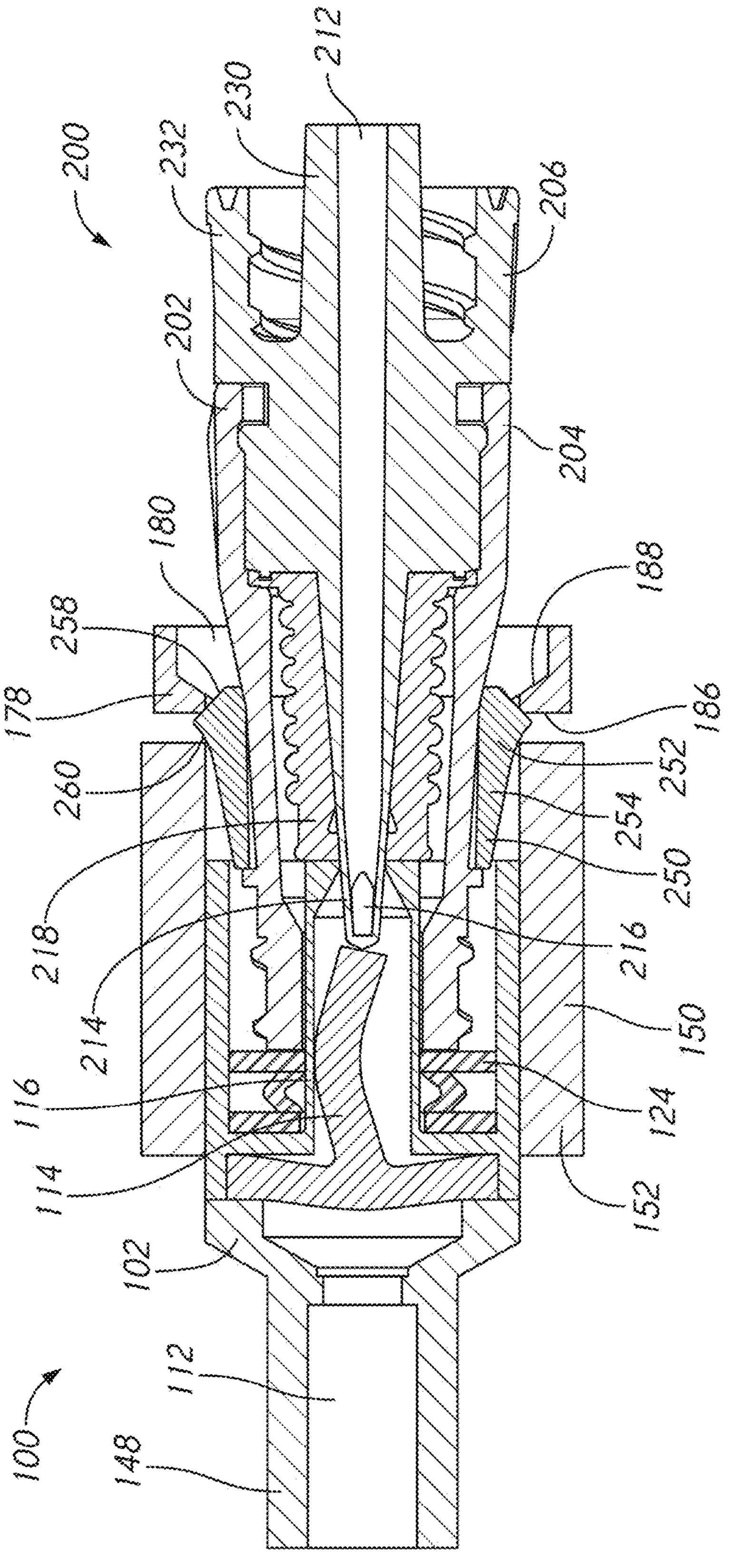
FIG. 26 is a cross-sectional view of the first connector coupled to the second connector (e.g., using the adapter).

In some embodiments, the second connector 200 can include an adapter 250. FIG. 22 shows a perspective view of an example embodiments of an adapter 250, which can be configured for use with a second connector 200. The adapter 250 can be configured to add a breakaway connection feature to a connector. FIG. 23 shows a side view of an example embodiments of a second connector 200, without the adapter 250 coupled thereto. FIG. 24 shows a side view of an example embodiments of a second connector 200, with the adapter 250 coupled thereto. FIG. 25 shows a cross-sectional view of the second connector 200, with the adapter 250 coupled thereto. FIG. 26 is a cross-sectional view of the first connector 100 coupled to the second connector 200 (e.g., using the adapter 250).

The second connector 200 can be a Clave® connector manufactured by ICU Medical, Inc., of San Clemente, California. The connector 200 can include various features disclosed in U.S. Pat. No. 5,685,866 (the "'866 Patent"), the entirety of which is incorporated herein by reference. Various other suitable connectors could be used for the second connector 200. The second connector 200 can be a needleless connector. The second connector 200 can have a female luer fitting, such as at its proximal end. The second connector 200 can have a male luer fitting, such as at its distal end. In some cases, the distal end of the second connector 200 can be connected to a catheter, or another fluid line, or some other medical implement.

The second connector 200 can have a housing 202, which can include a first (e.g., proximal) housing portion 204 and a second (e.g., distal) housing portion 206, which can be coupled together, such as by sonic welding, a threaded engagement, a snap-fit engagement, a friction engagement, or any other suitable coupling mechanism. The housing 202 (e.g., the first housing portion 204) can have a first (e.g., proximal) opening 208. The housing 202 (e.g., the second housing portion 206) can have a second (e.g., distal) opening 210. A fluid pathway 212 can connect the first opening 208 to the second opening 210. The connector 200 (e.g., the second housing portion 206) can have a projection 214, which can extend distally from a base portion 220 of the housing 202. The projection 214 can be hollow, and the interior of the projection 214 can form a portion of the fluid pathway 212 through the connector 100. The projection 214 can have one or more openings 216, which can permit fluid to pass out of, or into, the fluid pathway portion inside the projection 214. The one or more openings 216 can be formed on the side(s) of the projection 214. The tip or proximal end of the projection 214 can be solid, with no openings. The exterior of the projection 214 can be tapered, with a narrowing diameter or width moving proximally.

The connector 200 can include a valve 218, which can have a closed configuration that closes the fluid pathway 212 and an open configuration that opens the fluid pathway 212. The valve 218 can cover the one or more openings 216 and/or fill the proximal opening 208 in the closed configuration. When the connectors 100, 200 are connected, the projection 116 of the connector 100 can push the valve 218 (e.g., the proximal end thereof) distally (e.g., out of the opening 208) to open the valve 218. The valve 218 can be pushed past part or all of the one or more openings 216 in the open configuration. The closed configuration of the valve 218 is shown in FIG. 25. The open configuration of the valve 218 is shown in FIG. 26. When the connectors 100, 200 are disconnected, such as when pulled apart, the valve 218 can return to the closed configuration, such as to impede fluid from leaking out of the connector 200 and/or to impede contaminants from entering the fluid pathway 212. The valve 218 can include a biasing structure 222, which can bias the valve 218 toward the closed configuration. The valve 218 and/or biasing structure 222 can be made of silicone or any other suitable elastomeric or resilient material.

The exterior of the housing 202 (e.g., the first housing portion 204) can have at least one protrusion 224, such as a ridge which can extend partially or completely around a circumference of the connector 200. The exterior of the housing 202 (e.g., of the first housing portion 204) can be tapered, with a diameter or width that increases moving distally from the protrusion 224. In some implementations, the adapter 250 can be held between the protrusion 224 (e.g., a circumferential ridge) and the tapered housing, to couple the adapter 250 to the connector 200.

The adapter 250 can have generally cylindrical shape. The adapter 250 can have a body portion 252. The body portion 252 can be annular with an opening through the middle. One or more arms 254 can extend proximally from the body portion 252. The arms 252 can be separated by gaps 256 (e.g., slits). The arms 254 can be coupled to the body portion 252 are their distal ends. The arms 254 can include free proximal ends. In FIG. 22, the adapter 250 includes 9 arms 254, but any suitable number of arms 254 can be used (e.g., 1, 2, 3, 4, 5, 7, 9, 12, 15, or 20 arms 254, or any values or ranges therebetween, although other configurations are possible). The arms 254 can be configured to flex (e.g., laterally outward), such as to enable the adapter 250 to be coupled to the connector 200.

The proximal end of the connector 200 can be inserted into the distal end of the adapter 250. The opening through the body portion 250 can have a diameter or width that is larger than the diameter or width of the connector 200 at the protrusion 224, so that the protrusion 224 can pass through the body portion 252 of the adapter 250. The arms 254 can be angled inwardly. The diameter or distance between the proximal ends of opposing arms 254 can be smaller than the diameter of width of the opening through the body portion 252, and/or can be smaller than the dimeter or width of the connector at the protrusion 224. As the adapter 250 moves distally relative to the connector 200, the protrusion 224 can push the arm(s) 254 outward. Once the protrusion 224 moves proximally past the arm(s) 254, the arm(s) 254 can move inward (e.g., to provide a snap-fit engagement). As shown in FIGS. 24 and 25, the proximal ends of the arm(s) 254 can abut against the protrusion 224 to impede the adapter 250 from moving proximally off of the connector 200. The adapter 250 can move distally relative to the connector 200 until the body portion 252 abuts against the tapered exterior of the housing 202. The size of the adapter 250 (e.g., the longitudinal length) can be configured so that the adapter 250 can fit snugly between the protrusion 224 and the tapered housing 202, or with little longitudinal movement, such as less than about 3 mm, about 2 mm, about 1.5 mm, about 1 mm, about 0.75 mm, about 0.5 mm, about 0.3 mm, about 0.2 mm, about 0.1 mm, or less, or any values or ranges therebetween, although other configurations are also possible.

In some embodiments, the connector 200 can have multiple protrusions 224, which can be spaced around the circumference of the connector 200, rather than a continuous ridge. In some embodiments, the housing 202 can have a step from a proximal portion with a larger diameter or width to a distal portion with a smaller diameter or width, and the step can hold the adapter 250 onto the connector 200. In some embodiments, distal end or portion of the adapter 250 can abut against a step or at least one protrusion on the exterior of the housing 202, rather than a tapered housing, to restrict further movement of the adapter 250 in the distal direction.

The adapter 250 can include an engagement structure configured to provide a breakaway connection to the first connector 100. The adapter 250 (e.g., the body portion 252) can have an angled breakaway surface 258. The surface 258 can face generally distally. The surface 258 can be a distal surface, such as at the distal end of the adapter 250. As can be seen in FIG. 26, when the connectors 100, 200 are connected, the surface 258 can abut against the one or more protrusions 178 to impede the adapter 250, and the second connector 200, from moving distally away from the first connector 100. The engagement between the surface 258 and the at least one protrusion 178 can keep the connectors 100, 200 connected (e.g., until a sufficient axial force pulls the connectors 100, 200 apart).

When the first connector 100 is pulled proximally and/or when the second connector is pulled distally with sufficient force, the breakaway connection can permit the connectors 100, 200 to disconnect. When the connectors 100, 200 are pulled apart, the angled surface 258 can push the one or more protrusions 178 laterally outward, until the adapter 250 is able to move distally past the protrusion(s) 178, to disconnect the connectors 100, 200. The breakaway interface can be configured to disconnect when a pulling force above a threshold amount is applied. The threshold force can be defined at least by the angle of the surface 258 on the adapter, the angle of the proximal side 186 of the protrusion(s) 178, and the flexibility of the flexible member(s) on the shroud 150 (e.g., the ring 180 or arms 190). A steeper angle on the surface 258 on the adapter and/or on the surface 186 of the protrusion(s) 178 can provide a lower breakaway force threshold, and a flatter angle on the surface 258 or the surface 186 can provide a higher breakaway force threshold. Shroud members with more flexibility can provide a lower breakaway force threshold, and shroud members with less flexibility can provide a higher breakaway force threshold. For example, the breakaway force threshold can be about 0.5 pounds, about 1 pound, about 2 pounds, about 3 pounds, about 4 pounds, about 5 pounds, about 6 pounds, about 7 pounds, about 8 pounds, about 10 pounds, about 12 pounds, or about 15 pounds of force, or any values therebetween, or any ranges between any pair of these values (e.g., between about 2 pounds and about 8 pounds), although other configurations are possible.

The surface 258 and/or the surface 186 can be angled so that a line normal to the surface is offset from a line parallel to the longitudinal axis by an angle of about 20 degrees, about 30 degrees, about 35 degrees, about 40 degrees, about 45 degrees, about 50 degrees, about 55 degrees, about 60 degrees, about 70 degrees, or any values or ranges between these values (e.g., between about 30 degrees and about 60 degrees), although other configurations could be used. In some embodiments, the surface 258 or the surface 178 can be substantially flat or lateral, or can have a normal line that is offset from a line parallel to the longitudinal axis by an angle of about 20 degrees, about 15 degrees, about 10 degrees, about 5 degrees, about 3 degrees, about 2 degrees, about 1 degree, or less, or about 0 degrees, or any values or ranges therebetween, although other configurations can be used. In FIG. 26, for example, the surface 186 is flat and the surface 258 is angled. The angled surface 258 can ride along the corner at the end of the surface 186, which can reduce friction between as compared to the surfaces 258 and 186 being flush against each other. In some configurations, the surface 258 can be flat and the surface 186 can be angled, or the surfaces 258 and 186 can be angled at different angles. The surfaces 258 and 260 can be angled or tapered in opposite directions. The surface 258 can decrease in width moving distally. The surface 260 can decrease in width moving proximally.

The adapter 250 (e.g., the body portion 252) can have an angled connection surface 260, which can be used during connection of the connectors 100, 200. The surface 260 can face generally proximally. The surface 260 can be proximal surface, such as on a proximal side of the body portion 252. The surface 260 can be formed on the outward side of the arm(s) 254. The second connector 200 can be inserted into the distal end of the shroud 150. The surface 260 can abut against the distal side 188 of the protrusion(s) 178. When sufficient force is applied pressing the connectors 100, 200 together, the surface 260 can push the protrusion(s) 178 (e.g., laterally outward) so that the surface 260 can move past the protrusion(s) 178. The protrusion(s) 178 can then move (e.g., radially inward) behind the surface 260 to hold the connectors 100, 200 together. Accordingly, the connectors 100, 200 can have a push-to-connect interface and/or a pull-to-disconnect interface.

The connection interface can be configured to connect the connectors 100, 200 when a pushing force above a threshold amount is applied. The threshold force can be defined at least by the angle of the surface 260 on the adapter, the angle of the distal side 188 of the protrusion(s) 178, and the flexibility of the flexible member(s) on the shroud 150 (e.g., the ring 180 or arms 190). A steeper angle on the surface 260 on the adapter and/or on the surface 188 of the protrusion(s) 178 can provide a lower connection force threshold, and a flatter angle on the surface 260 or the surface 188 can provide a higher connection force threshold. Flexible shroud members with more flexibility can provide a lower connection force threshold, and shroud members with less flexibility can provide a higher connection force threshold. For example, a threshold force to couple the connectors 100, 200 can be about 0.5 pounds, about 1 pound, about 2 pounds, about 3 pounds, about 4 pounds, about 5 pounds, about 6 pounds, about 7 pounds, about 8 pounds, about 10 pounds, about 12 pounds, or about 15 pounds of force, or any values therebetween, or any ranges between any pair of these values (e.g., between about 2 pounds and about 8 pounds), although other configurations are possible. In some embodiments, the threshold disconnection force can be higher than the threshold connection force. In other configurations, the threshold disconnection force can be lower than the threshold connection force.

The surface 260 and/or the surface 188 can be angled so that a line normal to the surface is offset from a line parallel to the longitudinal axis by an angle of about 20 degrees, about 30 degrees, about 35 degrees, about 40 degrees, about 45 degrees, about 50 degrees, about 55 degrees, about 60 degrees, about 70 degrees, or any values or ranges between these values (e.g., between about 30 degrees and about 60 degrees), although other configurations could be used. In some embodiments, the surface 260 or the surface 188 can be substantially flat or lateral, or can have a normal line that is offset from a line parallel to the longitudinal axis by an angle of about 20 degrees, about 15 degrees, about 10 degrees, about 5 degrees, about 3 degrees, about 2 degrees, about 1 degree, or less, or about 0 degrees, or any values or ranges therebetween, although other configurations can be used. In FIG. 26, for example, the surface 188 and the surface 260 are both angled. In some configurations, the angled surface 260 or 188 can ride along the corner at the end of the flat surface 188 or 260, which can reduce friction between as compared to the surfaces 260 and 188 being flush against each other.

The adapter 250 can have a tip between the surface 258 and the surface 260. The tip can be the laterally outermost part of the adapter 250. The tip can be a hard angle, can be rounded, or can be somewhat flattened. When the connectors 100, 200 are coupled the tip of the adapter can be disposed in the gap 184 (e.g., the circumferential portion of the gap 184).

When the adapter 250 and/or the connector 200 are coupled the first connector 100, the shroud 150 can be impeded from moving to the second position (e.g., the retraced or proximal position). When the shroud is in the second position (e.g., the retracted or proximal position), the second connector 200 and/or the adapter 250 can be impeded from connecting to the first connector 100.

The first connector 100 and the second connector 200 can be configured so that when the connectors 100, 200 are coupled together, a substantially fluid-tight seal can be formed between the connectors. For example, as the adapter 250 moves proximally to engage with the protrusions 178 to mechanically couple the connectors 100, 200, the projection 214 can move proximally to engage the projection 116 to form a seal. The adapter 250 can be positioned on the connector 200 at the appropriate location so that the fluid seal is formed at substantially the same longitudinal position as the mechanical coupling between the connectors 100, 200. Specific adapters 250 can be configured for use with specific types of second connectors 200, so that multiple types of connectors can be made compatible with the same first connector 100.

Figure 27:
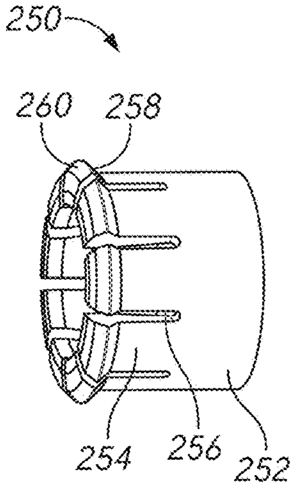
FIG. 27 shows a perspective view of another example embodiment of an adapter.
Figure 28:
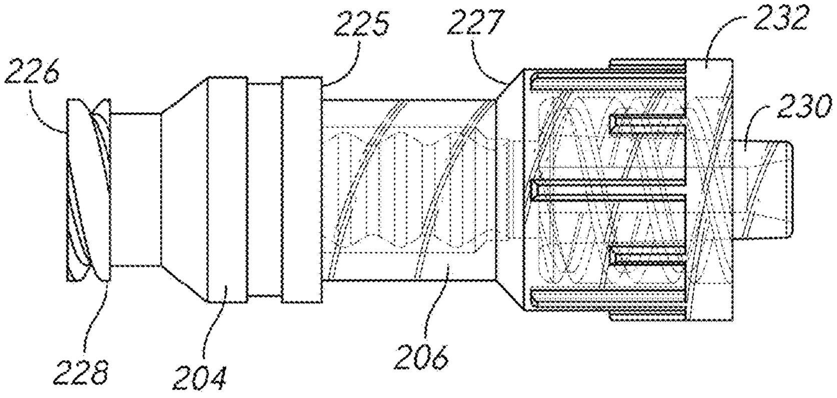
FIG. 28 shows a side view of another example embodiment of a second connector, which can be coupled to the first connector using the adapter.
Figure 29:
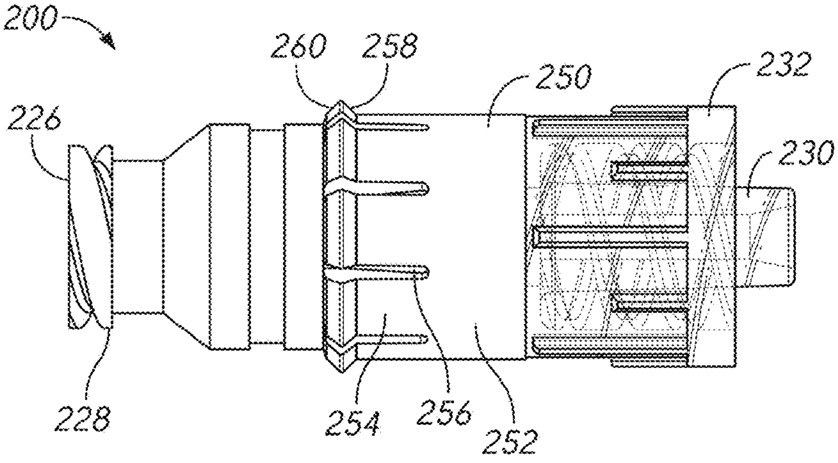
FIG. 29 shows the connector with the adapter coupled thereto.
Figure 30:
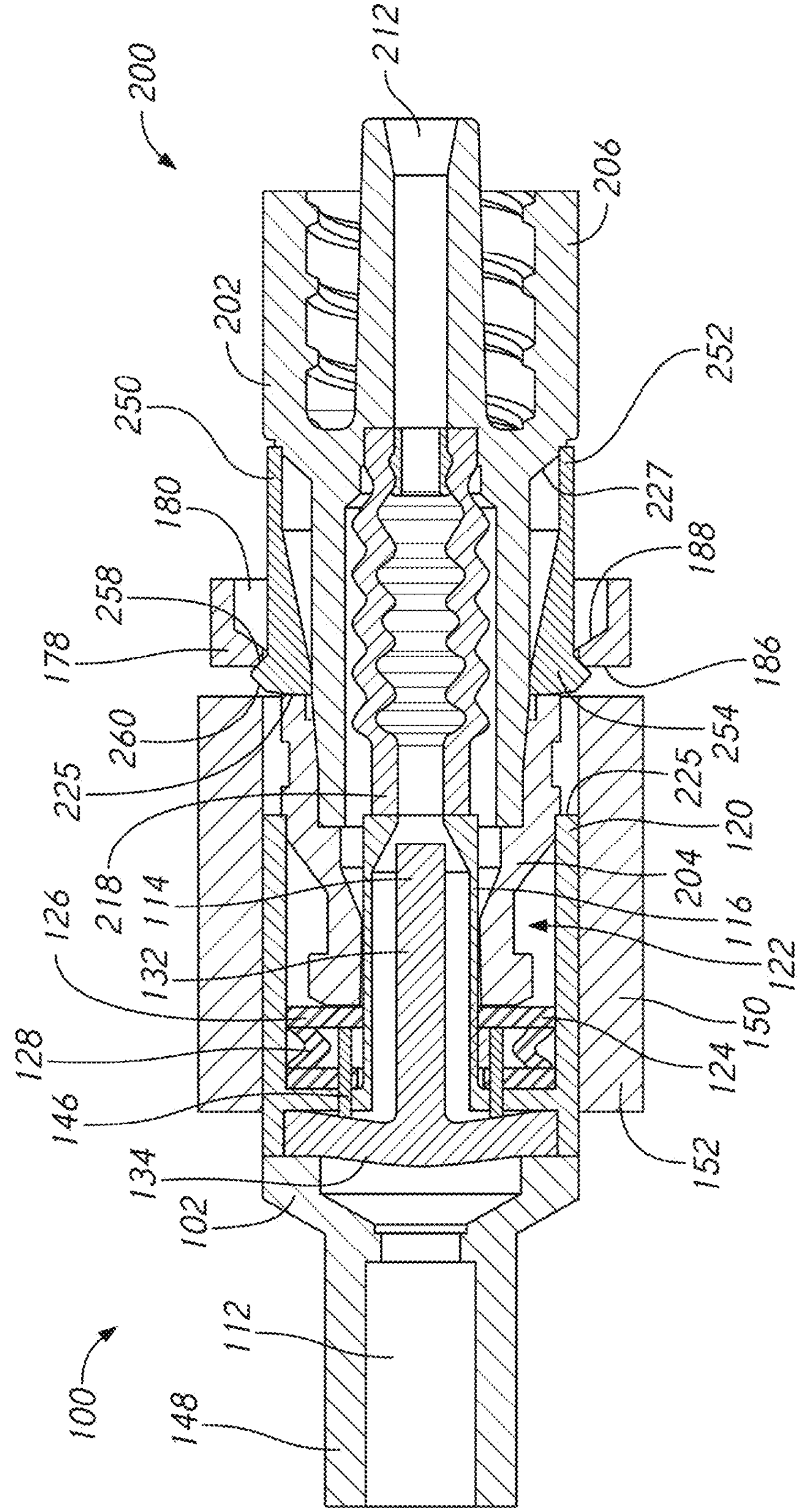
FIG. 30 shows a cross-sectional view of the first connector coupled to the second connector using the adapter.

FIG. 27 shows a perspective view of another example embodiment of an adapter 250. FIG. 28 shows a side view of another example embodiment of a second connector 200, which can be coupled to the first connector 100 using the adapter 250. FIG. 29 shows the connector 200 with the adapter 250 coupled thereto. FIG. 30 shows a cross-sectional view of the first connector 100 coupled to the second connector 200 using the adapter 250. The first connector 100, second connector 200, and adapter 250 can be similar to the other embodiments disclosed herein, except as discussed herein.

As shown in FIG. 27, the adapter 250 can have a body portion 252, and one or more arms 254 extending proximally from the body portion 252, with gaps 256 between the arms 254. The arms can flex laterally outward to permit coupling of the adapter 250 to the second connector 200. The second connector 200 can have a housing 202 with a step 225. The step 225 can be formed by a transition from a first housing portion 204 to a second housing portion 206. The second housing portion 206 is shown semi-transparent in FIGS. 28 and 29. The second housing portion 206 can be inserted into the first housing portion 204 to form the step 225. The housing 202 can include a distal step 227, which can be disposed distally from the step 225. The distal step 227 can be angled or tapered, although a flat step could be used. The adapter 250 can be configured (e.g., sized) so that a proximal end or portion of the adapter 250 abuts against the step 225 and a distal end or portion of the adapter 250 abuts against the step 227 to hold the adapter 250 in place relative to the housing 202 of the connector 200. The adapter 250 can fit snug onto the housing 202, or the adapter 250 can fit onto the housing 202 with little play, for example similar to the discussion of other embodiments.

The adapter 250 can have an angled breakaway surface 258 and an angled connection surface 260, which can be positioned at the proximal end or portion of the adapter 250. The angled breakaway surface(s) 258 and/or the angled connection surface(s) 260 can be disposed on the arms 254. The proximal ends of the arm(s) 254 can have outward protrusions that form the surfaces 258, 260. The surface 258 can provide a breakaway disconnection feature similar to other embodiments discussed herein. The surface 258 can provide a pull-to-disconnect configuration. When sufficient axial force is applied pulling the connectors 100, 200 apart, the surface 258 can displace the protrusions 178 outward so that the adapter 250 can pass by the protrusions 178 so that the second connector 200 disconnects from the first connector 100. The surface 260 can provide a push-to-connect feature. When sufficient axial force is applied pushing the connectors 100, 200 together, the surface 260 can displace the protrusions 178 outward so that the protrusions on the adapter 250 can pass by the protrusions 178 on the shroud 150 of the connector 100.

The first connector 100 can include posts 146, which can function similar to the embodiments of FIGS. 8 and 9. When the second connector 200 is inserted into the cavity 122, the posts 146 can be displaced proximally, which can displace at least a portion of the flange 134 proximally, which can pull the shaft 132 proximally, which can open the valve 114 to permit fluid flow into or out of the connector 100. In some embodiments, the shaft 132 can be rigid (e.g., since the shaft 132 does not need to bend to open the valve 114), although a flexible shaft 132 could be used (e.g., integrally formed with the flexible flange 134). When the second connector 200 enters the cavity 122, the cover 124 can be displaced proximally by the end of the connector 200. In some embodiments, a portion of the cover 124 (e.g., the distal portion or wiper 126) can be between the one or more posts 146 and the second connector 200. The second connector 200 can push the portion of the cover 124 proximally and the portion of the cover 124 can push the one or more posts 146 distally. In some embodiments, the biasing structure 128 can be disposed radially outward of the one or more posts 146. The biasing structure 128 can be disposed adjacent the outer wall 120. Positioning the one or more posts 146 laterally inward of the biasing structure 128 can enable the posts 146 to displace a portion of the flange 134 that is not bound between the housing portions 104, 106, and spaced therefrom. Other configurations are possible. For example, the one or more posts 146 can be positioned outward of the biasing structure 128. The biasing structure 128 can be adjacent to the projection 116.

The connector 200 can have a female luer fitting 226, such as at its proximal end. The interior wall of the female luer fitting 226 can be tapered, such as according to a standard luer taper (e.g., 6%). The female luer fitting 226 can be a female luer lock fitting, which can be configured to engage a male luer lock fitting. The housing 202 can have external threading 228. When the second connector 200 couples the first connector 100, the external threading 228 does not engage the first connector 100. The female luer fitting 226 (e.g., female luer lock fitting) can be bypassed, when coupling the connectors 100, 200. The adapter 250 can enable the second connector 200 to couple to another connector without engagement of the female luer lock fitting 226 and/or without engagement of the threading 228. The adapter 250 can convert the second connector 200 from twist-to-connect to push-to-connect, for engaging another connector.

The connector 200 can have a male luer fitting 230, such as at its distal end. The external wall of a male luer fitting 230 can be tapered, such as according to a standard luer taper (e.g., 6%). The male luer fitting 230 can be a male luer lock fitting, which can be configured to engage a female luer lock fitting. The housing 202 can have a shroud 232 with internal threading, which can at least partially surround the projection of the male luer fitting 230. Many variations are possible. For example, the female and luer fittings can be switched, or other non-luer fittings can be used.

Figure 32:
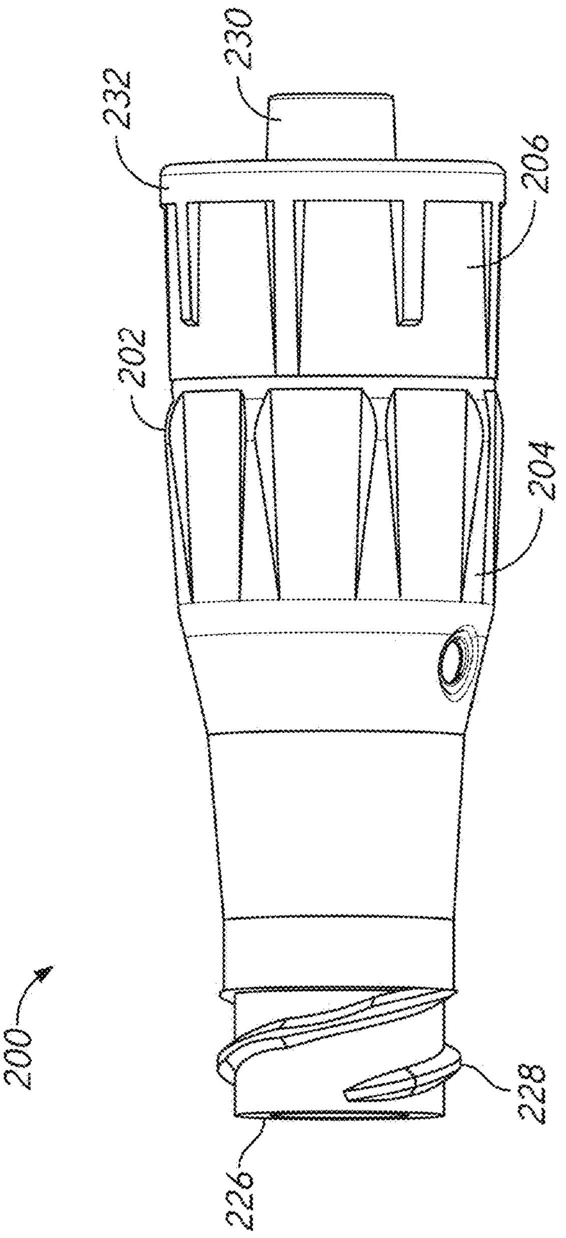
FIG. 32 shows an example connector, which can be compatible with the threaded adapter.
Figure 31:
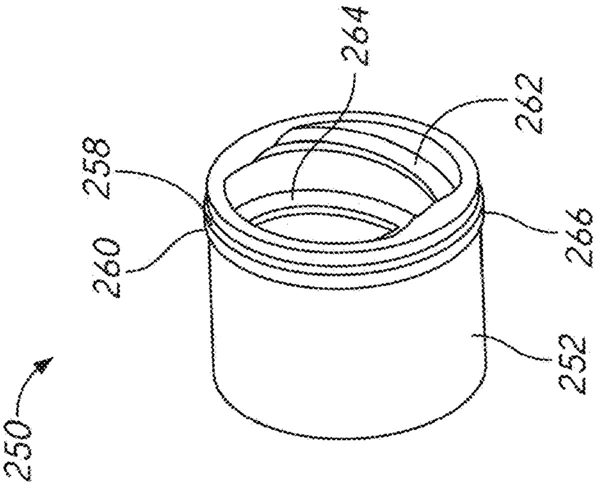
FIG. 31 shows a perspective view of an example embodiment of an adapter.

In some embodiments, the adapter 250 can couple to the second connector 200 without using the threading 228 of the second connector. The adapter 250 can be configured to fit onto a specific shape of connector 200, as discussed herein. In some embodiments, the adapter 250 can be configured to couple to the connector 200 using the threading 228, which can be the external thread(s) of a female luer lock fitting 226. FIG. 31 shows a perspective view of an example embodiment of an adapter 250, which can be configured for threaded engagement with connectors of various different shapes. FIG. 32 shows an example connector 200, which can be compatible with the threaded adapter 250. The threaded adapter 250 can be compatible with the connectors of FIGS. 23 and 28, and various other connectors as well, in some embodiments. The adapter 250 can be configured to engage a standard female luer lock on a connector 200. The adapter can convert the threading to a push-to-connect engagement feature, which can be compatible with the connector 100, as discussed herein.

The adapter 250 can have a body portion 252, which can be generally cylindrical in shape. The body portion 252 can be annular with an opening through the middle. The adapter 250 can have threading 262, such as one or more internal threads, which can be configured to engage the external threading 228 on the connector 200. The adapter 250 can have a stop 264, such as a step or ledge inside the body portion 252. When the adapter 250 is threaded on to the connector 200, the stop 264 can limit further threading of the adapter 250 onto the connector 200. For example, the proximal end of the housing 202 can abut against the ledge or step inside the adapter. The stop 264 can position the adapter 250 at a specific axial position on the connector 200, which position can facilitate sealing engagement with the first connector 100, such as when the first connector 100 and second connector 200 (e.g., and adapter 250) are pressed together, as discussed herein.

The adapter 250 can have one or more engagement features for providing a breakaway connection with the first connector 100, as discussed herein. The adapter 250 can have at least one protrusion 266, such as a ridge or tabs. The protrusion(s) 266 can have a proximal side or connection surface 260, which can be used to displace one or more features on the first connector 100 during the connecting of the adapter 250 (e.g., and the second connector 200) to the first connector 100. The surface 260 can be flat or angled, as discussed herein (e.g., depending on whether the surface 188 is angled or flat). The protrusion(s) 266 can have a distal side or disconnection surface 258, which can be used to displace one or more features on the first connector 100 during the breakaway disconnecting of the adapter 250 (e.g., and the second connector 200) from the first connector 100. The surface 258 can be flat or angled, as discussed herein (e.g., depending on whether the surface 186 is angled or flat).

The threaded adapter 250 can be compatible with a connector 200 that does not include the protrusion 224 or step 225. The connector 200 of FIG. 32 can be similar to the connector of FIG. 23, for example, except that the protrusion 224 is omitted. In some embodiments, the adapter 250 can add a protrusion 266 to a connector 200 that does not include the protrusion 224 built into the housing, and the protrusion 266 can function similar to the protrusion 224 discussed in connection with other embodiments. For example, the threaded adapter 250 of FIG. 31 can add the protrusion 266, which can be used to couple a second adapter (e.g., the adapter 250 of FIG. 22) to the connector 200. Alternatively, the distal end of the adapter 250 can form a step (e.g., similar to the step 225), which can be used to couple a second adapter 250 to the connector 200 (e.g., similar to FIGS. 29 and 30). The arms 254 of the second adapter 250 can snap inward behind the protrusion 266 or step at the distal end of the first adapter 250. This configuration could be beneficial to position the engagement features (e.g., surfaces 258 and/or 260) at a location that is spaced distally from the external threading 228.

Figure 33:
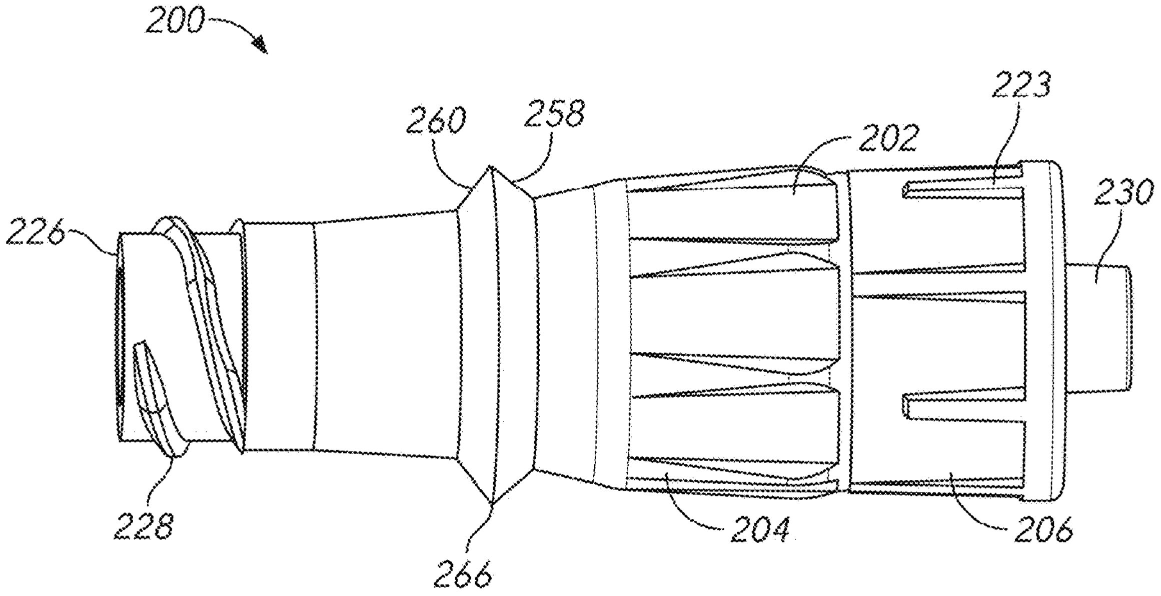
FIG. 33 shows an example embodiment of a connector, which can have the breakaway engagement features built into the housing of the connector.

FIG. 33 shows an example embodiment of a connector 200, which can have the breakaway engagement features built into the housing 202 of the connector 200. The connector 200 can have the push-to-connect and/or pull-to-disconnect features built into the housing 202. The housing 202 can have at least one protrusion 266 (e.g., a ridge or tabs), which can extend laterally outward from the exterior of the housing 202. The protrusion 266 can have a proximal side or connection surface 260, which can facilitate connection to the first connector 100, as discussed herein, such as by displacing a protrusion 178 on the connector 100. The surface 260 can be flat or angled, as discussed herein (e.g., depending on whether the surface 188 is angled or flat). The angle(s) used for the surface 260 and/or the surface 188 can at least partially define the connection threshold force. The protrusion 266 can have a distal side or disconnection surface 258, which can facilitate disconnection of the connector 200 from the connector 100, such as when sufficient force pulls the connectors 100, 200 apart, as discussed herein. The surface 258 can be flat or angled, as discussed herein (e.g., depending on whether the surface 186 is angled or flat). The angle(s) used for the surface 258 and/or the surface 186 can at least partially define the breakaway threshold force.

Figure 34:
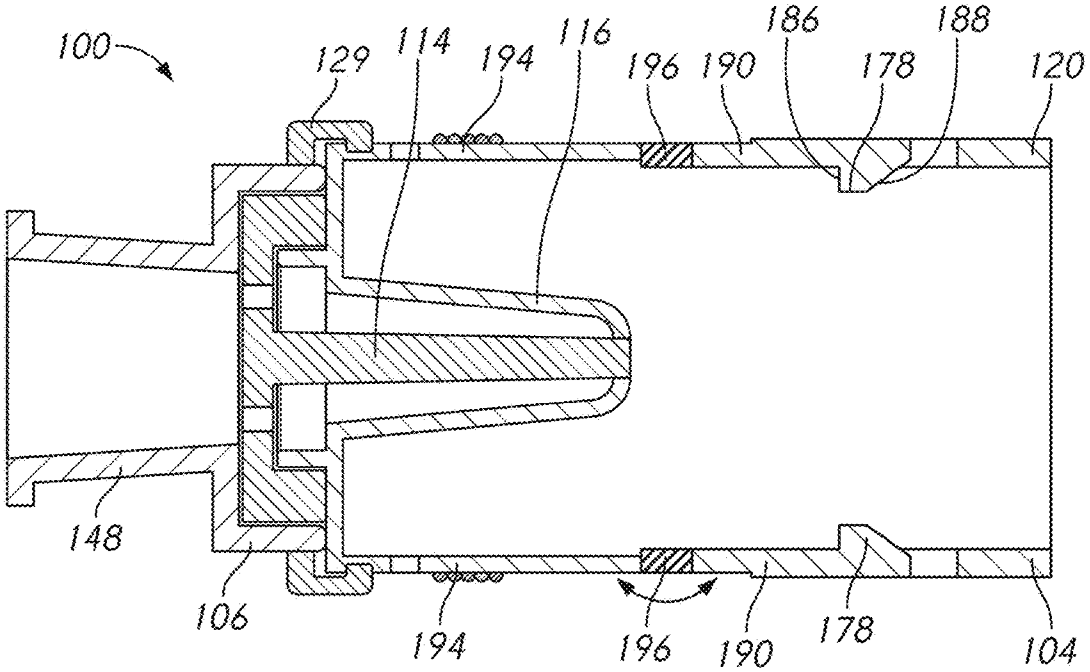
FIG. 34 shows an example embodiment of a first connector that can have a manual release mechanism.

FIG. 34 shows an example embodiment of a first connector 100. The connector 100 can have a manual release mechanism, such as one or more clips. The clips can be part of the outer wall 120 of the housing 102, in some embodiments, as shown in FIG. 34. The clips can be part of the shroud 150, in other embodiments. The connector 100 can have one or more protrusions 178 positioned on one or more arms 190. The connector 100 can have one or more tabs 194, which can be manipulated (e.g., pressed inward) to displace the corresponding one or more arms 190 and protrusions 178. A junction 196 can be positioned between the arm 190 and the tab 194. The junction 196 can couple the corresponding arm 190 and tab 194 to the outer wall 120 (or shroud 150, or other portion of the housing 102). The junction 196 can provide a fulcrum or pivot for the corresponding arm 190 and tab 194. When a tab is pressed laterally inward, the corresponding arm 190 can move laterally outward. A gap or opening can surround the arm 190 except where the arm 190 is joined to the junction 196 (e.g., at the proximal end of the arm 190). A gap or opening can surround the tab 194, except where the tab 194 is joined to the junction 196 (e.g., at the distal end of the tab 194).

In some embodiments, the one or more arms 190 can flex outward (e.g., during connection to or disconnection from the second connector 200, as discussed herein). In some embodiments, the arm(s) 190 pivot so that the protrusion(s) 178 are displaced outward (e.g., without substantial flexing of the arm(s) 190). The protrusion(s) 178 can have a first surface 186 (e.g., a proximal surface) which can hold the second connector 200 in engagement with the first connector 100 until a threshold disconnection force is applied pulling the connectors 100, 200 apart. The surface 186 can be flat or angled, as discussed herein. When the threshold disconnection force is applied, protrusion(s) 178 can move laterally outward so that a structure on the second connector 200 (e.g., the surface 258) can move past the protrusion(s) 178, to disconnect the connector 100, 200. When the protrusion(s) 178 are displaced outwardly, the arm(s) 190 and tab(s) 194 can pivot about the junction(s) 196. The arm(s) can pivot outward and the tab(s) can pivot inward. The user can press the tab(s) 194 inward to move the arm(s) 190 and protrusion(s) 178 outward so that the structure on the second connector 200 (e.g., the surface 258) can move past the protrusion(s) 178 to disconnect the connectors 100, 200 even with force below the disconnection threshold amount.

The protrusion(s) 178 can have a second surface 188 (e.g., a distal surface). The surface 188 can be flat or angled, as discussed herein. When a threshold connection force is applied pressing the connectors 100, 200 together, protrusion(s) 178 can move laterally outward so that a structure on the second connector 200 (e.g., the surface 260) can move past the protrusion(s) 178, to connect the connector 100, 200. When the protrusion(s) 178 are displaced outwardly, the arm(s) 190 and tab(s) 194 can pivot about the junction(s) 196. The arm(s) can pivot outward and the tab(s) can pivot inward. The user can press the tab(s) 194 inward to move the arm(s) 190 and protrusion(s) 178 outward so that the structure on the second connector 200 (e.g., the surface 260) can move past the protrusion(s) 178 to connect the connectors 100, 200 even with force below the connection threshold amount.

In some embodiments, the shroud 150 can be omitted from the connector 100, as shown in FIG. 34, for example. The connection features (e.g., the protrusions 178) can be incorporated into the outer wall 120 or other housing 102 portion in other embodiments as well. FIG. 34 shows the first housing portion 104 coupled to the second housing portion 106 using a clamp 129 or snap-fit mechanism, although any suitable coupling structure could be used.

Figure 35:
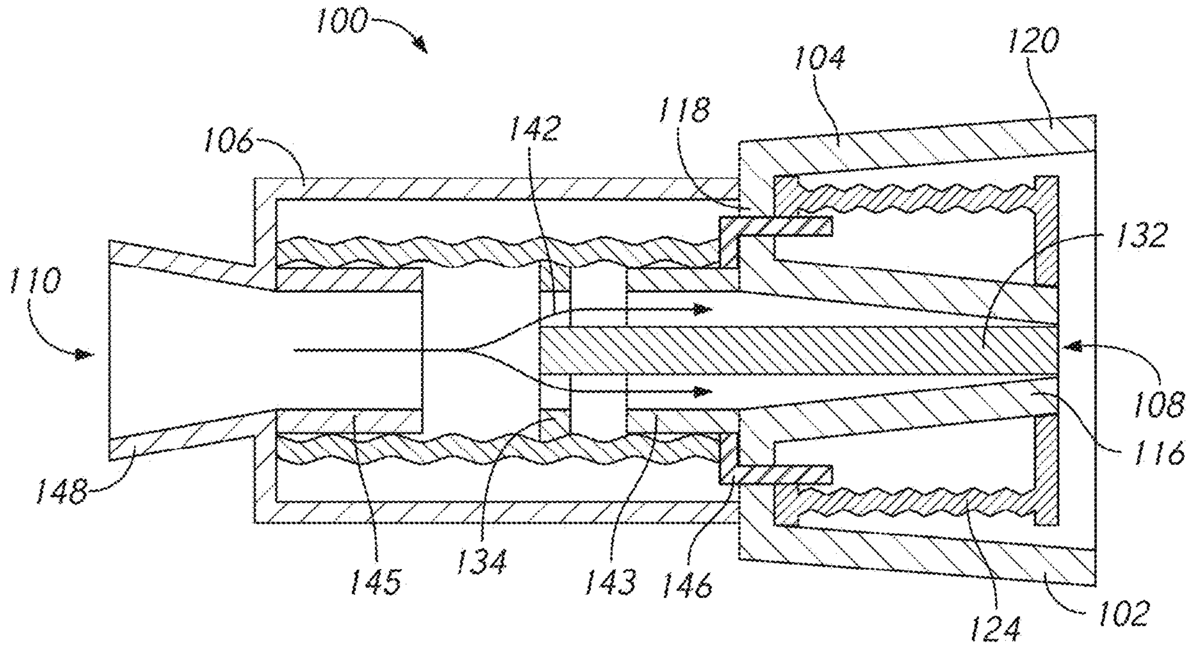
FIG. 35 shows a cross-section view of another example embodiment of a first connector.

FIG. 35 shows a cross-section view of another example embodiment of a first connector 100. The connector 100 can be similar to the other first connector 100 embodiments disclosed herein, except as described herein. The connector 100 can include a collapsible fluid path. The shaft 132 of the valve 114 can be coupled to the collapsible fluid path so that the shaft 132 is pulled to the open position when the fluid path collapses. The post(s) 146 can push or otherwise move the collapsible fluid path to the collapsed configuration, which can open the valve 214. The flange 134 of the valve 214 can be coupled to a flexible sidewall 131. The sidewall 131 can be generally cylindrical in shape. The flange 134 can be coupled to an inside surface of the flexible sidewall 131. A distal portion of the sidewall 131 can extend distally from the flange 134. The distal end or portion of the sidewall 131 can be coupled to the one or more posts 146, such as with an adhesive, clamp, friction fitting, or any other suitable coupling mechanism. The post(s) 146 can have a L-shaped configuration. A longitudinal portion of the post(s) 146 can extend through opening(s) in the base portion 118 of the housing 102. A lateral portion of the post(s) (e.g., at the proximal end) can be coupled to the flexible sidewall 131. A proximal portion of the sidewall 131 can extend proximally from the flange 134. The proximal end or portion of the sidewall 131 can be coupled to the housing 102 (e.g., to a proximal housing portion 106), such as near the proximal connection fitting 148, by an adhesive, clamp, friction fitting, or any other suitable coupling mechanism. In some embodiments, the sidewall 131 can be integrally formed with the shaft 132 and flange 134 of the valve 114. The sidewall 131 can be made of silicone, or some other elastomeric or resilient material. The flange 134 can include one or more openings 142, so that fluid can pass through the flange 134. A lumen 143 can extend proximally into the distal portion of the sidewall 131. The lumen 143 can extend proximally from the base portion 118 of the housing 102, for example. The lumen 143 can provide a guide surface for the sidewall 131 and/or the one or more posts 146. A lumen 145 can extend distally into the proximal portion of the sidewall 131. The lumen 145 can provide a support or guide surface for the sidewall 131. As the sidewall collapses, the lumen 145 and/or the lumen 143 can facilitate the shortening or collapsing of the sidewall 131, while impeding the sidewall from 131 from folding, which could block the fluid path through the sidewall 131. The sidewall 131 can be corrugated or ribbed, which can facilitate the collapse of the sidewall 131 and/or the resilient return of the sidewall 131 to the uncollapsed configuration.

When a second connector 200 is coupled to the first connector 100, the second connector 200 can press the one or more posts 146 proximally, as discussed herein. In some embodiments, the connector 200 can depress the cover 124, and the cover 124 can press the post(s) 146 proximally. When the post(s) 146 move proximally, the longitudinal length of the sidewall 131 can shorten, the flange 134 can move proximally, and/or the shaft 132 of the valve 114 can move proximally, which can open the valve 114 (e.g., at the distal opening 108). In the open configuration, fluid can flow from the proximal opening 110 through the proximal portion of the collapsible fluid path (e.g., formed by the sidewall 131), through the opening(s) 142 in the flange 134, through the distal portion of the collapsible fluid path (e.g., formed by the sidewall 131), through the projection 116, and out the distal opening 108. Fluid can flow in the opposite direction, in some implementations. Upon disconnection of the connectors 100, 200, the sidewall 131 can return to its original or uncollapsed configuration. The shaft 132 of the valve 114 can move distally to the closed configuration, to close the valve 114. The valve 114 can be actuated without a projection 214 on the second connector 200.

Figure 36:
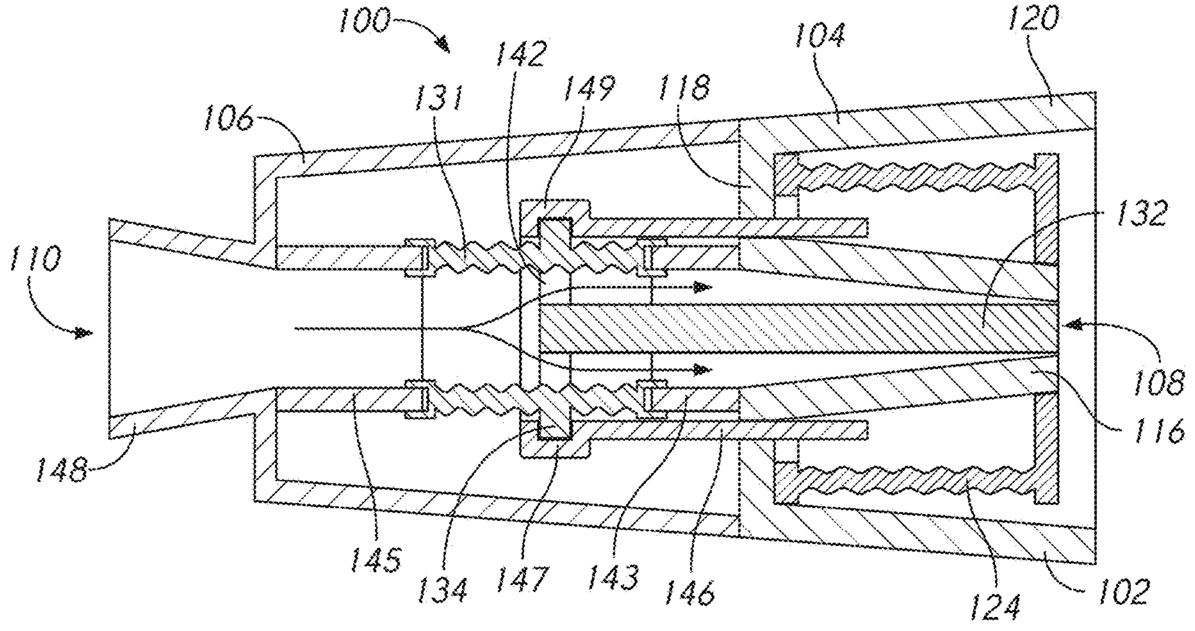
FIG. 36 shows a cross-section view of another example embodiment of a first connector.

FIG. 36 shows a cross-section view of another example embodiment of a first connector 100. The connector 100 of FIG. 36 can be similar to the connector 100 of FIG. 35, or other embodiments disclosed herein, except as described. The distal portion or end of the sidewall 131 can be coupled to a proximal end of the lumen 143, such as by an adhesive, clamp, friction fitting, etc. The proximal portion or end of the sidewall 131 can be coupled to a distal end of the lumen 145, such as by an adhesive, clamp, friction fitting, etc. The one or more posts 146 can be coupled to an exterior of the sidewall 131, such as by an adhesive, clamp, friction fitting, etc. For example, the exterior of the sidewall 131 can have one or more protrusions 147, which can extend laterally outward from the exterior of the sidewall 131. The protrusion(s) 147 can fit into coupling members 149 on the post(s)

146 (e.g., at the proximal ends of the post(s)). The coupling member(s) 149 can have a narrowed neck region, which can engage a narrowed neck region on the protrusion(s) 147, in some configurations. Various other coupling mechanisms could be used. The protrusion(s) 147 and coupling members 149 can be aligned longitudinally with the flange 134, in some configurations. A lateral plane can intersect the flange 134 and the protrusion(s) 147. The protrusion(s) 147 can be constructed as an extension of the flange 134.

When a second connector 200 is coupled to the first connector 100, the second connector 200 can press the one or more posts 146 proximally, as discussed herein. In some embodiments, the connector 200 can depress the cover 124, and the cover 124 can press the post(s) 146 proximally. When the post(s) 146 move proximally, the protrusions 147 on the sidewall 131 and/or the flange 134 can be pushed proximally. A proximal portion of the sidewall 131 can be compressed while distal portion of the sidewall 131 can be stretched, for example. The shaft 132 of the valve 114 can move proximally, which can open the valve 114 (e.g., at the distal opening 108). In the open configuration, fluid can flow from the proximal opening 110 through the proximal portion of the fluid path formed by the sidewall 131, through the opening(s) 142 in the flange 134, through the distal portion of the fluid path formed by the sidewall 131, through the projection 116, and out the distal opening 108. Fluid can flow in the opposite direction, in some implementations. Upon disconnection of the connectors 100, 200, the sidewall 131 can return to its original configuration. The shaft 132 of the valve 114 can move distally to the closed configuration, to close the valve 114.

Figure 37:
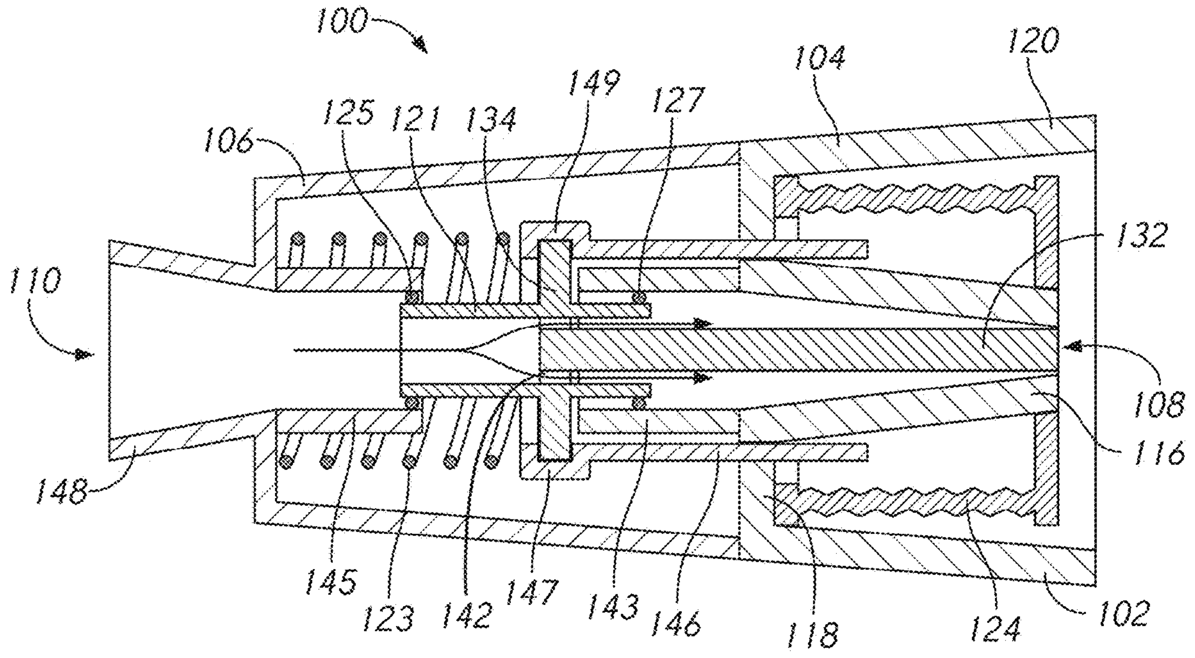
FIG. 37 shows a cross-sectional view of another example embodiment of a first connector.

FIG. 37 shows a cross-sectional view of another example embodiment of a first connector 100, which can be similar to the other embodiments disclosed herein, except as described. The shaft 132 of the valve 114 can be coupled to a movable fluid path so that the shaft 132 is pulled to the open position when the fluid path moves from the first position to a second position. The post(s) 146 can push or otherwise move the fluid path to the second position, which can open the valve 214. A movable sidewall 121 can define the movable fluid path. The sidewall 121 can be generally cylindrical in shape, with an opening through the middle, which can define the movable fluid pathway. The sidewall 121 can be a resilient, flexible, or rigid material. In some embodiments, the sidewall 121 can be integrally formed with the shaft 132 and flange 134 of the valve 114. The flange 134 can be coupled to an inside surface of the sidewall 121. A distal portion of the sidewall 121 can extend distally from the flange 134. A proximal portion of the sidewall 121 can extend proximally from the flange 134. The flange 134 can include one or more openings 142, so that fluid can flow through the flange 134. Protrusion(s) 147 can extend laterally outward from the sidewall 121 and can engage coupling members 149 to couple the sidewall 121 to the posts 146. A biasing mechanism 123 (e.g., a spring) can bias the sidewall 121 to a first or distal position. The biasing mechanism 123 can be a metal coil spring, or an elastomer spring that is compressed upon activation, or an extension spring, or any other suitable biasing structure. The sidewall 121 can be a tube or lumen. The sidewall 121 can be moved proximally to a second or proximal position, which can compress the biasing mechanism 123. The proximal portion of the sidewall 121 can be disposed inside the lumen 145. The proximal portion of the sidewall 121 can include an external O-ring 125 or protrusion, which can seal against the inside of the lumen 145 as the sidewall 121 moves between the first and second positions. The proximal portion of the sidewall 121 could be disposed outside the lumen 145, with an O-ring or protrusion on the inside of the sidewall to seal against the exterior of the lumen 145. The distal portion of the sidewall 121 can be disposed inside the lumen 143. The distal portion of the sidewall 121 can include an external O-ring 127 or protrusion, which can seal against the inside of the lumen 143 as the sidewall 121 moves between the first and second positions. The distal portion of the sidewall 121 could be disposed outside the lumen 143, with an O-ring or protrusion on the inside of the sidewall to seal against the exterior of the lumen 143.

When a second connector 200 is coupled to the first connector 100, the second connector 200 can press the one or more posts 146 proximally, as discussed herein. In some embodiments, the connector 200 can depress the cover 124, and the cover 124 can press the post(s) 146 proximally. When the post(s) 146 move proximally, the sidewall 121 can move from its first or distal position to is second or proximal position. The flange 134 can move with the sidewall 121. The shaft 132 of the valve 114 can move proximally with the sidewall 121, which can open the valve 114 (e.g., at the distal opening 108). In the open configuration, fluid can flow from the proximal opening 110 through the proximal portion of the fluid path formed by the sidewall 111, through the opening(s) 142 in the flange 134, through the distal portion of the fluid path formed by the sidewall 121, through the projection 116, and out the distal opening 108. Fluid can flow in the opposite direction, in some implementations. Upon disconnection of the connectors 100, 200, the biasing mechanism 123 can return the sidewall 121 to the first or distal position. The shaft 132 of the valve 114 can move distally to the closed configuration, to close the valve 114.

Figure 38:
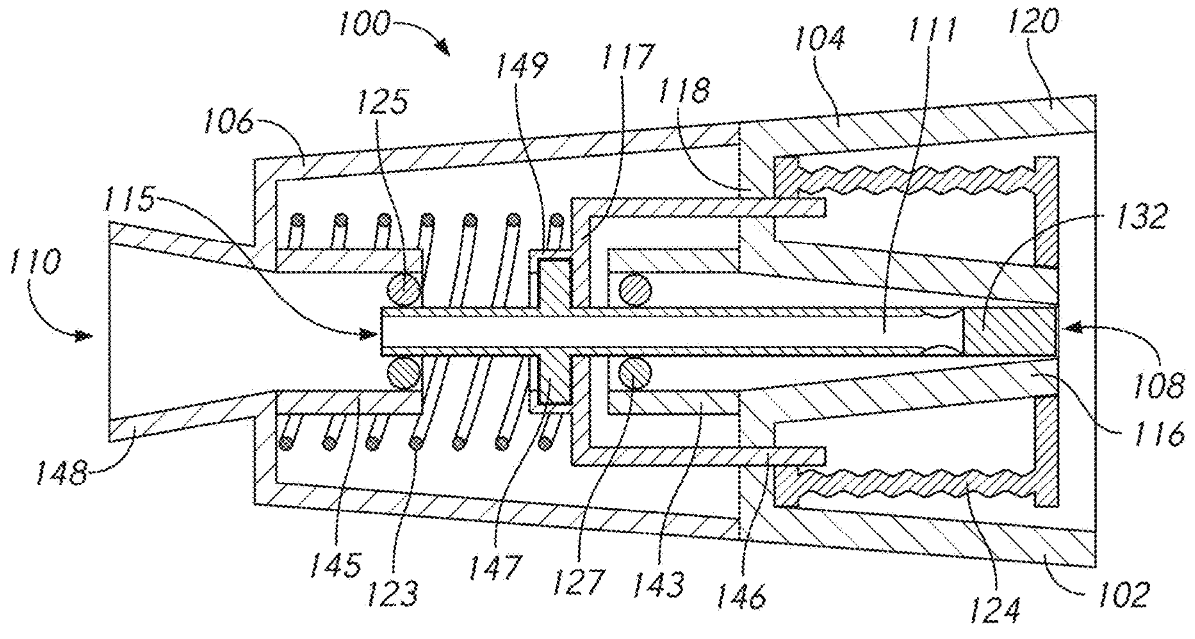
FIG. 38 shows a cross-sectional view of another example embodiment of a first connector.
Figure 39:
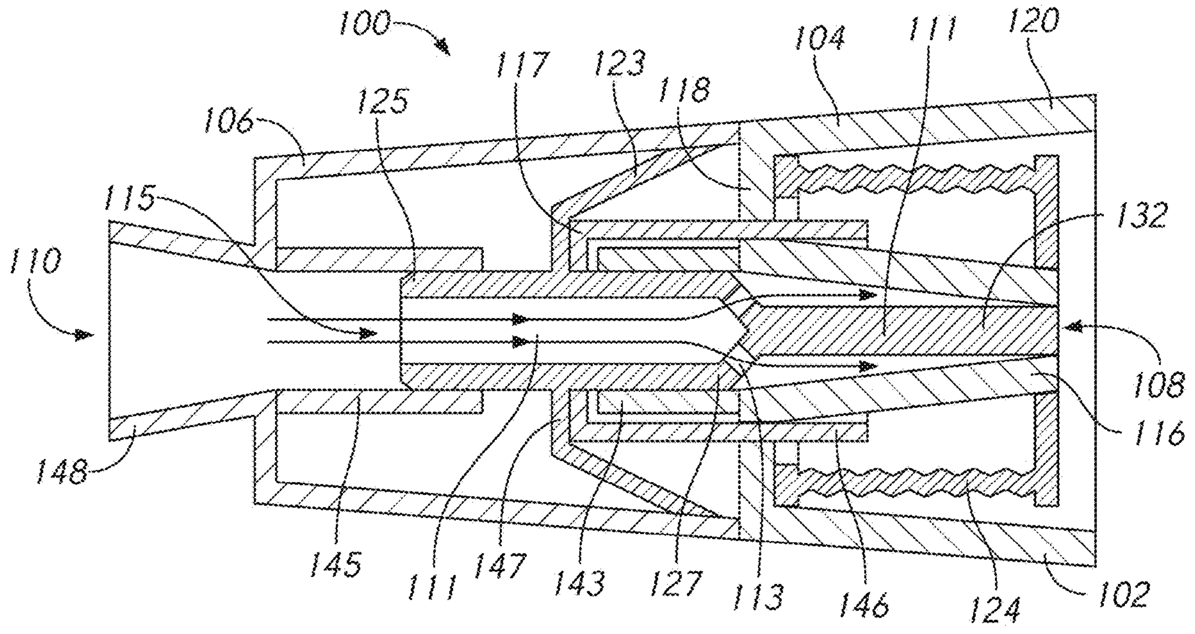
FIG. 39 shows a cross-sectional view of another example embodiment of a first connector.

FIG. 38 shows a cross-sectional view of another example embodiment of a first connector 100, which can be similar to the other embodiments disclosed herein, except as described. At least a portion of the shaft 132 can be hollow. A fluid pathway 111 can extend through at least a portion of the shaft 132. A distal end of the shaft 132 can be closed. The distal end and/or portion of the shaft 132 can close the distal opening 108 when the shaft is in a first position (e.g., a closed or distal position). The shaft 132 can include one or more openings 113 through the side of the shaft 132, which can permit fluid to flow between the fluid pathway 111 inside the shaft 132 and the interior of the projection 116. The shaft 132 can include an opening 115 at the proximal end or portion of the shaft 132. Protrusion(s) 147 can extend laterally outward from an exterior of the shaft 132, and the one or more posts 146 can be coupled to the protrusion(s) 147, such as by coupling members 149, although an adhesive or any other coupling manner could be used to couple the post(s) to the protrusion(s) 147. The protrusion 147 can be a flange, and the coupling member 149 can have a recess to receive the flange, with an opening that is narrower than the flange, so that the flange can snap or fit into the recess and be retained therein. In some embodiments, the post(s) 146 can be integrally formed with the shaft 132. The posts 146 can be coupled so that they move longitudinally together, such as be a flange 117 or other structure. An opening through the flange 117 or other structure can permit the shaft 132 (or the sidewall 121 or 131) to pass therethrough. The proximal portion of the shaft 132 can be disposed inside the lumen 145. The proximal portion of the shaft 132 can include an external O-ring 125 or protrusion, which can seal against the inside of the lumen 145 as the shaft 132 moves between the first and second positions. The distal portion of the shaft 132 can be disposed inside the lumen 143. The distal portion of the shaft 132 can include an external O-ring 127 or protrusion, which can seal against the inside of the lumen 143 as the shaft 132 moves between the first and second positions. The biasing mechanism 123 can bias the shaft 132 to the first position (e.g., the closed or distal position).

When a second connector 200 is coupled to the first connector 100, the second connector 200 can press the one or more posts 146 proximally, as discussed herein. In some embodiments, the connector 200 can depress the cover 124, and the cover 124 can press the post(s) 146 proximally. When the post(s) 146 move proximally, the shaft 132 of the valve 114 can move proximally from a first position (e.g., a closed or distal position) to a second position (e.g., an open or proximal position), which can open the valve 114 (e.g., at the distal opening 108). In the open configuration, fluid can flow from the proximal opening 110 through the opening 115 an into the fluid pathway 111 in the shaft 132, through the shaft 132 and out the openings 113, and out the distal opening 108. Fluid can flow in the opposite direction, in some implementations. Upon disconnection of the connectors 100, 200, the biasing mechanism 123 can return the shaft 132 to the first or distal position, to close the valve 114.

FIG. 38 shows a cross-sectional view of another example embodiment of a first connector 100, which can be similar to the embodiment of FIG. 28, or other embodiments disclosed herein, except as described. The shaft 132 can have a distal portion that does not include the fluid pathway 111 (e.g., that is solid or not hollow), and a proximal portion that includes the fluid pathway 111. The proximal portion of the shaft 132 can be wider than the distal portion of the shaft 132. The shaft 132 can include openings 103 at the transition between the proximal and distal portions of the shaft 132, and the openings can permit fluid to flow into or out of the fluid pathway 111. At least one protrusion 147 can extend outward from the exterior of the shaft 132. The post(s) 146 can push proximally on the protrusion 147 when the post(s) are moved proximally, which can thereby move the shaft 132 to open the valve 114. The biasing member 123 can be an elastomeric extension member that tethers the protrusion 147 and/or the shaft 132 to a portion of the housing 102 that is located distally of the connection to the shaft 132 or protrusion 147. When the shaft 132 is moved proximally, the elastomeric extension member can be stretched to bias the shaft 132 distally (e.g., to the closed configuration). The elastomeric extension member can have one or more elastic arms or an elastic diaphragm, which can be coupled to the housing 102 by an adhesive, clap, friction fitting, etc. In some cases, the end of the elastomeric extension member can be pinched between parts of the proximal housing portion 106 and the distal housing portion 104 (e.g., similar to the flange 134 discussed herein). The elastomeric member can be anchored to the interior of exterior of the connector 100.

Many variations are possible. In some embodiments, the connector 100 of FIGS. 34-39 can have shroud 150, similar to other embodiments disclosed herein. The connectors disclosed herein can utilize various features disclosed in U.S. Pat. No. 9,168,366 (the "'366 Patent"), the entirety of which is incorporated herein by reference. The connectors disclosed herein can utilize various features disclosed in U.S. Pat. No. 9,933,094 (the "'094 Patent"), the entirety of which is incorporated herein by reference. For example, various connector closure mechanisms or valves are disclosed in these references, as well as other features, such as coupling structures, which can be used by the connectors disclosed herein.

The connectors 100, 200 disclosed herein can be used for various fluid transfer actions. For example, fluid can be transferred from an IV bag, through the first connector 100, through the second connector 200, through a catheter, and to a patient (e.g., to the patient's vasculature system). In some implementations, blood or other bodily fluid can be drawn through the second connector 200 and through the first connector 100. In some implementations, fluid can be transferred between a first container and a second container (e.g., without directly involving a patient), such as to fill an IV bag, etc.

Figure 40:
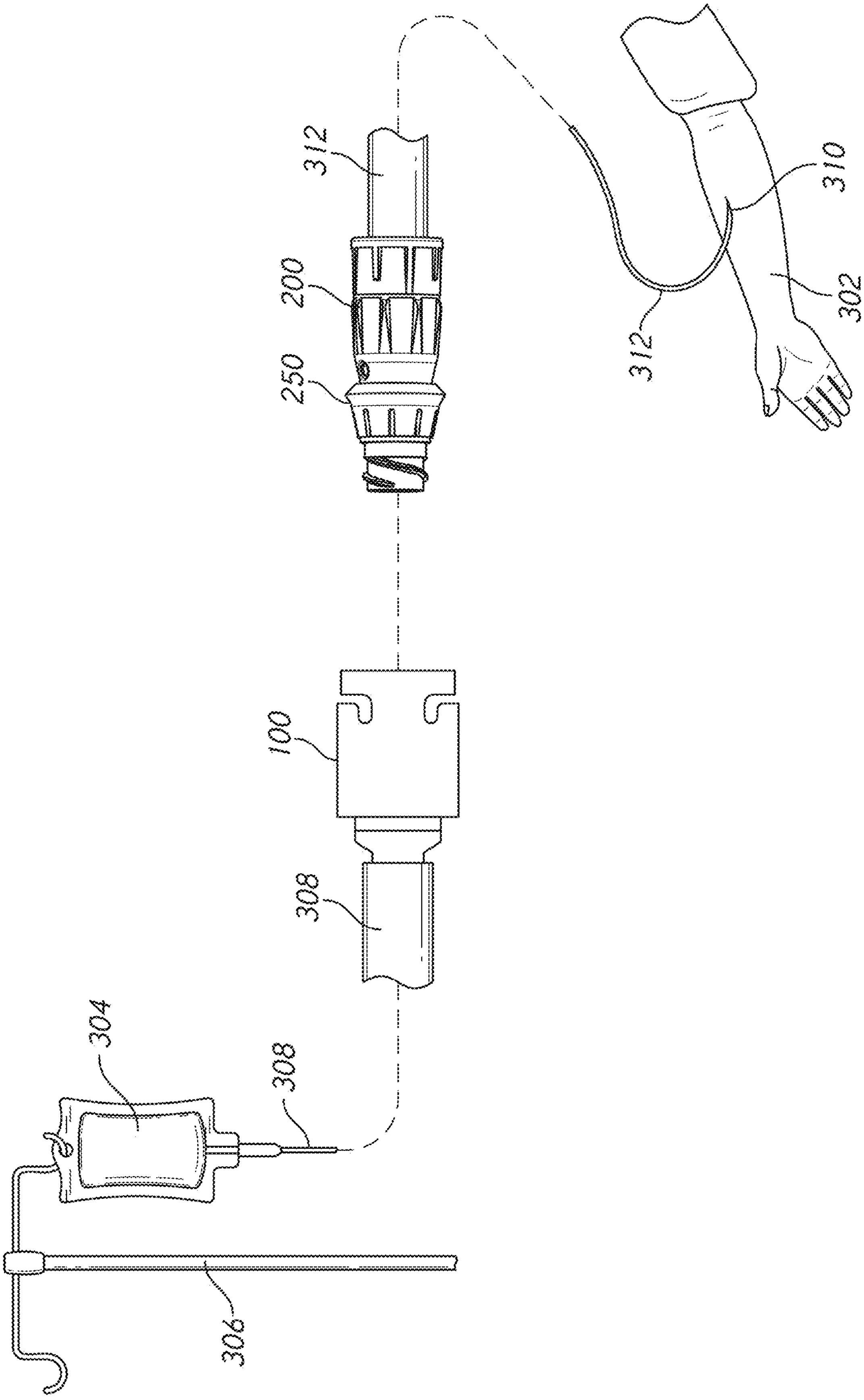
FIG. 40 shows an example embodiment of an IV delivery system, which can be used for fluid communication with a patient.

By way of example, FIG. 40 shows an example embodiment of an IV delivery system, which can be used for fluid communication with a patient 302. A first connector 100 can be attached to an IV bag 304, which can be filled with a medical fluid. The fluid bag 304 can be hanging from a pole stand 306. A section of tubing 308 can be attached at the bottom of the bag 304. The opposite end of the tubing 308 can be connected to the first connector 100 (e.g., to the proximal side thereof). A closure mechanism (e.g., on the distal end) of the luer connector 100 can prevent the fluid contained within the bag 304 from flowing through the tubing 308 and leaking out of the connector 100, as long as the connector 100 remains in the closed configuration. A catheter 310 can be inserted into the arm or other body portion of a patient 302. The catheter can 310 can penetrate the skin of the patient 302 and can be fluidly connected with the patient's bloodstream. The catheter 310 can be connected to a length of tubing 312, which can be attached to a second connector 200 (e.g., a female medical connector). The distal end of the second connector 200 can be connected to the tubing 312. A closure mechanism (e.g., on the proximal end) of the second connector 200 can prevent fluid contained within the tubing 312 from leaking out of the connector 200, as long as the connector 200 remains in the closed configuration. The closure mechanism can also impede contaminants from entering the tubing 312.

The first connector 100 can be brought into engagement with the second connector 200. When the first connector 100 and second connector 200 are engaged, fluid can be permitted to flow from the IV bag 304 into the patient 302. The second connector 200 can include an adapter 250, as discussed herein. The adapter 250 can provide a push-to-connect interface with the first connector 100. A user can press the connectors 100, 200 together axially with sufficient force that the adapter 250 engages with the first connector 100. In some embodiments, the user can retract a shroud 150 on the first connector 100, and the user can swab or otherwise disinfect the connector 100 (e.g., the distal end thereof), and/or the user can swab or otherwise disinfect the second connector 200 (e.g., the proximal end thereof) before connecting the connectors 100, 200.

The connectors 100, 200 can be configured to provide a breakaway connection, which can disconnect the first connector 100 from the second connector 200 when a sufficient axial force is applied that pulls the connectors 100, 200 apart from each other. For example, the patient 302 could be moved away from the IV bag 304 without first disconnecting the connectors 100, 200 (e.g., when transferring hospital beds), or the IV bag 304 (e.g., and the pole stand 306) could be moved away from the patient 302, or a person could trip on the fluid line. Various other situations could apply axial force that pulls on one or both of the connectors 100, 200. The threshold axial force to disconnect the connectors 100, 200 can be lower than the force that would pull out the catheter 310 from the patient 302, and/or can be lower than the force that would knock over the pole stand 306, etc.

When the connectors 100, 200 are disconnected, the closure mechanism of the first connector 100 can close to impede fluid from leaking from the first connector 100 and/or to impede contaminants from entering the fluid line. Upon disconnection, the closure mechanism of the second connector 200 can close to impede fluid from leaking from the second connector 200 and/or to impede contaminants from entering the fluid line. The connectors 100, 200 can be disconnected by axial force without twisting the connectors 100, 200 relative to each other.

In some cases, the first connector 100 can fall on the ground upon unintended disconnection from the connector 200. In some configurations, the fluid line 312 can be shorter than the fluid line 308. When the connectors 100, 200 become disconnected, in some situations, the 200 connector can fall onto the bed with the patient, and the first connector 100 can fall onto the ground, or onto another unsterile surface. The shroud 150 of the first connector 100 can cover the fluid connection portion of the connector 100, to impede the connector 100 for being contaminated upon accidental disconnection. A user can reconnect the connectors 100, 200 after disconnection. In some embodiments, the user can retract a shroud 150 on the first connector 100, and the user can swab or otherwise disinfect the connector 100 (e.g., the distal end thereof), and/or the user can swab or otherwise disinfect the second connector 200 (e.g., the proximal end thereof) before reconnecting the connectors 100, 200.

Figure 41:
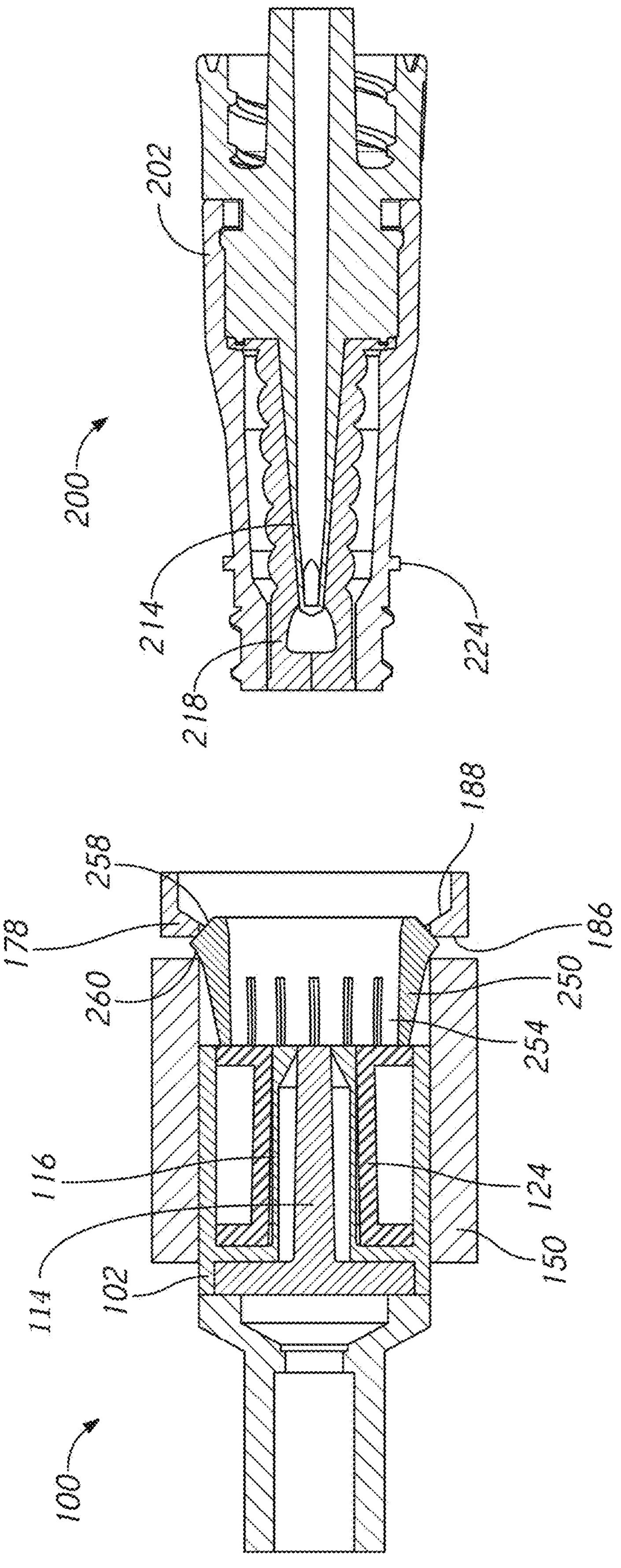
FIG. 41 shows an example embodiment with a first connector and a second connector.

The adapter can be coupled first to either the first connector 100 or the second connector 200. With reference to FIG. 41, in some embodiments, the adapter 250 can be coupled to the first connector 100, without the second connector 200. For example, the adapter 250 can be inserted into the distal end of the connector 100. The surface 258 on the adapter 250 can displace the protrusion(s) 178 outward so that an engagement portion of the adapter 250 can move past the protrusion(s) 178. The protrusion(s) 178 can move inward behind the engagement portion of the adapter 250 to hold the adapter 250 onto the connector 100. The adapter 250 can be coupled to the first connector by a push-to-connect engagement. The second connector 200 can then be coupled to the adapter 250, such as using a second push-to-connect engagement. The connector 200 can be inserted into the adapter 250 so that the arms 254 of the adapter 250 flex outward to let the ridge 224 of the connector 200 move past the arms 254. The arms 254 can move inwardly behind the ridge 224 to hold the connector 200 onto the adapter 250. When axial force is applied to separate the connectors 100, 200, the adapter 250 can detach from the first connector 100 and can remain attached to the second connector 200. Once attached to the second connector 200, the adapter 250 can be substantially permanently coupled thereto. In some embodiments, the adapter 250 does not have a release mechanism for detaching form the second connector 200, once attached thereto. The adapter 250 can be preassembled onto the second connector 200, or onto the first connector 100.

Figure 42:
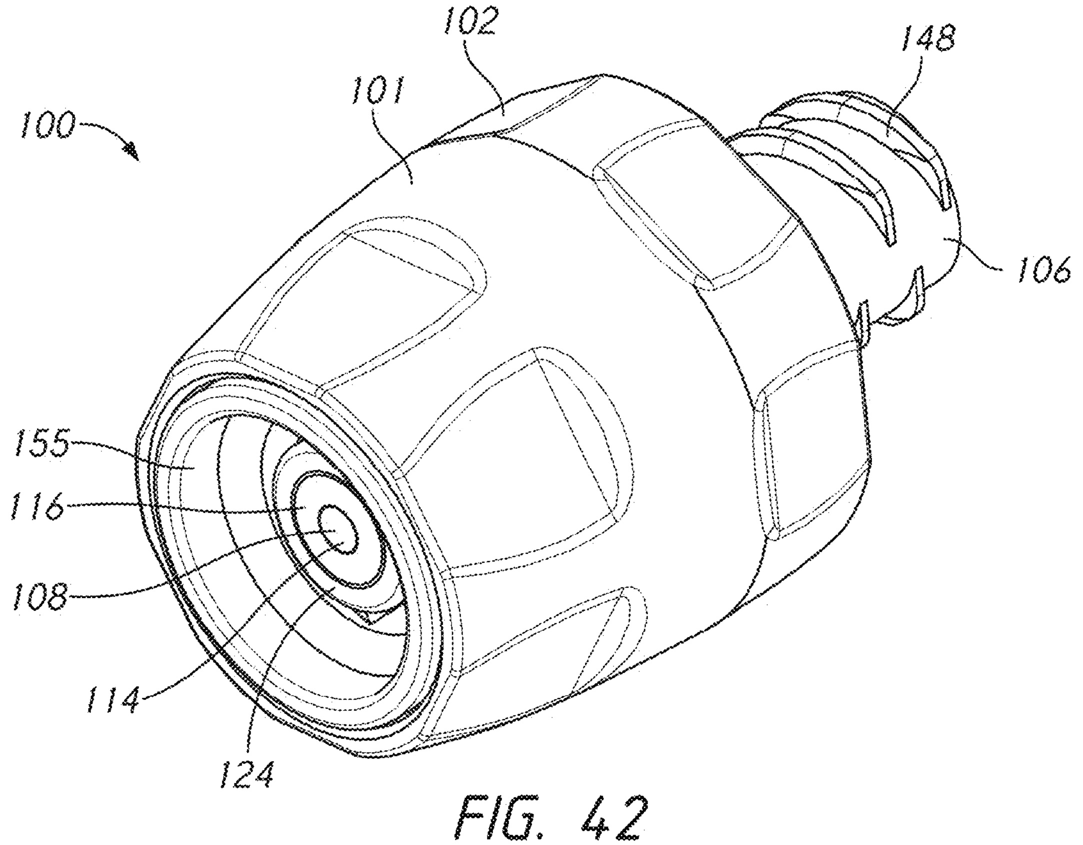
FIG. 42 shows a perspective view of another example embodiment of a first connector.
Figure 43:
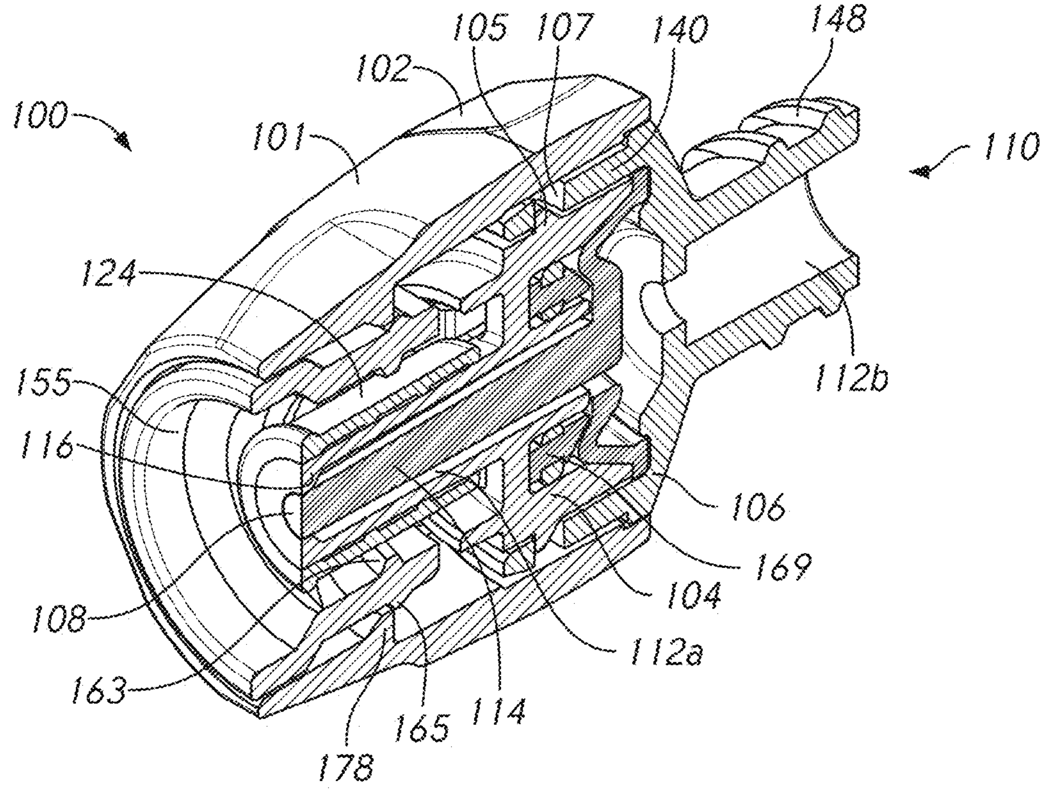
FIG. 43 shows a perspective cross-sectional view of the example first connector of FIG. 42.
Figure 44:
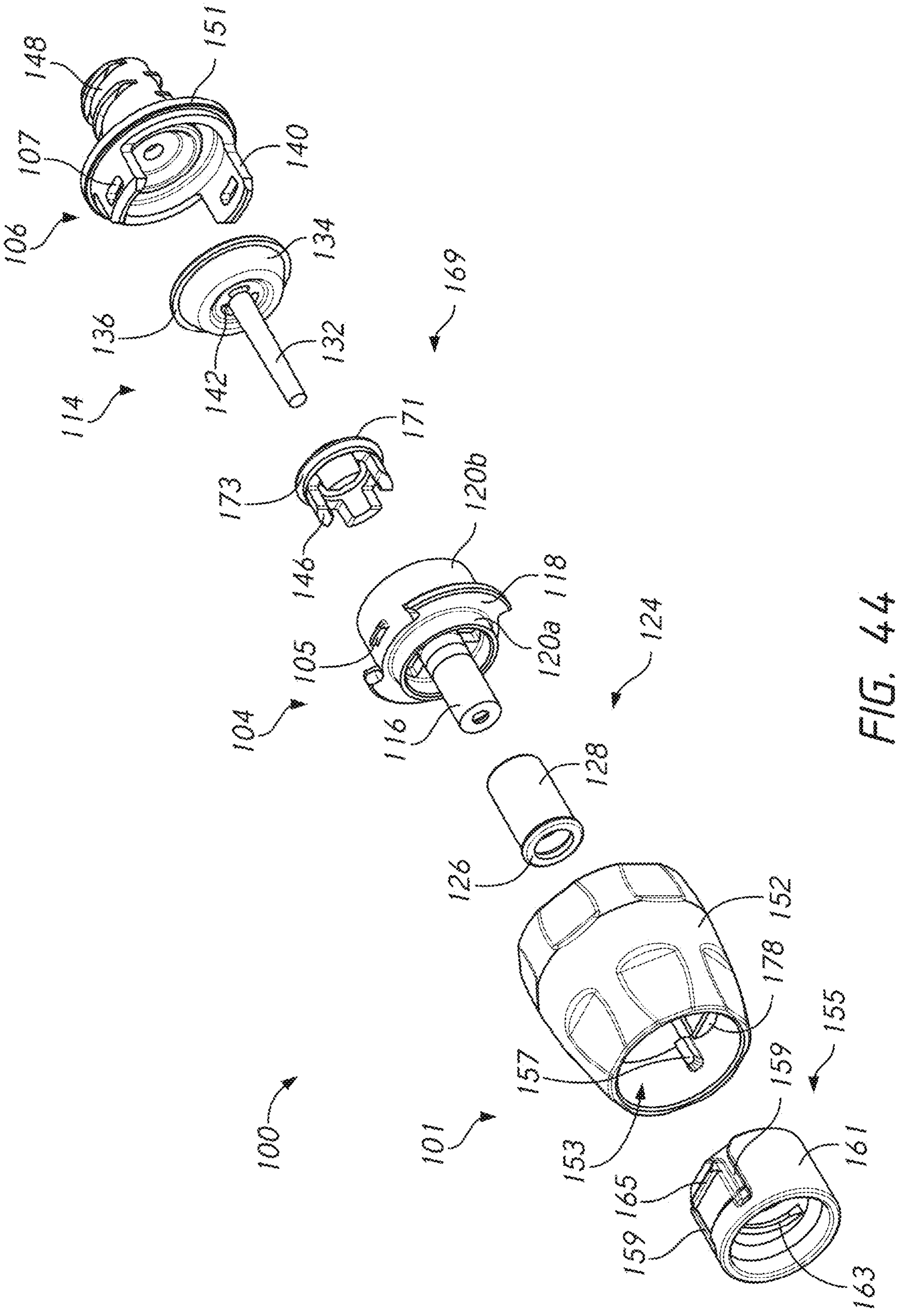
FIG. 44 is an exploded view of the example first connector.
Figure 45:
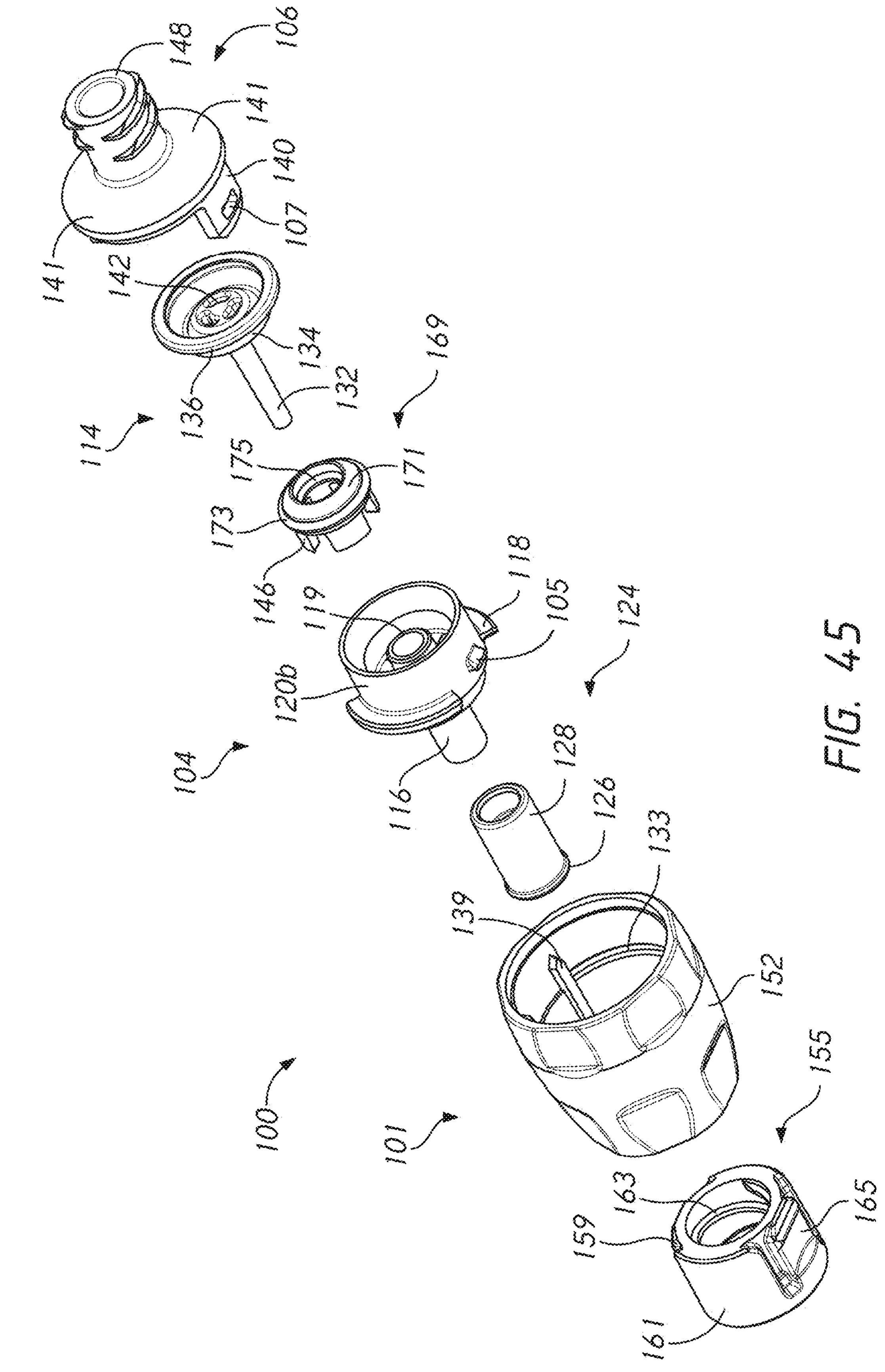
FIG. 45 is another exploded view of the example first connector.

FIG. 42 shows a perspective view of another example embodiment of a first connector 100. FIG. 43 shows a perspective cross-sectional view of the example first connector 100 of FIG. 42. FIG. 44 is an exploded view of the example first connector 100. FIG. 45 is another exploded view of the example first connector 100. The connector 100 can be similar to the other first connector 100 embodiments disclosed herein, except as described herein.

The first connector 100 can have a housing 102. The housing 102 can include a first (e.g., distal) housing portion 104 and a second (e.g., proximal) housing portion 106, which can be coupled together, such as by sonic welding, a threaded engagement, a snap-fit engagement, a friction engagement, adhesive, or any other suitable coupling mechanism. By way of example, first housing portion 104 can have protrusions 105 (e.g., one, two, or more) that are configured to engage corresponding recesses or openings 107 (e.g., one, two, or more) on the second housing portion 106 to provide a snap-fit engagement. In some embodiments, the first housing portion 104 can have the recesses or openings 107 and the second housing portion 106 can have the protrusions 105. Various other engagement mechanisms can be used. The housing 102 can include a third (e.g., outer) housing portion 101, which can at least partially surround the first housing portion 102 and/or the second housing portion 104. The third housing portion 101 is sometimes referred to herein as a shroud 150. The third housing portion 101 can be immovably coupled to the first housing portion 104 and/or the second housing portion 106, such as by sonic welding, a threaded engagement, a snap-fit engagement, a friction engagement, adhesive, or any other suitable coupling mechanism. In some embodiments, the third housing portion 101 can be moveable relative to the first housing portion 104 and/or the second housing portion 106, such as described herein relative to some implementations of the shroud 150, although in other embodiments, the third housing portion 101 does not move relative to the first housing portion 104 and/or the second housing portion 106.

The housing 102 (e.g., the first housing portion 104) can have a first (e.g., distal) opening 108. The housing 102 (e.g., the second housing portion 106) can have a second (e.g., proximal) opening 110. A fluid pathway 112 can connect the first opening 108 to the second opening 110. A first portion 112*a* of the fluid pathway can extend through the first housing portion 104, and a second portion 112*b* of the fluid pathway can extend through the second housing portion 106. The connector 100 can include a valve 114, which can have a closed configuration that closes the fluid pathway 112 and an open configuration that opens the fluid pathway 112, as discussed herein.

Figure 46:
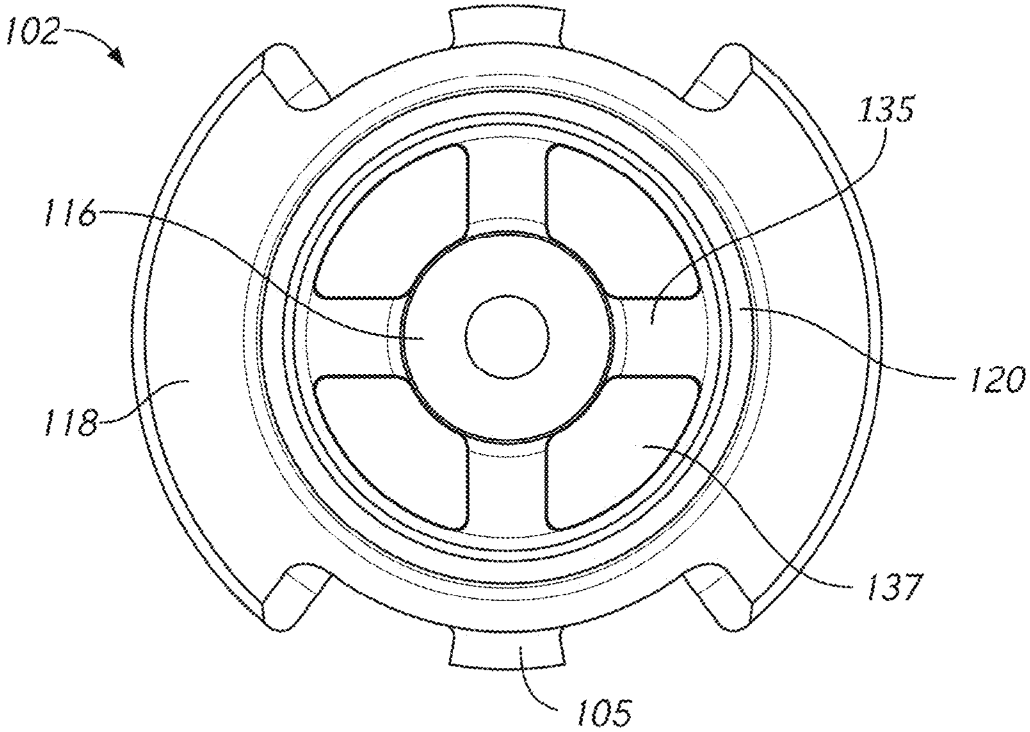
FIG. 46 shows the first housing portion.
Figure 47:
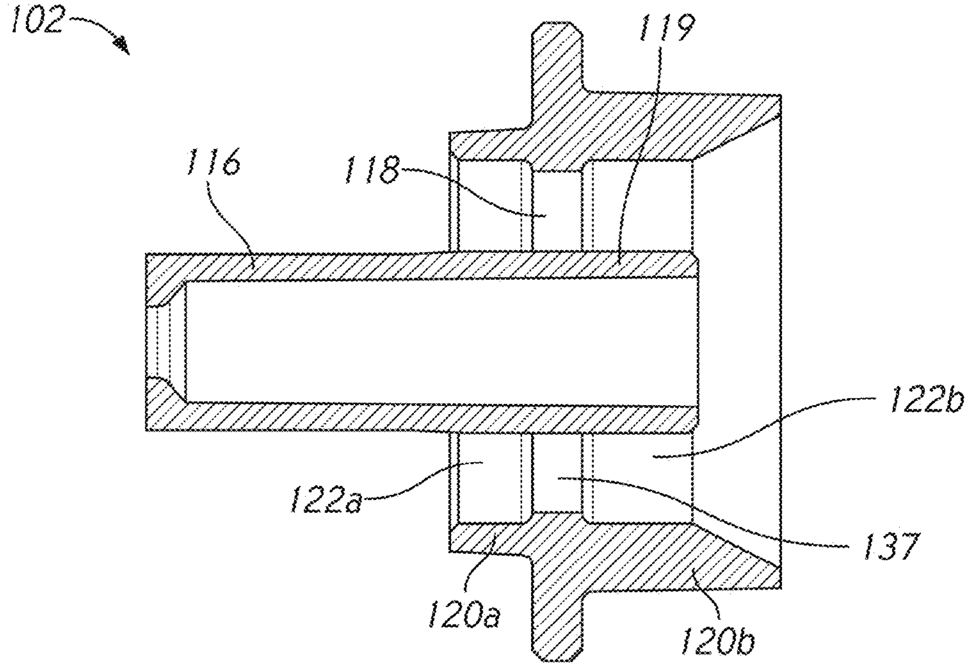
FIG. 47 is a cross-sectional view of the first housing portion.

The first housing portion 104 can be a hub piece, which can interconnect other portions of the connector 100. FIG. 46 shows the first housing portion 104, and FIG. 47 is a cross-sectional view of the first housing portion 104. The first housing portion 104 can have a base portion 118, which can extend laterally, such as a flange. A projection 116 can extend distally from the base portion 118 of the housing 102. The projection 116 can be hollow, and the interior of the projection 116 can form a portion 112*a* of the fluid pathway through the connector 100. The end of the projection 116 can have the first opening 108. The projection 116 can have a generally cylindrical shape. The exterior of the projection 116 can be tapered in the distal direction, such as by about 0.25 degrees, about 0.5 degrees, about 0.75 degrees, about 0.9 degrees, about 1 degree, about 1.1 degrees, about 1.25 degrees, about 1.5 degrees, about 1.75 degrees, about 2 degrees, about 2.5 degrees, about 3 degrees, about 4 degrees, about 5 degrees, or any values or ranges between any of these values (e.g., between about 0.5 degrees and about 1.5 degrees). The taper of the projection 116 can be different (e.g., less) than a standard male luer taper, so that the projection 116 does not function as a standard male luer and does not form a fluid seal with a standard female luer. The interior of the projection 116 can be tapered or sloped inward in the distal direction, such as by the same angles or ranges discussed in connection with the exterior. In some cases, the projection 116 can have a substantially uniform interior diameter and/or a substantially uniform outer diameter or shape, such as without the taper. The distal end of the interior of the projection can have a narrowed or tapered section, such as so that the distal end of the projection 116 can be configured to guide the valve 114 to the closed configuration, in some embodiments. The first housing portion 102 can have a projection 119 that can extend proximally from the base portion 118. The proximal projection 119 can be an extension of the distal projection 116, such as by extending the same shape (e.g., taper) of the interior and/or exterior of the distal projection 116.

The first housing portion 104 can have an outer wall 120, which can have a distal wall portion 120*a* that extends distally from the base portion 118 and/or a proximal wall portion 120*b* that extends proximally from the base portion 118. The distal wall portion 120*a* can be shorter than the projection 116. The projection 116 can extend distally further than the distal wall portion 120*a*. The distal outer wall portion 120*a* can be spaced radially outward from the projection 116 to form a gap or first (e.g., distal) cavity 122*a* therebetween. The proximal outer wall portion 120*b* can be spaced radially outward from the projection 119 to form a gap or second (e.g., proximal) cavity 122*b* therebetween. The base portion 118 can include fingers 135 that extend between the outer wall 120 and the projection 116. The base portion 118 can include one or more openings 137, such as between the finger 135. The distal cavity 122*a* can be connected with the proximal cavity 122*b* through the one or more openings 137. The connector 100 can have four fingers 135 that define four openings 137, although any suitable number can be used (e.g., 1, 2, 3, 4, 5, 6, 8, 10, etc.). The one or more protrusions 105 can be formed on the outer surface of the outer wall 120. In some cases, the base portion 118 can include a flange that extends laterally beyond the side wall 120. The flange can have gaps that can align with corresponding protrusions or ridges 139 on an inside of the third housing portion 101, such as to impede the third housing portion 101 from rotating relative to the first housing portion 101 and/or to facilitate alignment during assembly.

The second housing portion 104 can include a base portion 141. The second housing portion 104 can include a connection fitting 148, which can extend proximally from the base portion 141. The connection fitting 148 can be configured to couple to tubing, some other conduit, or other medical implement, which can be used to transport fluid (e.g., medical fluids). The tubing or other device can be coupled to the connection fitting 148 by a clamp, friction fitting, adhesive, threading, or any other suitable coupling mechanism. In some embodiments, the connection fitting 148 can be configured to couple to an additional connector that is configured to engage the connection fitting 148. For example, the connection fitting 148 can be female luer connection fitting, which can be configured to engage a male luer fitting on an additional connector. The connection fitting 148 can have threading (e.g., external thread(s)) for coupling to another connector, such as for a luer lock engagement). In some configurations, the connector 100 can be added to an existing fluid line and connector to add a breakaway connection feature to the system. The second housing portion 104 can include one or more walls 140, which can extend distally from the base portion 141. The walls 140 can include the recesses or openings 107, or other engagement features, that couple the second housing portion 106 to the first housing portion 104. A flange 151 can extend laterally outward of the one or more walls 140. The proximal end of the third housing portion 101 can engage the flange 151, or other structure, to couple the third housing portion 101 to the second housing portion 106 (e.g., by sonic welding, adhesive, or any other suitable coupler). The second housing portion 106 can form a cap on the proximal side of the connector 100.

The third housing portion 101 can form an outer body portion of the connector 100. The third housing portion 101 can surround the distal end of the first housing portion 104 and can impede contaminants from reaching the first housing portion 104 or other inner components (e.g., the valve 114, the projection 116, the cover 124, etc.). For example, in some instances when the connectors 100, 200 become disconnected, the first connector 100 can fall onto the floor or other non-sterile surface. The third housing portion 101 can tend to contact the floor or other non-sterile surface, thereby insulating the inner components from the contaminants. In some cases, the distal end of the third housing portion 101 can extend distally past the distal end(s) of the first housing portion 104, the valve 114, the projection 116, and/or the cover 124, such as by about 5 mm, about 7 mm, about 10 mm, about 12 mm, about 15 mm, about 17 mm, about 20 mm, about 25 mm, about 30 mm, or any values therebetween, or any ranges between any of these values, although other configurations are possible. The third housing portion 101 can have a generally cylindrical shape, with distal opening 153 at the distal end and/or a proximal opening at the proximal end. The distal opening 153 can be wide enough to enable a practitioner to reach into the connector 100 (e.g., to access the valve 114, the projection 116, the cover 124, etc.) for disinfection, such as by swabbing with alcohol or some other disinfectant. In some cases, after disconnection of the connectors 100, 200, the user can disinfect the connector 100, and recouple the connectors 100, 200. The distal opening can have a diameter or width of about 6 mm, about 7 mm, about 8 mm, about 9 mm, about 10 mm, about 11 mm, about 12 mm, about 13 mm, about 14 mm, about 15 mm, about 16 mm, about 18 mm, about 20 mm, about 22 mm, about 25 mm, or more, or any values or ranges between any of these values, although other configurations are also possible. The interior of the connector 100 from the distal opening 153 to the distal ends of the projection 116, valve 114, and cover 124 (e.g., which can form a substantially flush swabbing surface) can have a diameter or width of about 6 mm, about 7 mm, about 8 mm, about 9 mm, about 10 mm, about 11 mm, about 12 mm, about 13 mm, about 14 mm, about 15 mm, about 16 mm, about 18 mm, about 20 mm, about 22 mm, about 25 mm, or more, or any values or ranges between any of these values, although other configurations are also possible.

The third housing portion 101 can include one or more engagement features 133, which can be a ridge or protrusion, that is configured to engage with one or more corresponding engagement features on the first housing portion 104, such as the outer portions of the base member 118. The third housing portion 101 can be pushed proximally relative to the first housing portion 104 (e.g., which can be attached to the second housing portion 106 already), until the engagement features 133 snap onto, or otherwise move past, the portions of the babe member 118. The third housing portion 101 can include two engagement members, which can be on opposing sides, but any suitable number could be used (e.g., 1, 2, 3, 4, 6, 8, etc.). When the third housing portion 101 is engaged, it can cover the engagement between the engagement features 105 and 107 (e.g., the protrusion and opening), which can impede disengagement of the first and second housing portions 104, 106. The outer wall 152 can impede the walls 140 from flexing outward, which can impede the disengagement of the protrusion 105 from the opening 107. The third housing portion 101 can lock the engagement between the first housing portion 104 and the second housing portion 106.

The connector can be assembled by first attaching the first housing portion 104 to the second housing portion 106, such as by engaging a first snap-fit connection (e.g., between the protrusions 105 and the openings 107). Components such as the valve 114, activation member 169, valve spring 183, etc. can be disposed or captured between the housing portions 104 and 106. Then the third housing portion 101 can be assembled onto the assembly, such as by a second snap-fit connection (e.g., between the structure 133 and the base portion 118). The breakaway member 155 can be attached to the third housing portion 101, such as be a third snap-fit connection, either before or after the third housing portion 101 is coupled to the assembly.

The distal end of the housing (e.g., of the third housing portion) can have a substantially continuous edge, such as without slits, breaks, or gaps. The proximal opening can receive the first housing portion 104 therein during assembly and can engage the flange 151 and/or engagement feature 133 or other structure on the first housing portion 104 and/or second housing portion 106, as discussed herein. The third housing portion 101 can have a generally cylindrical shape. A side wall 152 can define a cavity, which can contain at least a portion of the first housing portion 104 and/or the second housing portion 106. In some embodiments, the side or outer wall 152 of the housing 102 can have no holes or openings that connect the internal cavity to the ambient environment, other than the opening 153. This can impede contaminants and/or debris from entering the connector 100. The opening 153 can a continuous (e.g., annular) shape. The opening 153 can substantially lie on a single plane. The opening 153 and/or the outer wall 152 do not include any slits or other openings to facilitate deformation of the outer wall 152. Rather, deformation of the outer wall 152 (e.g., for the breakaway features) can be provided and tuned based on the material used for the outer wall 152 and/or the thickness and/or the shape of the outer wall 152. [0202]

Figure 48:
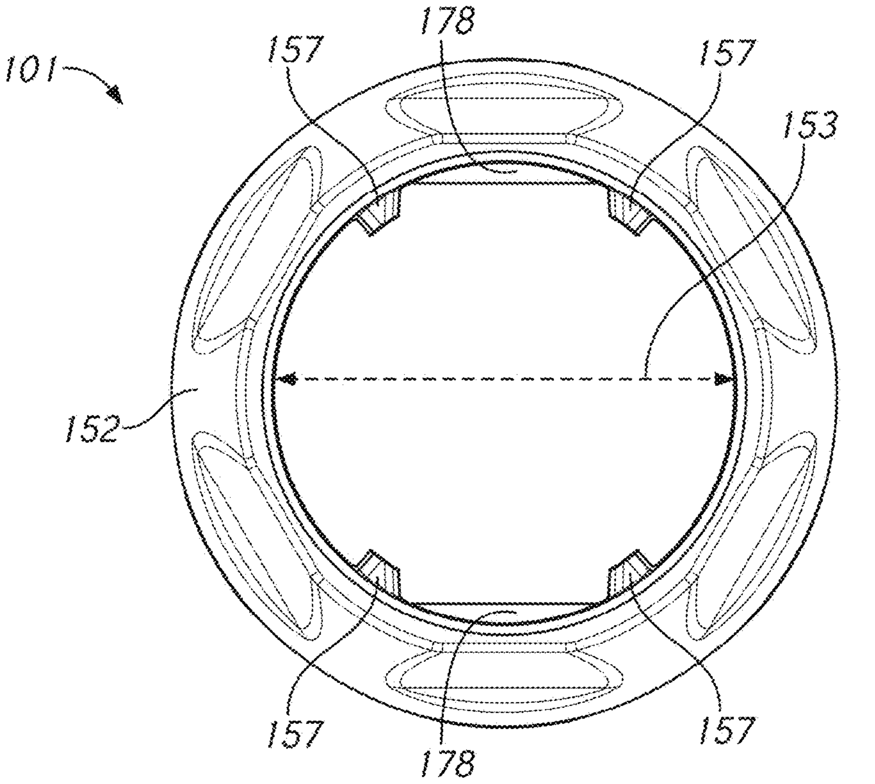
FIG. 48 is a view of the third housing portion from the distal end.
Figure 49:
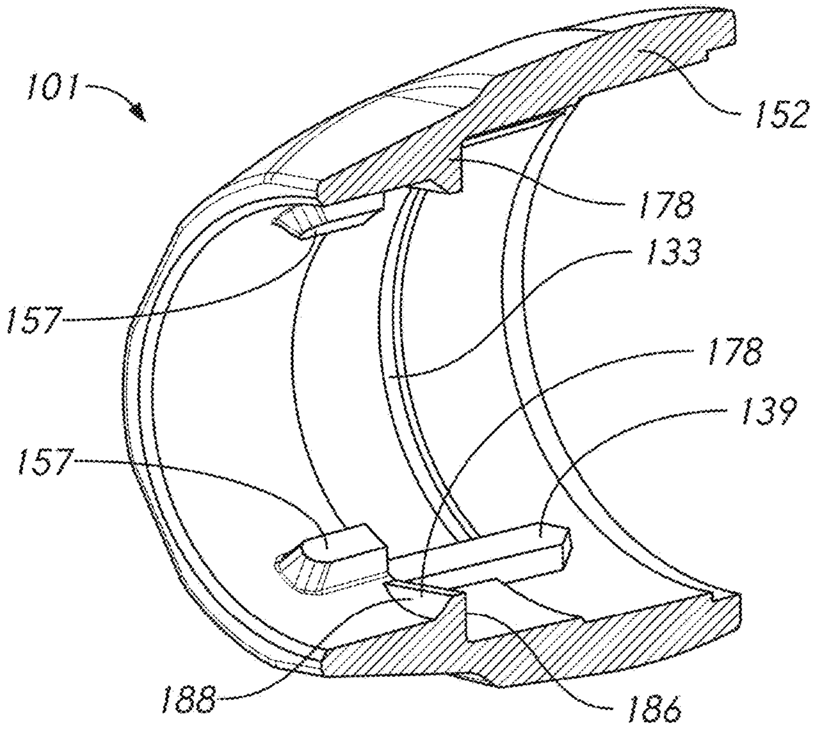
FIG. 49 is a perspective cross-sectional view of the third housing portion.

The third housing portion 101 can include an engagement structure configured to provide a breakaway connection with a breakaway member 155 that can couple to the second connector 200, as discussed herein. The connector 100 can include a breakaway engagement feature configured to couple the first connector 100 to the second connector 200 via the breakaway member 155 in a manner the permits the breakaway member 155 and the connector 200 to decouple from the rest of the first connector 100 when a sufficient force is applied that pulls the connectors 100, 200 apart (e.g., longitudinally). FIG. 48 is a view of the third housing portion 101 from the distal end. FIG. 49 is a perspective cross-sectional view of the third housing portion 101. The third housing portion 101 can have one or more protrusions 178, which can extend laterally inward. In some cases two protrusions 178 can be used, and can be positioned opposite each other, such as offset by about 180 degrees. Other designs are possible, such as three protrusions 178, which can be offset by about 120 degrees, or four protrusions, which can be offset by about 90 degrees, etc. In some cases, a single protrusion 178 can be used for the engagement mechanism. The distance between the protrusions can be less than the diameter of the distal opening 153. The third housing portion 101 can flex or deform when the breakaway engagement features engage, which can produce a removable snap engagement between the third housing portion 101 and the breakaway member 155. The one or more protrusions 178 can engage a corresponding structure on the breakaway member 155 to retain the breakaway member 155 in contact with the third housing portion 101, until a sufficient breakaway force is applied to overcome the engagement. When the connectors 100, 200 are pulled apart, the one or more protrusions 178 can be displaced (e.g., laterally outwardly) to disengage from the corresponding structure(s) on the breakaway member 155, to permit disconnection of the breakaway member 155 and the second connector 200 from the third housing portion 101 (e.g., and the remainder of the connector 100).

The protrusion(s) 178 can have a proximal side 186 and a distal side 188. The proximal side 186 can be flat (e.g., extending laterally). A line normal to the proximal side or surface 186 can extend substantially parallel to the longitudinal axis of the connector, or within about 2 degrees, about 5 degrees, about 10 degrees, or any values or ranges therebetween, although other configurations are possible, such as with different angles which can adjust the breakaway force that disengages the connectors 100, 200. The distal side or surface 188 can be angled. A line normal to the distal side or surface 188 can be angled inwardly by an angle of about 30 degrees, about 40 degrees, 45 degrees, 50 degrees, 60 degrees, or any values therebetween or any ranges between any of these values (e.g., between about 30 and 60 degrees), although other configurations are possible. The breakaway member 155 can form formed and then attached to the third housing portion 101. When the breakaway member 155 is being coupled to the third connector portion 101, a structure on the breakaway member 155 can press proximally on the distal surface 188, and the angled surface can facilitate displacing the protrusion(s) 178 outwardly as the structure slides along the distal surface 188. When the structure on the breakaway member 155 clears the protrusions 178, the protrusions 178 can move inward (e.g., to their unflexed positions), which can couple the breakaway member 155 to the third housing portion 101. The proximal side or surface 186 can abut against a portion of the breakaway member 155 to impede the breakaway member 155 from moving distally away from the connector 100 (e.g., unless sufficient force is applied to implement the breakaway disconnection feature, which can push the protrusions 178 outward to release the breakaway member 155 from the rest of the first connector 100). The third housing portion 101 can include one or protrusions 157, which can engage recesses 159 on the breakaway member 155, as discussed herein. The breakaway member 155 can be formed of polycarbonate, or various other polymers, or any other suitable (e.g., substantially rigid) material.

Various housing configurations can be used. In some cases, two or more housing portions can be combined into a single portion, or portions can be divided into additional housing portions. Features disclosed in connection with a certain housing portion can be considered features of the general housing 102 or of other housing components in different configurations. The housing 102 (e.g., the first housing portion 104, the second housing portion 106, and/or the third housing portion 101) can be made of polycarbonate, or various other polymers, or any other suitable (e.g., substantially rigid) material.

The first connector 100 can include a breakaway member 155, which can be configured to engage a second connector 200 and provide a breakaway connection (e.g., similar to the adapter 250 embodiments disclosed herein). The breakaway member 155 can be part of the first connector 100. When the second connector 200 is coupled to the first connector 100, the second connector can engage the breakaway member 155. If sufficient force is applied, the breakaway member

Figure 50:
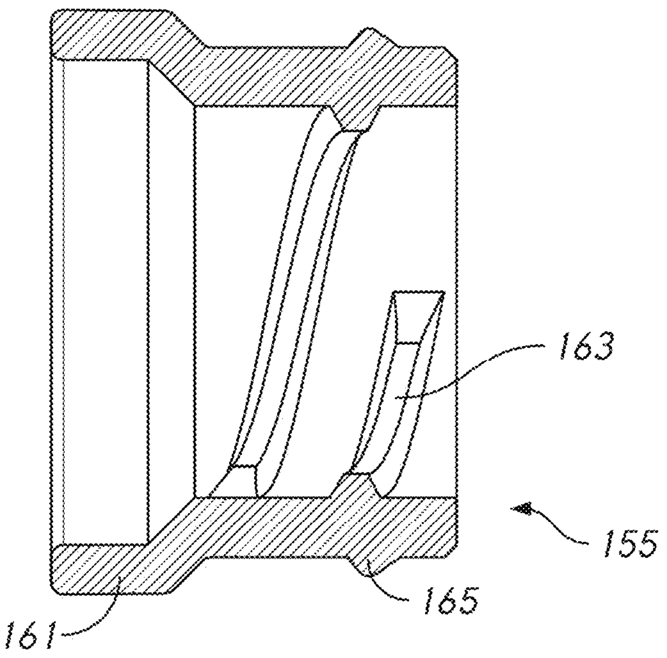
FIG. 50 is a cross-sectional view of the breakaway member.

155 can separate from the rest of the first connector 100 and can stay coupled to the second connector 200 after the breakaway disengagement. The breakaway member 155 can be a collar that encircles a portion of the housing of the second connector 200. FIG. 50 is a cross-sectional view of the breakaway member 155. The breakaway member 155 can have generally cylindrical shape. The breakaway member 155 can have a body portion 161. The body portion 161 can be annular with an opening through the middle. The breakaway member 155 can have threading 163, such as one or more internal threads, which can be configured to engage the external threading 228 on the connector 200. For example, the second connector 200 can have a threaded female luer fitting, such as at its proximal end.

The breakaway member 155 can include an engagement structure that can be configured to provide a breakaway connection to the rest of the first connector 100. The breakaway member 155 (e.g., the body portion 161) can have one or more protrusions 165, which can be configured to engage with the protrusions 178 on the housing 102. The protrusions 165 can be positioned proximally of the protrusions 178, so that the breakaway member 155 does not move distally unless enough force is applied to overcome the engagement of the protrusions 165 with the protrusions 178, such as by deforming one or both of the housing 102 and the breakaway member 155. In some cases two protrusions 165 can be used, and they can be positioned on opposing sides of the breakaway member 155, such as offset by about 180 degrees. Other designs are possible, such as three protrusions 165, which can be offset by about 120 degrees, or four protrusions 165, which can be offset by about 90 degrees, etc.

Figure 52:
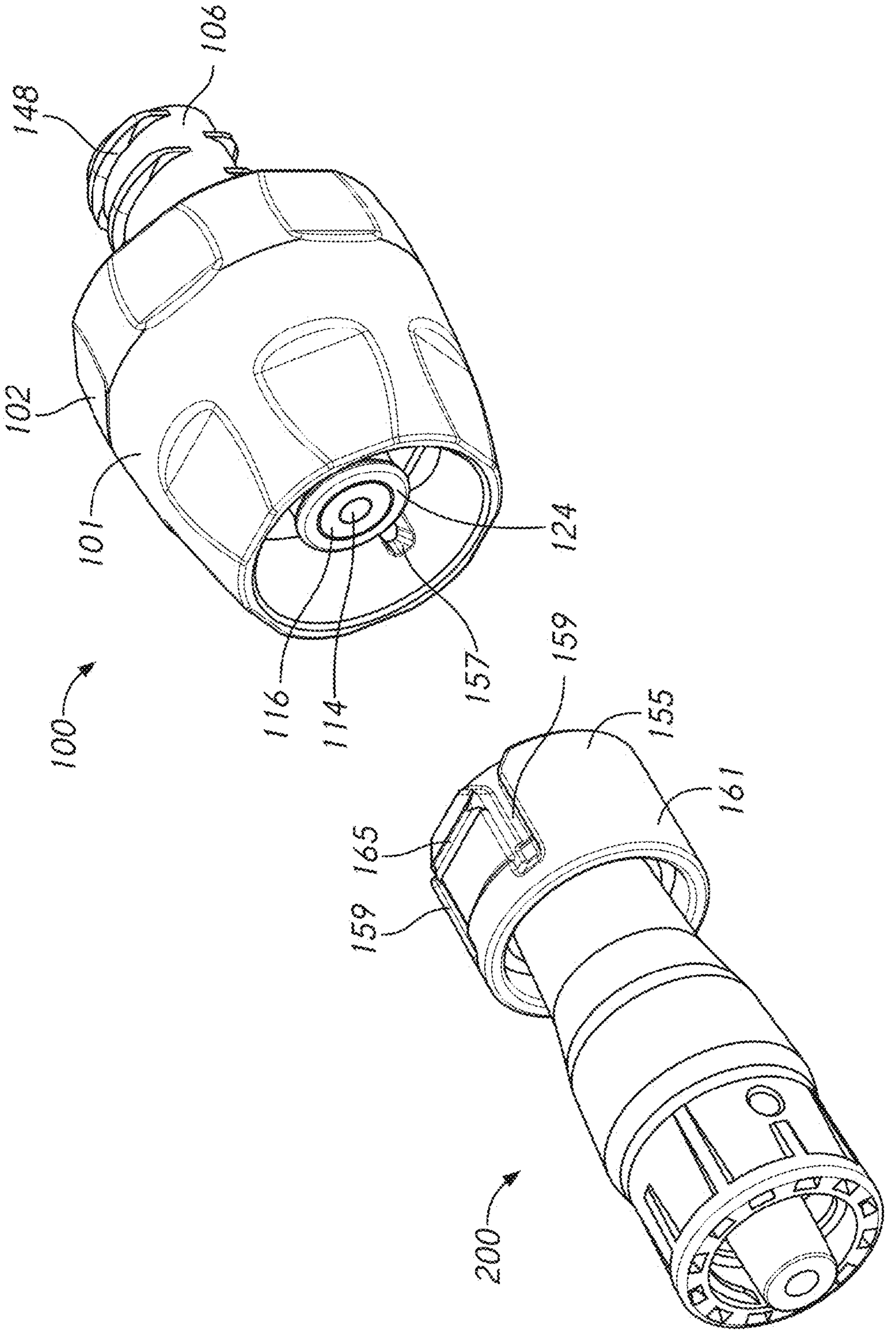
FIG. 52 shows a second connector coupled to the breakaway member, which are disconnected from the remainder of the first connector.

When the first connector 100 is pulled proximally and/or when the second connector 200 is pulled distally with sufficient force while coupled to the breakaway member 155, the breakaway connection can permit the second connector 200 and the breakaway member 155 to disconnect from the first connector 100, similar to the other embodiments disclosed herein. FIG. 52 shows a second connector 200 coupled to the breakaway member 155, which are disconnected from the remainder of the first connector, such as after the breakaway disengagement. The threshold breakaway force can be defined at least by the number, size, and shapes (e.g., surface angles) of the protrusions 165 and/or the protrusions 178, as discussed herein. For example, the breakaway force threshold can be about 0.5 pounds, about 1 pound, about 2 pounds, about 3 pounds, about 4 pounds, about 5 pounds, about 6 pounds, about 7 pounds, about 8 pounds, about 10 pounds, about 12 pounds, or about 15 pounds of force, or any values therebetween, or any ranges between any pair of these values (e.g., between about 2 pounds and about 8 pounds), although other configurations are possible. The one or more protrusions 165 can have an angled distal surface, which can influence the threshold breakaway force, similar to the other embodiments disclosed herein. The one or more protrusions 165 can have an angled proximal surface, which can facilitate assembly of the breakaway member 155 with the rest of the connector 100 and/or to facilitate reengagement of the second connector 200 and the breakaway member 155 with the rest of the first connector 100, such as to reconnect after an unintended disconnection. The surface angles and other disclosure provided herein relating to the adapter embodiments 250 can apply the breakaway member 155.

The connection interface can be configured to connect the breakaway member 155 to the housing 102 when a pushing force above a threshold amount is applied. The threshold force can be defined at least by the surface angles, the size, and the number of protrusions 165 and 178, as discussed herein. For example, a threshold force to couple the engagement member 155 to the housing 102 can be about 0.5 pounds, about 1 pound, about 2 pounds, about 3 pounds, about 4 pounds, about 5 pounds, about 6 pounds, about 7 pounds, about 8 pounds, about 10 pounds, about 12 pounds, or about 15 pounds of force, or any values therebetween, or any ranges between any pair of these values (e.g., between about 2 pounds and about 8 pounds), although other configurations are possible. In some embodiments, the threshold disconnection force can be higher than the threshold connection force. In other configurations, the threshold disconnection force can be lower than the threshold connection force. The surface angles and other disclosure provided herein relating to the adapter embodiments 250 can apply the breakaway member 155.

In some embodiments, the outer wall 152 can be somewhat compliant, such as to enable it to flex or otherwise deform to permit the engagement and/or disengagement of the breakaway engagement features (e.g., the protrusion(s) 178 and the protrusion(s) 165). For example, when the protrusions 165 move past the protrusion 178, the outer wall 152 can flex or deform so that the protrusions 178 can move outward. The substantially circular opening 153, and/or cross-sectional shape of the wall 152 at the location of the protrusions 178, can temporarily flex or deform into an oblong shape, for example. In some embodiments, the outer wall 152 (or the entire third housing portion 101) can be made of a less rigid (e.g., more flexible) material than the first housing portion 104, the second housing portion 106, and/or the breakaway member 155, such as a polyurethane material or a thermoplastic material (e.g., thermoplastic elastomer), or various other polymers or other suitable materials.

Force that causes the disengagement of the breakaway features can be tuned by adjusting any combination of various parameters, such as the material of the side wall 152, the thickness of the side wall 152, the shape of the side wall 152, the size of the opening 153, the number, size, and/or shape of the engagement features (e.g., protrusions 178 and/or protrusions 165), the angles of the engagement surfaces, etc. In some embodiments, the outer wall 152, or third housing portion 101, can be configured so that when 5 Newtons ($kg*m/s^2$) of force is applied to push outward on opposing sides, the opposing sides can displace apart by a distance of about 0.075 mm, about 0.1 mm, about 0.125 mm, about 0.15 mm, about 0.175 mm, about 0.2 mm, about 0.25 mm, about 0.3 mm, about 0.35 mm, about 0.4 mm, about 0.45 mm, about 0.5 mm, about 0.6 mm, about 0.7 mm, about 0.8 mm, about 0.9 mm, about 1 mm, about 1.25 mm, about 1.5 mm, about 1.75 mm, about 2 mm, about 2.5 mm, about 2.75 mm, about 3 mm, about 3.25 mm, about 3.5 mm, about 4 mm, about 4.5 mm, about 5 mm, about 5.5 mm, about 6 mm, or more, or any values or ranges between any of these distances, although other configurations are possible.

The breakaway member 155 can include one or more recesses 159, which can engage one or more corresponding protrusions 157 on the housing 102. Although four recesses 159 and four protrusions 157 are shown, any suitable number can be used (e.g., 1, 2, 3, 4, 5, 6, 8, 10, etc.). The recesses 159 can extend to the proximal end of the breakaway member 155, so that the protrusions 157 can slide into the recesses as the breakaway member 155 is inserted into the housing 102, which can serve to align the breakaway member 155 so that the protrusion 165 aligns to engage with the protrusion 178 on the housing 102. Also, the protrusions 157 and the recesses 159 can impede the breakaway member 155 (e.g., and the second connector 200 once it is coupled thereto) from rotating relative to the housing 102. In some embodiments, the protrusions 157 and recesses 159 can be swapped, or various other alignment and/or securement structures can be used.

Figure 51:
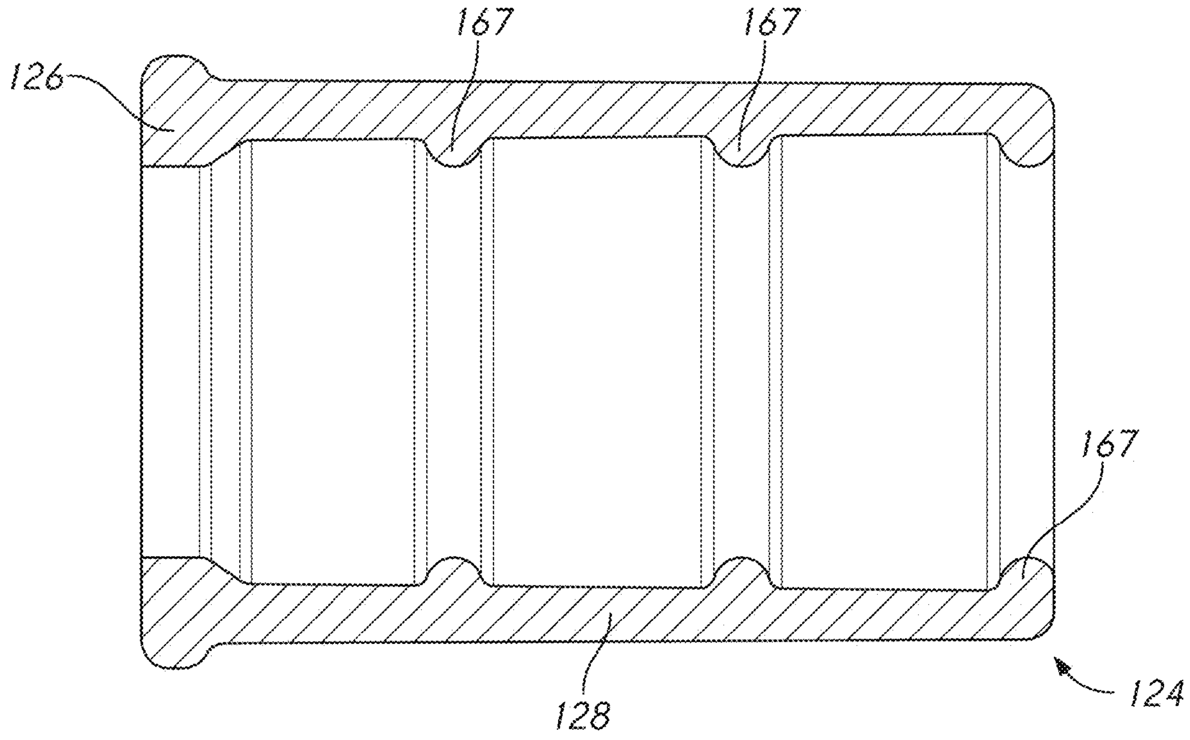
FIG. 51 is a cross-sectional view of the cover.

The first connector 100 can include a cover 124, which can be similar to the covers 124 of other embodiments disclosed herein. In some embodiments, the cover 124 can be a face seal, which can be configured to provide a substantially fluid-tight seal with the second connector 200, such as with the proximal face of the second connector 200, as discussed herein. FIG. 51 is a cross-sectional view of the cover 124. The cover 124 can be disposed around at least a portion of the projection 116. In some embodiments, a portion of the cover 124 (e.g., a proximal end thereof) can be disposed in the cavity 122*a* that is formed between the projection 116 and the outer wall portion 120*a*. In some cases, the proximal end of the cover 124 can be spaced apart from the base portion 118 (e.g., so that the cover 124 does not extend to the base of the projection 116), when the valve 114 is closed (e.g., when the connectors 100 and 200 are disengaged). The cover 124 can be configured to cover a majority of the exterior of the projection 116 when in its default configuration. The cover 124 can be movable between a default configuration and an actuated configuration. When the portion of the second connector 200 is inserted into the cavity formed between the projection 116 and the third housing member 101, the portion of the second connector 200 (e.g., the proximal face thereof) can compress or displace the cover 124 proximally, such as to transition the cover 124 from its default configuration to its actuated configuration. The cover 124 can be biased so that it returns to its default configuration when the second connector 200 is removed or detached from the connector 100.

The cover 124 can have a generally cylindrical shape. The cover 124 can include a narrowed distal portion, which can provide a wiper 126, which can be configured to wipe the exterior of the projection 116 as it moves between the actuated and default configurations. The distal end of the cover 124 can have a lip that extends laterally outward from the body, which can facilitate sealing against the housing of the second connector 102. In some embodiments, the distal end (e.g., the wiper 126) of the cover 124 does not extend laterally outward to a housing portion like in some of the other embodiments. The radially outward side of the cover 124 can be spaced apart from the housing 102, for example forming a cavity between the cover 124 and the outer housing (e.g., the third housing portion 101). The cover 124 can have a biasing structure 128. The biasing structure 128 can be a resilient sleeve that at least partially surrounds the projection 116. The resilient sleeve 128 can buckle, flex, compress, or otherwise deform as the wiper 126 or face seal is displaced proximally. The resilient sleeve 128 can resiliently return to its undeformed shape to return the cover 124 to its default position. As the wiper 126 moves distally, it can wipe the fluid off of the exterior of the projection 116, which can impede microbial growth in the connector 100 or other contaminants. Various biasing structures can be used, such as a coil spring, a compression spring, another type of spring, a resiliently compressible O-ring, etc. The cover 124 can have a plurality of ridges 167 or protrusions on the inside thereof, which can reduce friction as the cover 124 slides along the projection 116. The ridges 167 can contact the projection 116, while intermediate portions of the cover 124 between the ridges 167 can be spaced apart from the projection 116. The cover 124 can be made of silicone or any other suitable elastomeric or resilient material.

Figure 53:
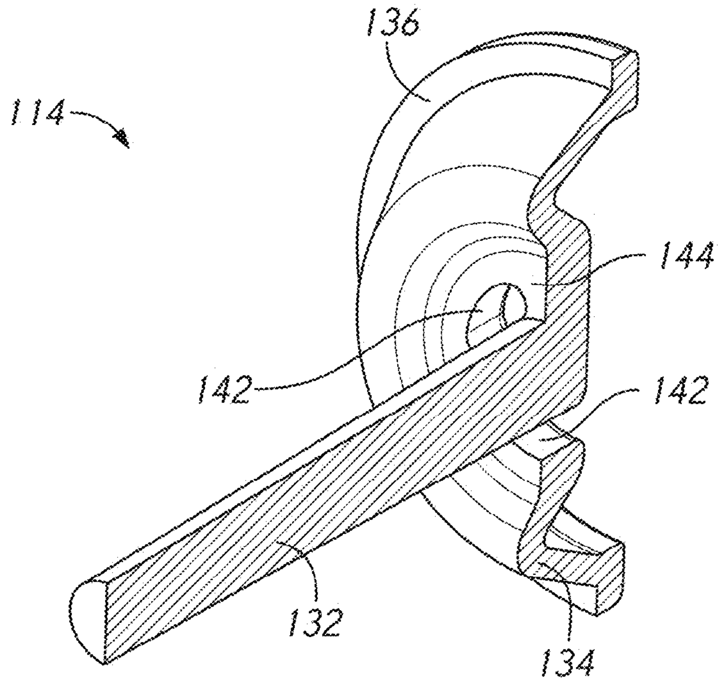
FIG. 53 is a perspective cross-sectional view of the valve.

The first connector 100 can have a valve 114, which can be used to open and close the fluid pathway through the connector 100. FIG. 53 is a perspective cross-sectional view of the valve 114. The valve 114 can have a shaft 132, which can extend axially, and a flange 134, which can extend laterally from a proximal end of the shaft 132. The valve 114 (e.g., the flange 134) can be coupled to the housing 100. The flange 134 can have a coupling portion 136, which can be the radially outer portion of the flange 134. The coupling portion 136 of the flange 134 can be pressed between the first housing portion 104 (e.g., the wall 120*b*) and the second housing portion 106 (e.g., the base 141). The coupling portion 136 of the flange 134 can be compressed between the housing portions, such as to secure the valve 114 to the housing 102.

The flange 134 can have one or more openings 142, which can permit fluid to pass through the flange 134. Although 3 openings are shown, any suitable number of openings can be used (e.g., 1, 2, 3, 4, 6, 8, 12, 16, 20 openings, or any values or ranges therebetween). In some embodiments, the openings are can fluidically couple the first fluid path portion 112*a* to the second fluid path portion 112*b* regardless of whether the valve 114 is open or closed. The openings 142 can be circular in shape or generally wedge shaped. In some cases, one or more spokes 144 can separate the openings 142. The flange 134 portion can provide a resilient force that can bias the valve 114 to the closed configuration. When the valve 114 is opened, the flange 134 can be deformed, and when the connectors 100 and 200 are disconnected, the flange 134 can return to its initial position, which can advance the shaft 132 of the valve 114 distally, so that it can close the distal opening 108. The flange 134 can operate as a diaphragm spring.

The shaft 132 can extend distally from the flange 134, such as along a longitudinal axis of the connector 100. The shaft 132 can be positioned inside the projection 116, such as inside the fluid pathway first portion 112*a*. The shaft 132 can have a diameter or thickness that is smaller than a diameter or width of the fluid pathway first portion 112*a* or hollow inside of the projection 116. The distal end of the fluid pathway first portion 112*a* can narrow to accommodate the distal tip of the shaft 132 so that the shaft 132 can close or seal the fluid pathway 112 (e.g., at the distal opening 108) when in the closed (e.g., default or undeformed) configuration. The narrowed distal end of the fluid pathway first portion 112*a* can have substantially the same diameter or width as the diameter or thickness of the distal tip of the shaft 132. The shaft 132 (e.g., at least the distal tip thereof) can be displaced proximally when the second connector 200 is coupled to the connector 100, which can open the distal opening 108, as discussed herein.

Figure 54:
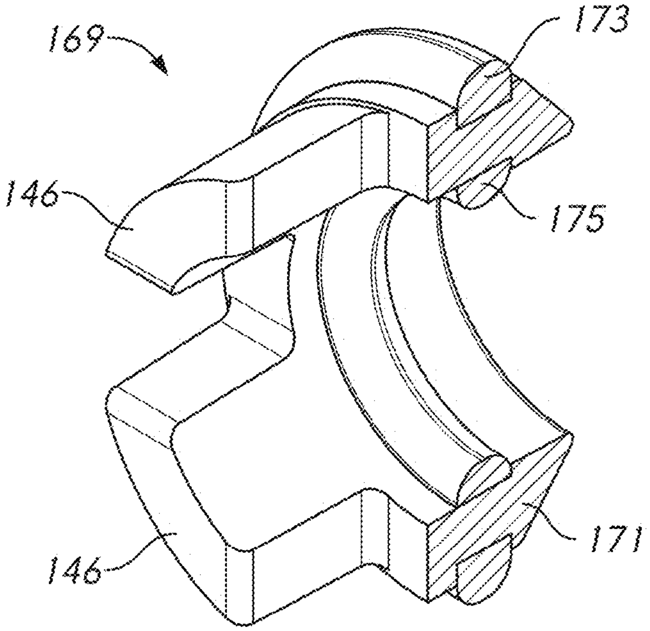
FIG. 54 is a perspective cross-sectional view of the activator member.

The connector 100 can include an activator member 169. FIG. 54 is a perspective cross-sectional view of the activator member 169. The activator member can have a body portion 171, which can be annular with an opening (e.g., through the middle). A seal 173 can be formed on or coupled to the outside surface of the body portion. For example, the seal 173 can be an O-ring. The body portion 171 can include a recess, and the O-ring can be seated in the recess. A seal 175 can be formed on or coupled to the inside surface of the body portion 171. For example, the seal 175 can be an O-ring, which can be seated in a recess on the inside surface of the body portion 171. In some cases, one or both of the seals 173 and 175 can be overmolded or otherwise formed on or coupled to the body portion 171. The activator member 169 can include one or more posts 146, which can extend distally from the body portion 171. Although four posts are shown, any suitable number could be used (e.g., 1, 2, 3, 4, 5, 6, 7, 8, etc.). The posts 146 be separated by gaps.

The activator member 169 can be inserted into the proximal cavity 122*b* of the first housing portion 104. The posts 146 can extend through the openings 137 and into the distal cavity 122*a*. The proximal end of the cover 124 can sit against or adjacent to the distal ends of the posts 146. Pushing the cover 124 proximally can move the posts 146, and the rest of the activator member 169, proximally, such as when attaching the connectors 100 and 200, as discussed herein. When the activator member 169 moves distally, the posts 146 can push the cover distally. The cover 124 and the posts 146, and the other components can be sized and configured so that the distal end of the cover 124 can be substantially flush with the distal end of the projection 116 when the activator member 169 is at its distal position. The flange 134 of the valve 114 can bias the activator member 169 distally. The proximal end of the body portion 171 can abut against the flange 134. The body portion 171 can hit the fingers 135 on the base portion 118 of the first housing member 104, which can impede the activator member 169 from moving further distally.

The outer seal 173 on the activator member 169 can seal against the inside surface of the proximal wall portion 120*b*. The inner seal 175 can seal against the proximal projection 119 portion, which can extend through the opening in the body portion 171. The activator portion 169 can slide longitudinally along the cavity between the projection 119 and the wall portion 120*b*.

Figure 55:
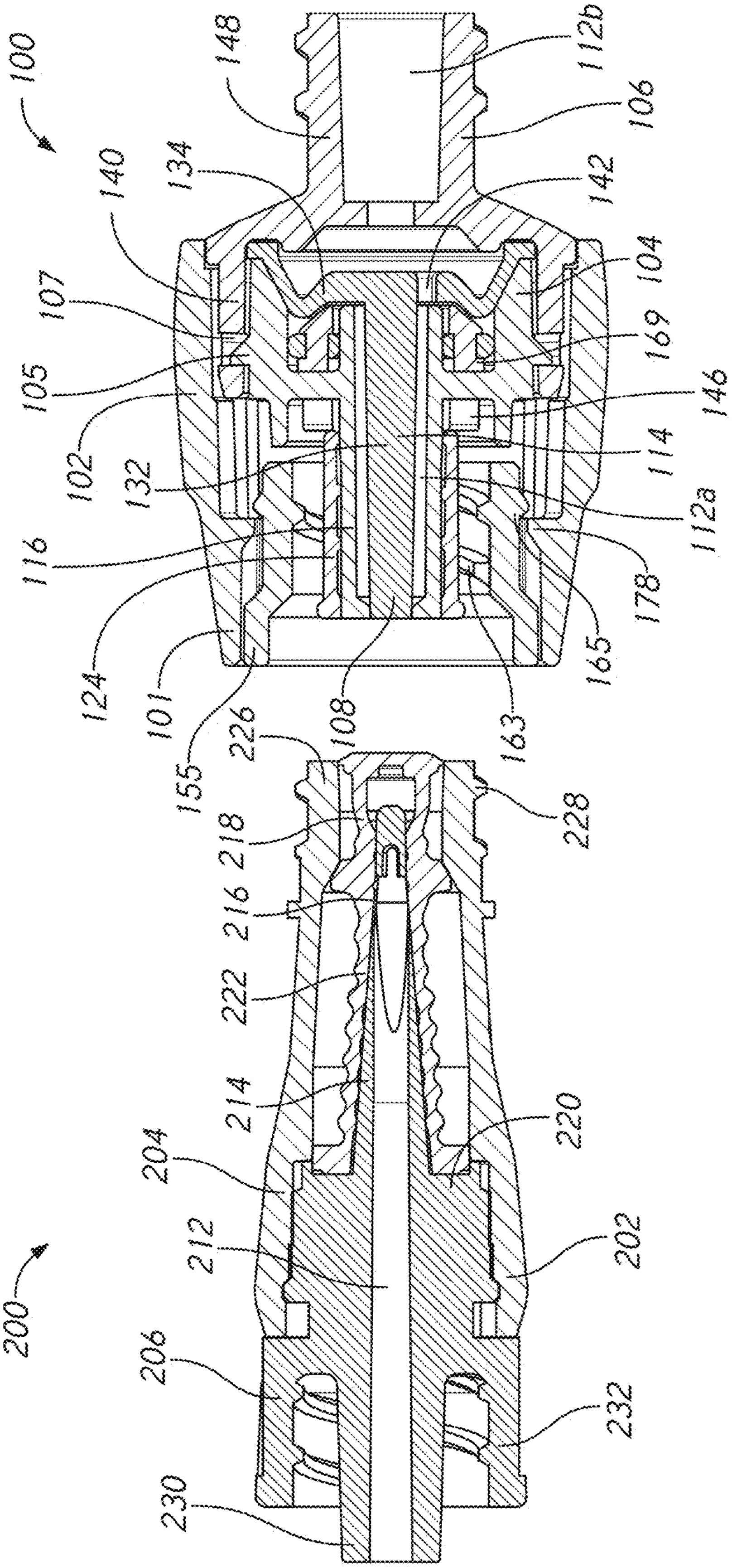
FIG. 55 shows a cross-sectional view of the first connector, with the breakaway member engaged, and with the second connector unconnected.
Figure 56:
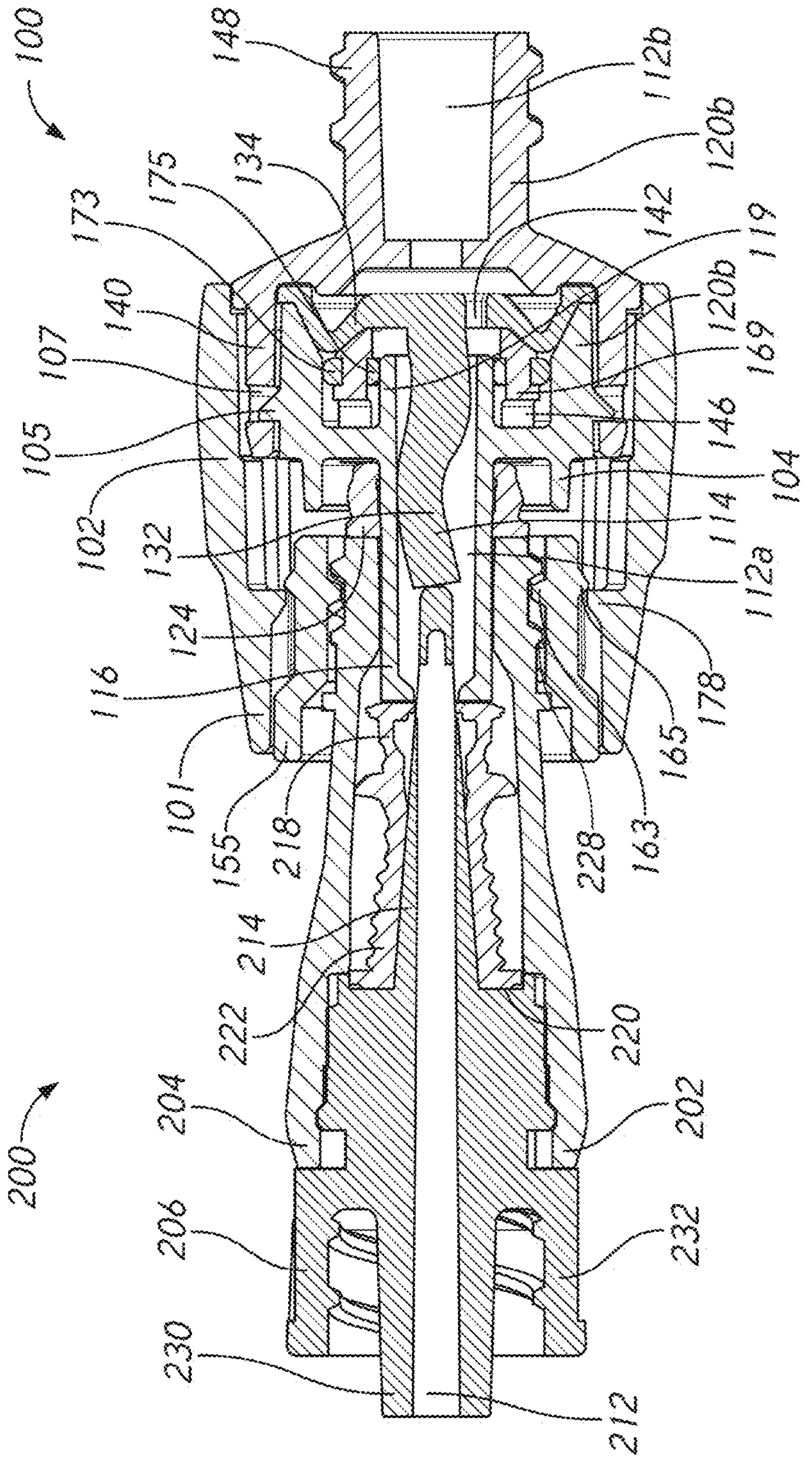
FIG. 56 shows a cross-sectional view of the first connector and the second connector coupled together.
Figure 57:
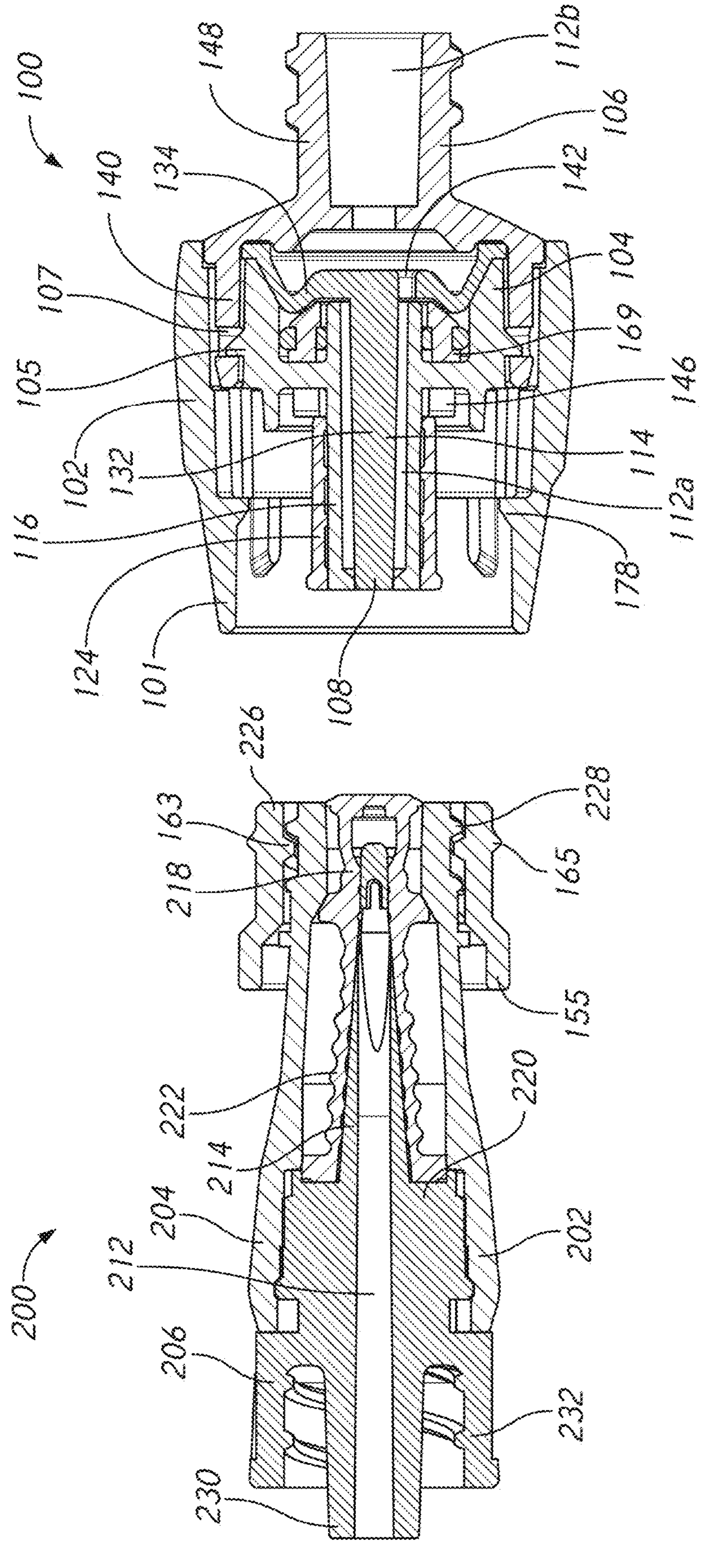
FIG. 57 shows the second connector detached from the main first connector, but still connected to the breakaway member portion thereof.
Figure 58:
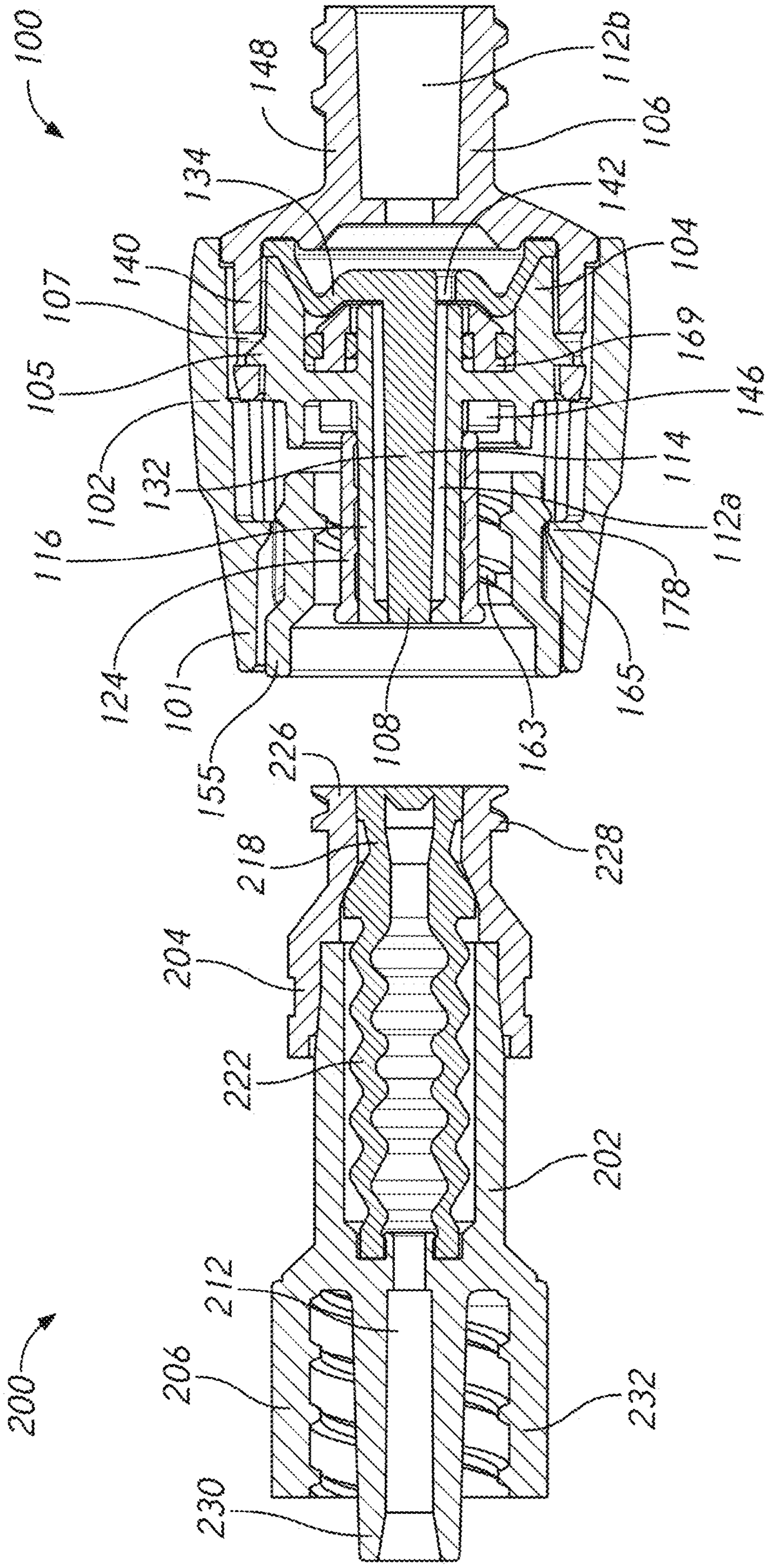
FIG. 58 shows a cross-sectional view of the first connector, with the breakaway member engaged, and with another second connector unconnected.
Figure 59:
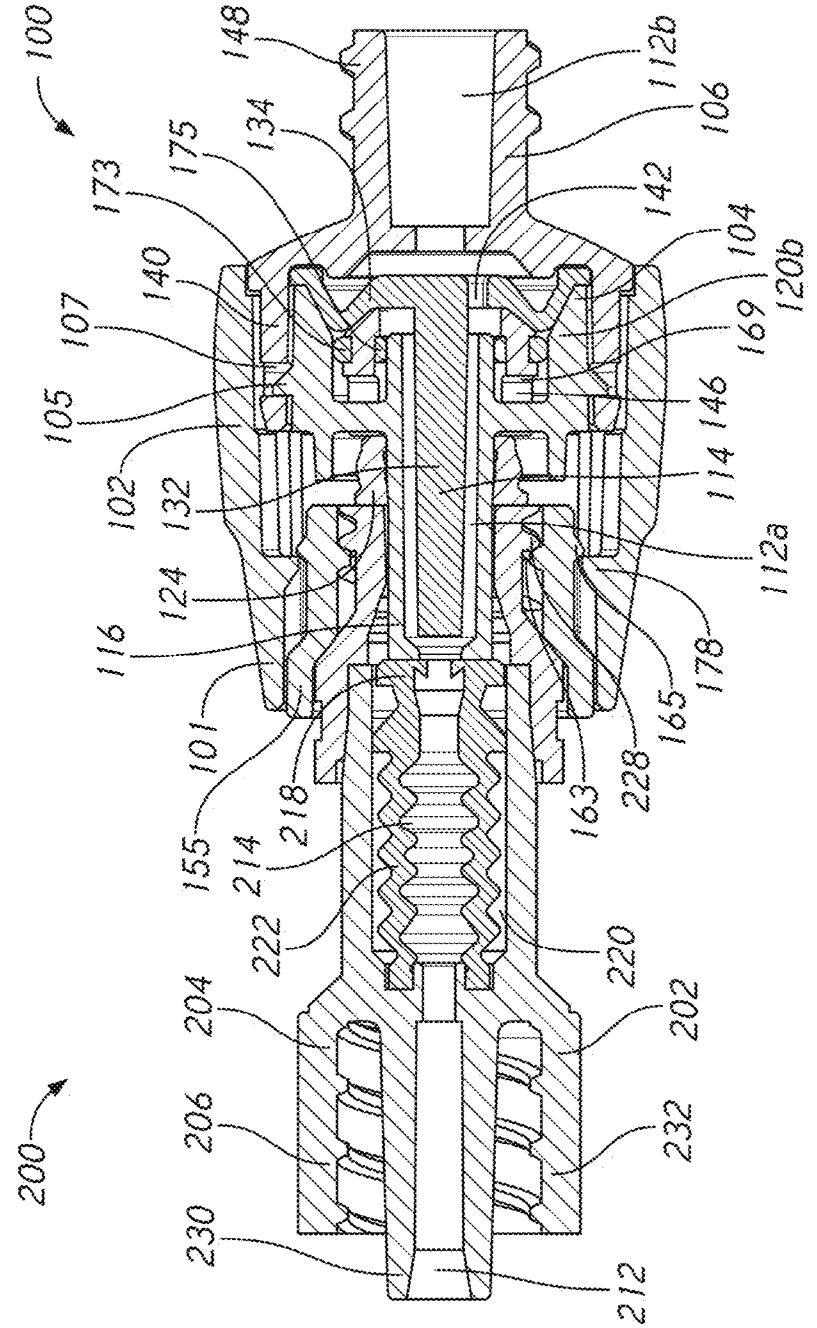
FIG. 59 shows a cross-sectional view of the first connector and the other second connector coupled together.
Figure 60:
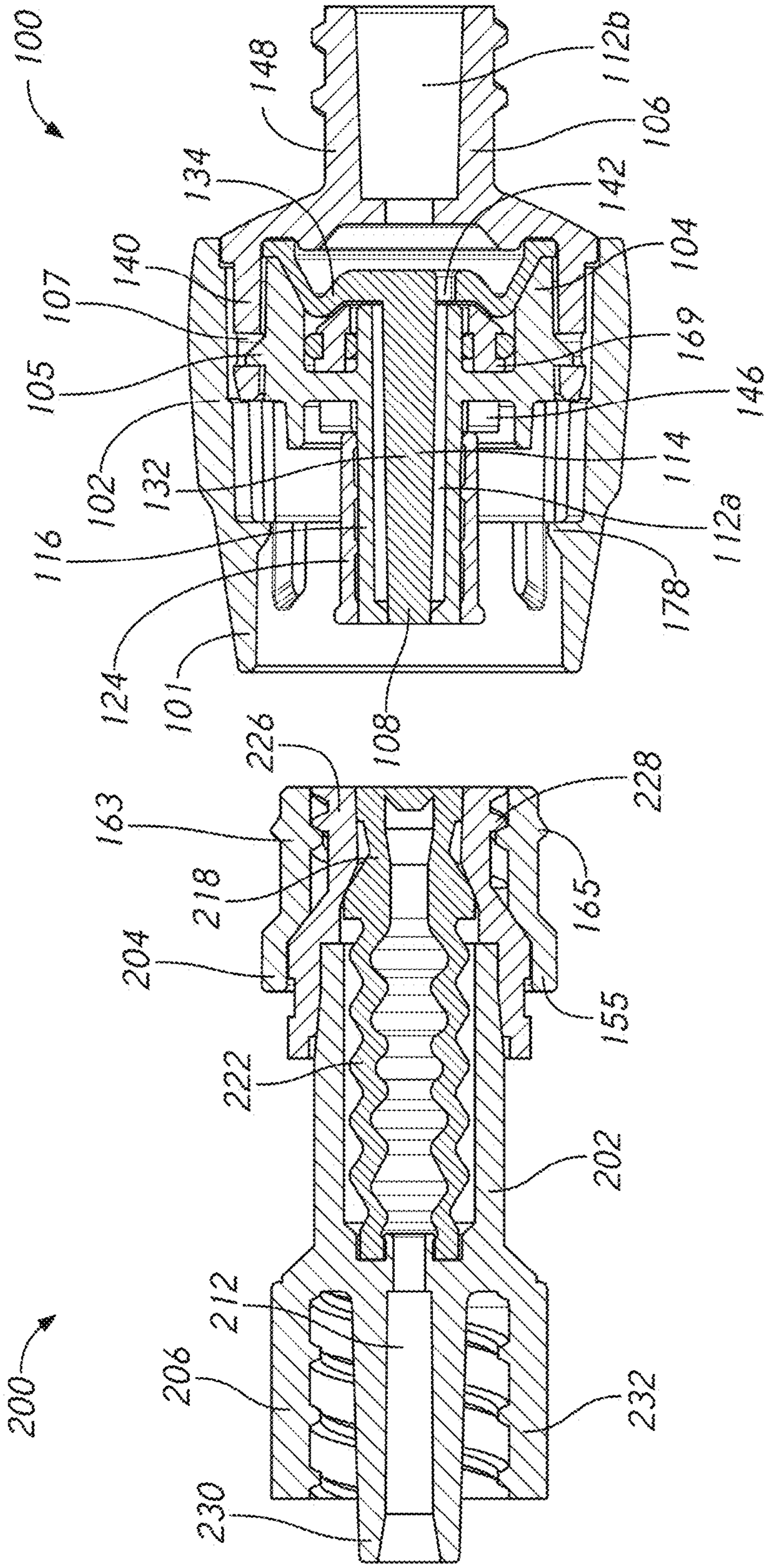
FIG. 60 shows the other second connector detached from the main first connector, but still connected to the breakaway member portion thereof.

The connector 100 can be compatible with multiple types of second connectors 200 (e.g., female luer connectors). FIGS. 55-57 show stages of using the first connector 100 with a second connector 200, which can be a Clave® connector discussed herein, for example. FIG. 58-60 show stages of using the first connector 100 with a different female luer connector that does not include an internal projection 214. FIG. 55 shows a cross-sectional view of the first connector 100, with the breakaway member 155 engaged, and with the second connector 200 unconnected. FIG. 56 shows a cross-sectional view of the first connector 100 and the second connector 200 coupled together. The second connector 200 can be inserted through the opening 153 in the housing 102, and the first connector 200 and/or the first connector 100 can be rotated to engage the one or more threads 163 on the breakaway member 155 with the one or more threads 228 on the connector 200. The internal diameter and threading on the breakaway member 155 can be configured to receive a standard female luer lock fitting 226. The second connector 200 can include a projection 214 (e.g., an internal cannula), which can be inserted into the opening 108 at the distal end of the projection 116 when the connector 200 is coupled to the connector 100. The projection 214 can push the distal end of the shaft 132 proximally to open the opening 108, such as to permit fluid to flow to or from the first connector 100. The shaft 132 can be compliant or resilient so that it can buckle, bend, compress, or otherwise deform, so that the distal end of the shaft 132 can disengage from the opening 108. The shaft 132 can be resilient and can return to the closed position (e.g., the default or undeformed position) when the second connector 200 is detached (e.g., see FIG. 56). The valve 114 can be made of silicone, or any other suitable elastomeric or resilient material. The fluid pathway first portion 112*a* in the projection 116 having a larger diameter or width than the shaft 132 can permit the shaft to bend or buckle. In some embodiments, the shaft 132 can be have sufficient rigidity to push a portion of the flange 134 proximally when the connectors 100, 200 are coupled. For example, a portion of the flange 134 at or near the junction with the shaft 132 (e.g., a center portion) can be pushed proximally by the shaft 132 when the projection 214 presses on the shaft 132. The flange 134 can provide biasing force that facilitate closing of the valve 114 when the second connector 200 is detached.

The projection 116 of the first connector 100 can be inserted into the housing 202 of the second connector 200. The projection 214 of the second connector 200 can include a fluid pathway 212 and one or more openings 216, which can permit fluid to flow to or from the fluid pathway 212. The projection 214 can be inserted so that the one or more openings 216 can be inside the projection 116 (e.g., in the fluid pathway 112 of the first connector 100). The second connector 200 can include a valve 218, which can have an open configuration (e.g., shown in FIG. 7) and a closed configuration. In the closed configuration, the valve 218 can cover the openings 216 on the projection 214 so that fluid is impeded from flowing to or from the connector 200. The projection 116 of the first connector 100 can push the valve 218 (e.g., at least the proximal end thereof) distally as the connectors 100, 200 are coupled, so that the opening(s) 216 are exposed to permit fluid flow. The distal face or portion of the projection 116 can engage the seal 218 (e.g., the proximal face thereof) to form a substantially fluid-tight seal, in some embodiments. When the connectors 100, 200 are disconnected, the valve 218 can resiliently return to its closed configuration. Many other suitable valve configurations may be used to open and close the connector 200, and can in some cases seal against the projection 116.

As the second connector 200 is coupled to the first connector 100, the proximal face of the housing 202 of the second connector 200 can contact the distal end of the cover 124 or face seal, and can push the cover 124 proximally. The engagement between the cover 124 or face seal with the housing 202 of the second connector (e.g., the proximal face surface thereof), can provide a substantially fluid-tight seal. In some embodiments, multiple seal locations can cooperate to seal the fluid path between the connectors 100 and 200.

As the cover 124 is pushed proximally, it can push the posts 146 of the activator member 169 proximally as well, so that the activator member 169 moves proximally to the position shown in FIG. 56. The activator member 169 can push the flange 134 of the valve proximally, which can pull the shaft 132 of the valve 114 proximally so that the distal portion of the shaft 132 disengages from the end of the projection 116, thereby opening the fluid path through the opening 108. In the embodiments of FIGS. 55 and 56, the valve 114 can be opened by the projection 214 pushing the shaft 132 proximally, and also by the housing 202 of the second connector pushing the activator member 269 proximally to pull the valve shaft 132 proximally. In the embodiments of FIGS. 58 and 59, the second connector 200 does not have a projection 214 that would push the shaft 132 of the valve 114 to the open configuration, so this embodiment opens the valve 214 only by the housing 202 of the second connector 200 pushing the cover 124 and the activation member 269 proximally so that the valve shaft 132 is pulled proximally to the open configuration.

As shown in FIGS. 56 and 59, when the connectors 100, 200 are coupled, fluid can flow from the second connector 200 to the first connector 100 (e.g., such as for drawing a bodily fluid from a patient). The fluid can flow through a fluid pathway 212 of the second connector 200, through the opening 108 and into the fluid pathway first portion 112*a* in the projection 116. The fluid can flow around the shaft 132, and through opening(s) 142 in the flange 134, through the fluid pathway second portion 112*b* in the second housing portion 106, and out the opening 110. In some embodiments, a catheter, tubing, another connector, or other medical implement can be attached to the proximal end of the connector 100 (e.g., to receive the fluid that flows out the opening 100. The fluid can flow in the other direction as well (e.g., such as for infusing a medication or other fluid into a patient). In some embodiments, the flange 134 of the valve 114 can be in the fluid pathway. The fluid can fill the are proximal of the flange 134, and fluid can also enter the space immediately distal of the flange 134. The outer seal 173 can seal against the wall 120*b*, and the inner seal 175 can seal against the outer wall of the projection 119, such as for form a barrier to the fluid path. The fluid path can contact the portion of the activation member 169 that is proximal of the seals 173 and 175. In some cases, the fluid path does not contact the portion of the activation member 169 that is distal of the seals 173 and 175. As the activation member 169 moves, the seals 173 and 175 can slide on the wall 120*b* and the projection 119 to maintain the seals.

FIGS. 57 and 60 show the respective second connectors 200 detached from the main first connector 100 (e.g., but still connected to the breakaway member portion 155 thereof), such as after a breakaway disconnection event. When sufficient force is applied, the one or more projections 165 on the breakaway member 155 can move past the projections 178 of the housing, so that the breakaway member 155 and the second connector 200 can disengage from the main body of the first connector 100. In some embodiments, at least the third housing portion 101 can flex or deform so that the projections 178 can move to enable the breakaway disengagement. When the connectors 100, 200 are disconnected, the valve 114 can resiliently return to the closed configuration to impede fluid from entering or exiting the first connector 100. When the connectors 100, 200 are disconnected, the valve 218 can resiliently return to the closed configuration to impede fluid from entering or exiting the second connector 200.

In some embodiments, the second connector 200 and the breakaway member 155 can be reattached to the main body of the first connector 100, such as by pressing the breakaway member 155 (e.g., with the second connector 200 attached thereto) into the opening at the distal end of the connector 100. The user can align the breakaway member 155 so that the recesses 159 on the breakaway member 55 align with the protrusions 157 on the housing 102, and/or so that the breakaway member protrusions 165 align with the corresponding protrusions 178 of the housing. The connectors 100 and 200 can have twist-to-connect features, can have pull-to-disconnect features, and/or can have push-to-reconnect features. In some embodiments, the breakaway member 155 (and the second medical connector 200) can be reattached to the main portion of the first connector 100 without the use of a tool. The user can merely push the breakaway member 115 into the housing 102 (e.g., after proper alignment), and the breakaway features can reengage to reconnect the connectors 100, 200.

When the connector 100 is in the closed configuration, the distal ends of the cover 124 or face seal, the projection 116, the valve 114, or any combination thereof, can be substantially flush with each other, for example to facilitate swabbing of the closed connector surface (e.g., with alcohol or other disinfectant). For example, the user can swab the first connector before reconnection with the second connector 200, or before an initial coupling.

In some embodiments, the second connector 200 can be detached from the first connector 100 in two ways. First, pulling the connectors 100 and 200 apart can detach the connectors 100 and 200 via the breakaway connection. The breakaway member 155 can remain attached to the second connector 200 and can separate from the first connector 100, as shown in FIGS. 57 and 60. Accordingly, a piece or portion of the first connector 100 can remain attached to the second connector 200 after detachment. Second, rotating the second connector 200 relative to the first connector 100 (e.g., in a loosening direction, which can e counter-clockwise), the first connector 100 can be unthreaded from threading 163 of the first connector 100 (e.g., on the breakaway member 155). The second connector 200 can then detach from the first connector 100, while leaving the breakaway member 155 coupled to the first connector 100 (e.g., transitioning back to the configuration of FIG. 55 or FIG. 58). When the connectors 100 and 200 are disengaged (e.g., by either approach), the valve 114 can close the fluid pathway 112 on the first connector and/or the valve 218 can close the fluid pathway 212 on the second connector 200. The connectors 100 and 200 can have a pull-to-detach disengagement as well as a twist-to-detach disengagement.

Figure 61:
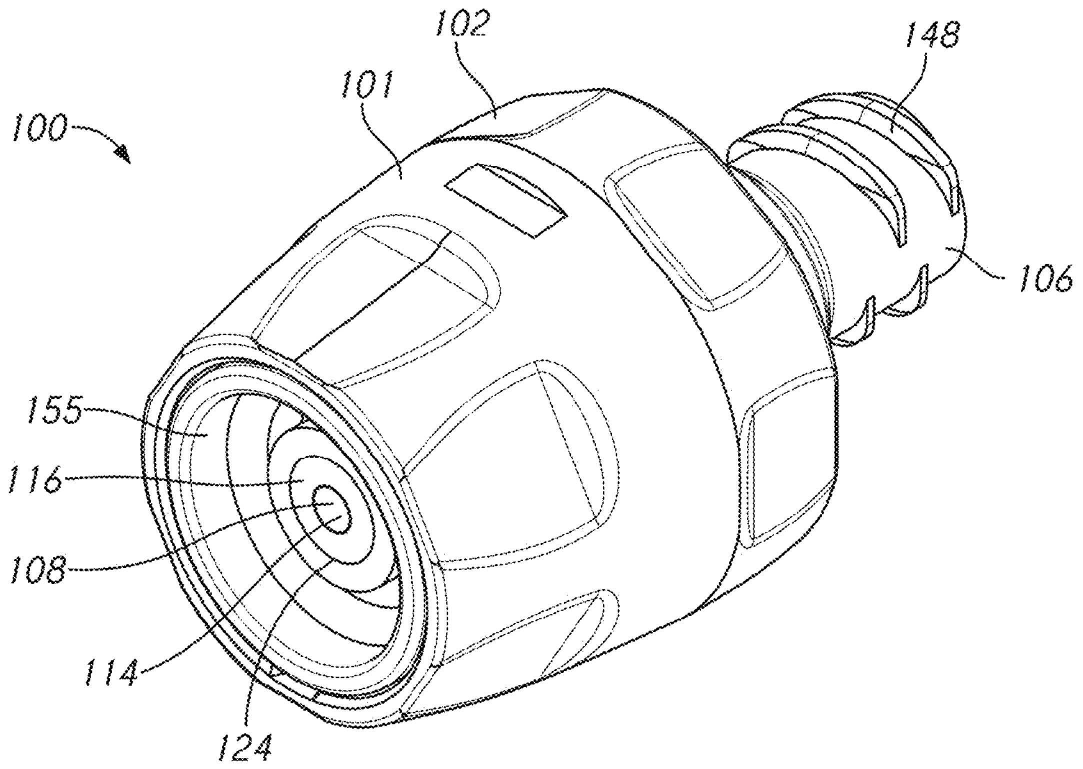
FIG. 61 shows a perspective view of another example embodiment of a first connector.
Figure 62:
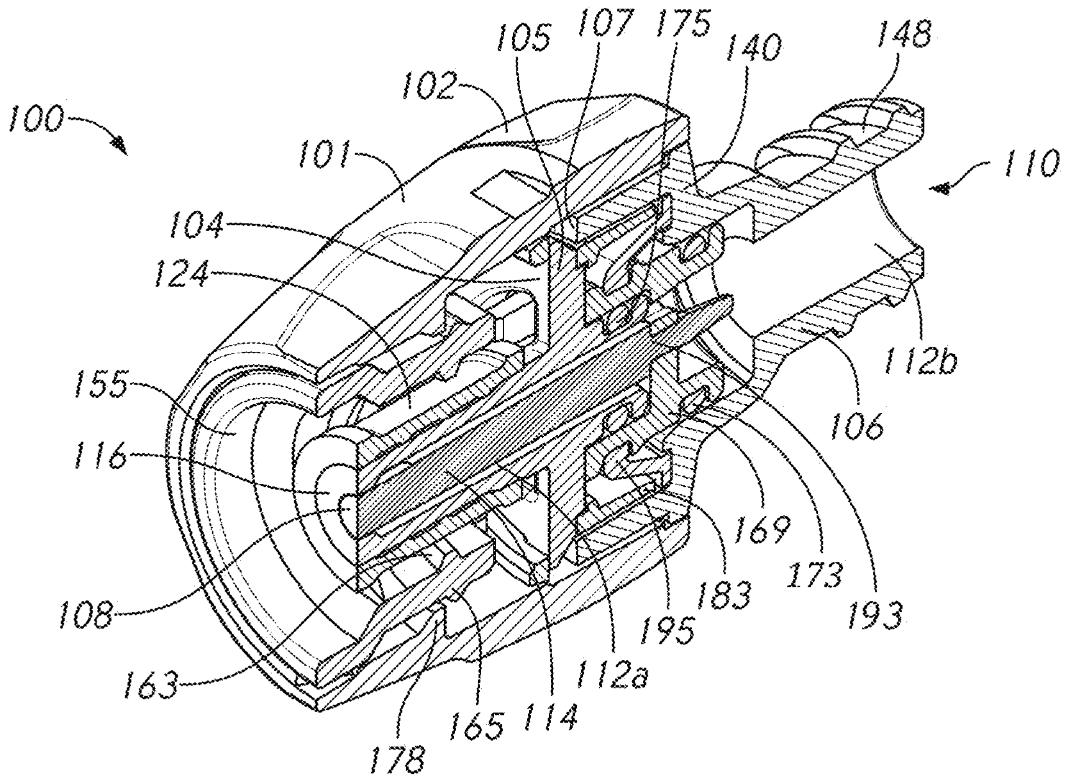
FIG. 62 shows a perspective cross-sectional view of the example first connector of FIG. 61.
Figure 63:
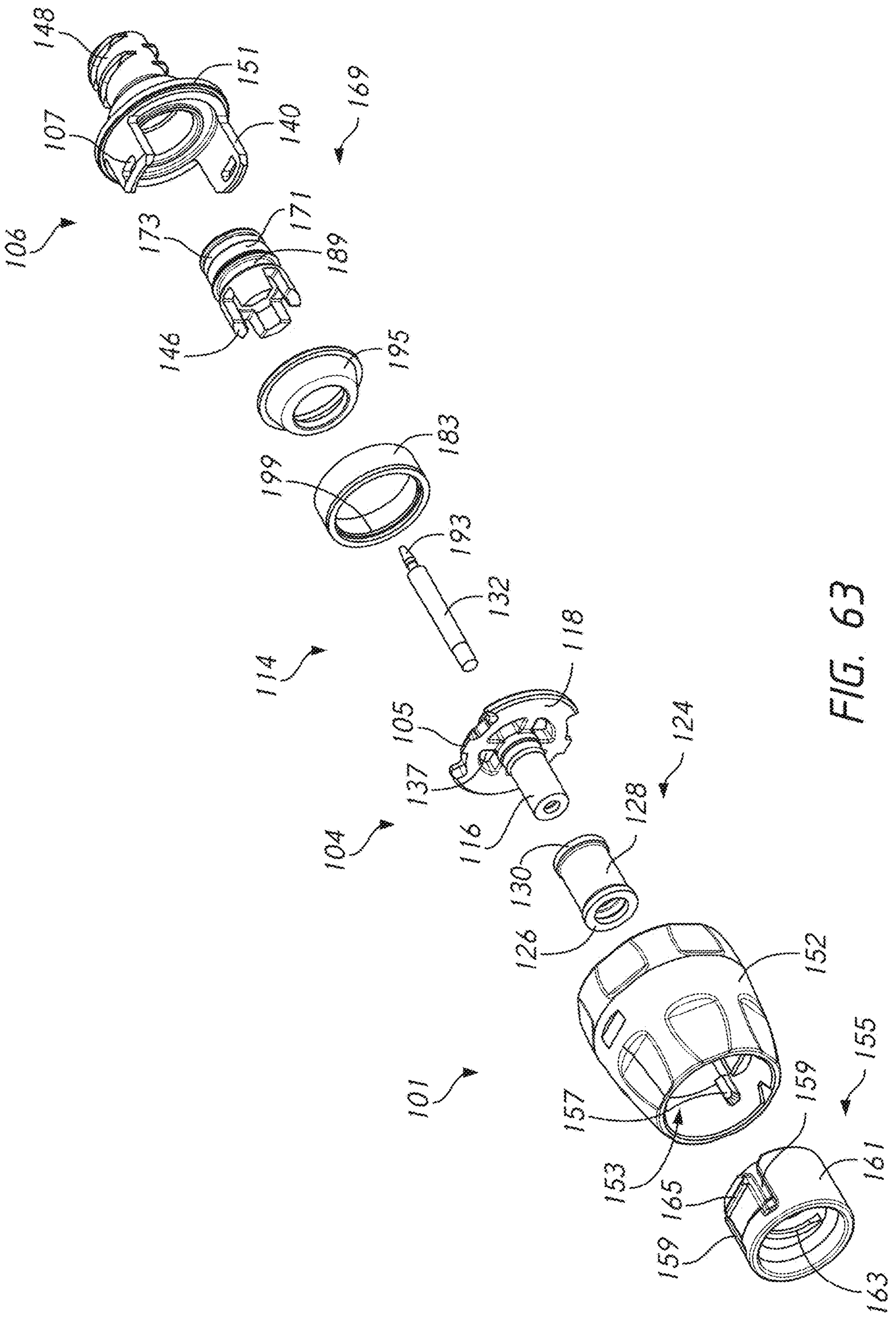
FIG. 63 is an exploded view of the example first connector.
Figure 64:
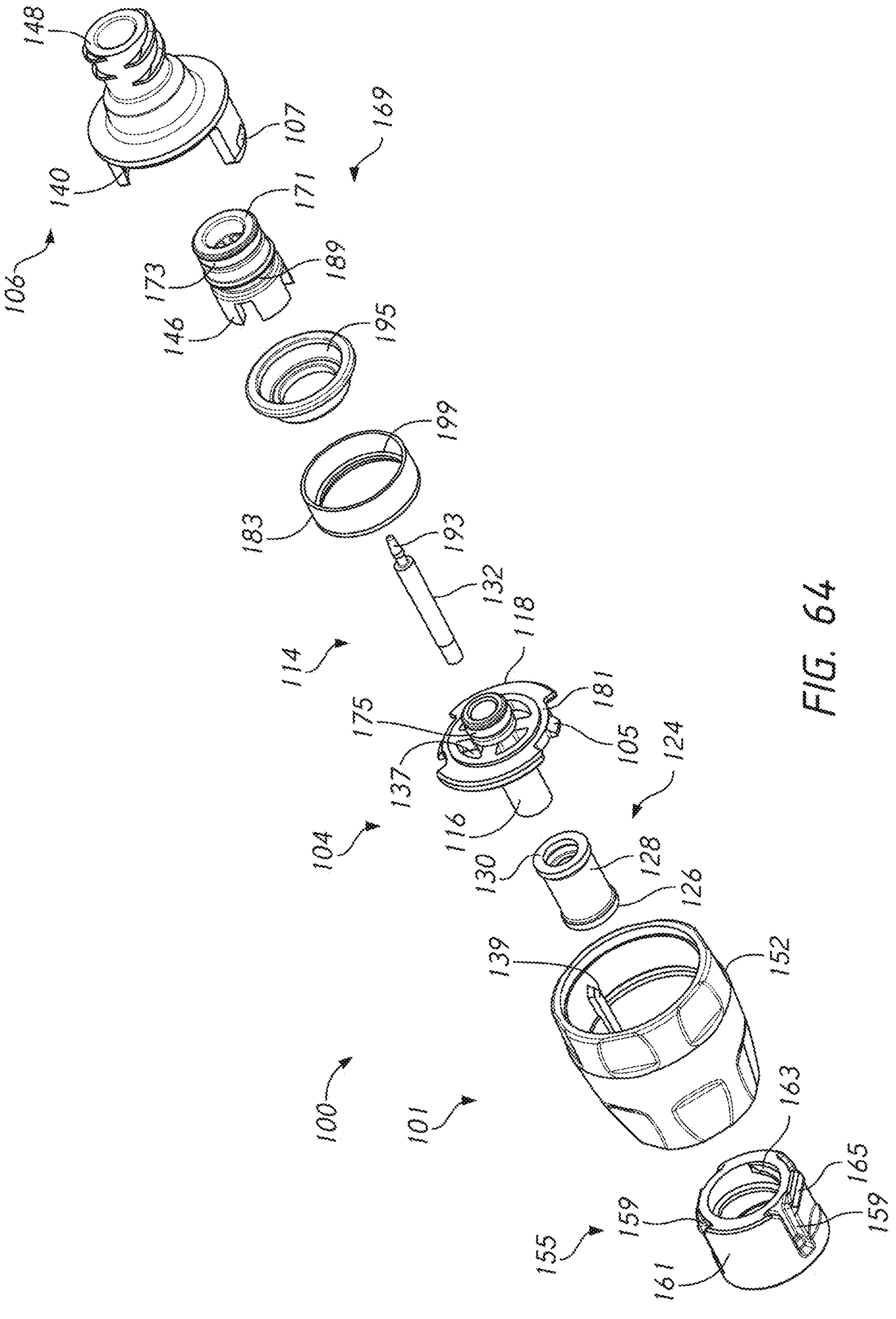
FIG. 64 is another exploded view of the example first connector.

FIG. 61 shows a perspective view of another example embodiment of a first connector 100. FIG. 62 shows a perspective cross-sectional view of the example first connector 100 of FIG. 61. FIG. 63 is an exploded view of the example first connector 100. FIG. 64 is another exploded view of the example first connector 100. This connector 100 can be similar to the other first connector 100 embodiments disclosed herein, except as described and shown herein, and the disclosure relating to FIGS. 42 to 60 can apply to this first connector 100 as well, except as noted.

Figure 65:
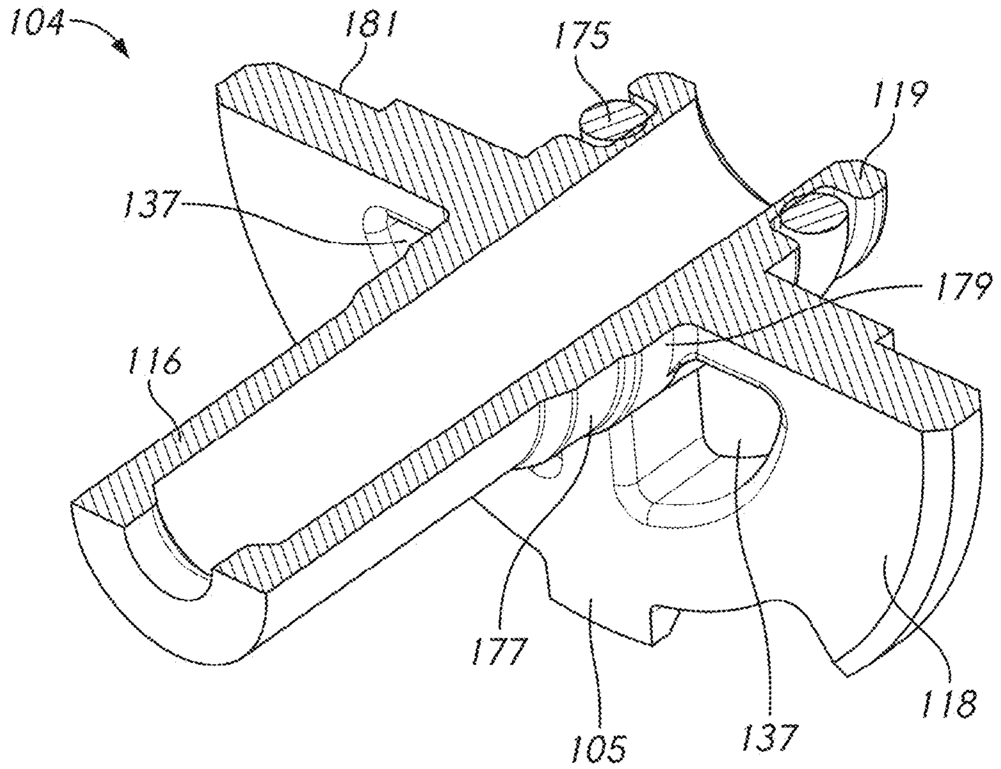
FIG. 65 is a perspective cross-sectional view of the first housing portion.

The connector 100 can have a housing 102, which can include a first housing portion 104, a second housing portion 106, and a third housing portion 101. FIG. 65 is a perspective cross-sectional view of the first housing portion. The projection 116 can have a first widened portion 177, which can have width that is larger than the portion of the projection 116 that is distal of the widened portion 177. A step or tapered portion can transition from the main projection portion to the first widened portion 177. The first widened portion 117 can be configured to engage a base 130 of the cover 124 or face seal, as discussed herein. The projection 116 can have a second widened portion 179, which can have a width that is larger than the portion of the projection 116 that is distal of the second widened portion 179 (e.g., including the first widened portion 177). A step or tapered portion can transition from the first widened portion 177 to the second widened portion 179. The second widened portion 179 can be configured to fill space to reduce the size of a gap between the projection 116 and the posts 146, which can impede the cover 124 or face seal from becoming stuck in the gap, such as during transitions between the closed and open states for the connector 100. The gap between the radially inward sides of the posts 146 and the radially outward side of the second widened portion 179 of the projection 116 can be about 0.5 mm, about 0.4 mm, about 0.3 mm, about 0.2 mm, about 0.15 mm, about 0.1 mm, about 0.07 mm, about 0.05 mm, or less, or any values or ranges between any of these distances, although other configurations are possible. In some cases, one or more of the posts 146 can be adjacent to or can touch (e.g., can slide against) the second widened portion 179.

The transition to the first widened portion 177 and/or the transition to the second widened portion 179 can have a taper angle of about 5 degrees, about 10 degrees, about 15 degrees, about 18 degrees, about 20 degrees, about 22 degrees, about 25 degrees, about 30 degrees, about 35 degrees, about 40 degrees, or any values or ranges between any of these values, although other designs are possible. The tapered transition(s) can facilitate movement of the cover 124 along the projection without sticking or binding. The thickness of the projection side wall can be thicker at the first widened portion 177 than at the portion of the projection distal of the widened portion 177, such as by about 10%, about 15%, about 20%, about 25%, about 30%, about 35%, about 40%, or any values or ranges between any of the these values, although other designs are possible. The thickness of the projection side wall can be thicker at the second widened portion 179 than at the portion of the projection distal of the widened portions 177 and 179, such as by about 20%, about 25%, about 30%, about 35%, about 40%, about 45%, about 50%, about 60%, about 70%, or more, or any values or ranges between any of the these values, although other designs are possible. In some cases, the first widened portion 177 and the second widened portion 179 can be combined as a single widened portion, such as with a single transition (e.g., tapered). One or both of the widened portions 177 and 179 can be omitted.

The first housing portion 104 can omit the outer wall 120*a* and the outer wall 120*b*. The connector 100 can include a seat member 183, which can form a structure similar to the outer wall 120*b*, as discussed herein. In some embodiments, the first housing portion 104 can have an outer wall 120*b* (e.g., similar to FIG. 47). The first housing portion 104 can have a base portion 118, which can extend laterally from the projection 116. The proximal side of the base portion 118 can have a step 181 around the periphery, which can be used to engage the seat member 183, as discussed herein. The base portion 118 can have protrusions 105, which can be used to engage structures (e.g., openings 107) on the second housing portion 106 to couple the first housing portion 104 to the second housing portion 106, such as with a snap-fit engagement.

The a proximal projection 119 can extend proximally from the base portion 118. The proximal projection 119 can be a continuation of the distal projection 116 forming a continuous inner lumen. A seal 175 can be disposed on the projection 119. For example, the seal 175 can be an O-ring, and the projection 119 can include an annular recess that is configured to receive the O-ring. In some embodiments, the seal 175 can be on the inside of the activation member 169, and in some cases the seal 175 can be on the outside of the projection 119.

Figure 66:
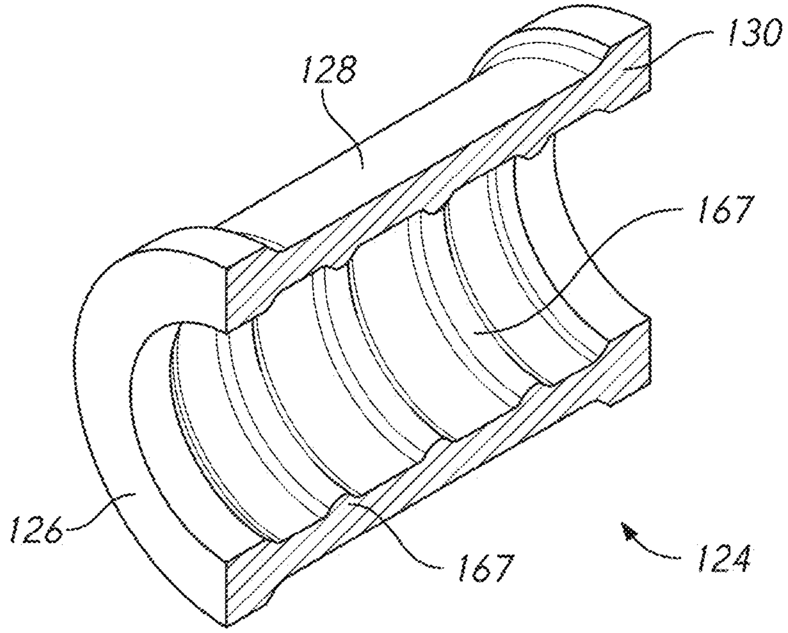
FIG. 66 is a cross-sectional view of the cover.

FIG. 66 is a cross-sectional view of the cover 124, which can be similar to the other cover or face seal embodiments disclosed herein. The cover 124 can include a base portion 130, such as at the proximal end thereof. The base portion 130 can be thicker than the side walls of the cover 124. The base portion 130 can provide a tighter engagement with the projection 116, such as with the first widened portion 177 of the projection 116. The distal face of the cover 124 can be configured seal against a housing of the second connector 200, as with other embodiments disclosed herein.

Figure 67:
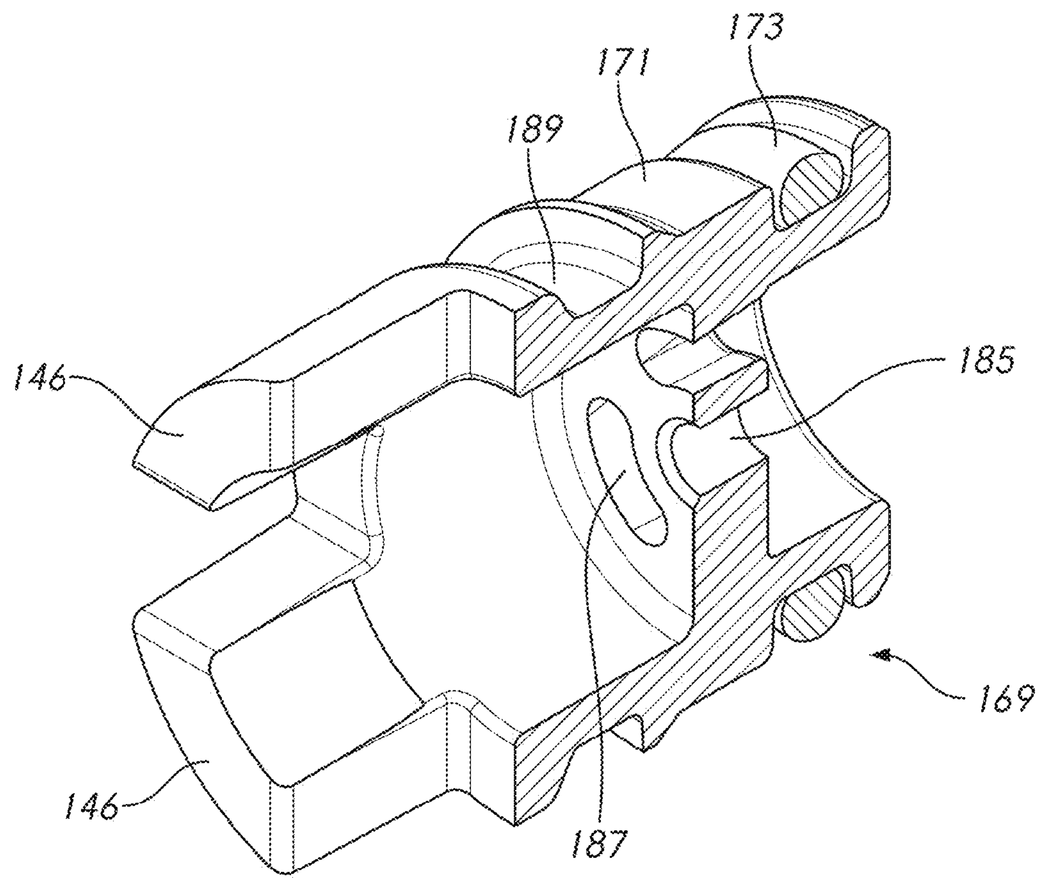
FIG. 67 is a perspective cross-sectional view of the activator member.

FIG. 67 is a perspective cross-sectional view of the activator member 169. The activation member 169 can have a body portion 171, which can be generally cylindrical in shape. The distal end of the body portion 171 can be open so that the projection 119 can be received therein. The seal 175 can seal against the inside surface of the boy portion 171 of the activator member 169. The body portion 171 can have a wall disposed laterally across the inside of thereof. The body portion 171 can have an engagement structure 185 for engaging the valve 114, as discussed herein. The engagement structure 185 can be a hole or opening through the wall, which can receive a portion of the valve 114, as discussed herein. The wall can include additional opening s 187, which can permit fluid to pass through the wall and to travel through the channel through the inside of the activation member 169. Any suitable number of openings 187 can be used (e.g., 1, 2, 3, 4, 6, 8, 10, 12, etc.). The body portion 171 can extend proximally of the lateral wall. A seal 73, such as an O-ring, can be coupled to the proximal part of the body portion 171, such as by being seated in an annual recess. The seal 173 can seal against a side wall on the second housing portion 106. The outside of the activation member 169 can include an annular recess 189, which can be used to engage the valve spring 195, as discussed herein. The activation member 169 can include posts 146, similar to other embodiments discussed herein.

Figure 68:
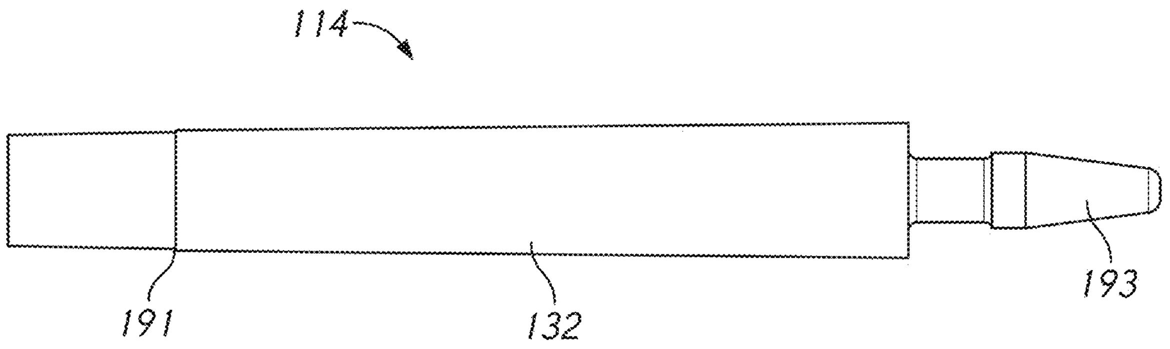
FIG. 68 shows a side view of the valve.

FIG. 68 shows a side view of the valve 114. The valve 114 can have a shaft 132, which can be flexible and can deform when the valve 114 is opened, similar to other embodiments. In some embodiments, the valve 114 can have a step, which can define a narrower distal tip portion of the shaft 132. The valve 114 can have an engagement structure that is configured to couple the valve 114 to the activation member 169, so that movement of the activation member 169 causes movement of the valve 114. The valve 114 can have a finger 193, which can extend from the proximal end of the shaft 132. The finger 193 can be narrower than the shaft 132. The finger 193 can include a notch or narrower portion, and a bulb or wider portion that is proximal of the notch or narrower portion. The bulb can be tapered narrowing in the proximal direction, which can facilitate feeding of the finger 193 through the opening 185. The bulb portion can be pulled once is exposed on the proximal side of the opening 185, and the pulling can stretch the valve to enable the bulb portion to squeeze through the opening 185. The notch portion can engage the opening. The shaft 132 can be wider, and does not fit through the opening 185. Once release, the bulb portion of the finger 193 can have a width that is larger than the opening 185, which can impede the valve from pulling out of engagement with the activation member 169.

The finger 193 can anchor the valve to the activation member 169. Various other coupling mechanisms or approaches could be used to couple the valve 114 to the activation member 169, such as adhesive, a clamp, a clip, a friction fitting, a between housing portions or other components, a screw or other fastener, a knot, an overmolded portion, etc.

Figure 69:
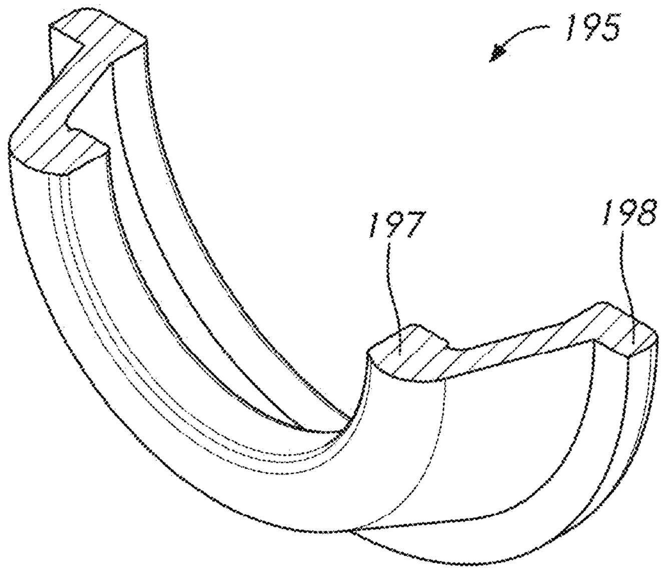
FIG. 69 is a perspective cross-sectional view of the valve spring.

The flange 134 portion of the valve can be omitted. Instead the connector 100 can include a biasing member that is a separate component from the valve 114. The connector 100 can include a valve spring 195. FIG. 69 is a perspective cross-sectional view of the valve spring 195. The valve spring 195 can be configured to bias the activation member 169 and/or the valve 114 distally. The valve spring 195 can have an opening through the center. The valve spring 195 can be a diaphragm spring, although various types of springs can be used. The inner portion 197 of the valve spring 195 can fit into the annular recess 189, which can couple the valve spring 195 to the activation member 169. The outer portion 198 of the valve spring 195 can be secured to the housing 102, such as by being clamped or pinched between two housing portions or other components. The inner portion 197 and the outer portion 198 of the valve spring can be coupled with a flexible wall, which can bend, bow, or otherwise deform to store energy that can provide a resilient biasing force. The valve spring 195 can be made of silicone or any other suitable elastomeric or resilient material.

Figure 70:
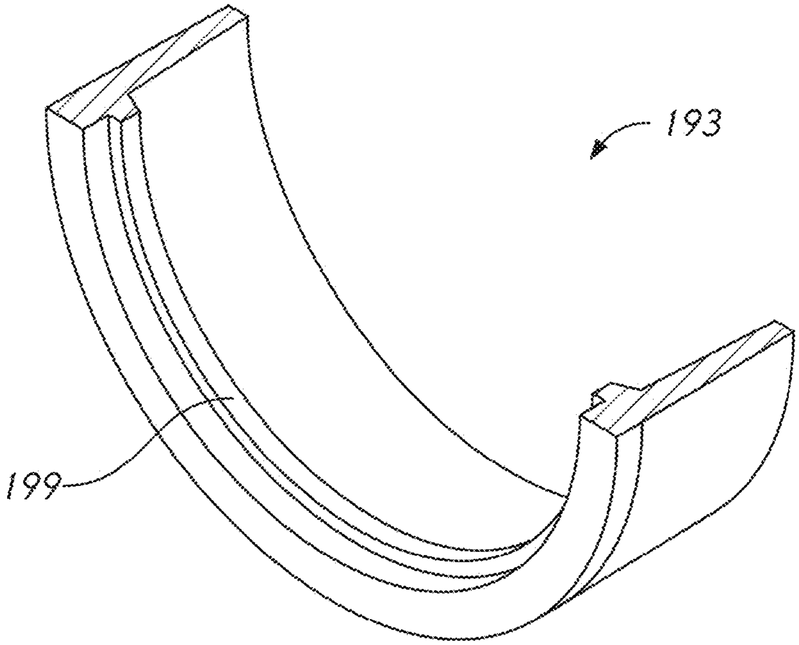
FIG. 70 is a perspective cross-sectional view of the seat member.

FIG. 70 is a perspective cross-sectional view of the seat member 183. The connector 100 can include a seat member 183, which can be used to seat the valve spring 195 or biasing member. The seat member 183 can be generally cylindrical in shape. The inside of the seat member 183 can have an annual ridge 199, which can form a step, which can engage the step 181 on the first housing portion 104, such as to secure, align, or support the seat member 183. The seat member 183 can be formed of polycarbonate, or various other polymers, or any other suitable (e.g., substantially rigid) material. When the first housing portion 104 is coupled to the second housing portion 106 (such as by the snap-fit engagement, or otherwise), the seat member 183 can be positioned so that the proximal end of the seat member 183 can engage the outer portion 198 of the valve spring 195. The outer portion 198 can be pinched between the seat member 183 and a wall 140 or other portion of the second housing portion 106, as can be seen in FIG. 62. In some embodiments, the housing 102 can include an outer wall portion (e.g., extending proximally from the base portion 118), which can function similar to the seat member 183, but can be integrally formed with other housing components. Various housing and other components can be combined or subdivided into additional sub-components.

The valve spring 195 can be positioned outside the fluid flow path through the connector 100. The seal 173 can seal between the outside of the activation member 169 can the sidewall of the second housing portion 106, which can impede the fluid from reaching the proximal side of the valve spring 195. The seal 175 can seal between the inside of the activation member 169 and the projections 119 on the first housing portion 104, which can impede the fluid from reaching the distal side of the valve spring 195.

Figure 71:
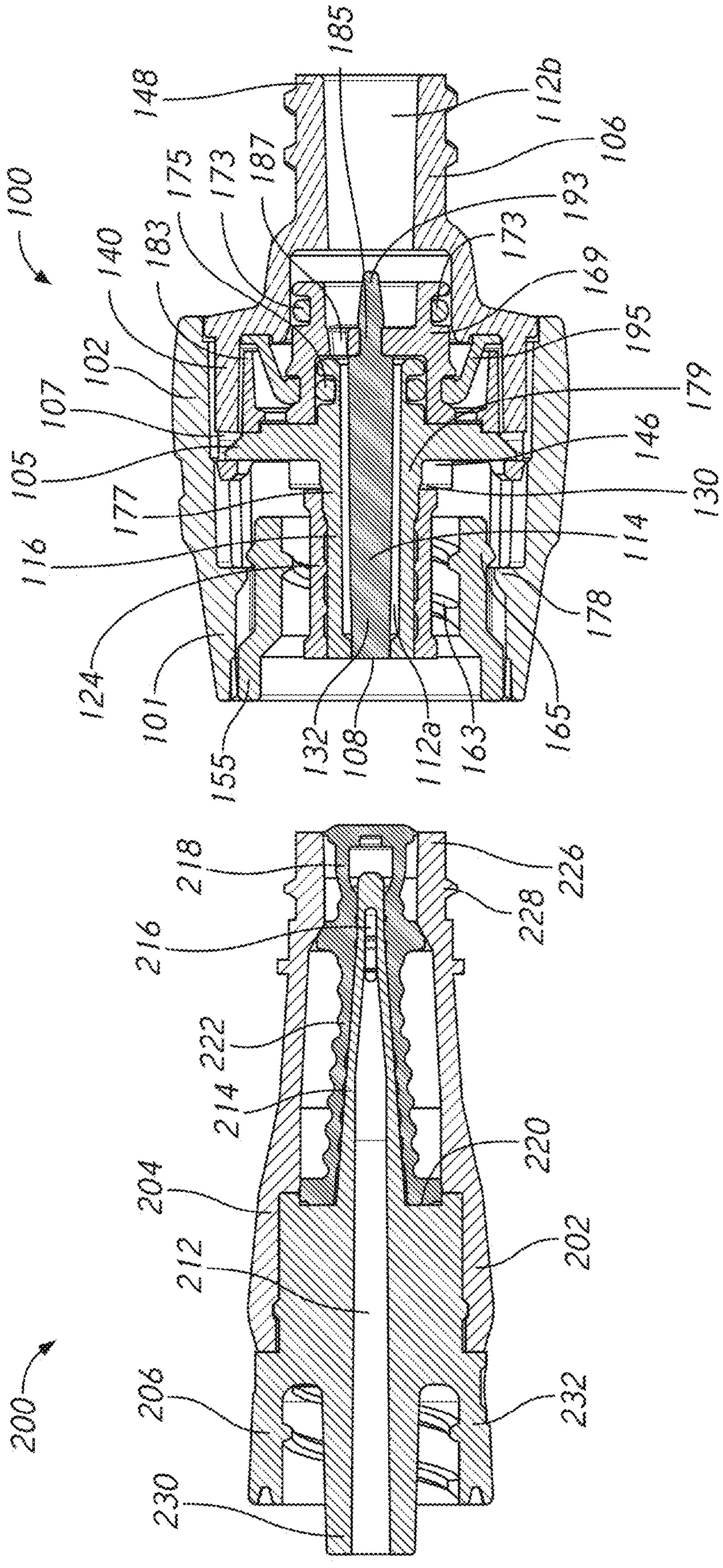
FIG. 71 shows a cross-sectional view of the first connector, with the breakaway member engaged, and with the second connector unconnected.
Figure 72:
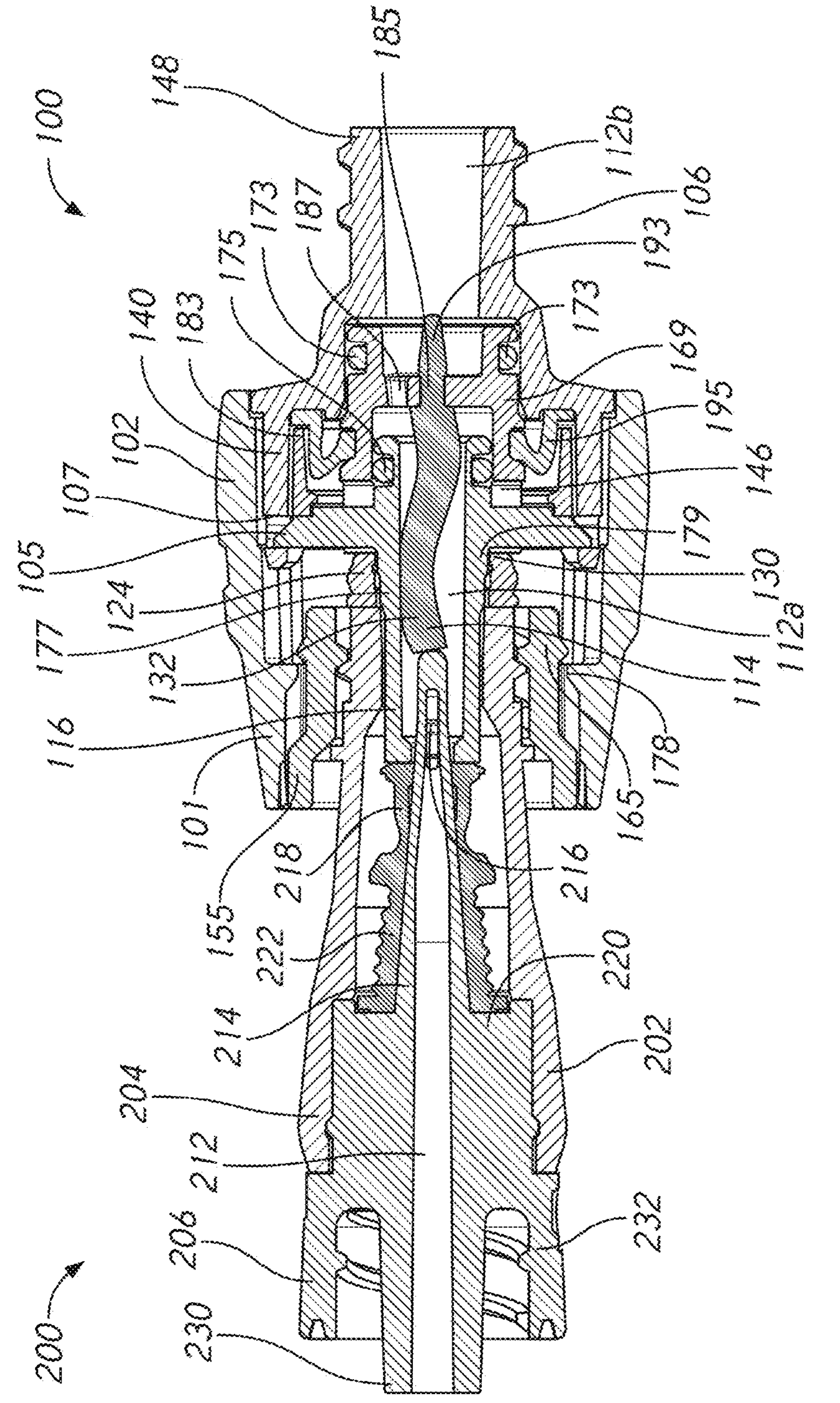
FIG. 72 shows a cross-sectional view of the first connector and the second connector coupled together.
Figure 73:
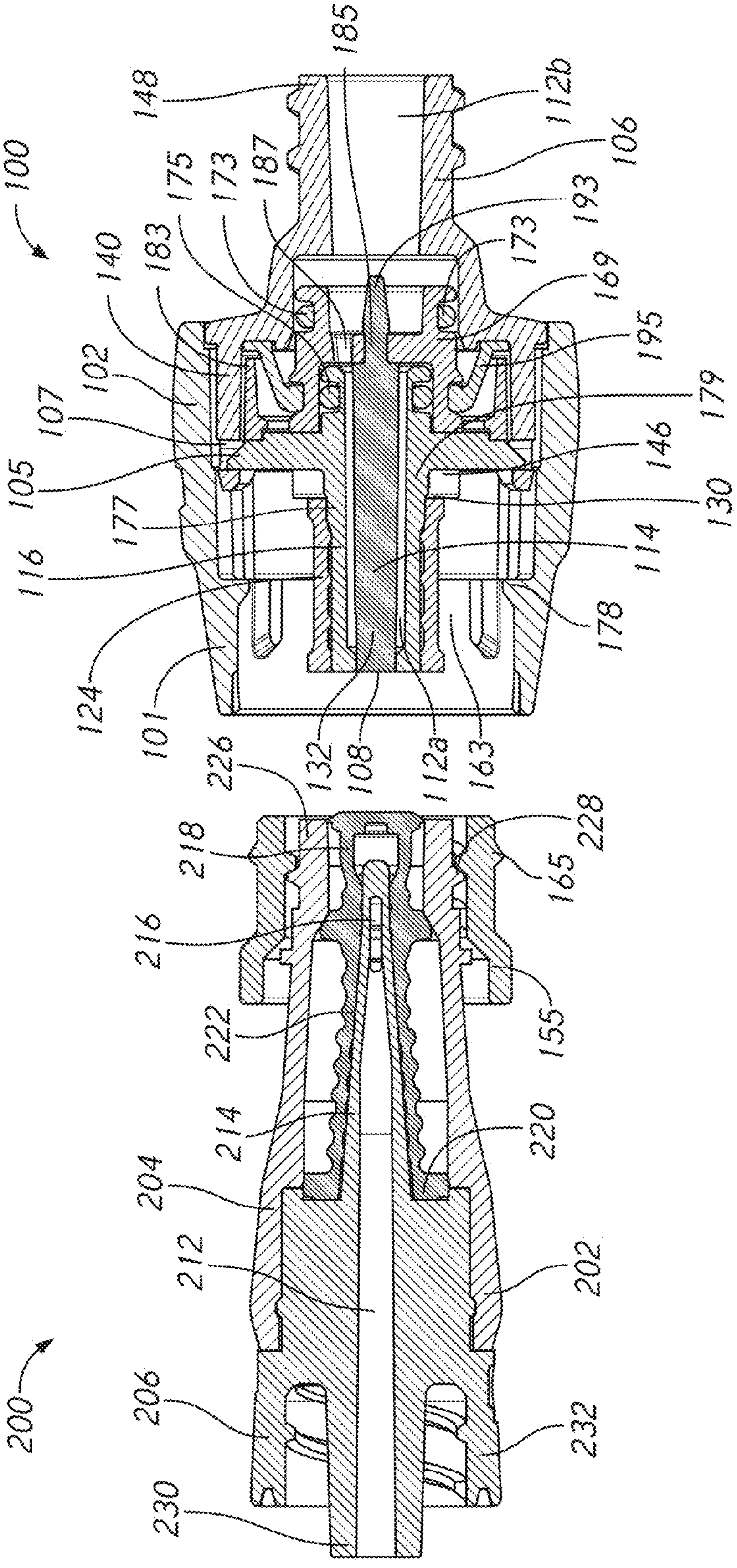
FIG. 73 shows the second connector detached from the main first connector, but still connected to the breakaway member portion thereof.

FIG. 71 shows a cross-sectional view of the first connector 100, with the breakaway member 155 engaged, and with the second connector 200 unconnected. FIG. 72 shows a cross-sectional view of the first connector 100 and the second connector 200 coupled together. FIG. 73 shows the second connector 200 detached from the main first connector 100, but still connected to the breakaway member 155 portion thereof. The first connector 100 can operate similar to other embodiments disclosed herein when coupled to a second connector 200. Although not shown in the Figures, a different type of second connector 200 can be used that does not have a projection 214, and that second connector 200 can engage the posts 101 to displace the activator member 169 and open the valve 114 (e.g., similar to FIGS. 68 to 70).

Many variations are possible. For example, various structures can be used to provide the breakaway engagement, such as pawl arms, recesses, ridges, notches, detents, etc. As discussed, the first connector 100 can be compatible with various types of second connectors 200, which may not include a projection 214. In some embodiments, the shaft 132 can be rigid.

In some embodiments, the recesses 159 and the associated protrusions 157 can be omitted. The breakaway member 155 can have a shape that is keyed to fit into the shape of the opening 153 in the housing 102. For example, both the breakaway member 155 and the opening 153 can the shape of a hexagon or other polygon. In some cases, an irregular shape can be used, for example to control the alignment of the breakaway member 155.

Figure 74:
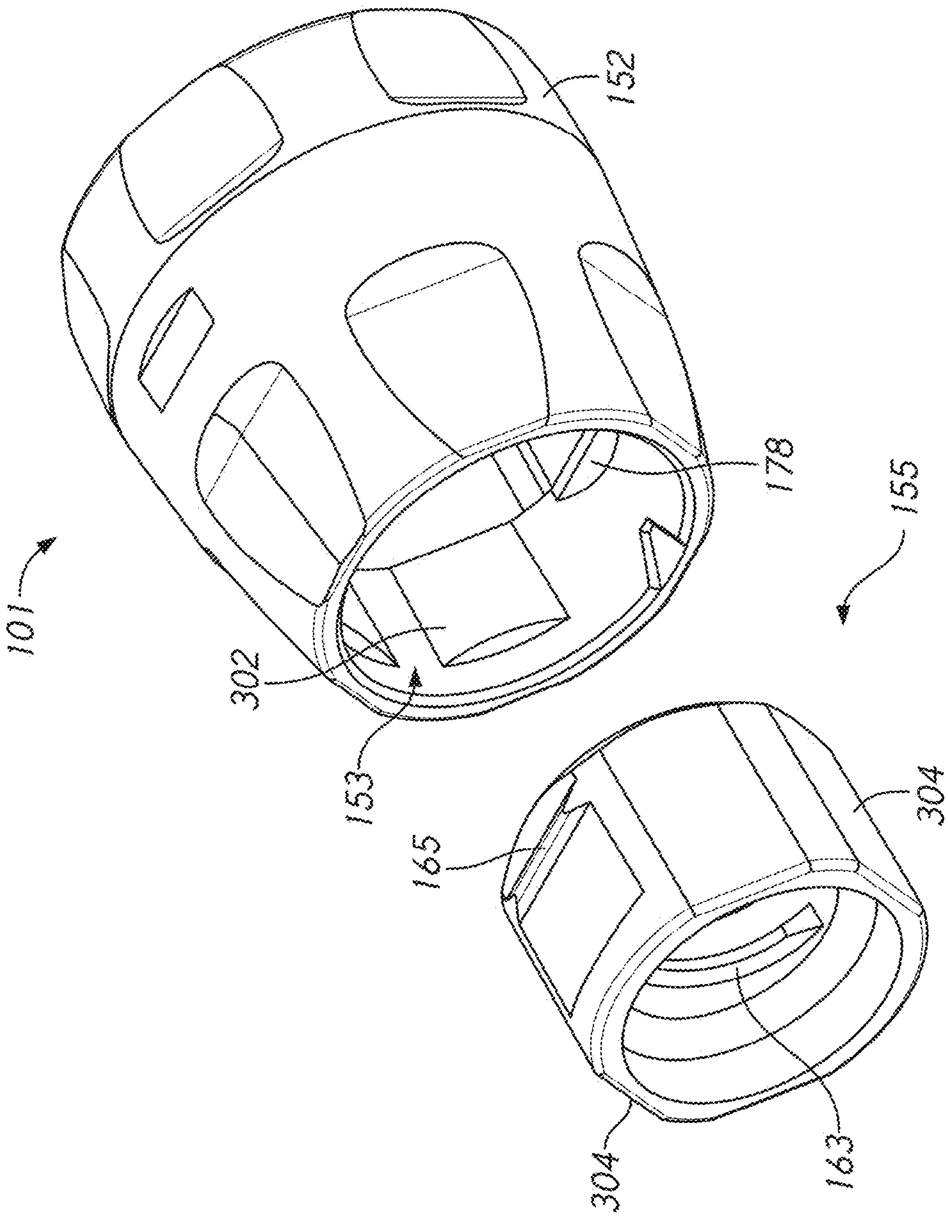
FIG. 74 shows an exploded view of an example embodiment of a housing portion and a breakaway member.
Figure 75:
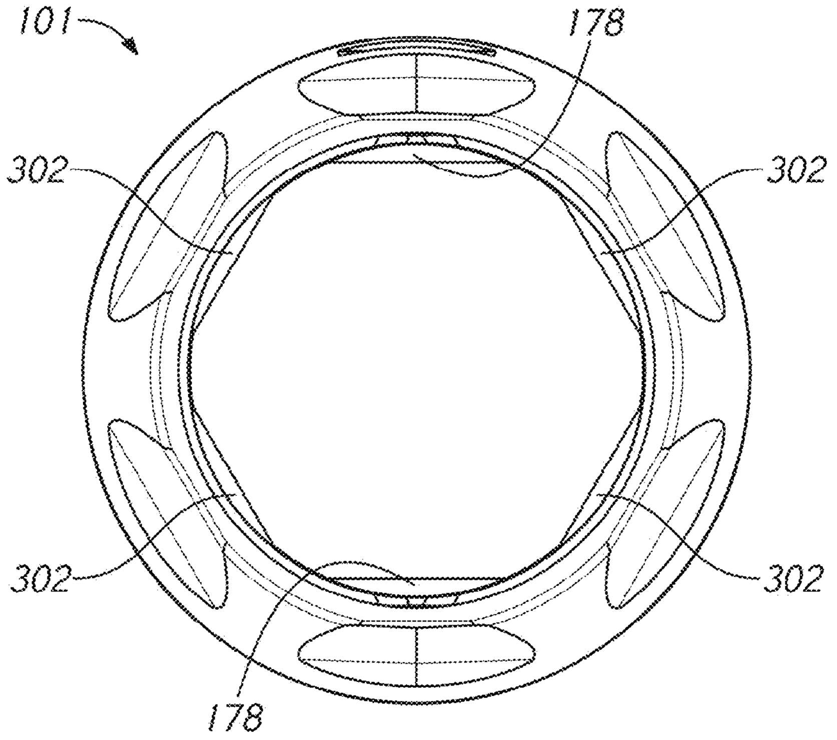
FIG. 75 shows the distal side of the housing portion.
Figure 76:
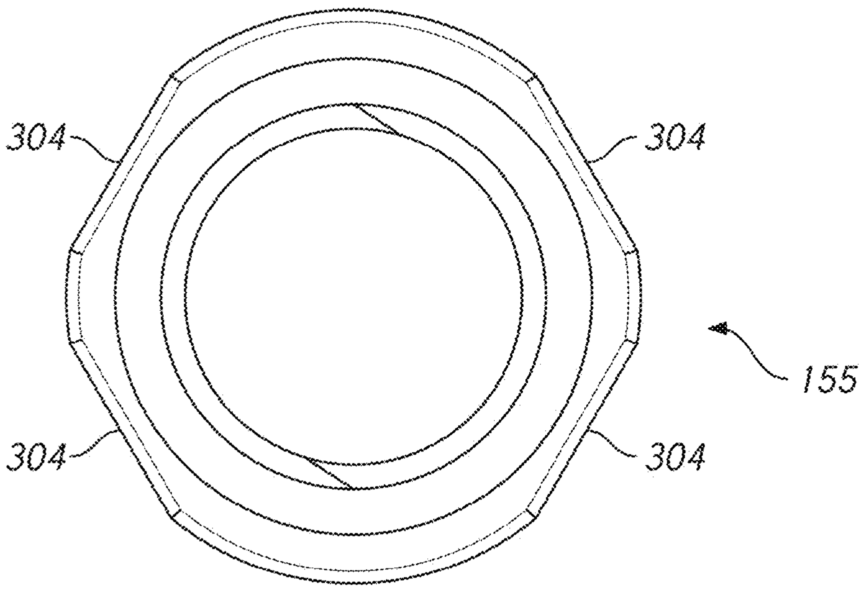
FIG. 76 shows the distal side of the breakaway member.

FIG. 74 shows an exploded view of an example embodiment of a housing portion 101 and a breakaway member 155. The other features of the connector are omitted from view, and could be similar to the other embodiments disclosed herein. FIG. 75 shows the distal side of the housing portion 101, and FIG. 76 shows the distal side of the breakaway member 155. The breakaway member 155 can have four flat surface 304, which can engage with four flat surfaces 302 on the inside of the housing portion 101. The breakaway member 155 can have two protrusions 165, which can engage with two corresponding protrusions 178 on the housing portion 101 to provide the breakaway connection. The engagement of the surfaces 302 and 304 can cause the protrusions 165 on the breakaway member 155 to be aligned with the protrusions 178 on the housing portion 101.

Figure 77:
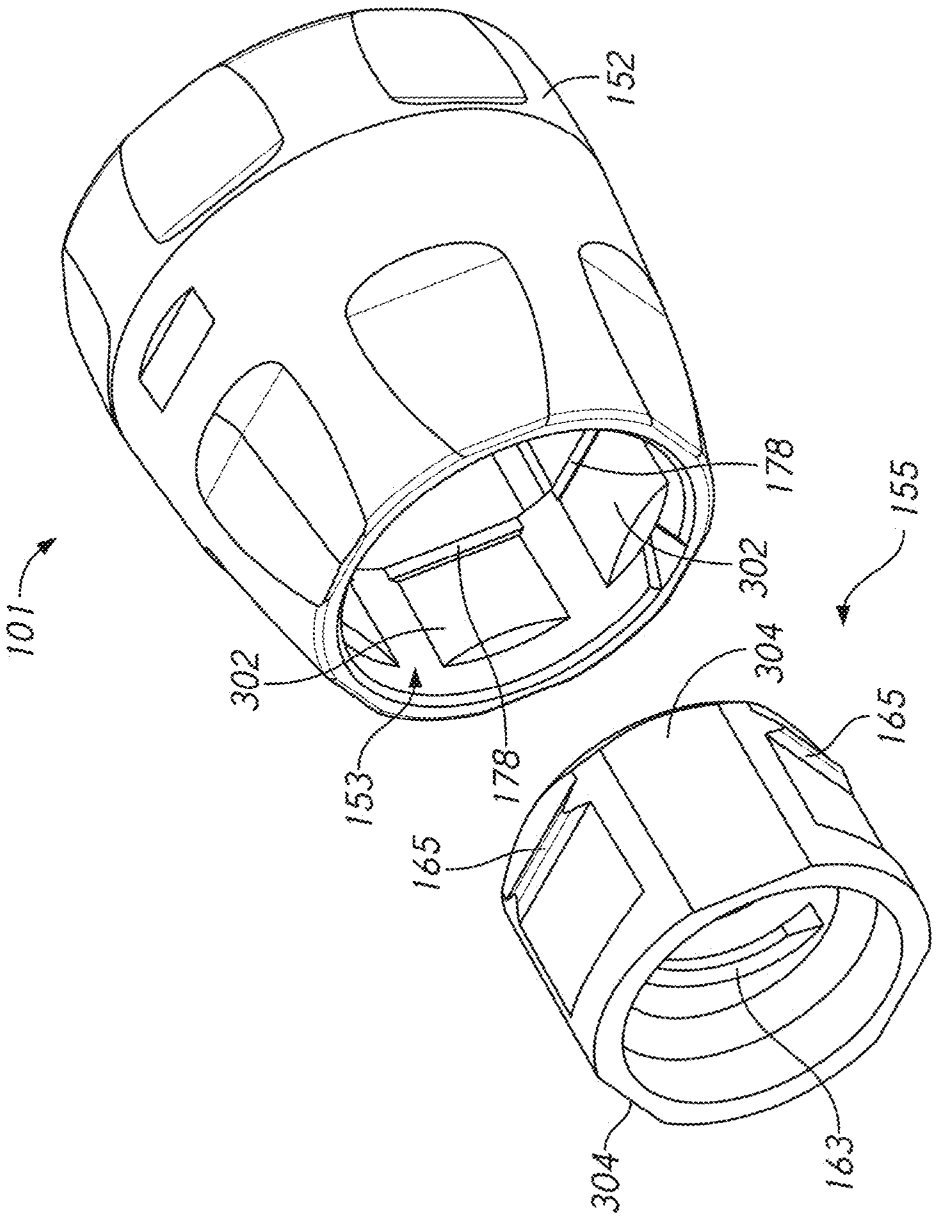
FIG. 77 shows another exploded view of an example embodiment of a housing portion and a breakaway member.

FIG. 77 shows an exploded view of another example embodiment of a housing portion 101 and a breakaway member 155. In the example of FIG. 77, the breakaway member can have three sides with the protrusions 165 that provide the breakaway connection, and three sides with the keyed surfaces 304, which can be flat. The housing portion 101 can have corresponding keyed surfaces 302 on each of the six sides, with protrusions 178 formed proximally of the keyed surface 302 on each of the six sides. In this embodiment, the breakaway member 155 can be inserted into the housing in any of the six configurations, since each side of the housing portion 101 can interface with either the keyed surfaces 304 or the breakaway protrusions 165. The keyed surfaces 302 and 304 can impede the breakaway member 155 from rotating relative to the housing portion 101.

Figure 78:
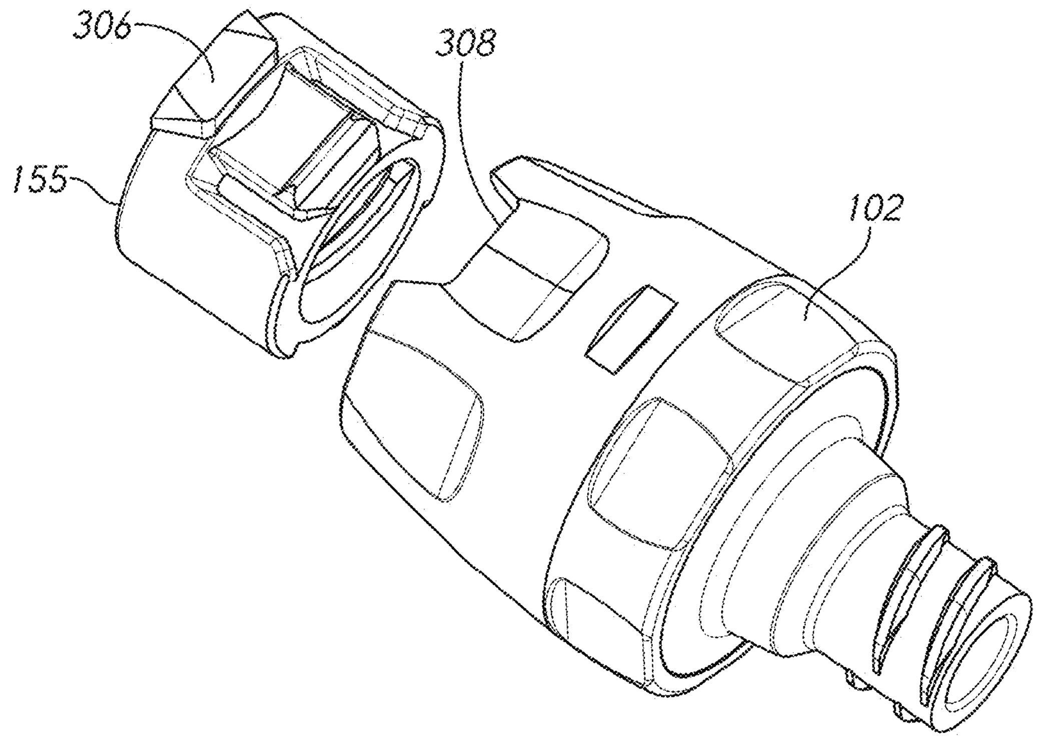
FIG. 78 shows another example embodiment of a breakaway member and housing.

FIG. 78 shows another example embodiment in which the breakaway member 155 can have a protrusion 306 that has a particular shape that is configured to fit into a corresponding notch in the housing 102. The engagement of the protrusion 306 and the notch 308 can impede the breakaway member 155 from rotating relative to the housing 102.

Figure 79:
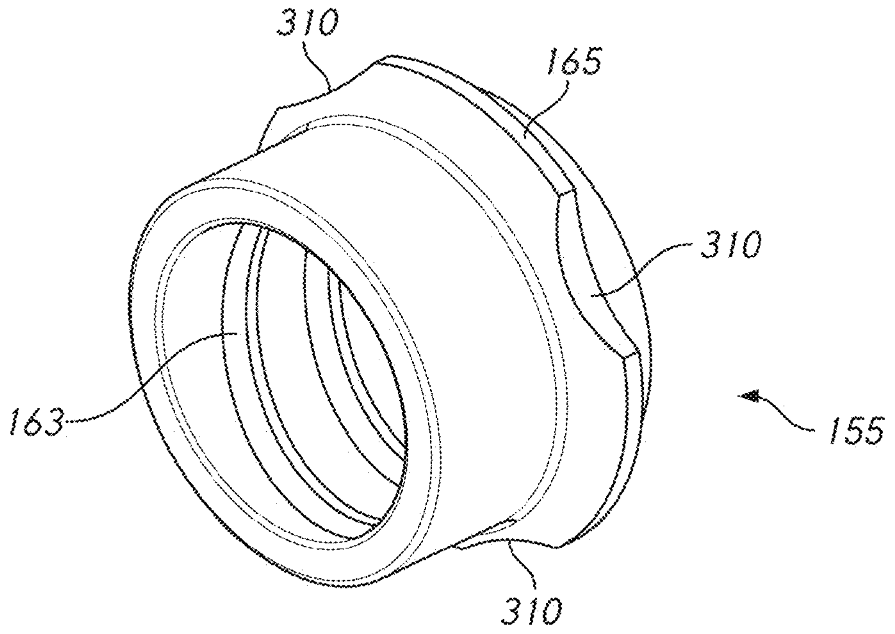
FIG. 79 shows another example embodiment of a breakaway member.

FIG. 79 shows another example embodiment of a breakaway member 155, which can have threads 163 to engage threading on a second connector 200 (e.g., standard female luer lock threading). The breakaway member 155 can have a protrusion 165 configured to engage breakaway features, similar to other embodiments disclosed herein. The protrusion 165 can be a ridge that extends along part or all of the periphery. The breakaway member 155 can have notches 310 formed in the protrusion 165 or ridge, which can provide gripping features for the user to grip the breakaway member 155, which can facilitate screwing the breakaway member 155 onto a second connector 200.

Figure 80:
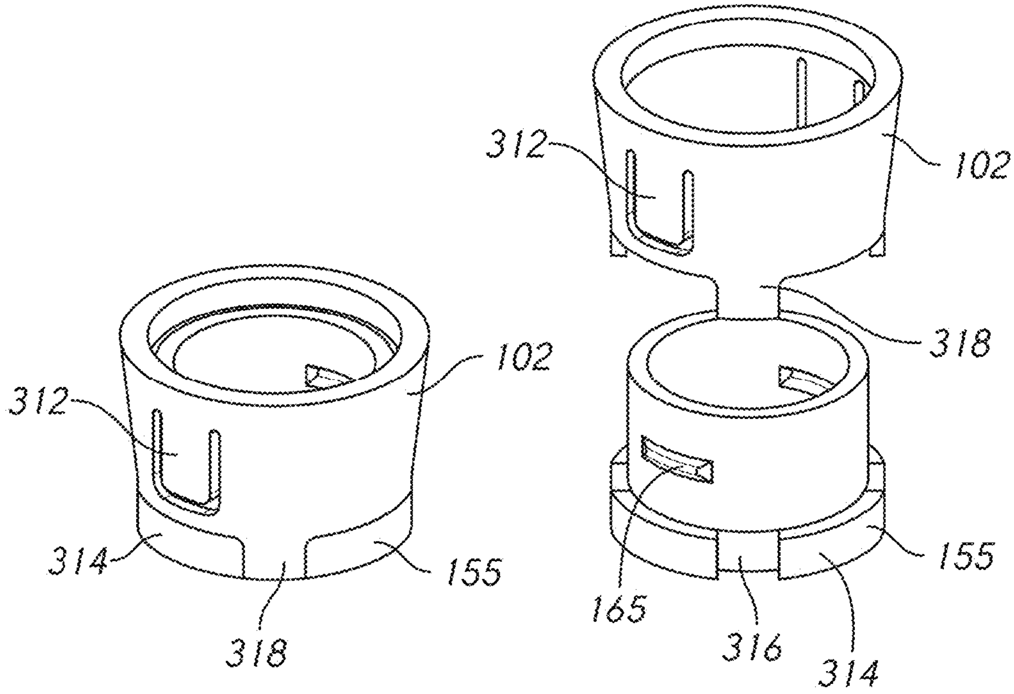
FIG. 80 shows an example embodiment of a housing portion and a breakaway member.
Figure 81:
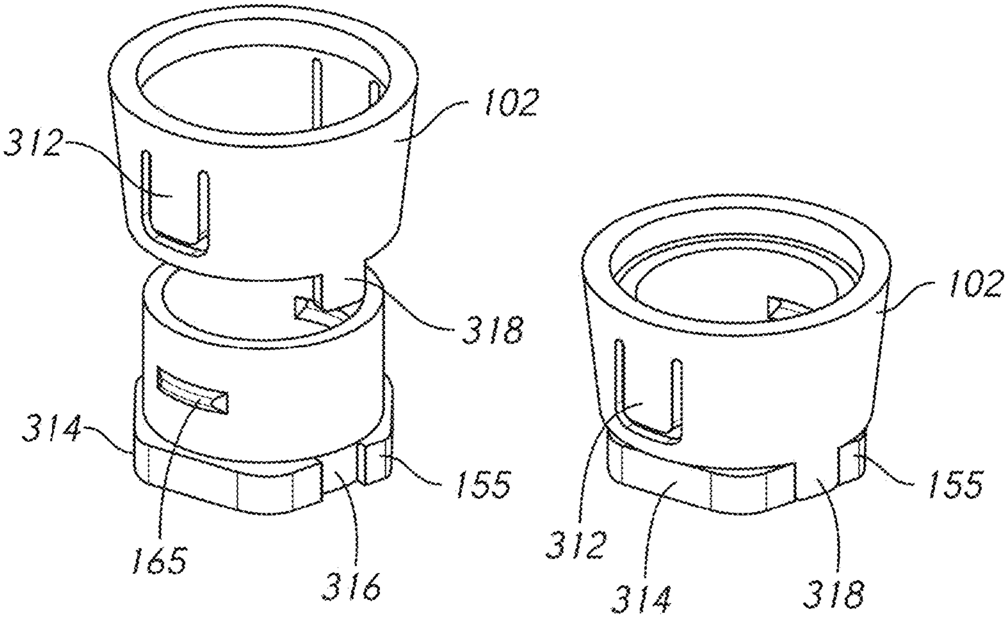
FIG. 81 shows another example embodiment of a housing portion and a breakaway member.

FIG. 80 shows an example embodiment of a housing 102 portion and a breakaway member 155. Other portions of the connector 100 are omitted from view and can be similar to the other embodiments disclosed herein. In FIG. 80, the left side shows the housing 102 and breakaway member 155 in an assembled configuration, and the right side shows the housing 102 and the breakaway member in a disengaged configuration. FIG. 81 shows another example embodiment of a housing 102 portion and a breakaway member 155. Other portions of the connector 100 are omitted from view and can be similar to the other embodiments disclosed herein. In FIG. 81, the right side shows the housing 102 and breakaway member 155 in an assembled configuration, and the left side shows the housing 102 and the breakaway member in a disengaged configuration. The housing 102 can include engagement features, which can be pawl arms 312, which can be configured to removably engage with protrusions 165 on the breakaway member 155. The pawl arms 312 can have teeth configured to engage the protrusions 165. The pawl arms 312 can flex outward during engagement and/or during disengagement. The pawl arm 312 can be coupled to the rest of the housing on one side, and can be uncoupled on 3 sides, which can enable the pawl arm 312 to flex outward.

The breakaway member 155 can have internal threading to engage a second connector 200, similar to other embodiments disclosed herein. The breakaway member 155 can have a first portion that is configured to be inserted into the housing 102, and a second portion that is configured to remain outside the housing 102, even when engaged with the housing 102. The breakaway member 155 can have a step or lip 314, which can impede further insertion of the breakaway member 155. In some embodiments, the lip 314 can have one or more notches 316, and the housing 102 can have one or more corresponding distal projections 318 that can engage the notches 316. In FIG. 81, the lip 314 can have a polygonal (e.g., hexagon) shape, which can facilitate threading the breakaway member 155 onto the second connector 200.

Figure 82:
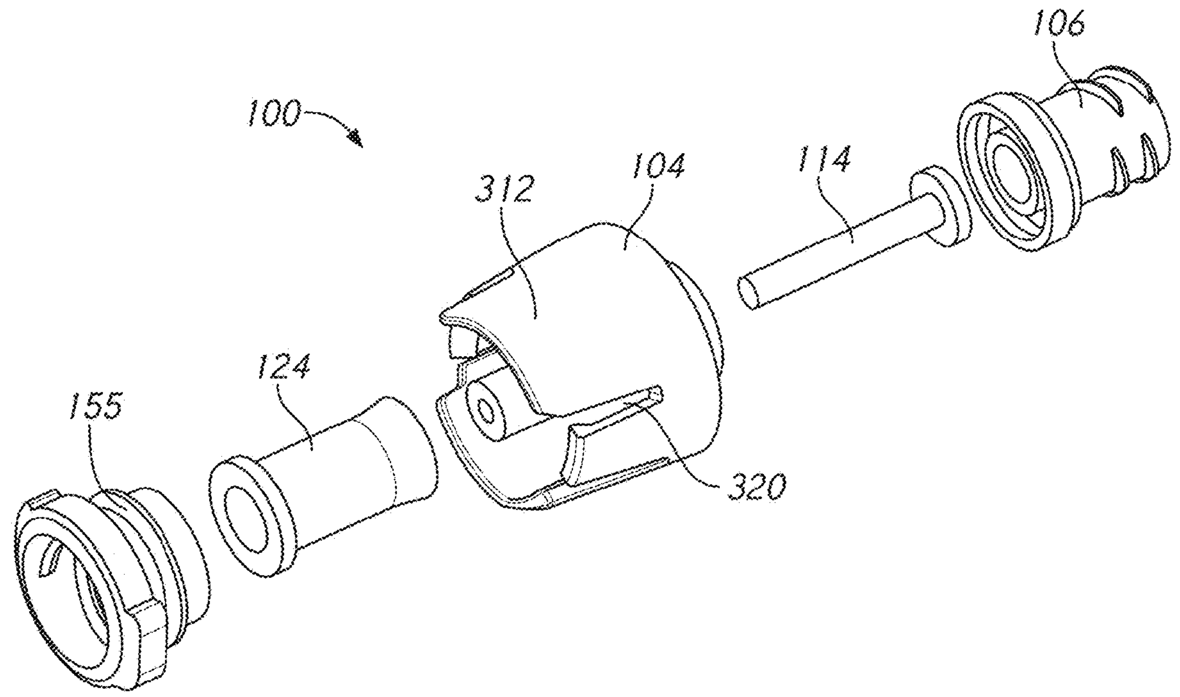
FIG. 82 shows an exploded view of another example embodiment of a connector.

FIG. 82 shows an exploded view of another example embodiment of a connector 100. The connector 100 can have a first housing portion 104, a second housing portion 106, a valve 114, a cover 124, and breakaway member 155. The housing first portion 104 can include slits 320, which can facilitate flexing of the housing portion 104 during the engagement and/or disengagement of the breakaway member 155 from the rest of the connector. The housing 102 can have fours slits 320, or any other suitable number (e.g., 1, 2, 3, 4, 6, 8, etc.). The slits 320 can define pawl arms 312, which can have teeth or other engagement features to engage the breakaway adapter 155. In some embodiments, the housing 102 has no slits and the distal end of the housing 102 can have a substantially continuous (e.g., annular) surface.

Figure 83:
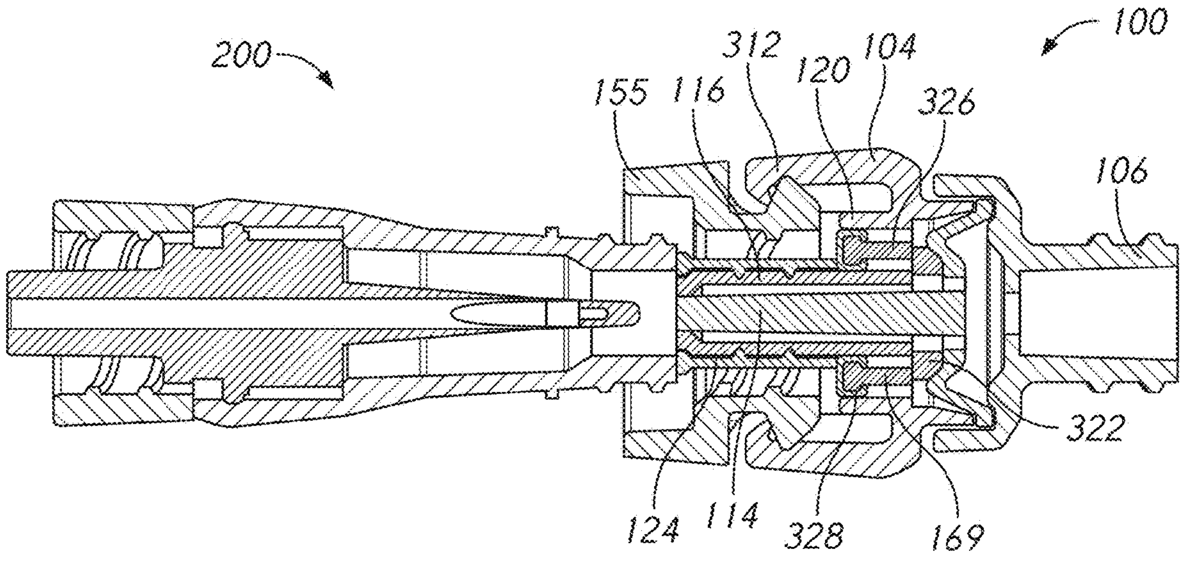
FIG. 83 is a cross-sectional view of an example embodiment of a connector with a second connector position partially inserted into the housing.
Figure 84:
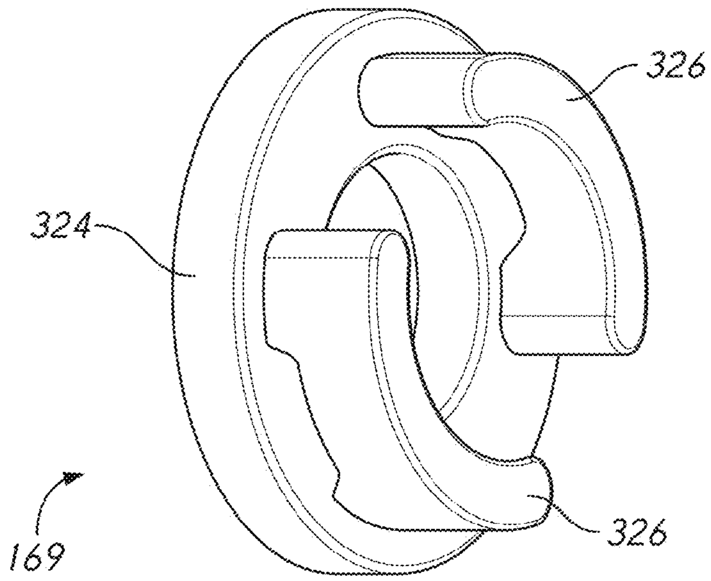
FIG. 84 shows an example of the activation member.

FIG. 83 is a cross-sectional view of an example embodiment of a connector 100 with a second connector 200 position partially inserted into the housing 102, but before engaging the valve 114 or the breakaway member 155. The connector 100 can include a housing (e.g., with first housing portion 104 and second housing portion 106), a valve 114, a cover 124, a breakaway member 155, and an activation member 169, which can be similar to the other embodiments disclosed herein. FIG. 84 shows an example of the activation member 169. The activation member 169 can include a distal body portion 324, which can have an opening therethrough. The projection 116 can be received into the opening. The body portion 324 can be an annular piece. In some embodiments, the proximal end of the cover 124 can contact or otherwise interface with the body portion 324 so that the cover 124 can push the activation member 169 proximally when the second connector 200 is coupled to the first connector 100. The activation member 169 can include arms 326, which can extend proximally from the body portion 324. The arms 324 can extend through a hole or gap in the housing 102, in some embodiments. In some cases, the arms 326 can push the valve 114 proximally to unseat the valve shaft to open the fluid pathway when the second connector 200 is coupled to the first connector 100.

Figure 86:
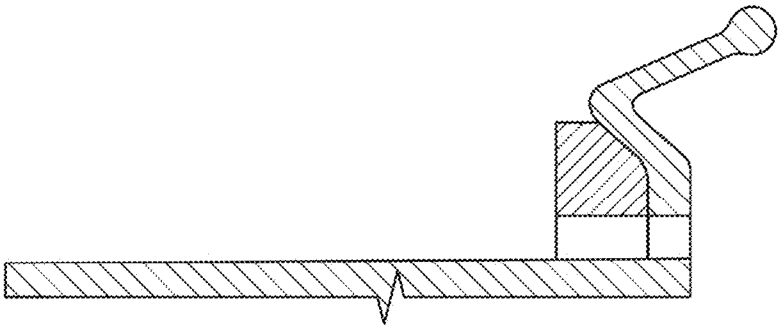
FIG. 86 shows an example of a valve with a washer.
Figure 87:
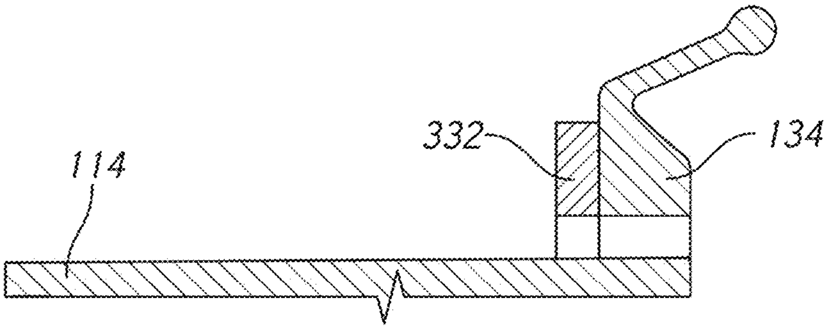
FIG. 87 shows another example of a valve with a washer.
Figure 88:
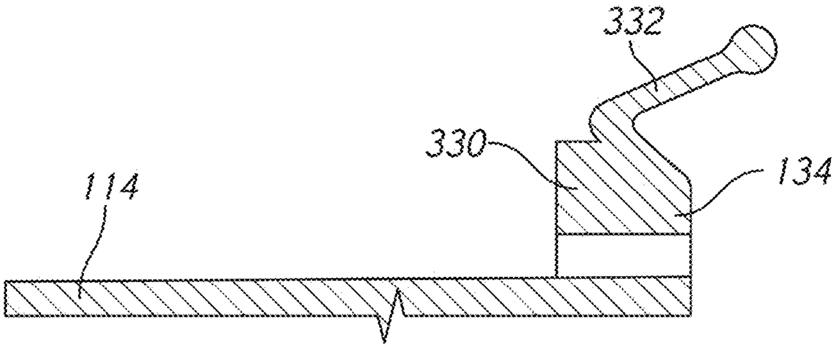
FIG. 88 shows an example of a valve with a thick region for interfacing with the activation member.

As shown in FIG. 83, the connector 100 can include a washer 322 between the arms 326 and the valve 114. The washer can have an annular shape with an opening therethrough. The washer 322 can distribute the force of the arms 326 on the valve 114 (e.g., on a flange portion thereof). The opening through the washer 322 can be sufficiently large that it permits fluid to flow therethrough with the valve shaft also extending through the opening. In some embodiments the washer 322 can be omitted, and the arms 326 can press directly on the valve 114. The proximal end of the washer 322 can be shaped corresponding to the contour of the valve 114 (e.g., the flange portion 134) at the location where the washer 322 contacts the valve 114, as shown in FIGS. 83 and 86. In some embodiments, the valve 114 can have a thickened region, which can receive a washer 322 with a flat proximal side, as shown in FIG. 87. In some cases, the valve 114 can have a thick region 330 at least at the locations where the arms 326 will push on the valve 114, which can serve to distribute the force, and more reliably open the valve, so that the washer 322 can be omitted, as shown in FIG. 88, for example. The thick region 330 can have a thickness that is about double the thickness, about 2.5 times, about 3 times, about 3.5 times, about 4 times, about 4.5 times, about 5 times, or more, the thickness of the biasing portion 332.

Figure 85:
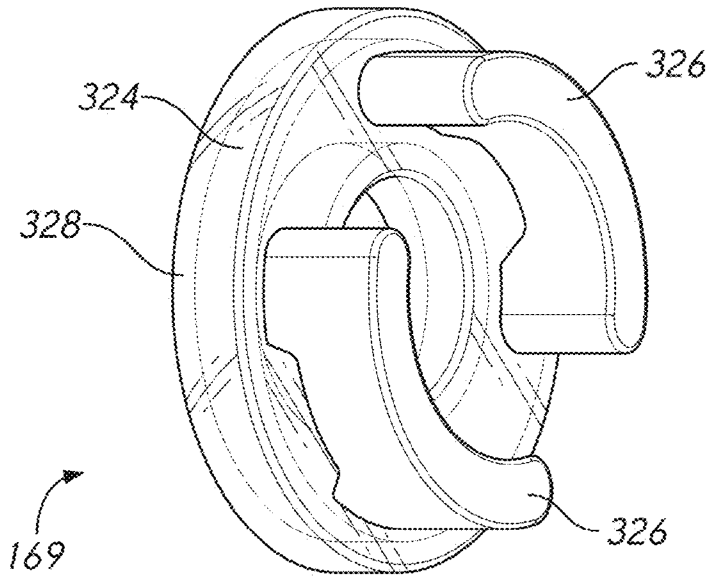
FIG. 85 shows an example of the activation member with an overmolded seal.

As shown in FIG. 83, the activation member 169 can have one or more seals 324, which can seal against the housing portions (e.g., against the outside of the projection 116 and/or against the inside of the outer wall 120, such as to impede the fluid from leaking out of the fluid path or out of the connector 100. When the activation member 169 moves, the seal(s) 328 can slide longitudinally against the housing portions and can maintain a substantially fluid-tight seal as they move. In some embodiments, the seals 324 can be overmolded onto the activation member 169, such as over a distal portion thereof. The overmolded seal 328 can be one continuous body of material, but it can seal against at least two different surfaces, and can be considered to be multiple seals. The body portion of the activation member 169 can be formed of polycarbonate or another relatively rigid material, and the seal(s) 328 can be formed of silicone or another relatively soft or resilient material, which in some cases can be overmolded over the posts 146. FIG. 85 shows an example of an activation member 169, with an overmolded seal 328.

Figure 89:
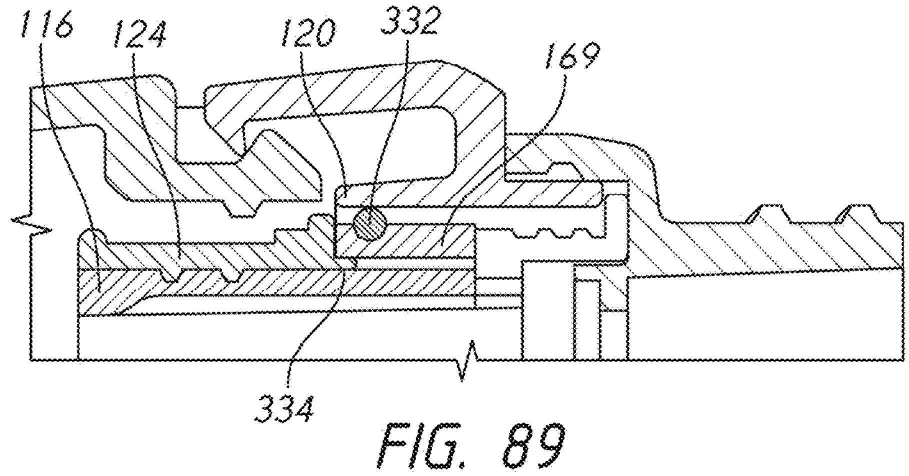
FIG. 89 is a partial view of a connector that has an O-ring and a face seal that seal the activation member.

In some cases, O-rings can be used for the seals. For example, an O-ring 332 can be mounted on the radially outside surface of the body portion 324 of the activation member 169, and the O-ring 332 can seal against the wall 120. In some embodiments, the proximal end of the cover 124 or face seal can form a seal between the projection 116 and the activation member 169, as shown in FIG. 89. The cover 124 or face seal can be coupled to the activation member by an adhesive, by over-molding, by a clamp, by a fastener, or any other suitable manner, which can enable the seal between the projection 116 and the activation member 169.

Figure 90:
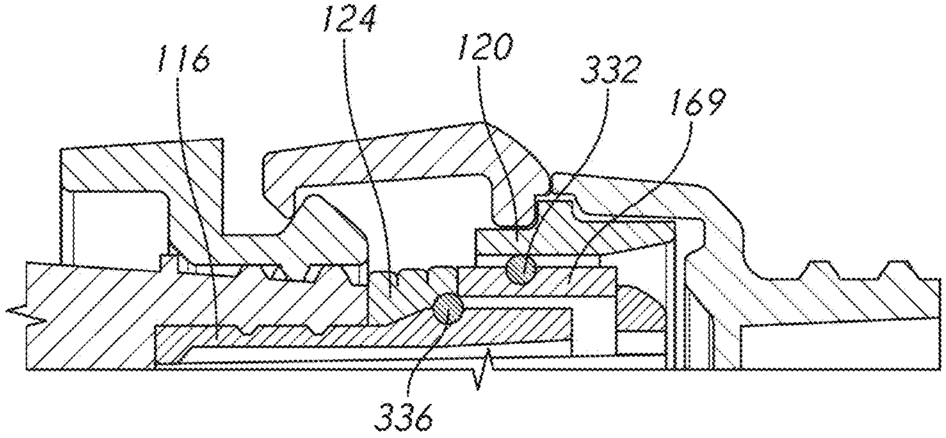
FIG. 90 is a partial view of a connector that has two O-rings for sealing the activation member.
Figure 91:
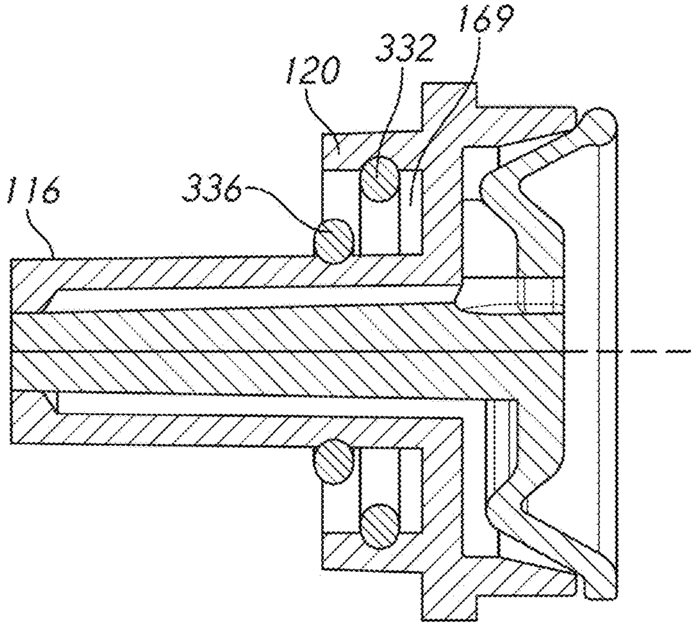
FIG. 91 is another example of a connector that has two O-rings for sealing the activation member.

With reference to FIG. 90, in some embodiments, a first O-ring 332 can be disposed on an outside of the activation member 169 (e.g., to seal against the wall 120), and a second O-ring 336 can be disposed on an inside of the activation member 169 (e.g., to seal against the projection 116). In some embodiments, an O-ring 336 can be mounted to the exterior of the projection 116, such as for sealing between the projection 116 and the activation member 169. In some embodiments, an O-ring 332 can be mounted on the inside of the wall 120, as shown for example in FIG. 91.

Figure 92:
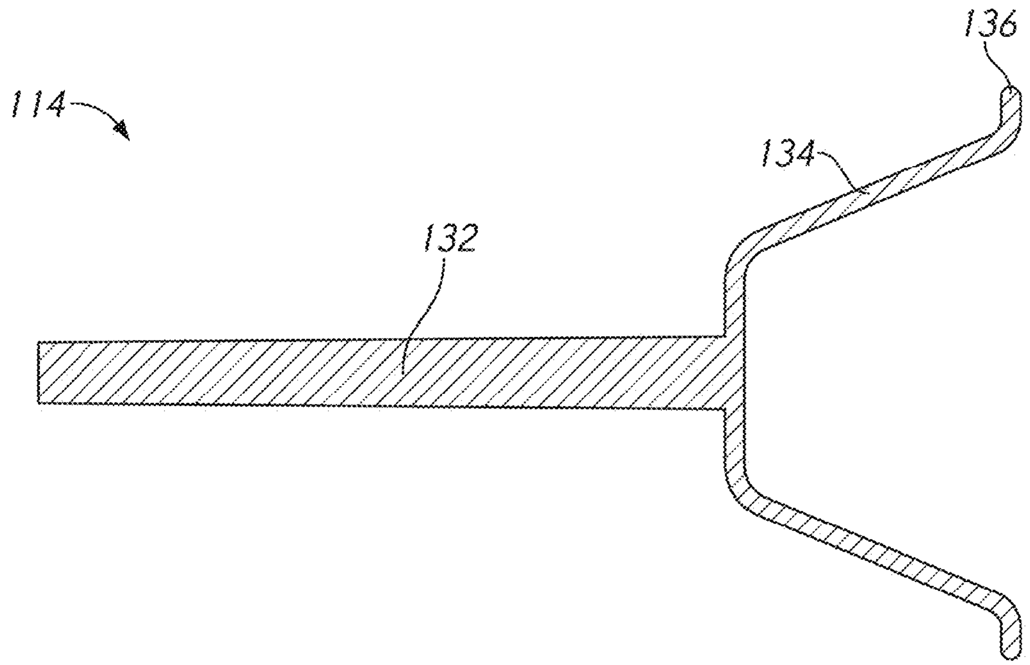
FIG. 92 shows an example embodiments of a valve in an as-molded or un-deformed state
Figure 93:
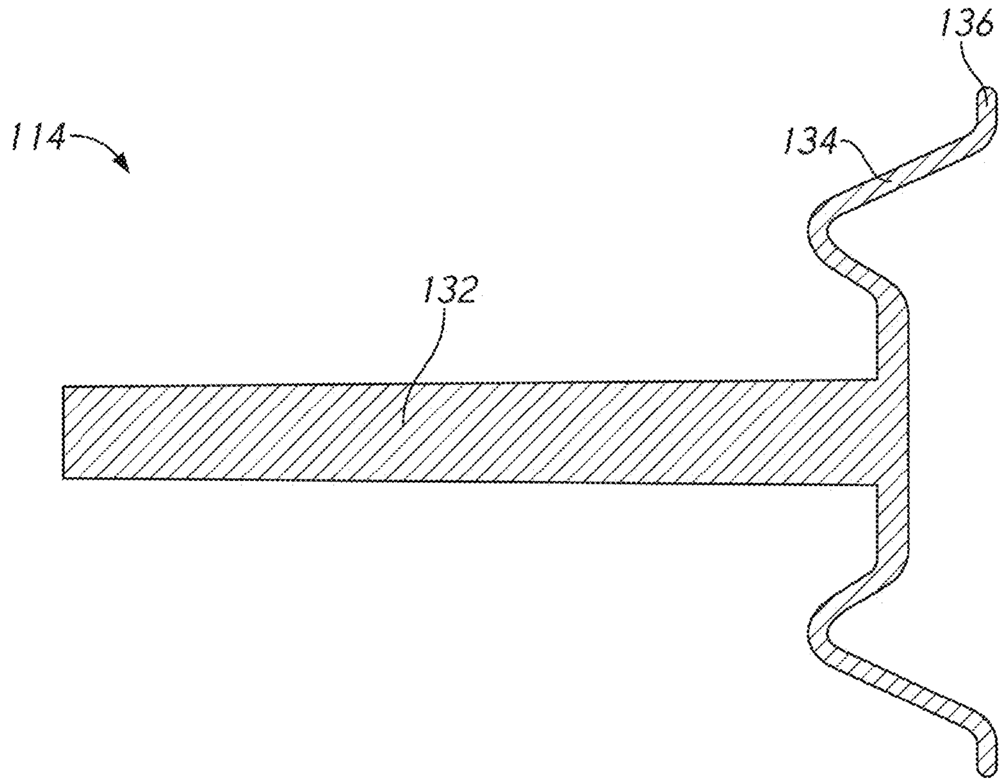
FIG. 93 shows an example embodiment of the valve in an assembled state.

FIG. 92 shows an example embodiments of a valve 114 in an as-molded or un-deformed state. FIG. 93 shows an example embodiment of the valve 114 in the assembled state, with the rest of the connector 100 omitted from view. The valve 114 can be preloaded distally. When the valve 114 is displaced proximally, such as by the activation member 169, the valve 114 can become further loaded with energy.

Figure 94:
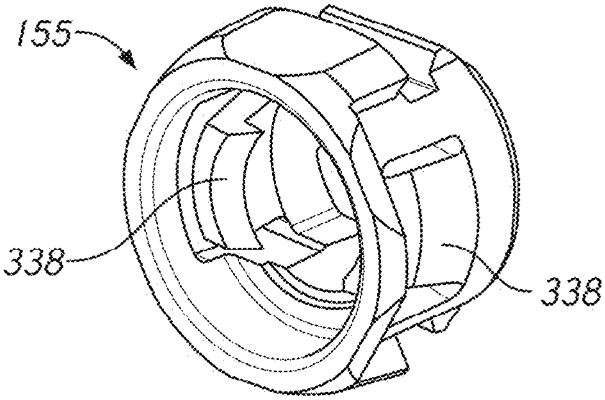
FIG. 94 is a perspective view of a distal end of an example embodiment of a breakaway member.
Figure 95:
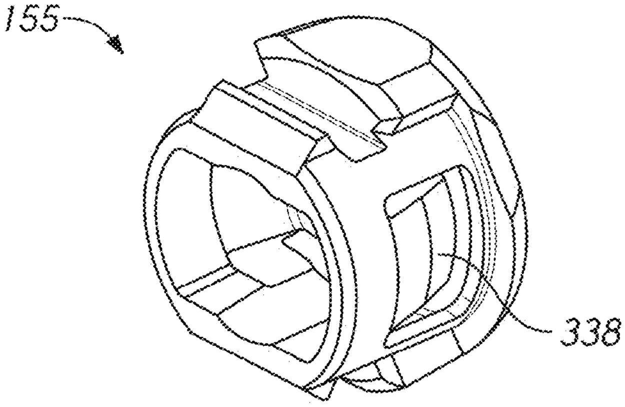
FIG. 95 is a perspective view of a proximal end of the example embodiment of a breakaway member.
Figure 96:
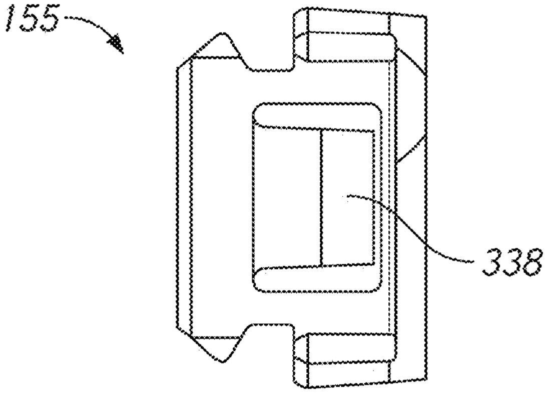
FIG. 96 is a side view of the example embodiment of a breakaway member.
Figure 97:
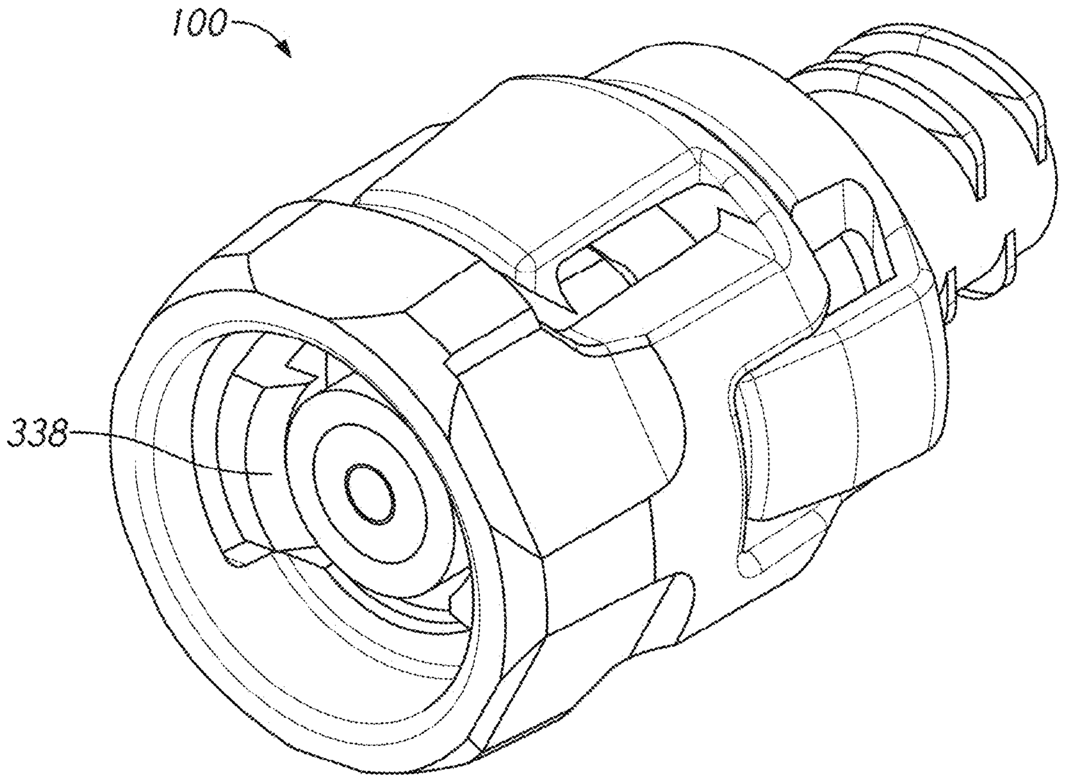
FIG. 97 shows the example breakaway member engaged with the rest of a corresponding first connector.
Figure 98:
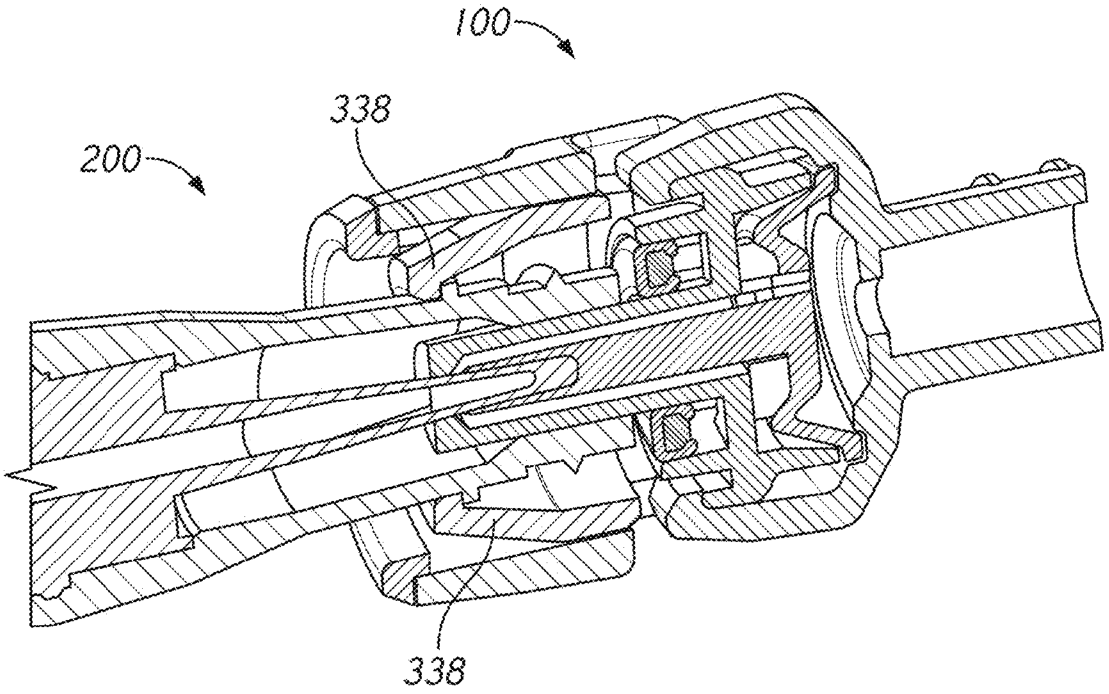
FIG. 98 shows a second connector coupled to the first connector using the breakaway member of FIGS. 94-96.

FIG. 94 is a perspective view of a distal end of an example embodiment of a breakaway member 155. FIG. 95 is a perspective view of a proximal end of the example embodiment of a breakaway member 155. FIG. 96 is a side view of the example embodiment of a breakaway member 155. FIG. 97 shows the example breakaway member 155 engaged with the rest of a corresponding first connector 100. FIG. 98 shows a second connector 200 coupled to the first connector 100 using the breakaway member 155 of FIGS. 94-96. The breakaway member 155 can include a plurality (e.g., 2 or any suitable number) of arms configured to engage the second connector 200 with snap-fit engagement. The connector 200 can be coupled to the first connector 100 with a push-to-connect action.

Figure 99:
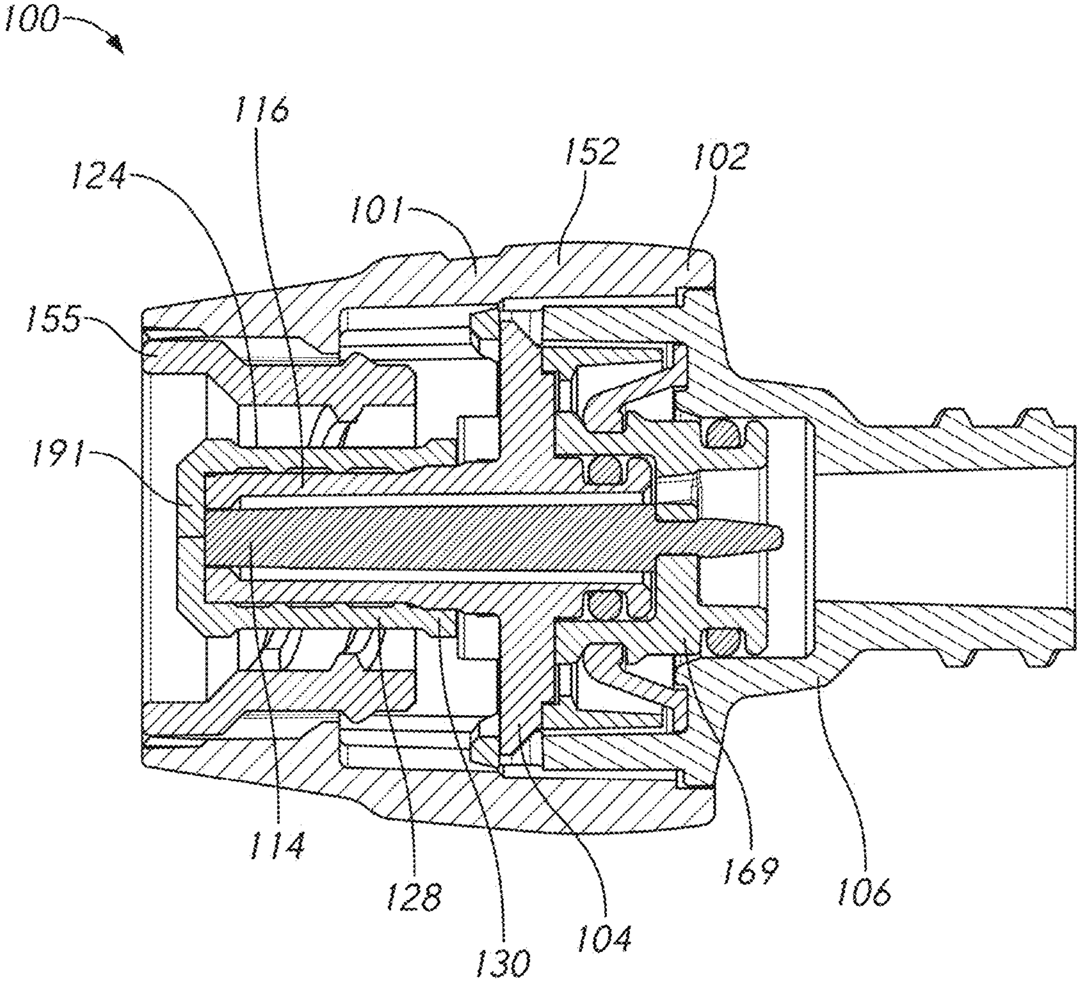
FIG. 99 shows a cross-sectional view of another example embodiment of a medical connector.

FIG. 99 shows a cross-sectional view of another example embodiment of a medical connector 100, which can be similar to the other embodiments disclosed herein except as described herein. The connector 100 can include a cover 124 or face seal that can have a closed position that covers the distal end of the projection 116 and/or the distal end of the valve 114. The cover 124 can have an wall 191, which can be at the distal end of the cover 124. The wall 191 can have a slit that can have a closed configuration (e.g., as shown in FIG. 99) and an open configuration. The cover 124 can have a closed distal end in its default assembled configuration. When the second connector 200 is attached to the first connector 100, the housing of the second connector 200 can engage the cover 124 (e.g., the wall 191) and can push the cover proximally, which can open the slit in the wall 191. In some cases, the projection 116 can extend through the slit when the cover 124 is displaced to its open configuration. When the second connector 200 is detached from the first connector, the cover 124 can return to its default or closed configuration. The biasing structure 128 (e.g., the resilient sleeve) can push the wall 191 portions back over the end of the projection 116, and the slit can close. In the closed configuration, a portion of the cover 124 (e.g., the proximal or inside surface of the wall 191) can contact a portion of the valve 114 (e.g., the distal end thereof). As can be seen in FIG. 99, when the cover 124 is closed the wall 191 (e.g., the distal end thereof) can be recessed in the cavity. The outer wall 152 or third housing portion 101 can extend further distally than the distal end of the cover 124, such as be any of the distances or ranges discussed herein.

ADDITIONAL INFORMATION

Various alternatives and combinations of the disclosed features can be used. Also, the proportions and ratios of the sizes of various components, edges, and surfaces that are shown in the Figures are intended to form part of this disclosure, even when not specifically discussed.

Unless the context clearly requires otherwise, throughout the description and the claims, the words "comprise," "comprising," "include," "including," and the like are to be construed in an inclusive sense, as opposed to an exclusive or exhaustive sense; that is to say, in the sense of "including, but not limited to." The words "coupled" or connected," as generally used herein, refer to two or more elements that can be either directly connected, or connected by way of one or more intermediate elements. Additionally, the words "herein," "above," "below," and words of similar import, when used in this application, shall refer to this application as a whole and not to any particular portions of this application. Where the context permits, words in the Detailed Description using the singular or plural number can also include the plural or singular number, respectively. The words "or" in reference to a list of two or more items, is intended to cover all of the following interpretations of the word: any of the items in the list, all of the items in the list, and any combination of the items in the list. All numerical values provided herein are intended to include similar values within a range of measurement error.

Although this disclosure contains certain embodiments and examples, it will be understood by those skilled in the art that the scope extends beyond the specifically disclosed embodiments to other alternative embodiments and/or uses and obvious modifications and equivalents thereof. In addition, while several variations of the embodiments have been shown and described in detail, other modifications will be readily apparent to those of skill in the art based upon this disclosure. It is also contemplated that various combinations or sub-combinations of the specific features and aspects of the embodiments may be made and still fall within the scope of this disclosure. It should be understood that various features and aspects of the disclosed embodiments can be combined with, or substituted for, one another in order to form varying modes of the embodiments. Any methods disclosed herein need not be performed in the order recited. Thus, it is intended that the scope should not be limited by the particular embodiments described above.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment. Any headings used herein are for the convenience of the reader only and are not meant to limit the scope.

Further, while the devices, systems, and methods described herein may be susceptible to various modifications and alternative forms, specific examples thereof have been shown in the drawings and are herein described in detail. It should be understood, however, that the disclosure is not to be limited to the particular forms or methods disclosed, but, to the contrary, this disclosure covers all modifications, equivalents, and alternatives falling within the spirit and scope of the various implementations described. Further, the disclosure herein of any particular feature, aspect, method, property, characteristic, quality, attribute, element, or the like in connection with an implementation or embodiment can be used in all other implementations or embodiments set forth herein. Any methods disclosed herein need not be performed in the order recited. The methods disclosed herein may include certain actions taken by a practitioner; however, the methods can also include any third-party instruction of those actions, either expressly or by implication.

The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers and should be interpreted based on the circumstances (e.g., as accurate as reasonably possible under the circumstances, for example ±5%, ±10%, ±15%, etc.). For example, "about 3.5 mm" includes "3.5 mm." Phrases preceded by a term such as "substantially" include the recited phrase and should be interpreted based on the circumstances (e.g., as much as reasonably possible under the circumstances). For example, "substantially constant" includes "constant." Unless stated otherwise, all measurements are at standard conditions including ambient temperature and pressure.

The following is claimed:

1. A breakaway medical connector comprising:

a base portion;

a projection that extends distally from the base portion;

a distal opening at a distal end of the projection;

a proximal end with a proximal opening;

a fluid pathway that extends between the distal opening and the proximal opening, wherein the fluid pathway extends inside the projection;

a valve disposed inside the projection and having a closed configuration that closes the fluid pathway at the distal opening and an open configuration that opens the fluid pathway at the distal opening;

an outer wall that extends distally further than the distal end of the projection, a cavity formed between the projection and the outer wall;

one or more first engagement features;

a breakaway member disposed in the cavity between the projection and the outer wall, the breakaway member comprising:

one or more second engagement features that are configured to engage with the first engagement features to retain the breakaway member in the cavity; and a coupling interface configured to couple to a second medical connector and to position the second medical connector to open the valve and to establish fluid communication between the second medical connector and fluid pathway when the second medical connector is coupled to the breakaway member when the second engagement features are engaged with the first engagement features;

wherein the first engagement features and the second engagement features are configured to disengage if a force above a threshold pulls the breakaway member in a distal direction, to thereby provide a breakaway disconnection.

2. The breakaway medical connector of claim 1, further comprising a face seal disposed outside the projection, wherein the face seal has a first configuration with the distal end of the face seal substantially flush with the distal end of the projection and substantially flush with the distal end of the valve, wherein connecting the second medical connector moves the face seal to a second configuration with the face seal displaced proximally from the distal end of the projection.

3. The breakaway medical connector of claim 2, wherein the face seal is configured to form a seal with the proximal end of the second connector when the second connector is coupled to the breakaway member.

4. The breakaway medical connector of claim 2, wherein the projection includes a widened portion, and wherein a proximal portion of the face seal is configured to engage the widened portion of the projection.

5. The breakaway medical connector of claim 2, wherein connection of the second connector to the breakaway member moves the proximal end of the face seal in a proximal direction.

6. The breakaway medical connector of claim 5, further comprising an activation member configured to move proximally with the proximal movement of the proximal end of the face seal, and wherein the activation member is configured to pull the valve proximally to open the valve.

7. The breakaway medical connector of claim 6, wherein the activation member is biased distally.

8. The breakaway medical connector of claim 7, wherein the activation member is configured to push the valve distally to close the valve upon breakaway disconnection of the second connector.

9. The breakaway medical connector of claim 6, wherein the base portion includes openings, and wherein the activation member includes a body portion on a first side of the base portion and posts that extend through the openings of the base portion.

10. The breakaway medical connector of claim 1, wherein the breakaway member is configured to be reattached after the breakaway disconnection to reestablish fluid communication between the second medical connector and the fluid pathway of the breakaway medical connector.

11. The breakaway medical connector of claim 10, wherein the outer wall defines an opening that is sufficiently large to permit swabbing of the distal ends of the projection and the distal end of the valve before reattachment.

12. The breakaway medical connector of claim 1, wherein the coupling interface on the breakaway member includes internal threading configured to engage threads of a standard female luer lock.

13. The breakaway medical connector of claim 12, wherein the breakaway medical connector is configured to form a seal with the second connector without using a standard luer taper connection.

14. The breakaway medical connector of claim 1, wherein the valve is a dual-mode valve that is configured to open when either:

a projection of the second medical connector is inserted into the distal opening of the projection of the breakaway connector to push the valve proximally; or a housing of the second medical connector pushes an activation member proximally when the activation member is coupled to the valve to thereby pull the valve proximally.

15. The breakaway medical connector of claim 1, wherein the valve includes a flexible shaft.

16. The breakaway medical connector of claim 1, wherein the outer wall has a distal opening formed by a continuous distal surface with no slits, the distal opening configured to permit the breakaway member to pass therethrough.

17. The breakaway medical connector of claim 16, wherein the outer wall has no openings that connect the cavity to the area outside the connector, other than the distal opening.

18. The breakaway medical connector of claim 1, wherein the outer wall has a distal opening having a first shape, and wherein the breakaway member has a second shape that is keyed with the first shape to impede rotation of the breakaway member relative to the outer wall.

19. A medical connector comprising:

a housing having:

an outer wall;

a first opening; and a second opening;

a fluid pathway between the first opening and the second opening;

a hollow projection that defines an interior cavity that forms a portion of the fluid pathway, the projection disposed inward of the outer wall to form a cavity between the projection and the outer wall;

a valve disposed inside the projection, the valve having a closed position with an end of the valve substantially flush with an end of the projection to close the fluid pathway and an open position with the end of the valve recessed inside the projection to open the fluid pathway, wherein the valve includes a shaft that is made of a resilient material, wherein pressing on an end of the shaft causes the shaft to bend so that the end of the shaft is recessed within the projection to open the valve; and a cover disposed in the cavity between the projection and the outer wall, wherein the cover has a first configuration with the cover disposed substantially flush with the end of the valve and substantially flush with the end of the projection.

20. A medical connector comprising:

a housing having:

an outer wall;

a first opening; and a second opening;

a fluid pathway between the first opening and the second opening;

a hollow projection that defines an interior cavity that forms a portion of the fluid pathway, the projection disposed inward of the outer wall to form a cavity between the projection and the outer wall;

a valve disposed inside the projection, the valve having a closed position with an end of the valve substantially flush with an end of the projection to close the fluid pathway and an open position with the end of the valve recessed inside the projection to open the fluid pathway;

a cover disposed in the cavity between the projection and the outer wall, wherein the cover has a first configuration with the cover disposed substantially flush with the end of the valve and substantially flush with the end of the projection; and a breakaway member that is configured to removably couple to the housing and to receive a second medical connector to establish fluid communication between the second medical connector and the fluid pathway, wherein the breakaway member is configured to disengage from the housing when a threshold amount of force pulls the breakaway member or the second medical connector away from the medical connector.

21. The medical connector of claim 20, wherein the breakaway member is configured to reengage the housing after the disengagement to reestablish fluid communication between the second medical connector and the fluid pathway of the breakaway medical connector.

22. The medical connector of claim 21, wherein the end of the valve, the end of the projection, and the end of the cover provide a substantially flush swabbing surface upon disengagement.

23. The medical connector of claim 22, wherein the outer wall has an opening that is at least about 6 mm wide to provide access to the swabbing surface.

24. The medical connector of claim 20, wherein the cover is configured to be pushed along an exterior of the projection when the second medical connector is coupled to the medical connector.

25. The medical connector of claim 24, wherein the cover is configured to form a seal with a housing of the second medical connector.

26. A medical connector comprising:

a housing having:

an outer wall;

a first opening; and a second opening;

a fluid pathway between the first opening and the second opening;

a hollow projection that defines an interior cavity that forms a portion of the fluid pathway, the projection disposed inward of the outer wall to form a cavity between the projection and the outer wall;

a valve disposed inside the projection, the valve having a closed position with an end of the valve substantially flush with an end of the projection to close the fluid pathway and an open position with the end of the valve recessed inside the projection to open the fluid pathway;

a cover disposed in the cavity between the projection and the outer wall, wherein the cover has a first configuration with the cover disposed substantially flush with the end of the valve and substantially flush with the end of the projection, wherein the cover is configured to be pushed along an exterior of the projection when a second medical connector is coupled to the medical connector; and an activation member configured to move with the cover, wherein the activation member is configured to pull the valve to the open position.

27. The medical connector of claim 26, wherein the activation member is biased so that the activation member is configured to push the valve to the closed position upon breakaway disconnection from a second connector.

28. The medical connector of claim 26, comprising a hub that divides an interior of the connector into a first portion and a second portion, wherein the hub includes one or more openings, wherein the activation member includes a body portion on a first side of the hub and one or more posts that extend through the openings in the hub.

29. The medical connector of claim 26, wherein the fluid pathway extends through the activation member.

30. The medical connector of claim 26, wherein the valve includes a shaft that is made of a resilient material, wherein pressing on an end of the shaft causes the shaft to bend so that the end of the shaft is recessed within the projection to open the valve.

31. A method of using a breakaway medical connector, the method comprising:

accessing a first medical connector that includes a main body with a fluid pathway and a breakaway member attached to the main body;

coupling a second medical connector to the breakaway member, wherein coupling the second medical connector to the breakaway member establishes fluid communication between the second medical connector and the fluid pathway of the main body;

detaching the breakaway member and the second medical connector from the main body of the first medical connector by pulling the second connector away from the first connector, wherein the breakaway member remains coupled to the second medical connector after the detachment; and reattaching the breakaway member to the main body of the first medical connector without needing the use of a tool by pushing the breakaway member into the main body of the first medical connector to reestablish fluid communication between the second medical connector and the fluid pathway of the main body of the first medical connector.

32. The method of claim 31, further comprising swabbing the main body of the first medical connector with a disinfectant before reattaching.

33. The method of claim 32 wherein the main body of the first connector includes a projection, a valve internal to the projection, and a face seal external to the projection, wherein the end of the projection, the end of the valve, and the end of the face seal are substantially flush after the detaching.

34. The method of claim 33, wherein the main body of the first medical connector includes an outside wall that creates a cavity, and wherein the projection, valve, and face seal are recessed within the cavity.

35. The method of claim 34, wherein the cavity has an opening that is at least about 6 mm wide to facilitate the swabbing.

36. The method of claim 31, comprising moving an activation member within the first medical connector with a housing of the second medical connector when the second medical connector is attached to the first medical connector, and wherein moving the activation member pulls a valve to an open position to open the fluid pathway.

37. The method of claim 36, wherein the activation member is biased so that is closes the valve upon detachment of the second medical connector from the main body of the first medical connector.

38. The method of claim 31, wherein coupling a second medical connector to the breakaway member comprises rotating the second medical connector relative to the breakaway member so that threading on the second medical connector engages threading on the breakaway member.

* * * * *